(12) United States Patent
Pasamontes et al.

(10) Patent No.: US 6,291,204 B1
(45) Date of Patent: *Sep. 18, 2001

(54) FERMENTATIVE CAROTENOID PRODUCTION

(75) Inventors: Luis Pasamontes, Trimbach (CH); Yuri Tsygankov, Moscow (RU)

(73) Assignee: Roche Vitamins Inc., Parsippany, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/980,832

(22) Filed: Dec. 1, 1997

(30) Foreign Application Priority Data

Dec. 2, 1996 (EP) .................................... 96810839

(51) Int. Cl.⁷ .................................... C12P 23/00
(52) U.S. Cl. .................... 435/67; 435/132; 435/155; 435/252.33; 536/23.2
(58) Field of Search .................. 435/67, 183, 252.3, 435/252.33; 536/23.2, 23.7

(56) References Cited

U.S. PATENT DOCUMENTS

| | | | |
|---|---|---|---|
| 5,607,839 | 3/1997 | Tsubokura et al. | 435/67 |
| 5,858,761 | 1/1999 | Tsubokura et al. | 435/252.1 |
| 6,087,152 | * 7/2000 | Hohmann et al. | 435/252.31 |

FOREIGN PATENT DOCUMENTS

| | | |
|---|---|---|
| 393 690 | 10/1990 | (EP) . |
| 635 576 A1 | 1/1995 | (EP) . |
| 0 735 137 A1 | 10/1996 | (EP) . |
| 747-483 | * 12/1996 | (EP) . |
| WO 91/13078 | 9/1991 | (WO) . |
| WO 95/18220 | 7/1995 | (WO) . |

OTHER PUBLICATIONS

Pasamontes, et al., "Isolation and characterization of the carotenoid biosynthesis genes of *Flavobacterium* sp. strain R1534," *Gene*, vol. 185, pp. 35–41 (1997).

Misawa et al., "Canthaxanthin Biosynthesis by the Conversion of Methylene to Keto Groups in a Hydrocarbon β–Carotene by a Singele Gene", Biochemical and Biophysical Research, vol. 209, No. 3, pp. 867–876 (1995).

Misawa et al., "Structure and Functional Analysis of a Marine Bacterial Carotenoid Biosynthesis Gene Cluster and Astaxanthin Biosynthetic Pathway Proposed at the Gene Level", Journal of Bacteriology, vol. 177, No. 22., pp. 6575–6584 (Nov. 1995).

Kajiwara et al., "Isolation and functional identification of a novel cDNA for astaxathin biosynthesis from *Haematococcus pluvialis*, and astaxathin synthesis in *Escherichia coli*", Plant Molecular Biology, 29:343–352 (1995).

Hundle et al., "Functional assignment of Erwinia herbicola Eho 10 carotenoid genes expressed in *Escherichia coli*", Mol. Gen. Genet., 245:406–416 (1994).

* cited by examiner

Primary Examiner—Nashaat T. Nashed
(74) Attorney, Agent, or Firm—Stephen M. Haracz; Kevin C. Hooper; Bryan Cave LLP

(57) ABSTRACT

Novel proteins of microorganism E-396 (FERM BP-4283) and the DNA sequences which encode these proteins have been discovered to provide an improved biosynthetic pathway from farnesyl pyrophosphate and isopentyl pyrophosphate to various carotenoids, especially zeaxanthin, astaxanthin, adonixanthin and canthaxanthin.

3 Claims, 87 Drawing Sheets

```
                                                     orf-5 -->  D  P  R  L  A  V  R  D  Q  Q  P  P  L  R  I  G  Q
  1    GGATCCGCGCCTGGCCGTTCGCCGATCAGCAGCCGCCCTTGCGGATCGGTC                                                              AGATGATGTGCTGATCCATGGCCCCGTCATTGCAAAACCGATCACCGATCC
       ----+----+----+----+----+----+----+----+----+----+--  50                                                        ----+----+----+----+----+----+----+----+----+----+--  350
       CCTAGGCGCGGACCGGCAAGCGGCTAGTCGTCGGCGGGAACGCCTAGCCAG                                                              TCTACTACACGACTAGTACGGGCAGTAAGTTTTGGCTAGTGGCTAGG
                                                                                                                         D  D  V  L  I  H  G  P  S  L  Q  N  R  S  P  I  L H  H  P  H  E  P  Q  R  T  T  Q  R  A  P  Q  I
 51    AGCATCATCCCCATGAACCGCAGCGCCACGACCCAGCGCGCGCCCCAGATC                                                              TGTCGCGTGATGGCATTGTTTGCAATGCCCAGGGGTAGGATGGCGCGA
       ----+----+----+----+----+----+----+----+----+----+--  100                                                       ----+----+----+----+----+----+----+----+----+----+--  400
       TCGTAGTAGGGGTACTTGGCGTCGCGGTGCTGGGTCGCGCGCGGGGTCTAG                                                              ACAGGCCACTACCGTAACAAACGTTACGGGCTCCCGATCCTACCGCGCT
                                                                                                                         S  R  D  G  I  V  C  N  A  P  R  A  R  M  A  R G  R  V  Q  H  G  M  R  H  H  R  E  G  P  R  R  H
101    GGGCCGCGTCCAGCACGGCATGCGCCATCATCGCGAAGGCCCCCGGCGGCA                                                              AGGATCAAGGGGGGAGAGACATGGAAATCGAGGGACGGGTCTTTGTCGT
       ----+----+----+----+----+----+----+----+----+----+--  150                                                       ----+----+----+----+----+----+----+----+----+----+--  450
       CCCCGGCGCAGGTCGTGCCGTACGCGGTAGTAGCGCTTCCGGGGCCGCCGT                                                              TCCTAGTTCCCCCCTCTCTGTACCTTTAGCTCCCTGCCCAGAAACAGCA
                                                                                                                         R  I  K  G  G  R  D  M  E  I  E  G  R  V  F  V  V G  A  R  A  H  S  E  E  L  A  A  C  P  L  R  K  V
151    TGGGGGCGCGTGCCCATTCCGAACAACTCCGAGGAGCTGGCCGCCTGCCCG                                                              CACGGGCCGCGCATCGGGTCTTGGGGGGCGGCCGCTCGGCGGCGGATGCTGGCCC
       ----+----+----+----+----+----+----+----+----+----+--  200                                                       ----+----+----+----+----+----+----+----+----+----+--  500
       ACCCCCGCGCACGGGTAAGGCTTGTTGAGGCTCCTCGACCGGCGGACGGGC                                                              GTGCCCGGCGCGTAGCCCAGACCCCGCCGAGCGCCGCCGCCTACGACCGGG
                                                                                                                         T  G  A  A  S  G  L  G  A  A  S  A  R  M  L  A  Q A  P  D  R  A  V  F  R  C  S  D  G  P  D  A  R
201    TCGGCCCAGATCGCGCCGTATTCCGATGCAGTGACGGGCCCCGATGCGCGT                                                              AAGGCGGCGGCGAAGGTCGTGCTGGCCGATCTGGCCGAACCGAAGGACGCG
       ----+----+----+----+----+----+----+----+----+----+--  250                                                       ----+----+----+----+----+----+----+----+----+----+--  550
       AGCCGGGTCTAGCGCGGCATAAGGCTACGTCACTGCCCGGGGCTACGCGCA                                                              TTCCGCCGCCGCTTCCAGCAGCACCGGCTAGACCGGCTTGGCTTCCTGCGC
                                                                                                                         G  G  A  K  V  V  L  A  D  L  A  E  P  K  D  A G  P  A  L  P  R  R  H  Q  R  I  A  H  E  P  F  R
251    GGGCCCCGCGCCCTGCCCCGCCGCCACCAGCGCATCGCGCACGAACCCTTCCG                                                            CCCGAAGGCGCGGTTCACGCGGCCTGCCGACTGCGACGTGACCGACGCTGC
       ----+----+----+----+----+----+----+----+----+----+--  300                                                       ----+----+----+----+----+----+----+----+----+----+--  600
       CCCGGGGCGCGGGACGGGGGCGGCGGTGGTCGCGTAGCGCGTGCTTGGGAAGGC                                                            GGGCTTCCGCGCCAAGTGCGCCGGACGCTGCACTGGCTGCTGGCCACG
                                                                                                                         P  E  G  A  V  H  A  A  C  D  V  T  D  A  T  A  A
```

FIG. 7A

```
601  GCAGACGGGCCATCGCGTGGCGACCGACCGCTTCGGGCAGGCTGGACGGGCC
     --------+---------+---------+---------+---------+   650
     CGTCTGCCCGGTAGCGCACCGCTGGCTGCCGAAGCCCGTCCGACCTGCCGG

Q  T  A  I  A  L  A  T  D  R  F  G  R  L  D  G  L

651  TTGTGAACTGCCGCGGCCATCGCGCCCGGCCCGAACGGATGCTGGGGCGGAC
     --------+---------+---------+---------+---------+   700
     AACACTTGACGGCGCCGGTAGCGCGGGCCGGGCTTGCCTACGACCCCGCCTG

V  N  C  A  G  I  A  P  A  E  R  M  L  G  R  D

701  GGGCCGCATGGACTGGACAGCTTTGCCCGTGCGGTCACGATCAACCTGAT
     --------+---------+---------+---------+---------+   750
     CCCGGCGTACCTGACCTGTCGAAACGGGCACGCCAGTGCTAGTTGGACTA

G  P  H  G  L  D  S  F  A  R  A  V  T  I  N  L  I

751  CGGCCAGCTTCAACATGGCCCGGCCCTTCAGCGCCGAGGCGATGGCCGAACG
     --------+---------+---------+---------+---------+   800
     GCCGGTCGAAGTTGTACCGGGCCGGGAAGTCGCGGCTCCGCTACCGGCTTGC

G  S  F  N  M  A  R  L  A  A  E  A  M  A  R  N  E

801  AGCCCGTCCGGGGCGAGCGTGGCGTGAATCGTCAACACGGCCTCGATCGG
     --------+---------+---------+---------+---------+   850
     TCGGGCAGGCCCCGCTCGCACCGCACTAGCAGTTGTGCCGGAGCTAGCC

P  V  R  G  E  R  G  V  I  V  N  T  A  S  I  A

851  GCGCAGGACGGACAGATCGGACAGGTCGCCTATGCGGCCAGCAAGGCGGG
     --------+---------+---------+---------+---------+   900
     CGGTCCTGCCTGTCTAGCCTGTCCAGCGGATACGCCGGTCGTTCCGCCC

A  Q  D  G  Q  I  G  Q  V  A  Y  A  A  S  K  A  G

901  CGTGGCGGGCATGACGACGCTGCCGATGGCCCGCGACCTTGCGCGGCACGGCA
     --------+---------+---------+---------+---------+   950
     GCACCGCCCGTACTGCTGCGACGGCTACCGGGCGCTGGAACGCGCCGTGCCGT

V  A  G  M  T  L  P  M  A  R  D  L  A  R  H  G  I

951  TCCGGCGTCATGACCATCGCGCCCGGCATCTTCCGCACCCCGATGCTGGAG
     --------+---------+---------+---------+---------+   1000
     AGGCCGCAGTACTGGTAGCGCGGGCCGTAGAAGGCGTGGGGCTACGACCTC

R  V  M  T  I  A  P  G  I  F  R  T  P  M  L  E

1001 GGGCTGCCGCAGGACGTTCAGGACAGCCTGGGCGCCGTGCCGTTCCC
     --------+---------+---------+---------+---------+   1050
     CCCGACGGCGTCCTGCAAGTCCTGTCGGACCCGCGGCACGGCCAAGGG

G  L  P  Q  D  V  Q  D  S  L  G  A  A  V  P  F  P

1051 CTCGCGGGCTGGGAGAGCCGTCGGAATACGGCGGCTGTTGCACCACATCA
     --------+---------+---------+---------+---------+   1100
     GAGCGCCCGACCCTCTCGGCAGCCTTATGCCGCCGACAACGTGTGTAGT

S  R  L  G  E  P  S  E  Y  A  A  L  L  H  H  I  I

1101 TCGGAACCCCATGCTGAACTGAAGGAGAGGTCATCCGCCTCGACGGCGCATTG
     --------+---------+---------+---------+---------+   1150
     AGCCTTGGGGTACGACTTGCTTCCTCTCCAGTAGGCGGAGCTGCCGCGTAAC

A  N  P  M  L  N  G  E  V  I  R  L  D  G  A  L

1151 CGCATGCCCCCAAGTGAAGGAGCGTTTCATGGACCCCATCGTCATCACC
     --------+---------+---------+---------+---------+   1200
     GCGTACCGGGGGTTCACTTCCTCGCAAAGTACCTGGGGTAGCAGTAGTGG

R  M  A  P  K  *          M  D  P  I  V  I  T
                                  orf-1 -->
```

FIG. 7B

```
1201 GGCGCGATGCGACCCCGATGGGGGCCATTCCAGGCGGATCTTGCGCCGAT              1250
     CCGCGCTACGCTGGGGCTACCCCCGGTAAGGTCCCGCTAGAACGGCGCTA
     G  A  M  R  T  P  M  G  A  F  Q  G  D  L  A  A  M

1251 GGATGCCCCGACCCTTGGCGCGGACGGATCCGCCGCGCTGAACGGGCC                 1300
     CCTACGGGGCTGGGAACCGCGCCCTAGGCGTCGGCGCGACTTGCCGG
     D  A  P  T  L  G  A  D  A  I  R  A  A  L  N  G  L

1301 TGTCGCCCGACATGGTGGACCAGGTCGATGGGCTGCGTCTTCGCGCCG                 1350
     ACAGCGGGCTGTACCACCTGGTCCAGCTACCCGACGCAGGAGCGGCGC
     S  P  D  M  V  D  E  V  L  M  G  C  V  L  A  A

1351 GGCCAGGGTCAGGCACCGGCACGTCAGGCGGCGCTTGGCGCCGGACTGCC               1400
     CCGGTCCCAGTCCGTGGCCGTGCAGTCCGCCGCGAACCGGCGGCCTGACGG
     G  Q  G  Q  A  P  A  R  Q  A  A  L  G  A  G  L  P

1401 GCTGTCGACGGGGCACGACCACCATCAACGAGATGTGCGGATCGGGCATGA              1450
     CGACAGCTGCCCCGTGCTGGTGGTAGTTGCTCTACACGCCTAGCCCGTACT
     L  S  T  G  T  T  I  N  E  M  C  G  S  G  M  K

1451 AGGCCCGACATGCTGGGCCATGACCTGATCGCCGCGGGATCGGCGGGCATC             1500
     TCCGGGCTGTACGACCCGGTACTGGACTAGCGGCGCCCTAGCCGCCCGTAG
     A  A  M  L  G  H  D  L  I  A  A  G  S  A  G  I
```

```
1501 GTCGTCGCCGGCGGGGATGGAGAGCATGTCGAACGCCCCCTACCTGCTGCC              1550
     CAGCAGCGGCCGCCCCTACCTCTCGTACAGCTTGCGGGGATGGACGACGG
     V  V  A  G  G  M  E  S  M  S  N  A  P  Y  L  L  P

1551 CAAGGCGCGGTCGGGGATGCGCATGGGCCATGACCGTGTGCTGGATCACA              1600
     GTTCCGCGCCAGCCCCTACGCGTACCCGGTACTGGCACACGACCTAGTGT
     K  A  R  S  G  M  R  M  G  H  D  R  V  L  D  H  M

1601 TGTTCCTCGACGGGTTGGAGGACGCCTATGACAAGGGGCCGCCTGATGGGC              1650
     ACAAGGAGCTGCCCAACCTCCTGCGGATACTGTTCCCGGCGGACTACCCG
     F  L  D  G  L  E  D  A  Y  D  K  G  R  L  M  G

1651 ACCTTCGCCGAGGATTGCGCCGGGGATCACGGTTTCACCCGGAGGGCCA               1700
     TGGAAGCGGCTCCTAACGCGGCCCCTAGTGCCAAAGTGGGCGCTCCGGT
     T  F  A  E  D  C  A  G  D  H  G  F  T  R  E  A  Q

1701 GGACGACTATGCCTTGACCAGCCTTGCGCGCGCAGGACGCCATCGCCA               1750
     CCTGCTGATACGGAACTGGTCGGAACGCGCGCGTCCTGCGGTAGCGGT
     D  D  Y  A  L  T  S  L  A  R  A  Q  D  A  I  A  S

1751 GCGGTGCCTTCGCCGCCGCCGAGATCGCCCGTGACCGTCACGGCACGCAAG             1800
     CGCCACGGAAGCGGCGGCGGCTCTAGCGGGCACTGGCAGTGCCGTGCGTTC
     G  A  F  A  A  E  I  A  P  V  T  V  T  A  R  K
```

FIG. 7C

```
1801  GTGCAGAGACCACCGTCGATACCGACGAGATGCCCGGCAAGGCCCCGCCCGA                    1850
      CACGTCCTGGTGGCAGCGTATGGCTGCTCTACGGGCCGTTCCGGGGCGGGCT
         V  Q  T  T  V  D  T  D  E  M  P  G  K  A  R  P  E

1851  GAAGATCCCCCATCTGAAGCCCGCCTTCCGTGACGGTGGCGGCACGGTCACG                    1900
      CTTCTAGGGGGTAGACTTCGGGCGGAAGGCACTGCCACCGTGCCAGTGCC
         K  I  P  H  L  K  P  A  F  R  D  G  G  T  V  T  A

1901  CGGCGAACAGCTGTCCGATCTCGACGGGCGCGGCGCGCTGGTGATGATG                      1950
      GCCGCTTGTCGACAGGCTAGAGCTGCCCGCGCCGCGCGACCACTACTAC
         A  N  S  S  S  I  S  D  G  A  A  A  L  V  M  M

1951  CGGCCAGTCGCAGGCCGAGAAGCTGGGCCTGACGCCGATCGCGCGGATCAT                    2000
      GCCGGTCAGCGTCCGGCTCTTCGACCCGGACTGCGGCTAGCGCGCCTAGTA
         R  Q  S  Q  A  E  K  L  G  L  T  P  I  A  R  I  I

2001  CGGGTCATGCCGACCATGCCGACCGTCCCGGCCTGTTCCCGACGGCCCCA                     2050
      GCCAGTACGGCTGGTACGGCTGGCAGGGCCGGACAAGGGCTGCCGGGGT
         G  H  A  T  H  A  D  R  P  G  L  F  P  T  A  P  I

2051  TCGGGCGCGATGCGCAAGCTGCTGGACCGCACGGACACCCGCCTTGGCGAT                    2100
      AGCCCGCGCTACGCGTTCGACGACCTGGCGTGCCTGTGGGCGGAACCGCTA
         G  A  M  R  K  L  L  D  R  T  D  T  R  L  G  D

2101  TACGACCTGTTCGAGGTGAACGAGGCATTCGCCGTCGTCGCCATGATCGC                     2150
      ATGCTGGACAAGCTCCACTTGCTCCGTAAGCGGCAGCAGCGGTACTAGCG
         Y  D  L  F  E  V  N  E  A  F  A  V  V  A  M  I  A

2151  GATGAAGGAGCTTGGCCTGCCACACGATGCCACGAACATCAACGGCGGG                      2200
      CTACTTCCTCGAACCGGACGGTGTGCTACGGTGCTTGTAGTTGCCGCCCC
         M  K  E  L  G  L  P  H  D  A  T  N  I  N  G  G  A

2201  CCTGCGCGCTTGGGCATCCCATCGGCGTCGGGGCGCGGATCATGTC                         2250
      GGACGCGCGAACCCGTAGGGTAGCCGCAGCCCGCGCCTAGTACCAG
         C  A  L  G  H  P  I  G  A  S  G  A  R  I  M  V

2251  ACCCTGCTGAACGCGATGCGGCCGCGGGGCGCGACGCGCGGGCCCATC                       2300
      TGCCGACGACTTGCGCTACCGCCGGCGCCCCGCGCTGCGCGCCCGGGTAG
         T  L  L  N  A  M  A  A  R  G  A  T  R  G  A  A  S

2301  CGTCTGCATCGGCGGGGGCGAGGCGACGGCCATCGCGCTGGAACGGCTGA                     2350
      GCAGACGTAGCCGCCCCCGCTCCGCTGCCGGTAGCGCGACCTTGCCGACT
         V  C  I  G  G  G  E  A  T  A  I  A  L  E  R  L  S

2351  GCTAATTCATTTGCGCGAATCCGCGTTTCGTGCACGATGGGGAACCG                        2400
      CGATTAAGTAAACGCGCTTAGGCGCAAAAGCACGTGCTACCCCCTTGGC
         *
```

FIG. 7D

```
2401 GAAACGGCCACGCCCTGTGTTGGTTGCGTCGACCTGTCTTCGGGCCATGCC        GTCTGCGATGCCATGGTCGATGCCGCTGCGCCGGTCGAGATGGTCCATGC 2750
     -------+---------+---------+---------+---------+--        -------+---------+---------+---------+---------+--
     CTTTGCCGGTGCGGACAACACCAACCGAGCAGAAGCCCGGTACGG              CAGACGCTACGGTACCAGCTACGGCGACGGCCAGCTCTACCAGGTACG
                                                               V  C  D  A  M  V  D  A  A  C  A  V  E  M  V  H  A

2451 CGTGACGCGATGTGGCAGGCCGCATGGGCCTTGCCGATCCGGTCGCATGA         CGCATGCTGCTGATCTTCGACGACATGCCCTGCATGGACGATGCCAGGACCC 2800
     -------+---------+---------+---------+---------+--        -------+---------+---------+---------+---------+--
     GCACTGCGCTACACCGTCCGGCGTACCCGGAACGGCTAGGCCAGCGTACT         GCGTAGCGACTAGAAGCTGCTGTACGGGACGTACCTGCTACGGTCCTGGG
                                                               A  S  L  I  F  D  D  M  P  C  M  D  D  A  R  T  R
2501 CTGAGCGCAACGAAGGCACCGATGACGCCCAAGCAGCAATTCCCCCTACGC         GTCGGGGTCAGCCCGCCACCATGTGCCCATGGGAGGGGCGGGTG 2850
     -------+---------+---------+---------+---------+--        -------+---------+---------+---------+---------+--
     GACTCGCGTTGCTTCCGTGGCTACTGCGGCGTTCGTCGTTAAGGGGGATGCG       CAGCCGCCAGTCGGGCGGTGGTACACGGGTACCCTCCCCGCGCCAC
         crtE --> M  T  P  K  Q  Q  F  P  L  R                 R  G  Q  P  A  T  H  V  A  H  G  E  G  R  A  V 2551 GATCTGGTCGAGATCAGGCTGGCGCAGATCTCGGGCCAGTTCGGCGTGGT         CTTGCGGGGATCGCCCTGATCACCGAGCGCATGCGGATTTTGGGCGAGGC 2900
     -------+---------+---------+---------+---------+--        -------+---------+---------+---------+---------+--
     CTAGACCAGCTCTAGTCCGACCGCGTCTAGAGCCCGGTCAAGCCGCACCA         GAACGCCCGTAGCGGGACTAGTGGCTCGCGTACGCCTAAAACCCGCTCCG
     D  L  V  E  I  R  L  A  Q  I  S  G  Q  F  G  V  V         L  A  G  I  A  L  I  T  E  A  M  R  I  L  G  E  A 2601 CTTCGGCCCCGTCGGCGGGCGGGCCATGAGCGATGCCGCCCTGTCCCCGGCA       GCGCGGCGCGAGCCGGATCAGCGCGATCAGCGCGCCAAGGCTGGTCGCATCCATGTCGC 2950
     -------+---------+---------+---------+---------+--        -------+---------+---------+---------+---------+--
     GAGCCGGGGCAGCCGCCCGCCCGGTACTCGCTACGGCGGGACAGGGGCCGT       CGCGCCGCGCTCGGCCTAGTCGCGCTAGTCGCGCGGTTCCGACCAGCTAGGTACAGCG
     S  A  P  L  G  A  A  M  S  D  A  A  L  S  P  G  K         R  G  A  T  P  D  Q  R  A  R  L  V  A  S  M  S  R 2651 AACGCTTTCGCGCCGTCGTGATGCTGATGGTCGCCGAAAGCTCGGGCGGG         GCGGATGGGACCGGTCGGGGCTGTGCCGCAGGGCAGGATCTGGACCTGCAC 3000
     -------+---------+---------+---------+---------+--        -------+---------+---------+---------+---------+--
     TTGCGAAAGCGCGGCACGCACTACGACTACCAGCGGCTTTCGAGCCCGCCC       CGCCTACCCTGGCCAGCCCGACACGGCGTCCCGTCCTAGACCTGGACGTG
     R  F  R  A  V  L  M  L  M  V  A  E  S  S  G  G           A  M  G  P  V  G  L  C  A  G  Q  D  L  D  L  H
```

```
4201 GCATAGAGCCATGACCGTATCCTCCGGATGCCGGGCGGCATCAGCTTGCC
     ----+----+----+----+----+----+----+----+----+----+  4250
     CGTATCTCGGTACTGGCATAGGAGGCCTACGGCCCGCCGTAGTCGAACCG
        A  Y  L  M  V  T  D  E  R  I  G  P  P  M  L  K  A

4251 CGGCCTGCGCGAAGCTTTGCGAACCCTGCGCGATGGCCGGCTTCGGAAGTCG
     ----+----+----+----+----+----+----+----+----+----+  4300
     GCCGGACGCGCTTCGAAACGCTTGGGACGCGCTACCGGCCGAAGCCTTCAGC
        A  Q  A  F  S  Q  S  G  Q  A  I  A  A  E  S  T

4301 CCGTCAGATCGGTCATGCGACGGCCAGTCTCCGACAGCATGACCTGGCCG
     ----+----+----+----+----+----+----+----+----+----+  4350
     GGCAGTCTAGCCAGTAGCTGCCGGTCAGAGGCTGTCGTACTGGACCGGCC
        A  T  L  D  T  M   A  V  A  L  D  S  L  M  V  Q  A
        <-- crtB 4351 TGGCCTTGGCGCTGCCAACGACACCCGGGATGCCCGGATGCGTG
     ----+----+----+----+----+----+----+----+----+----+  4400
     ACCGGAACCGCGACGGTTGCTGTGTGGGCCCTACGGGCCTACGCAC
        T  A  K  A  S  G  V  V  G  P  I  G  A  G  P  H  T 4401 CCCGCCCCCACGATGTAGAAGTTCGGGATCGCGGCGGTTATGCGG
     ----+----+----+----+----+----+----+----+----+----+  4450
     GGGCGGGGGGTGCTACATCTTCAAGCCCTAGCGCCGCCAATACGCC
        G  A  G  V  I  Y  F  N  P  I  A  R  D  R  N  H  P 4451 GCGGAACCAGGGCCGGATTGCGTCAGGATCGCTCGACCGAGAAGGCGCTGC
     ----+----+----+----+----+----+----+----+----+----+  4500
     CGCCTTGGTCCCGGCCTAACGCAGTCCTAGCGAGCTGGCTCTTCCGCGACG
        R  F  W  A  S  Q  T  L  I  P  E  V  S  F  A  S 4501 CTGACGGTCAGGTCGTTGCTGCGCAGGTCGGGGATGGCGGCGCTCCAGTTC
     ----+----+----+----+----+----+----+----+----+----+  4600
     GACTGCCAGTCCAGCAACGACGCGTCCAGCCCCTACCGCCGCGAGGTCAAG
        S  V  T  L  H  K  R  L  D  P  I  A  R  R  E  L  E 4551 CGTGATGGGCCGACAGTTCGGTGCTGAAATCGGCGGGGCTGAAGATGCGG
     ----+----+----+----+----+----+----+----+----+----+  4550
     GCACTACCCGGCTGTCAAGCCACGACTTTAGCCGCCCCGACTTCCTACGCC
        G  H  H  A  S  L  E  T  S  F  D  A  P  S  F  I  R 4601 CTCGAAGATGCCTCGGCATAGCCCGGGCCTCGGCTTCCCAATCGACAT
     ----+----+----+----+----+----+----+----+----+----+  4650
     GAGCTTCTACGGAGCCGTATCGGGCCCGGAGCCGAAGGTTAGCTGTA
        E  F  I  R  E  A  Y  G  P  A  E  A  E  W  D  V 4651 CGGCGCGGCCCAGATGCGGAACGGCGCAAGGACGCTAATGCGTGGACATC
     ----+----+----+----+----+----+----+----+----+----+  4700
     GCCGCGCCGGGTCTACGCCTTGCCGCGTTCCTGCGATTACGCACCTGTAG
        D  A  R  G  L  H  P  V  P  A  L  V  H  T  S  M 4701 CCCTCGGGGGCCAGGCTGGGATCGGTCACGCAGGCGGAATGCAGATACAT
     ----+----+----+----+----+----+----+----+----+----+  4750
     GGGAGCCCCCGGTCCGACCCTAGCACTGCGTCCGCCTTACGTCTATGTA
        G  E  P  A  L  S  P  D  T  V  C  P  S  H  L  Y  M 4751 CGAGAAATCTCCGGCAGGCGTGCCCGGTTGAAGATCTCGTTCACCAGCC
     ----+----+----+----+----+----+----+----+----+----+  4800
     GCTCTTTAGAGGCCGTCCGCACGGGCCAACTTCTAGAGCAAGTGGTCGG
        S  F  D  D  P  L  R  P  G  N  F  I  E  N  V  L
```

```
6001  CCGGTTCAGCAGCCCGCAGGAAGCGGTCGCGGATCCGCGGATCGATGGCCC
      ---------+---------+---------+---------+---------+  6050
      GGCCAAGTCGTCGGGCGTCCTTCGCCAGCGCCTAGCGCGCCTAGCTACCGGG
       R  N  L  L  P  L  F  R  D  A  R  D  I  A

6051  AGCCCGCGCACCGCGACGGGCGGACGCGGTCGTTCAGGTCGCGCCGCCGCG
      ---------+---------+---------+---------+---------+  6100
      TCGGGCGCGTGGCGCTGCCCGCCTGCGCCAGCAAGTCCAGCGCGGCGGCGC
       W  G  R  V  A  R  R  A  S  A  T  T  L  D  R  A  A

6101  ATGGCATCCGCGACCTGCGCGGACATAGGGCAGGAATATCCGGTGACGGGG
      ---------+---------+---------+---------+---------+  6150
      TACCGTAGGCGCTGGACGCGCCTGTATCCCGTCCTTATAGGCCACTGCCC
       I  A  D  A  V  Q  A  A  Y  P  L  S  Y  G  T  V  P

6151  GTGAACAGCCCTGCCCCCAGCCCCAACCGGCGGGGGGGGGACGGCCACCA
      ---------+---------+---------+---------+---------+  6200
      CACTTGTCGGGACGGGGTCGGGTTGGCCGCCCCCCCCCCTGCCGGTGGT
       H  F  L  G  A  G  L  G  V  P  V  A  G  Q  A  H

6201  CGCGCCAGAAGCCTATGGCGTCATGGGCCAGCGCGGATGGCAGGATGCCC
      ---------+---------+---------+---------+---------+  6250
      GCGCGGTCTTCGGATACCGCAGTACCCGGTCGCGCCTACCGTCCTACGGG
       D  R  W  F  G  I  A  D  H  A  L  A  I  P  L  I  G

6251  CTTTCGCGCCGCATCCTGCCCGGGTCCAGCCCCGCCTGGCGGCATAGTC
      ---------+---------+---------+---------+---------+  6300
      GAAAGCGCGGCGTAGGACGGGCCAGGTCGGGGCGGACCGCCGTATCAG
       R  E  R  R  M  E  Q  G  T  W  G  R  R  A  A  Y  D

6301  CAGGCGACGGCCCTGCGCCAGCGGCCAGCGTCCATGTCTCAGATGCCGCCGTCGCTGT
      ---------+---------+---------+---------+---------+  6350
      GTCGCTGCGGGACGCGGTCGCCGGTCGCAGGGTACAGAGTCTACGGCGGCAGCGACA
       L  S  A  Q  A  L  A  G  D  D  L  D  G  G  D  S

6351  AGCGGCTATCTCGATCAGGATGCGGTGGGACTGGAAGGGCAGCAGATAG
      ---------+---------+---------+---------+---------+  6400
      TCGCCGATAGAGCTAGTCCTACGCCACCCTGACCTTCCCGTCGTCTATC
       Y  R  T  D  E  I  L  I  R  T  P  S  F  P  L  L  Y

6401  ATGAAGCGGTACCGTCCATCGGAACGGTCGGTCTCCATGATCATCGG
      ---------+---------+---------+---------+---------+  6450
      TACTTCGCCATGGCAGGTAGACGCTTGCCAGCGCAGGTACTAGTAGCC
       I  F  R  Y  G  D  M  Q  P  V  T  A  D  M  I  M  P

6451  GCGCTCGACGCCATGGGGGCGTCGGTCTGATTCGACGCCCACGAATT
      ---------+---------+---------+---------+---------+  6500
      CGCGAGCTGCGGTACCCCGCAGCAGCCAGAGCTAGAGCTGCGGGTGCTTAA
       R  E  V  G  H  P  A  D  T  E  I  E  V  G  V  F

6501  TCTGAAACCACGGTCAGGTGCCGGGGTCTCGACGGCACCACGGGCGTCG
      ---------+---------+---------+---------+---------+  6550
      AGACTTTGGGTGCCAGTCCACGGCCCCAGAGCTGCCGTGGTGCCCGCAGC
       K  Q  F  G  V  T  L  H  P  T  E  V  A  G  R  A  D

6551  ATCACGCAGGCAGCCTGCGATCCCGAGCCGTCGTTCGGCGGTCGCGCCGGT
      ---------+---------+---------+---------+---------+  6600
      TAGTGCGTCCGTCGGACGCTAGGGCTCGGCAGCAAGCCGCCAGCGCGGCCA
       I  V  C  A  A  E  I  R  S  G  D  T  L  T  A  G  T
```

FIG. 7K

```
6601 ATCGTCCAGCGTCGCGACATGCGTATTCCACCGCAGATCGACACCCTGCA
     ----+----+----+----+----+----+----+----+----+----+  6650
     TAGCAGGTCGCAGCGCTGTACGCATAAGGTGGCGTCTAGCTGTGGACGT
       D  D  L  T  A  V  H  T  N  W  R  L  D  V  G  Q

6651 GCAGCCCGAATGGTCGGGAAACGCCGACCTCCTGATCCGTCCATTCGCCGCG
     ----+----+----+----+----+----+----+----+----+----+  6700
     CGTCGGGCTTAGCCAGCCCTTTGCGGCTGGAGGACTAGGCAGGTAAGCGGCGC
       L  L  G  I  L  A  G  A  E  I  S  G  Y  G  T  T  L

6701 CGGGCCGAATGGTCGGGAAACGCCGACCTCCTGATCCGTCCATTCGCCGCG
     ----+----+----+----+----+----+----+----+----+----+  6750
     GCCGGGCTTACCAGCCCTTTGCGGCTGGAGGACTAGGCAGGTAAGCGGCGC
       R  R  S  H  D  P  F  A  V  E  Q  D  T  W  E  G  R

6751 ACGAATGGGCGACAGGCGCGCCAGCCATTCGGGCGAAAGATCCGTGTCGT
     ----+----+----+----+----+----+----+----+----+----+  6800
     TGCTTACCCGCTGTCCGCGCGGTCGGTAAGCCCGCTTTCTAGGCACAGCA
       R  I  P  S  L  R  A  L  W  E  P  S  L  D  T  D

6801 GGCAGGACCAGGTGTGCTGTCCGAGGGGCCCGGACCGCGCGTCGAGCATC
     ----+----+----+----+----+----+----+----+----+----+  6850
     CCGTCCTGGTCCACACGACAGGCTCCCCGGGCCTGGCGCGCAGCTCGTAG
       H  C  S  W  T  H  Q  D  S  P  G  S  R  A  D  L  M

6851 ACGATGCGCGATCCGGTCTGCGGTCGCGACGCCCAGCCGCTTGCCGTTGCCGGTTGCCTTGCCGCTTGCCGTTCGCCTAGTCGCG
     ----+----+----+----+----+----+----+----+----+----+  6900
     TGCTACGCGCTAGGCCAGACGCCAGCGCCTGCGGGTCGGCGAACGGCAAGCGGCCAACGGCAAGCGGCGAACGGCAAGCGGATCAGCGC
       V  I  R  A  D  P  R  R  D  R  V  A  L  A  I  L  A

6901 ACCGGACAGCCCCGCGGCCCGCGATCAGCAGCAGATCATGCTCATGTATTGCG
     ----+----+----+----+----+----+----+----+----+----+  6950
     TGGCCTGTCGGGGCGCCGGGCGCTAGTCGTCGTCTAGTACCGAGTACATAACGC
       G  S  L  G  A  G  A  I  L  L  D  H  S  M  T  N  R
                                        <-- crtY 6951 ATCCCGCCCTTCGCGGTCCTTCAGCAGCCGCGCCCGAGCGTTTCAGCTCTG
     ----+----+----+----+----+----+----+----+----+----+  7000
     TAGGGCGGGAAGCCCAGGAAGTCGTCGGCGCGGGCTCGCAAAGTCGAGAC
       D  A  G  E  R  D  K  L  L  A  G  S  R  K  L  E 7001 CCTTGAGGCTGTGTCGACCGAGGGCGGCCCAGATGAAACCGAAGCTGACGCAG
     ----+----+----+----+----+----+----+----+----+----+  7050
     GGAACTCCGACACAGCTGGCTCCCCGCCGGGTCTACTTGGCTTCGACTGCGTC
       A  K  L  S  D  V  S  P  A  W  I  F  G  F  S  V  C 7051 TTTCTGCGGCCATGGACCGGCGCTGAGTCATCCTGTGTGCCTGGTAGACGCG
     ----+----+----+----+----+----+----+----+----+----+  7100
     AAGAGCCGCCGGTACCTGGCCGCTACTCAGTAGGACACACGGACCATCTGCGC
       N  E  R  G  H  V  A  H  H  M  R  H  A  Q  Y  V  R 7101 ACGAAGATAGCCGCGCTTGGGGACATAGCGGACATGGCAACGGCCAGCGCCCATGCA
     ----+----+----+----+----+----+----+----+----+----+  7150
     TGCTTCTATCGGCGCGAACCCCTGTATCGCCTGTACCGTTGCCGGTCGCGGGTACGT
       R  L  Y  G  R  K  P  V  Y  R  F  P  W  R  G  H 7151 CCAAGCCCTCATGCAGGAATAGTAGATCAGCCCGTAGCAGGTGACCCCC
     ----+----+----+----+----+----+----+----+----+----+  7200
     GGTTCGGCAGTACGTCCTTTATCATCTAGTCGGGCATCGTCCACTGGGGG
       V  L  G  D  H  L  F  Y  Y  I  L  G  Y  C  T  V  G
```

```
      CACGAGGTCCGAGAAGCCCGAATGACGGAGCACCTCGATATCGATGAACA
8401  --------+---------+---------+---------+---------+  8450
      GTGCTCCAGGCTCTTCGGCCTTACTGCCTCGTGGAGCTATACCTACTTGT

CGTCCTCGGGGTGGCCGAAGATGTTGGCGAACCGGGAAAAGGCCCTTGGC
8451  --------+---------+---------+---------+---------+  8500
      GCAGGAGCCCCACCGGCTTCTACAACCGCTTGGCCCTTTTCCGGGAACCG

CTTGTCGAACTCACTTGACGCGGGCCGGACGCAGCGGCAnnCGTCCAGATG
8501  --------+---------+---------+---------+---------+  8550
      GAACAGCTTGGTGAACTGCGCCCGGCCTGCGTCGCCGTnnGCAGGTCTAC

CTCGATCACCTCGGCATCCAGATCGGCGATnGGGGGGGTGnChGTCGCTTT
8551  --------+---------+---------+---------+---------+  8600
      GAGCTAGTGGAGCCCTAGGTCTAGCCGCTAnCCCCCACnGnCAGCGAAA

ChnnCGGTTCGATCGACAGGACCTC
8601  --------+---------+------  8625
      GnnnGCCAAGCTAGCTGTCCTGGAG
```

FIG. 70

```
  1  MTPKQQFPLR DLVEIRLAQI SGQFGVVSAP LGAAMSDAAL SPGKRFRAVL
 51  MLMVAESSGG VCDAMVDAAC AVEMVHAASL IFDDMPCMDD ARTRRGQPAT
101  HVAHGEGRAV LAGIALITEA MRILGEARGA TPDQRARLVA SMSRAMGPVG
151  LCAGQDLDLH APKDAAGIER EQDLKTGVLF VAGLEMLSII KGLDKAETEQ
201  LMAFGRQLGR VFQSYDDLLD VIGDKASTGK DTARDTAAPG PKGGLMAVGQ
251  MGDVAQHYRA SRAQLDELMR TRLFRGGQIA DLLARVLPHD IRRSA
```

FIG. 8

```
  1  MTDLTATSEA AIAQGSQSFA QAAKLMPPGI REDTVMLYAW CRHADDVIDG
 51  QVMGSAPEAG GDPQARLGAL RADTLAALHE DGPMSPPFAA LRQVARRHDF
101  PDLWPMDLIE GFAMDVADRE YRSLDDVLEY SYHVAGVVGV MMARVMGVQD
151  DAVLDRACDL GLAFQLTNIA RDVIDDAAIG RCYLPADWLA EAGATVEGPV
201  PSDALYSVII RLLDAAEPYY ASARQGLPHL PPRCAWSIAA ALRIYRAIGT
251  RIRQGGPEAY RQRISTSKAA KIGLLARGGL DAAASRLRGG EISRDGLWTR
301  PRA
```

FIG. 9

```
  1  MSSAIVIGAG FGGLALAIRL QSAGIATTIV EARDKPGGRA YVWNDQGHVF
 51  DAGPTVVTDP DSLRELWALS GQPMERDVTL LPVSPFYRLT WADGRSFEYV
101  NDDDELIRQV ASFNPADVDG YRRFHDYAEE VYREGYLKLG TTPFLKLGQM
151  LNAAPALMRL QAYRSVHSMV ARFIQDPHLR QAFSFHTLLV GGNPFSTSSI
201  YALIHALERR GGVWFAKGGT NQLVAGMVAL FERLGGTLLL NARVTRIDTE
251  GDRATGVTLL DGRQLRADTV ASNGDVMHSY RDLLGHTRRG RTKAAILNRQ
301  RWSMSLFVLH FGLSKRPENL AHHSVIFGPR YKGLVNEIFN GPRLPDDFSM
351  YLHSPCVTDP SLAPEGMSTH YVLAPVPHLG RADVDWEAEA PGYAERIFEE
401  LERRAIPDLR KHLTVSRIFS PADFSTELSA HHGSAFSVEP ILTQSAWFRP
451  HNRDRAIPNF YIVGAGTHPG AGIPGVVGSA KATAQVMLSD LAVA
```

FIG. 10

```
  1  MSHDLLIAGA GLSGALIALA VRDRRPDARI VMLDARSGPS DQHTWSCHDT
 51  DLSPEWLARL SPIRRGEWTD QEVAFPDHSR RLTTGYGSIE AGALIGLLQG
101  VDLRWNTHVA TLDDTGATLT DGSRIEAACV IDARGAVETP HLTVGFQKFV
151  GVEIETDAPH GVERPMIMDA TVPQMDGYRF IYLLPFSPTR ILIEDTRYSD
201  GGDLDDGALA QASLDYAARR GWTGQEMRRE RGILPIALAH DAIGFWRDHA
251  QGAVPVGLGA GLFHPVTGYS LPYAAQVADA IAARDLTTAS ARRAVRGWAI
301  DRADRDRFLR LLNRMLFRGC PPDRRYRLLQ RFYRLPQPLI ERFYAGRLTL
351  ADRLRIVTGR PPIPLSQAVR CLPERPLLQE RA
```

FIG. 11

```
  1  MSTWAAILTV ILTVAAMELT AYSVHRWIMH GPLGWGWHKS HHDEDHDHAL
 51  EKNDLYGVIF AVISIVLFAI GAMGSDLAWW LAVGVTCYGL IYYFLHDGLV
101  HGRWPFRYVP KRGYLRRVYQ AHRMHHAVHG RENCVSFGFI WAPSVDSLKA
151  ELKRSGALLK DREGADRNT
```

FIG. 12

```
                                      ┌→ crtE
#100:  5'tatatactagtaagaggagaaattacatATGACGCCCAAGCAGCAGCAATTC  3'
            ─────    ─────────────    ─────
             SpeI         RBS           NdeI

#101:  5'TATATACCCGGGTCAGCCGCGACGGCCTGTGG  3'
             ─────
              SmaI

┌→ crtZ
#104:  5'tatatgaattcaagaggagaaattacatATGAGCACTTGGGCCGCAATCC  3'
            ──────   ─────────────    ─────
             EcoRI       RBS            NdeI

105:  5'GTTTCAGCTCTGCCTTGAGGC  3' crtZ →                         ┌→ crtY
MUT1:  5'GCGAAGGGGCGGGATCGCAATACgTGaaaggaggacacgtgATGAGCCATGATCTGCTGATCG  3'
                                ──────────────────
                                       PmlI crtY →                     ┌→ crtI
MUT2:  5'GCCCCCTGCTGCAGGAGAGAGCtTGaaaggaggcaattgagATGAGTTCCGCCATCGTCATCG  3'
                                ──────────────────
                                       MunI crtI →                    ┌→ crtB
MUT3:  5'GGTCATGCTGTCGGACCTGGCCGTCGCtTGaaaggaggatccaatcATGACCGATCTGACGGCGACTTCC  3'
                                     ────────────────────
                                            BamHI MUT5:  5'ATATATctcaattgcctccttttcaaGCTCTCTCCTGCAGCAGGG  3'
               ────────────────────
                    MunI      ←─ crtY MUT6:  5'atgattggatcctccttttcaaGCGACGGCCAGGTCCGACAGC  3'
            ──────
             BamHI      ←─ crtI

CAR17:  5'CAGAACCCATCACCTGCCCGTC  3' cat3:   5'CGCGAATTCTCGCCGGCAATAGTTACC  3'
             ──────
              EcoRI cat4:   5'GTCACATGCATGCATGTTACGAGCTCATAAGCATGTGACGTCTTCAACTAACGGGGCAGG  3'
                  ──────       ──────       ──────
                   SphI         SacI         AatII
```

FIG. 14

```
                    HindIII   AfIII   XbaI              EcoRI
CS1:  5' AGCTTGGATCCTTAAGTACTCTAGAGTTTAAACG      3'
CS2:  3'     ACCTAGGAATTCATGAGATCTCAAATTTGCTTAA  5'
                             ScaI         PmeI SalI  AvrII       MluI      BamHI       HindIII
MUT7: 5' TCGACCCTAGGCACGTGACGCGTTCAATTGGATCCGCATGCAAGCTT  3'
MUT8: 3'     GGGATCCGTGCACTGCGCAAGTTAACCTAGGCGTACGTTCGAACTAG 5'
                         PmlI         MunI          SphI PmlI                                                                                              SalI
MUT9:  5' gtgtcctccttTcacGTATTGCGATCCGCCCCTTCGCGGTCCTTCAGCAGCGGCGCCGAGCGTTTCAGCTCTGCTTGAGGCTG           3'
MUT10: 3' cacaggaggaagtgCATAACGCTAGGCGGGGAAGCGCCAGGAAGTCGTCGCCGCGGCTCGCAAAGTCGAGACGAACGGAACTCCGACAGCT   5'
               RBS            ⊢crtZ SpeI
MUT11: 5' TAAGAAACCctccttA   3'
MUT12: 3'     TCTTTGggaggaaTGATC 5'
                    RBS
```

FIG. 15

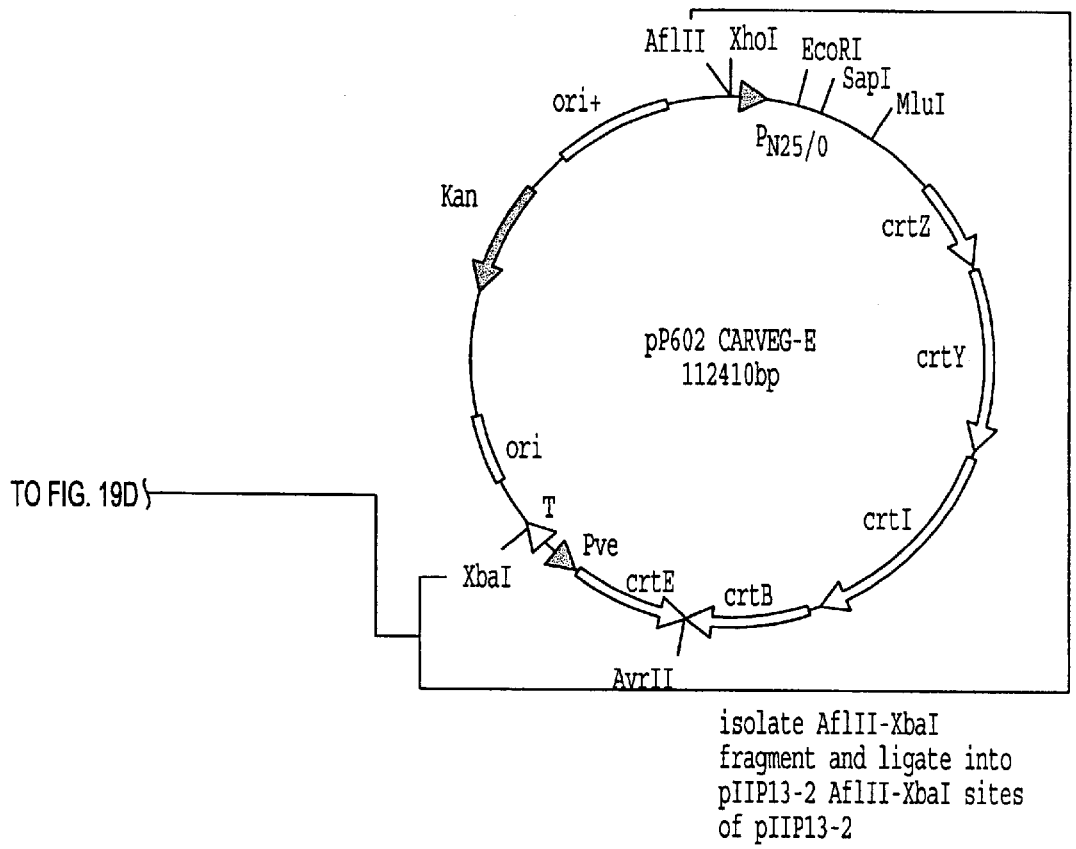
isolate AflII-XbaI fragment and ligate into pIIP13-2 AflII-XbaI sites of pIIP13-2
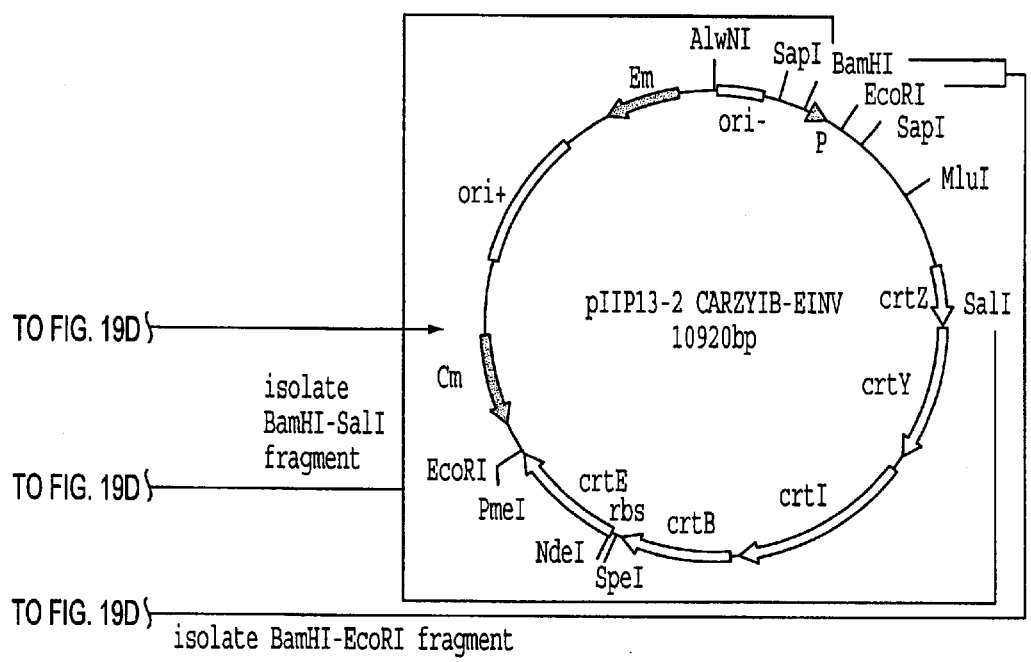
isolate BamHI-SalI fragment
isolate BamHI-EcoRI fragment
FIG. 19C

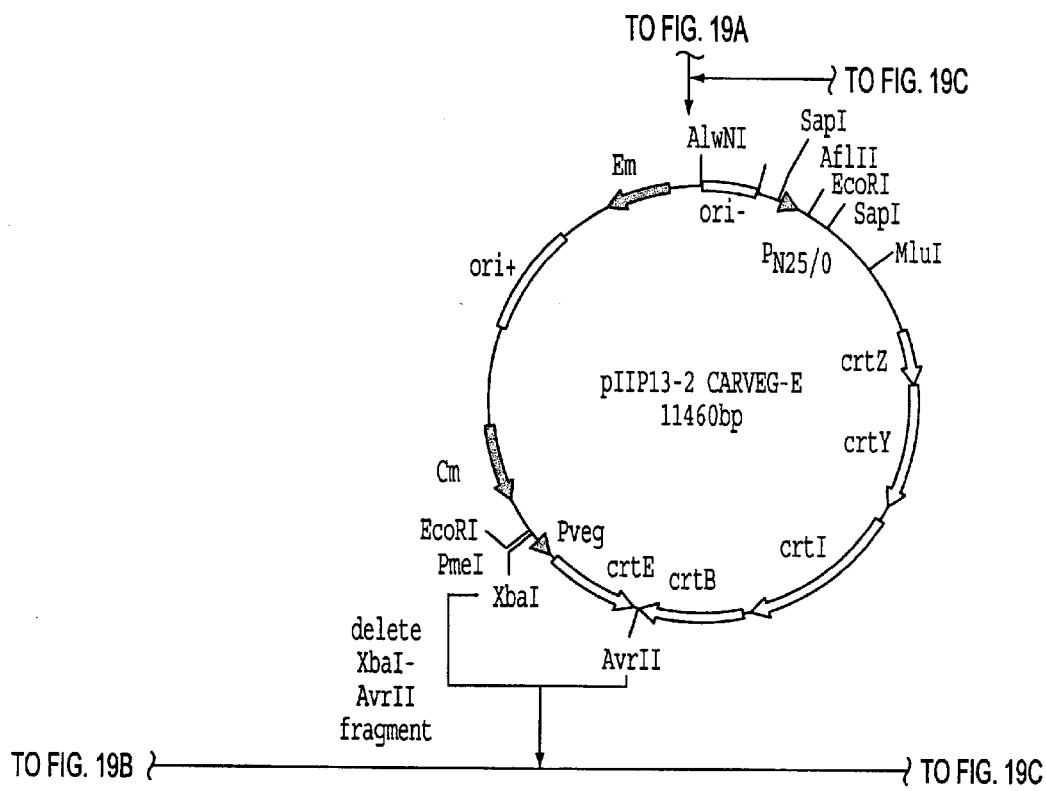
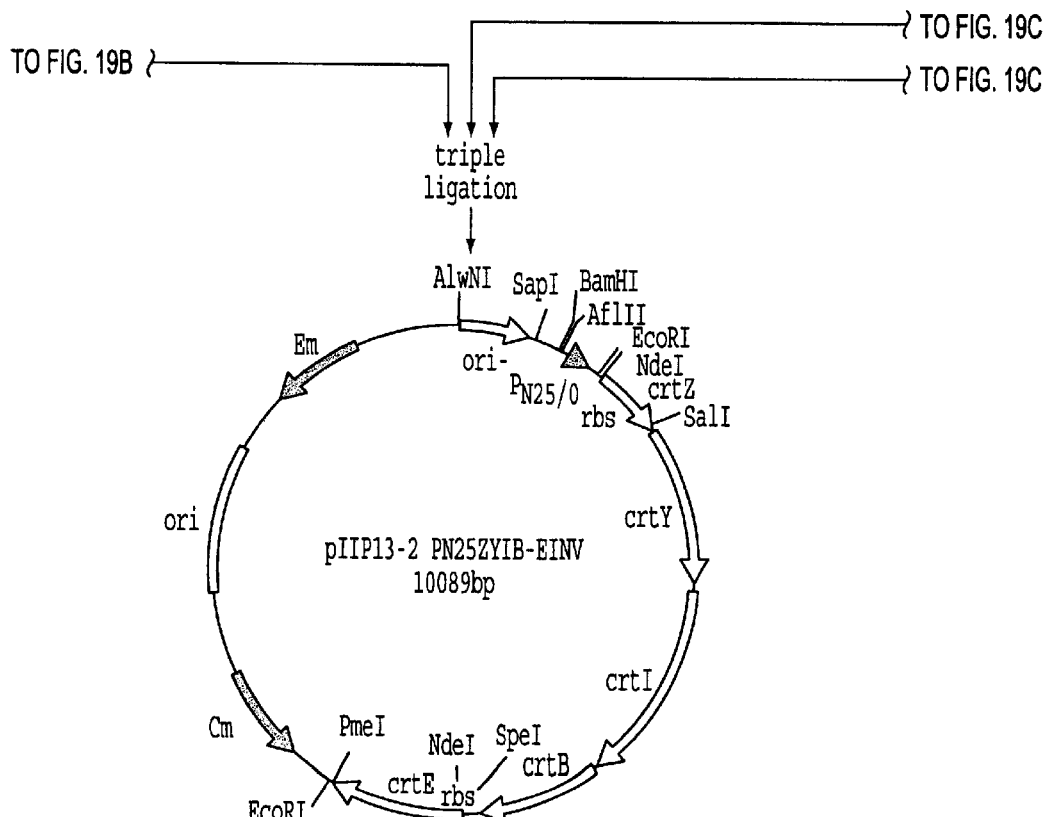
FIG. 19D

```
    CTAAATTGTAAGCGTTAATATTTTGTTAAAATTCGCGTTAAATTTTTGTTAAATCAGCTC
  1 ---------+---------+---------+---------+---------+---------+ 60
    GATTTAACATTCGCAATTATAAAACAATTTTAAGCGCAATTTAAAAACAATTTAGTCGAG

ATTTTTTAACCAATAGGCCGAAATCGGCAAAATCCCTTATAAATCAAAAGAATAGACCGA
 61 ---------+---------+---------+---------+---------+---------+ 120
    TAAAAAATTGGTTATCCGGCTTTAGCCGTTTTAGGGAATATTTAGTTTTCTTATCTGGCT

GATAGGGTTGAGTGTTGTTCCAGTTTGGAACAAGAGTCCACTATTAAAGAACGTGGACTC
121 ---------+---------+---------+---------+---------+---------+ 180
    CTATCCCAACTCACAACAAGGTCAAACCTTGTTCTCAGGTGATAATTTCTTGCACCTGAG

CAACGTCAAAGGGCGAAAAACCGTCTATCAGGGCGATGGCCCACTACGTGAACCATCACC
181 ---------+---------+---------+---------+---------+---------+ 240
    GTTGCAGTTTCCCGCTTTTTGGCAGATAGTCCCGCTACCGGGTGATGCACTTGGTAGTGG

CTAATCAAGTTTTTTGGGGTCGAGGTGCCGTAAAGCACTAAATCGGAACCCTAAAGGGAG
241 ---------+---------+---------+---------+---------+---------+ 300
    GATTAGTTCAAAAAACCCCAGCTCCACGGCATTTCGTGATTTAGCCTTGGGATTTCCCTC

CCCCCGATTTAGAGCTTGACGGGGAAAGCCGGCGAACGTGGCGAGAAAGGAAGGGAAGAA
301 ---------+---------+---------+---------+---------+---------+ 360
    GGGGGCTAAATCTCGAACTGCCCCTTTCGGCCGCTTGCACCGCTCTTTCCTTCCCTTCTT

AGCGAAAGGAGCGGGCGCTAGGGCGCTGGCAAGTGTAGCGGTCACGCTGCGCGTAACCAC
361 ---------+---------+---------+---------+---------+---------+ 420
    TCGCTTTCCTCGCCCGCGATCCCGCGACCGTTCACATCGCCAGTGCGACGCGCATTGGTG

CACACCCGCCGCGCTTAATGCGCCGCTACAGGGCGCGTCCCATTCGCCATTCAGGCTGCG
421 ---------+---------+---------+---------+---------+---------+ 480
    GTGTGGGCGGCGCGAATTACGCGGCGATGTCCCGCGCAGGGTAAGCGGTAAGTCCGACGC

CAACTGTTGGGAAGGGCGATCGGTGCGGGCCTCTTCGCTATTACGCCAGCTGGCGAAAGG
481 ---------+---------+---------+---------+---------+---------+ 540
    GTTGACAACCCTTCCCGCTAGCCACGCCCGGAGAAGCGATAATGCGGTCGACCGCTTTCC

GGGATGTGCTGCAAGGCGATTAAGTTGGGTAACGCCAGGGTTTTCCCAGTCACGACGTTG
541 ---------+---------+---------+---------+---------+---------+ 600
    CCCTACACGACGTTCCGCTAATTCAACCCATTGCGGTCCCAAAAGGGTCAGTGCTGCAAC

TAAAACGACGGCCAGTGAGCGCGCGTAATACGACTCACTATAGGGCGAATTGGAGCTCCA
601 ---------+---------+---------+---------+---------+---------+ 660
    ATTTTGCTGCCGGTCACTCGCGCGCATTATGCTGAGTGATATCCCGCTTAACCTCGAGGT

CCGCGGTGGCGGCCGCTCTAGTGGATCCGCGCCTGGCCGTTCGCGATCAGCAGCCGCCCT
661 ---------+---------+---------+---------+---------+---------+ 720
    GGCGCCACCGCCGGCGAGATCACCTAGGCGCGGACCGGCAAGCGCTAGTCGTCGGCGGGA

TGCGGATCGGTCAGCATCATCCCCATGAACCGCAGCGCACGACGCAGCGCGCGCCCCAGA
721 ---------+---------+---------+---------+---------+---------+ 780
    ACGCCTAGCCAGTCGTAGTAGGGGTACTTGGCGTCGCGTGCTGCGTCGCGCGCGGGGTCT

TCGGGCGCGTCCAGCACGGCATGCGCCATCATCGCGAAGGCCCCCGGCGGCATGGGGCGC
781 ---------+---------+---------+---------+---------+---------+ 840
    AGCCCGCGCAGGTCGTGCCGTACGCGGTAGTAGCGCTTCCGGGGGCCGCCGTACCCCGCG

GTGCCCATTCCGAAGAACTCGCAGCCTGTCCGCTGCGCAAGGTCGCGCCAGATCGCGCCG
841 ---------+---------+---------+---------+---------+---------+ 900
    CACGGGTAAGGCTTCTTGAGCGTCGGACAGGCGACGCGTTCCAGCGCGGTCTAGCGCGGC

TATTCCGATGCAGTGACGGGCCCGATGCGCGTGGGCCCGCCCTGCCCCGCCGCCACCAGC
901 ---------+---------+---------+---------+---------+---------+ 960
    ATAAGGCTACGTCACTGCCCGGGCTACGCGCACCCGGGCGGGACGGGGCGGCGGTGGTCG
```

FIG. 24A

```
            GCATCGCGCACGAACCCTTCCGAGATGATGTGCTGATCCATGGCCCGTCATTGCAAAACC
       961  ------------+---------+---------+---------+---------+---------+  1020
            CGTAGCGCGTGCTTGGGAAGGCTCTACTACACGACTAGGTACCGGGCAGTAACGTTTTGG

GATCACCGATCCTGTCGCGTGATGGCATTGTTTGCAATGCCCCGAGGGCTAGGATGGCGC
      1021  ------------+---------+---------+---------+---------+---------+  1080
            CTAGTGGCTAGGACAGCGCACTACCGTAACAAACGTTACGGGGCTCCCGATCCTACCGCG

GAAGGATCAAGGGGGGGAGAGACATGGAAATCGAGGGACGGGTCTTTGTCGTCACGGGCG
      1081  ------------+---------+---------+---------+---------+---------+  1140
            CTTCCTAGTTCCCCCCCTCTCTGTACCTTTAGCTCCCTGCCCAGAAACAGCAGTGCCCGC

CCGCATCGGGTCTGGGGGCGGCCTCGGCGCGGATGCTGGCCCAAGGCGGCGCGAAGGTCG
      1141  ------------+---------+---------+---------+---------+---------+  1200
            GGCGTAGCCCAGACCCCCGCCGGAGCCGCGCCTACGACCGGGTTCCGCCGCGCTTCCAGC

TGCTGGCCGATCTGGCGGAACCGAAGGACGCGCCCGAAGGCGCGGTTCACGCGGCCTGCG
      1201  ------------+---------+---------+---------+---------+---------+  1260
            ACGACCGGCTAGACCGCCTTGGCTTCCTGCGCGGGCTTCCGCGCCAAGTGCGCCGGACGC

ACGTGACCGACGCGACCGCTGCGCAGACGGCCATCGCGCTGGCGACCGACCGCTTCGGCA
      1261  ------------+---------+---------+---------+---------+---------+  1320
            TGCACTGGCTGCGCTGGCGACGCGTCTGCCGGTAGCGCGACCGCTGGCTGGCGAAGCCGT

GGCTGGACGGCCTTGTGAACTGCGCGGGCATCGCGCCGGCCGAACGGATGCTGGGCCGCG
      1321  ------------+---------+---------+---------+---------+---------+  1380
            CCGACCTGCCGGAACACTTGACGCGCCCGTAGCGCGGCCGGCTTGCCTACGACCCGGCGC

ACGGGCCGCATGGACTGGACAGCTTTGCCCGTGCGGTCACGATCAACCTGATCGGCAGCT
      1381  ------------+---------+---------+---------+---------+---------+  1440
            TGCCCGGCGTACCTGACCTGTCGAAACGGGCACGCCAGTGCTAGTTGGACTAGCCGTCGA

TCAACATGGCCCGCCTTGCAGCCGAGGCGATGGCCCGGAACGAGCCCGTCCGGGGCGAGC
      1441  ------------+---------+---------+---------+---------+---------+  1500
            AGTTGTACCGGGCGGAACGTCGGCTCCGCTACCGGGCCTTGCTCGGGCAGGCCCCGCTCG

GTGGCGTGATCGTCAACACGGCCTCGATCGCGGCGCAGGACGGACAGATCGGACAGGTCG
      1501  ------------+---------+---------+---------+---------+---------+  1560
            CACCGCACTAGCAGTTGTGCCGGAGCTAGCGCCGCGTCCTGCCTGTCTAGCCTGTCCAGC

CCTATGCGGCCAGCAAGGCGGGCGTGGCGGGCATGACGCTGCCGATGGCCCGCGACCTTG
      1561  ------------+---------+---------+---------+---------+---------+  1620
            GGATACGCCGGTCGTTCCGCCCGCACCGCCCGTACTGCGACGGCTACCGGGCGCTGGAAC

CGCGGCACGGCATCCGCGTCATGACCATCGCGCCCGGCATCTTCCGCACCCCGATGCTGG
      1621  ------------+---------+---------+---------+---------+---------+  1680
            GCGCCGTGCCGTAGGCGCAGTACTGGTAGCGCGGGCCGTAGAAGGCGTGGGGCTACGACC

AGGGGCTGCCGCAGGACGTTCAGGACAGCCTGGGCGCGGCGGTGCCCTTCCCCTCGCGGC
      1681  ------------+---------+---------+---------+---------+---------+  1740
            TCCCCGACGGCGTCCTGCAAGTCCTGTCGGACCCGCGCCGCCACGGGAAGGGGAGCGCCG

TGGGAGAGCCGTCGGAATACGCGGCGCTGTTGCACCACATCATCGCGAACCCCATGCTGA
      1741  ------------+---------+---------+---------+---------+---------+  1800
            ACCCTCTCGGCAGCCTTATGCGCCGCGACAACGTGGTGTAGTAGCGCTTGGGGTACGACT

ACGGAGAGGTCATCCGCCTCGACGGCGCATTGCGCATGGCCCCCAAGTGAAGGAGCGTTT
      1801  ------------+---------+---------+---------+---------+---------+  1860
            TGCCTCTCCAGTAGGCGGAGCTGCCGCGTAACGCGTACCGGGGGTTCACTTCCTCGCAAA

CATGGACCCCATCGTCATCACCGGCGCGATGCGCACCCCGATGGGGGCATTCCAGGGCGA
      1861  ------------+---------+---------+---------+---------+---------+  1920
            GTACCTGGGGTAGCAGTAGTGGCCGCGCTACGCGTGGGGCTACCCCCGTAAGGTCCCGCT

TCTTGCCGCGATGGATGCCCCGACCCTTGGCGCGGACGCGATCCGCGCCGCGCTGAACGG
      1921  ------------+---------+---------+---------+---------+---------+  1980
            AGAACGGCGCTACCTACGGGGCTGGAACCGCGCCTGCGCTAGGCGCGGCGCGACTTGCC
```

FIG. 24B

```
      CCTGTCGCCCGACATGGTGGACGAGGTGCTGATGGGCTGCGTCCTCGCCGCGGGCCAGGG
1981  ------------+---------+---------+---------+---------+---------+ 2040
      GGACAGCGGGCTGTACCACCTGCTCCACGACTACCCGACGCAGGAGCGGCGCCCGGTCCC

TCAGGCACCGGCACGTCAGGCGGCGCTTGGCGCCGGACTGCCGCTGTCGACGGGCACGAC
2041  ------------+---------+---------+---------+---------+---------+ 2100
      AGTCCGTGGCCGTGCAGTCCGCCGCGAACCGCGGCCTGACGGCGACAGCTGCCCGTGCTG

CACCATCAACGAGATGTGCGGATCGGGCATGAAGGCCGCGATGCTGGGCCATGACCTGAT
2101  ------------+---------+---------+---------+---------+---------+ 2160
      GTGGTAGTTGCTCTACACGCCTAGCCCGTACTTCCGGCGCTACGACCCGGTACTGGACTA

CGCCGCGGGATCGGCGGGCATCGTCGTCGCCGGCGGGATGGAGAGCATGTCGAACGCCCC
2161  ------------+---------+---------+---------+---------+---------+ 2220
      GCGGCGCCCTAGCCGCCCGTAGCAGCAGCGGCCGCCCTACCTCTCGTACAGCTTGCGGGG

CTACCTGCTGCCCAAGGCGCGGTCGGGGATGCGCATGGGCCATGACCGTGTGCTGGATCA
2221  ------------+---------+---------+---------+---------+---------+ 2280
      GATGGACGACGGGTTCCGCGCCAGCCCCTACGCGTACCCGGTACTGGCACACGACCTAGT

CATGTTCCTCGACGGGTTGGAGGACGCCTATGACAAGGGCCGCCTGATGGGCACCTTCGC
2281  ------------+---------+---------+---------+---------+---------+ 2340
      GTACAAGGAGCTGCCCAACCTCCTGCGGATACTGTTCCCGGCGGACTACCCGTGGAAGCG

CGAGGATTGCGCCGGCGATCACGGTTTCACCCGCGAGGCGCAGGACGACTATGCGCTGAC
2341  ------------+---------+---------+---------+---------+---------+ 2400
      GCTCCTAACGCGGCCGCTAGTGCCAAAGTGGGCGCTCCGCGTCCTGCTGATACGCGACTG

CAGCCTGGCCCGCGCGCAGGACGCCATCGCCAGCGGTGCCTTCGCCGCCGAGATCGCGCC
2401  ------------+---------+---------+---------+---------+---------+ 2460
      GTCGGACCGGGCGCGCGTCCTGCGGTAGCGGTCGCCACGGAAGCGGCGGCTCTAGCGCGG

CGTGACCGTCACGGCACGCAAGGTGCAGACCACCGTCGATACCGACGAGATGCCCGGCAA
2461  ------------+---------+---------+---------+---------+---------+ 2520
      GCACTGGCAGTGCCGTGCGTTCCACGTCTGGTGGCAGCTATGGCTGCTCTACGGGCCGTT

GGCCCGCCCCGAGAAGATCCCCCATCTGAAGCCCGCCTTCCGTGACGGTGGCACGGTCAC
2521  ------------+---------+---------+---------+---------+---------+ 2580
      CCGGGCGGGGCTCTTCTAGGGGGTAGACTTCGGGCGGAAGGCACTGCCACCGTGCCAGTG

GGCGGCGAACAGCTCGTCGATCTCGGACGGGGCGGCGGCGCTGGTGATGATGCGCCAGTC
2581  ------------+---------+---------+---------+---------+---------+ 2640
      CCGCCGCTTGTCGAGCAGCTAGAGCCTGCCCCGCCGCCGCGACCACTACTACGCGGTCAG

GCAGGCCGAGAAGCTGGGCCTGACGCCGATCGCGCGGATCATCGGTCATGCGACCCATGC
2641  ------------+---------+---------+---------+---------+---------+ 2700
      CGTCCGGCTCTTCGACCCGGACTGCGGCTAGCGCGCCTAGTAGCCAGTACGCTGGGTACG

CGACCGTCCCGGCCTGTTCCCGACGGCCCCCATCGGCGCGATGCGCAAGCTGCTGGACCG
2701  ------------+---------+---------+---------+---------+---------+ 2760
      GCTGGCAGGGCCGGACAAGGGCTGCCGGGGGTAGCCGCGCTACGCGTTCGACGACCTGGC

CACGGACACCCGCCTTGGCGATTACGACCTGTTCGAGGTGAACGAGGCATTCGCCGTCGT
2761  ------------+---------+---------+---------+---------+---------+ 2820
      GTGCCTGTGGGCGGAACCGCTAATGCTGGACAAGCTCCACTTGCTCCGTAAGCGGCAGCA

CGCCATGATCGCGATGAAGGAGCTTGGCCTGCCACACGATGCCACGAACATCAACGGCGG
2821  ------------+---------+---------+---------+---------+---------+ 2880
      GCGGTACTAGCGCTACTTCCTCGAACCGGACGGTGTGCTACGGTGCTTGTAGTTGCCGCC

GGCCTGCGCGCTTGGGCATCCCATCGGCGCGTCGGGGGCGCGGATCATGGTCACGCTGCT
2881  ------------+---------+---------+---------+---------+---------+ 2940
      CCGGACGCGCGAACCCGTAGGGTAGCCGCGCAGCCCCCGCGCCTAGTACCAGTGCGACGA

GAACGCGATGGCGGCGCGGGGCGCGACGCGCGGGGCCGCATCCGTCTGCATCGGCGGGGG
2941  ------------+---------+---------+---------+---------+---------+ 3000
      CTTGCGCTACCGCCGCGCCCCGCGCTGCGCGCCCCGGCGTAGGCAGACGTAGCCGCCCCC
```

FIG. 24C

```
      CGAGGCGACGGCCATCGCGCTGGAACGGCTGAGCTAATTCATTTGCGCGAATCCGCGTTT
3001  ------------------------------------------------------------ 3060
      GCTCCGCTGCCGGTAGCGCGACCTTGCCGACTCGATTAAGTAAACGCGCTTAGGCGCAAA

TTCGTGCACGATGGGGGAACCGGAAACGGCCACGCCTGTTGTGGTTGCGTCGACCTGTCT
3061  ------------------------------------------------------------ 3120
      AAGCACGTGCTACCCCCTTGGCCTTTGCCGGTGCGGACAACACCAACGCAGCTGGACAGA

TCGGGCCATGCCCGTGACGCGATGTGGCAGGCGCATGGGGCGTTGCCGATCCGGTCGCAT
3121  ------------------------------------------------------------ 3180
      AGCCCGGTACGGGCACTGCGCTACACCGTCCGCGTACCCCGCAACGGCTAGGCCAGCGTA

GACTGACGCAACGAAGGCACCGATGACGCCCAAGCAGCAATTCCCCCTACGCGATCTGGT
3181  ------------------------------------------------------------ 3240
      CTGACTGCGTTGCTTCCGTGGCTACTGCGGGTTCGTCGTTAAGGGGGATGCGCTAGACCA

CGAGATCAGGCTGGCGCAGATCTCGGGCCAGTTCGGCGTGGTCTCGGCCCCGCTCGGCGC
3241  ------------------------------------------------------------ 3300
      GCTCTAGTCCGACCGCGTCTAGAGCCCGGTCAAGCCGCACCAGAGCCGGGGCGAGCCGCG

GGCCATGAGCGATGCCGCCCTGTCCCCCGGCAAACGCTTTCGCGCCGTGCTGATGCTGAT
3301  ------------------------------------------------------------ 3360
      CCGGTACTCGCTACGGCGGGACAGGGGGCCGTTTGCGAAAGCGCGGCACGACTACGACTA

GGTCGCCGAAAGCTCGGGCGGGGTCTGCGATGCGATGGTCGATGCCGCCTGCGCGGTCGA
3361  ------------------------------------------------------------ 3420
      CCAGCGGCTTTCGAGCCCGCCCCAGACGCTACGCTACCAGCTACGGCGGACGCGCCAGCT

GATGGTCCATGCCGCATCGCTGATCTTCGACGACATGCCCTGCATGGACGATGCCAGGAC
3421  ------------------------------------------------------------ 3480
      CTACCAGGTACGGCGTAGCGACTAGAAGCTGCTGTACGGGACGTACCTGCTACGGTCCTG

CCGTCGCGGTCAGCCCGCCACCCATGTCGCCCATGGCGAGGGGCGCGCGGTGCTTGCGGG
3481  ------------------------------------------------------------ 3540
      GGCAGCGCCAGTCGGGCGGTGGGTACAGCGGGTACCGCTCCCCGCGCGCCACGAACGCCC

CATCGCCCTGATCACCGAGGCCATGCGGATTTTGGGCGAGGCGCGCGGCGCGACGCCGGA
3541  ------------------------------------------------------------ 3600
      GTAGCGGGACTAGTGGCTCCGGTACGCCTAAAACCCGCTCCGCGCGCCGCGCTGCGGCCT

TCAGCGCGCAAGGCTGGTCGCATCCATGTCGCGCGCGATGGGACCGGTGGGGCTGTGCGC
3601  ------------------------------------------------------------ 3660
      AGTCGCGCGTTCCGACCAGCGTAGGTACAGCGCGCGCTACCCTGGCCACCCCGACACGCG

AGGGCAGGATCTGGACCTGCACGCCCCCAAGGACGCCGCCGGGATCGAACGTGAACAGGA
3661  ------------------------------------------------------------ 3720
      TCCCGTCCTAGACCTGGACGTGCGGGGGTTCCTGCGGCGGCCCTAGCTTGCACTTGTCCT

CCTCAAGACCGGCGTGCTGTTCGTCGCGGGCCTCGAGATGCTGTCCATTATTAAGGGTCT
3721  ------------------------------------------------------------ 3780
      GGAGTTCTGGCCGCACGACAAGCAGCGCCCGGAGCTCTACGACAGGTAATAATTCCCAGA

GGACAAGGCCGAGACCGAGCAGCTCATGGCCTTCGGGCGTCAGCTTGGTCGGGTCTTCCA
3781  ------------------------------------------------------------ 3840
      CCTGTTCCGGCTCTGGCTCGTCGAGTACCGGAAGCCCGCAGTCGAACCAGCCCAGAAGGT

GTCCTATGACGACCTGCTGGACGTGATCGGCGACAAGGCCAGCACCGGCAAGGATACGGC
3841  ------------------------------------------------------------ 3900
      CAGGATACTGCTGGACGACCTGCACTAGCCGCTGTTCCGGTCGTGGCCGTTCCTATGCCG

GCGCGACACCGCCGCCCCCGGCCCAAAGGGCGGCCTGATGGCGGTCGGACAGATGGGCGA
3901  ------------------------------------------------------------ 3960
      CGCGCTGTGGCGGCGGGGCCGGGTTTCCCGCCGGACTACCGCCAGCCTGTCTACCCGCT

CGTGGCGCAGCATTACCGCGCCAGCCGCGCGCAACTGGACGAGCTGATGCGCACCCGGCT
3961  ------------------------------------------------------------ 4020
      GCACCGCGTCGTAATGGCGCGGTCGGCGCGCGTTGACCTGCTCGACTACGCGTGGGCCGA
```

FIG. 24D

```
     GTTCCGCGGGGGGCAGATCGCGGACCTGCTGGCCCGCGTGCTGCCGCATGACATCCGCCG
4021 ------------+---------+---------+---------+---------+---------+ 4080
     CAAGGCGCCCCCCGTCTAGCGCCTGGACGACCGGGCGCACGACGGCGTACTGTAGGCGGC

CAGCGCCTAGGCGCGCGGTCGGGTCCACAGGCCGTCGCGGCTGATTTCGCCGCCGCGCAG
4081 ------------+---------+---------+---------+---------+---------+ 4140
     GTCGCGGATCCGCGCGCCAGCCCAGGTGTCCGGCAGCGCCGACTAAAGCGGCGGCGCGTC

GCGCGATGCGGCCGCGTCCAAGCCTCCGCGCGCCAGAAGCCCGATCTTGGCAGCCTTCGA
4141 ------------+---------+---------+---------+---------+---------+ 4200
     CGCGCTACGCCGGCGCAGGTTCGGAGGCGCGCGGTCTTCGGGCTAGAACCGTCGGAAGCT

CGTGCTGATCCGCTGGCGATAGGCCTCGGGGCCACCCTGCCGGATGCGCGTCCCGATTGC
4201 ------------+---------+---------+---------+---------+---------+ 4260
     GCACGACTAGGCGACCGCTATCCGGAGCCCCGGTGGGACGGCCTACGCGCAGGGCTAACG

GCGATAGATACGCAGCGCGGCGGCGATCGACCACGCGCAGCGCGGCGGCAGATGCGGAAG
4261 ------------+---------+---------+---------+---------+---------+ 4320
     CGCTATCTATGCGTCGCGCCGCCGCTAGCTGGTGCGCGTCGCGCCGCCGTCTACGCCTTC

CCCCTGCCGCGCCGAGGCATAATAGGGCTCGGCCGCGTCAAGCAGGCGGATGATGACGGA
4321 ------------+---------+---------+---------+---------+---------+ 4380
     GGGGACGGCGCGGCTCCGTATTATCCCGAGCCGGCGCAGTTCGTCCGCCTACTACTGCCT

ATAGAGCGCGTCCGAAGGCACCGGACCCTCAACCGTCGCCCCGCCTCGGCCAGCCAGTC
4381 ------------+---------+---------+---------+---------+---------+ 4440
     TATCTCGCGCAGGCTTCCGTGGCCTGGGAGTTGGCAGCGGGGGCGGAGCCGGTCGGTCAG

GGCAGGCAGATAGCAGCGCCCGATGGCGGCATCGTCGATCACGTCGCGAGCGATGTTCGT
4441 ------------+---------+---------+---------+---------+---------+ 4500
     CCGTCCGTCTATCGTCGCGGGCTACCGCCGTAGCAGCTAGTGCAGCGCTCGCTACAAGCA

CAGCTGGAACGCAAGGCCCAGATCGCAGGCGCGATCCAGCACCGCATCGTCCTGCACGCC
4501 ------------+---------+---------+---------+---------+---------+ 4560
     GTCGACCTTGCGTTCCGGGTCTAGCGTCCGCGCTAGGTCGTGGCGTAGCAGGACGTGCGG

CATCACCCGCGCCATCATCACGCCCACGACCCCCGCGACGTGGTAGGAATATTCCAGCAC
4561 ------------+---------+---------+---------+---------+---------+ 4620
     GTAGTGGGCGCGGTAGTAGTGCGGGTGCTGGGGGCGCTGCACCATCCTTATAAGGTCGTG

GTCATCCAGGCTGCGGTATTCGCGATCCGCGACATCCATCGCGAAACCCTCGATCAGGTC
4621 ------------+---------+---------+---------+---------+---------+ 4680
     CAGTAGGTCCGACGCCATAAGCGCTAGGCGCTGTAGGTAGCGCTTTGGGAGCTAGTCCAG

CATCGGCCAAAGGTCCGGGAAATCATGCCGCCGGGCGACCTGGCGCAGCGCCGCGAAGGG
4681 ------------+---------+---------+---------+---------+---------+ 4740
     GTAGCCGGTTTCCAGGCCCTTTAGTACGGCGGCCCGCTGGACCGCGTCGCGGCGCTTCCC

CGGCGACATCGGGCCGTCCTCGTGCAGCGCGGCCAGCGTGTCGGCGCGCAGCGCCCCCAG
4741 ------------+---------+---------+---------+---------+---------+ 4800
     GCCGCTGTAGCCCGGCAGGAGCACGTCGCGCCGGTCGCACAGCCGCGCGTCGCGGGGGTC

CCGCGCCTGTGGGTCGCCGCCCGCCTCGGGGGCAGAACCCATCACCTGCCCGTCGATCAC
4801 ------------+---------+---------+---------+---------+---------+ 4860
     GGCGCGGACACCCAGCGGCGGGCGGAGCCCCCGTCTTGGGTAGTGGACGGGCAGCTAGTG

GTCATCCGCATGCCTGCACCAGGCATAGAGCATGACCGTATCCTCGCGGATGCCGGGCGG
4861 ------------+---------+---------+---------+---------+---------+ 4920
     CAGTAGGCGTACGGACGTGGTCCGTATCTCGTACTGGCATAGGAGCGCCTACGGCCCGCC

CATCAGCTTGGCCGCCTGCGCGAAGCTTTGCGAACCCTGCGCGATGGCCGCTTCGGAAGT
4921 ------------+---------+---------+---------+---------+---------+ 4980
     GTAGTCGAACCGGCGGACGCGCTTCGAAACGCTTGGGACGCGCTACCGGCGAAGCCTTCA

CGCCGTCAGATCGGTCATGCGACGGCCAGGTCCGACAGCATGACCTGCGCCGTGGCCTTG
4981 ------------+---------+---------+---------+---------+---------+ 5040
     GCGGCAGTCTAGCCAGTACGCTGCCGGTCCAGGCTGTCGTACTGGACGCGGCACCGGAAC
```

FIG. 24E

```
     GCGCTGCCAACGACACCCGGGATGCCCGCACCCGGATGCGTGCCCGCCCCCACGATGTAG
5041 ----------+---------+---------+---------+---------+---------+ 5100
     CGCGACGGTTGCTGTGGGCCCTACGGGCGTGGGCCTACGCACGGGCGGGGGTGCTACATC

AAGTTCGGGATCGCGCGGTCGCGGTTATGCGGGCGGAACCAGGCGGATTGCGTCAGGATC
5101 ----------+---------+---------+---------+---------+---------+ 5160
     TTCAAGCCCTAGCGCGCCAGCGCCAATACGCCCGCCTTGGTCCGCCTAACGCAGTCCTAG

GGCTCGACCGAGAAGGCGCTGCCGTGATGGGCCGACAGTTCGGTGCTGAAATCGGCGGGG
5161 ----------+---------+---------+---------+---------+---------+ 5220
     CCGAGCTGGCTCTTCCGCGACGGCACTACCCGGCTGTCAAGCCACGACTTTAGCCGCCCC

CTGAAGATGCGGCTGACGGTCAGGTGCTTGCGCAGGTCGGGGATGGCGCGGCGCTCCAGT
5221 ----------+---------+---------+---------+---------+---------+ 5280
     GACTTCTACGCCGACTGCCAGTCCACGAACGCGTCCAGCCCCTACCGCGCCGCGAGGTCA

TCCTCGAAGATGCGCTCGGCATAGCCCGGGGCCTCGGCTTCCCAATCGACATCGGCGCGG
5281 ----------+---------+---------+---------+---------+---------+ 5340
     AGGAGCTTCTACGCGAGCCGTATCGGGCCCCGGAGCCGAAGGGTTAGCTGTAGCCGCGCC

CCCAGATGCGGAACGGGCGCAAGGACGTAATGCGTGGACATCCCCTCGGGGCCAGGCTG
5341 ----------+---------+---------+---------+---------+---------+ 5400
     GGGTCTACGCCTTGCCCGCGTTCCTGCATTACGCACCTGTAGGGGAGCCCCCGGTCCGAC

GGATCGGTCACGCAGGGCGAATGCAGATACATCGAGAAATCGTCCGGCAGGCGTGGCCCG
5401 ----------+---------+---------+---------+---------+---------+ 5460
     CCTAGCCAGTGCGTCCCGCTTACGTCTATGTAGCTCTTTAGCAGGCCGTCCGCACCGGGC

TTGAAGATCTCGTTCACCAGCCCCTTGTAGCGCGGGCCGAAGATGACGCTGTGGTGGGCC
5461 ----------+---------+---------+---------+---------+---------+ 5520
     AACTTCTAGAGCAAGTGGTCGGGGAACATCGCGCCCGGCTTCTACTGCGACACCACCCGG

AGGTTCTCGGGGCGCTTGGACAGGCCGAAATGCAGCACGAACAGCGACATCGACCAGCGC
5521 ----------+---------+---------+---------+---------+---------+ 5580
     TCCAAGAGCCCCGCGAACCTGTCCGGCTTTACGTCGTGCTTGTCGCTGTAGCTGGTCGCG

TGCCGGTTCAGGATCGCGGCCTTGGTGCGCCCGCGGCGGGTATGGCCCAGCAGGTCGCGA
5581 ----------+---------+---------+---------+---------+---------+ 5640
     ACGGCCAAGTCCTAGCGCCGGAACCACGCGGGCGCCGCCCATACCGGGTCGTCCAGCGCT

TAGCTGTGCATCACGTCGCCGTTGCTGGCCACCGTATCCGCGCGCAACTGCCGCCCGTCC
5641 ----------+---------+---------+---------+---------+---------+ 5700
     ATCGACACGTAGTGCAGCGGCAACGACCGGTGGCATAGGCGCGCGTTGACGGCGGGCAGG

AGCAGCGTGACGCCCGTGGCGCGATCGCCCTCGGTGTCGATCCGCGTGACGCGGGCATTC
5701 ----------+---------+---------+---------+---------+---------+ 5760
     TCGTCGCACTGCGGGCACCGCGCTAGCGGGAGCCACAGCTAGGCGCACTGCGCCCGTAAG

AGCAGCAGCGTGCCGCCAAGACGCTCGAACAGGGCGACCATGCCCGCGACCAGCTGGTTG
5761 ----------+---------+---------+---------+---------+---------+ 5820
     TCGTCGTCGCACGGCGGTTCTGCGAGCTTGTCCCGCTGGTACGGGCGCTGGTCGACCAAC

GTGCCGCCCTTGGCGAACCAGACGCCGCCGCGCCGTTCCAGCGCATGGATCAGCGCATAG
5821 ----------+---------+---------+---------+---------+---------+ 5880
     CACGGCGGGAACCGCTTGGTCTGCGGCGGCGCGGCAAGGTCGCGTACCTAGTCGCGTATC

ATCGAGCTGGTCGAAAACGGGTTCCCGCCGACCAGCAGCGTGTGGAACGAGAAGGCCTGC
5881 ----------+---------+---------+---------+---------+---------+ 5940
     TAGCTCGACCAGCTTTTGCCCAAGGGCGGCTGGTCGTCGCACACCTTGCTCTTCCGGACG

CGCAGATGCGGGTCCTGGATGAAGCGCGCCACCATGCTGTGGACCGAGCGGTATGCCTGC
5941 ----------+---------+---------+---------+---------+---------+ 6000
     GCGTCTACGCCCAGGACCTACTTCGCGCGGTGGTACGACACCTGGCTCGCCATACGGACG

AGGCGCATCAGCGCCGGCGCGGCGTTCAGCATCTGGCCCAGCTTCAGGAAGGGCGTGGTC
6001 ----------+---------+---------+---------+---------+---------+ 6060
     TCCGCGTAGTCGCGGCCGCGCCGCAAGTCGTAGACCGGGTCGAAGTCCTTCCCGCACCAG
```

FIG. 24F

```
      CCCAGCTTCAGATACCCCTCGCGATAGACCTCCTCGGCGTAATCGTGGAAGCGGCGATAG
6061  ------------+---------+---------+---------+---------+---------+ 6120
      GGGTCGAAGTCTATGGGGAGCGCTATCTGGAGGAGCCGCATTAGCACCTTCGCCGCTATC

CCATCGACATCGGCGGGATTGAAGGAGGCGACCTGGCGGATCAGCTCGTCGTCGTCGTTC
6121  ------------+---------+---------+---------+---------+---------+ 6180
      GGTAGCTGTAGCCGCCCTAACTTCCTCCGCTGGACCGCCTAGTCGAGCAGCAGCAGCAAG

ACGTATTCGAAGCTGCGGCCGTCCGCCCATGTCAGCCGGTAGAAGGGCGAGACCGGCAGC
6181  ------------+---------+---------+---------+---------+---------+ 6240
      TGCATAAGCTTCGACGCCGGCAGGCGGGTACAGTCGGCCATCTTCCCGCTCTGGCCGTCG

AGCGTCACGTCACGCTCCATCGGTTGGCCGCTGAGGGCCCACAGCTCTCGCAGGCTGTCG
6241  ------------+---------+---------+---------+---------+---------+ 6300
      TCGCAGTGCAGTGCGAGGTAGCCAACCGGCGACTCCCGGGTGTCGAGAGCGTCCGACAGC

GGGTCGGTCACGACCGTCGGGCCTGCATCGAAGACGTGGCCCTGATCGTTCCAGACATAG
6301  ------------+---------+---------+---------+---------+---------+ 6360
      CCCAGCCAGTGCTGGCAGCCCGGACGTAGCTTCTGCACCGGGACTAGCAAGGTCTGTATC

GCGCGGCCGCCGGGCTTGTCGCGGGCCTCGACGATGGTGGTCGCGATGCCGGCCGATTGC
6361  ------------+---------+---------+---------+---------+---------+ 6420
      CGCGCCGGCGGCCCGAACAGCGCCCGGAGCTGCTACCACCAGCGCTACGGCCGGCTAACG

AGGCGGATGGCAAGCGCAAGCCCGCCGAAACCTGCGCCGATGACGATGGCGGAACTCATG
6421  ------------+---------+---------+---------+---------+---------+ 6480
      TCCGCCTACCGTTCGCGTTCGGGCGGCTTTGGACGCGGCTACTGCTACCGCCTTGAGTAC

CTCTCTCCTGCAGCAGGGGGCGTTCGGGCAGGCAGCGCACGGCCTGCGACAGCGGAATGG
6481  ------------+---------+---------+---------+---------+---------+ 6540
      GAGAGAGGACGTCGTCCCCCGCAAGCCCGTCCGTCGCGTGCCGGACGCTGTCGCCTTACC

GCGGGCGTCCGGTGACGATGCGAAGCCGGTCGGCCAATGTCAGGCGCCCGGCATAGAAGC
6541  ------------+---------+---------+---------+---------+---------+ 6600
      CGCCCGCAGGCCACTGCTACGCTTCGGCCAGCCGGTTACAGTCCGCGGGCCGTATCTTCG

GCTCGATCAGCGGCTGCGGCAGGCGGTAGAACCGCTGCAGCAGGCGATAGCGACGGTCGG
6601  ------------+---------+---------+---------+---------+---------+ 6660
      CGAGCTAGTCGCCGACGCCGTCCGCCATCTTGGCGACGTCGTCCGCTATCGCTGCCAGCC

GCGGGCAGCCGCGGAACAGCATCCGGTTCAGCAGCCGCAGGAAGCGGTCGCGATCCGCGC
6661  ------------+---------+---------+---------+---------+---------+ 6720
      CGCCCGTCGGCGCCTTGTCGTAGGCCAAGTCGTCGGCGTCCTTCGCCAGCGCTAGGCGCG

GATCGATGGCCCAGCCGCGCACCGCGCGACGGGCGGACGCGGTCGTCAGGTCGCGCGCCG
6721  ------------+---------+---------+---------+---------+---------+ 6780
      CTAGCTACCGGGTCGGCGCGTGGCGCGCTGCCCGCCTGCGCCAGCAGTCCAGCGCGCGGC

CGATGGCATCCGCGACCTGCGCGGCATAGGGCAGCGAATATCCGGTGACGGGGTGGAACA
6781  ------------+---------+---------+---------+---------+---------+ 6840
      GCTACCGTAGGCGCTGGACGCGCCGTATCCCGTCGCTTATAGGCCACTGCCCCACCTTGT

GCCCTGCCCCCAGCCCAACCGGCACCGCCCCTGCGCGTGGTCGCGCCAGAAGCCTATGG
6841  ------------+---------+---------+---------+---------+---------+ 6900
      CGGGACGGGGGTCGGGTTGGCCGTGGCGGGGGACGCGCACCAGCGCGGTCTTCGGATACC

CGTCATGGGCCAGCGCGATGGGCAGGATGCCCCTTTCGCGCCGCATCTCCTGCCCCGGTCC
6901  ------------+---------+---------+---------+---------+---------+ 6960
      GCAGTACCCGGTCGCGCTACCCGTCCTACGGGGAAAGCGCGGCGTAGAGGACGGGCCAGG

AGCCCCGCCTGGCGGCATAGTCCAGCGACGCCTGCGCCAGCGCGCCATCGTCCAGATCGC
6961  ------------+---------+---------+---------+---------+---------+ 7020
      TCGGGGCGGACCGCCGTATCAGGTCGCTGCGGACGCGGTCGCGCGGTAGCAGGTCTAGCG
```

FIG. 24G

```
       CGCCGTCGCTGTAGCGCGTATCCTCGATCAGGATGCGGGTGGGACTGAAGGGCAGCAGAT
7021   ----------+---------+---------+---------+---------+---------+ 7080
       GCGGCAGCGACATCGCGCATAGGAGCTAGTCCTACGCCCACCCTGACTTCCCGTCGTCTA

AGATGAAGCGGTACCCGTCCATCTGCGGAACGGTCGCGTCCATGATCATCGGGCGCTCGA
7081   ----------+---------+---------+---------+---------+---------+ 7140
       TCTACTTCGCCATGGGCAGGTAGACGCCTTGCCAGCGCAGGTACTAGTAGCCCGCGAGCT

CGCCATGGGGGGCGTCGGTCTCGATCTCGACGCCCACGAATTTCTGGAAACCCACGGTCA
7141   ----------+---------+---------+---------+---------+---------+ 7200
       GCGGTACCCCCCGCAGCCAGAGCTAGAGCTGCGGGTGCTTAAAGACCTTTGGGTGCCAGT

GGTGCGGGGTCTCGACGGCACCACGGGCGTCGATCACGCAGGCAGCCTCGATCCGCGAGC
7201   ----------+---------+---------+---------+---------+---------+ 7260
       CCACGCCCCAGAGCTGCCGTGGTGCCCGCAGCTAGTGCGTCCGTCGGAGCTAGGCGCTCG

CGTCCGTCAGCGTCGCGCCGGTATCGTCCAGCGTCGCGACATGCGTATTCCACCGCAGAT
7261   ----------+---------+---------+---------+---------+---------+ 7320
       GCAGGCAGTCGCAGCGCGGCCATAGCAGGTCGCAGCGCTGTACGCATAAGGTGGCGTCTA

CGACACCCTGCAGCAGCCCGATCAGCGCGCCCGCCTCGATCGAGCCATAGCCTGTCGTCA
7321   ----------+---------+---------+---------+---------+---------+ 7380
       GCTGTGGGACGTCGTCGGGCTAGTCGCGCGGGCGGAGCTAGCTCGGTATCGGACAGCAGT

GGCGGCGCGAATGGTCGGGAAACGCGACCTCCTGATCCGTCCATTCGCCGCGACGAATGG
7381   ----------+---------+---------+---------+---------+---------+ 7440
       CCGCCGCGCTTACCAGCCCTTTGCGCTGGAGGACTAGGCAGGTAAGCGGCGCTGCTTACC

GCGACAGGCGCGCCAGCCATTCGGGCGAAAGATCCGTGTCGTGGCAGGACCAGGTGTGCT
7441   ----------+---------+---------+---------+---------+---------+ 7500
       CGCTGTCCGCGCGGTCGGTAAGCCCGCTTTCTAGGCACAGCACCGTCCTGGTCCACACGA

GGTCCGAGGGGCCGGACCGCGCGTCGAGCATCACGATGCGCGCATCCGGTCTGCGGTCGC
7501   ----------+---------+---------+---------+---------+---------+ 7560
       CCAGGCTCCCCGGCCTGGCGCGCAGCTCGTAGTGCTACGCGCGTAGGCCAGACGCCAGCG

GAACGGCAAGCGCGATCAGCGCACCGGACAGCCCCGCGCCCGCGATCAGCAGATCATGGC
7561   ----------+---------+---------+---------+---------+---------+ 7620
       CTTGCCGTTCGCGCTAGTCGCGTGGCCTGTCGGGGCGCGGGCGCTAGTCGTCTAGTACCG

TCATGTATTGCGATCCGCCCCTTCGCGGTCCTTCAGCAGCGCGCCCGAGCGTTTCAGCTC
7621   ----------+---------+---------+---------+---------+---------+ 7680
       AGTACATAACGCTAGGCGGGGAAGCGCCAGGAAGTCGTCGCGCGGGCTCGCAAAGTCGAG

TGCCTTGAGGCTGTCGACCGAGGGCGCCCAGATGAAACCGAAGCTGACGCAGTTCTCGCG
7681   ----------+---------+---------+---------+---------+---------+ 7740
       ACGGAACTCCGACAGCTGGCTCCCGCGGGTCTACTTTGGCTTCGACTGCGTCAAGAGCGC

GCCATGGACCGCGTGATGCATCCTGTGTGCCTGGTAGACGCGACGAAGATAGCCGCGCTT
7741   ----------+---------+---------+---------+---------+---------+ 7800
       CGGTACCTGGCGCACTACGTAGGACACACGGACCATCTGCGCTGCTTCTATCGGCGCGAA

GGGGACATAGCGGAACGGCCAGCGCCCATGCACCAAGCCGTCATGCAGGAAATAGTAGAT
7801   ----------+---------+---------+---------+---------+---------+ 7860
       CCCCTGTATCGCCTTGCCGGTCGCGGGTACGTGGTTCGGCAGTACGTCCTTTATCATCTA

CAGCCCGTAGCAGGTGACCCCCACCGCCAGCCACCAGGCCAGATCCGACCCCATCGCGCC
7861   ----------+---------+---------+---------+---------+---------+ 7920
       GTCGGGCATCGTCCACTGGGGGTGGCGGTCGGTGGTCCGGTCTAGGCTGGGGTAGCGCGG

GATCGCGAACAGCACGATCGAGATTACCGCGAAGATGACGCCATAGAGGTCGTTCTTCTC
7921   ----------+---------+---------+---------+---------+---------+ 7980
       CTAGCGCTTGTCGTGCTAGCTCTAATGGCGCTTCTACTGCGGTATCTCCAGCAAGAAGAG
```

FIG. 24H

```
      GAGCGCGTGGTCGTGATCCTCGTCGTGGTGCGATTTATGCCAGCCCCAGCCCAGGGGGCC
7981  ------------+---------+---------+---------+---------+---------+  8040
      CTCGCGCACCAGCACTAGGAGCAGCACCACGCTAAATACGGTCGGGGTCGGGTCCCCCGG

ATGCATGATCCACCGATGGACGGAGTAGGCCGTCAGCTCCATCGCGGCGACGGTCAGGAT
8041  ------------+---------+---------+---------+---------+---------+  8100
      TACGTACTAGGTGGCTACCTGCCTCATCCGGCAGTCGAGGTAGCGCCGCTGCCAGTCCTA

GACGGTCAGGATTGCGGCCCAAGTGCTCATGCCGGCCCCTTGCTTGATATGACAGGGAAC
8101  ------------+---------+---------+---------+---------+---------+  8160
      CTGCCAGTCCTAACGCCGGGTTCACGAGTACGGCCGGGGAACGAACTATACTGTCCCTTG

AGGCTACGCTGCCGCGCGGTGCATGACCAGCCCATCGGGGTGCGACCAAAGGGCATCGCG
8161  ------------+---------+---------+---------+---------+---------+  8220
      TCCGATGCGACGGCGCGCCACGTACTGGTCGGGTAGCCCCACGCTGGTTTCCCGTAGCGC

TGACATCTGCGTTCAGGGCTCATAGGCGGATCATCCGTGACATTCGCCGCCGAACGCGGC
8221  ------------+---------+---------+---------+---------+---------+  8280
      ACTGTAGACGCAAGTCCCGAGTATCCGCCTAGTAGGCACTGTAAGCGGCGGCTTGCGCCG

AGGCGCATCACGCGTTCCGTCGCTGGAAATATTAATGTTTTCCCGAAGATGGTCGGGGCG
8281  ------------+---------+---------+---------+---------+---------+  8340
      TCCGCGTAGTGCGCAAGGCAGCGACCTTTATAATTACAAAAGGGCTTCTACCAGCCCCGC

AGAGGATTCGAACCTCCGACCTACGGTACCCAAAACCGTCGCGCTACCAGGCTGCGCTAC
8341  ------------+---------+---------+---------+---------+---------+  8400
      TCTCCTAAGCTTGGAGGCTGGATGCCATGGGTTTTGGCAGCGCGATGGTCCGACGCGATG

GCCCCGACTGCGGAAGGCTTTAGCCGATTGTTCCGGCAAGGGAAAGACCTAGTCGCAGGC
8401  ------------+---------+---------+---------+---------+---------+  8460
      CGGGGCTGACGCCTTCCGAAATCGGCTAACAAGGCCGTTCCCTTTCTGGATCAGCGTCCG

CAGGACCGCATTGTCGCCCATGCCCGGATGCGCCATCGGCTGACCGGGCTTCAGGCCAAG
8461  ------------+---------+---------+---------+---------+---------+  8520
      GTCCTGGCGTAACAGCGGGTACGGGCCTACGCGGTAGCCGACTGGCCCGAAGTCCGGTTC

GCGATCCGCCTCTCCGCCCGCGATTTCGAGGACGAACAGCCGGTCGGGGTCCGGATCGCC
8521  ------------+---------+---------+---------+---------+---------+  8580
      CGCTAGGCGGAGAGGCGGGCGCTAAAGCTCCTGCTTGTCGGCCAGCCCCAGGCCTAGCGG

GACCGCCGCGCCCGGAATGGGCGTCTCGTCCAGCGGGCGCGCATTGCGGTGGATGTGGCG
8581  ------------+---------+---------+---------+---------+---------+  8640
      CTGGCGGCGCGGGCCTTACCCGCAGAGCAGGTCGCCCGCGCGTAACGCCACCTACACCGC

GATGACGCCGGTTTCATCCGCAAAGACCATGTCCAGCGGGATCAGTGTGTTGCGCATCCA
8641  ------------+---------+---------+---------+---------+---------+  8700
      CTACTGCGGCCAAAGTAGGCGTTTCTGGTACAGGTCGCCCTAGTCACACAACGCGTAGGT

GAAGGACACCGGCTGGGGCGATTCGTAGATGAACAGCATTCCGGTGCCCGCAGGCAGCTC
8701  ------------+---------+---------+---------+---------+---------+  8760
      CTTCCTGTGGCCGACCCCGCTAAGCATCTACTTGTCGTAAGGCCACGGGCGTCCGTCGAG

CTTGCGGAACATCAGGCCCTGCGCGCGCTCTTCGGGGCTGTCCGCGACCTCGACCCGAAA
8761  ------------+---------+---------+---------+---------+---------+  8820
      GAACGCCTTGTAGTCCGGGACGCGCGCGAGAAGCCCCGACAGGCGCTGGAGCTGGGCTTT

CCCGAGCGTTTCCGCACCGGTATCGACGACAAGACTGCCGGGCGCGCATTCCACCGCCGC
8821  ------------+---------+---------+---------+---------+---------+  8880
      GGGCTCGCAAAGGCGTGGCCATAGCTGCTGTTCTGACGGCCCGCGCGTAAGGTGGCGGCG

CGCGGCGGCGGGCATCAGGACCGCAAGAAGCGCTGCGGCCTTACTCGGCCACATGGGCAA
8881  ------------+---------+---------+---------+---------+---------+  8940
      GCGCCGCCGCCCGTAGTCCTGGCGTTCTTCGCGACGCCGGAATGAGCCGGTGTACCCGTT

GATAGGACTGCTCGGCGCCGAGATCCCCCGGGCTGCAGGAATTCGATATCAAGCTTATCG
8941  ------------+---------+---------+---------+---------+---------+  9000
      CTATCCTGACGAGCCGCGGCTCTAGGGGGCCCGACGTCCTTAAGCTATAGTTCGAATAGC
```

FIG. 24I

```
      ATACCGTCGACCTCGAGGGGGGGCCCGGTACCCAGCTTTTGTTCCCTTTAGTGAGGGTTA
9001  ---------+---------+---------+---------+---------+---------+ 9060
      TATGGCAGCTGGAGCTCCCCCCCGGGCCATGGGTCGAAAACAAGGGAAATCACTCCCAAT

ATTGCGCGCTTGGCGTAATCATGGTCATAGCTGTTTCCTGTGTGAAATTGTTATCCGCTC
9061  ---------+---------+---------+---------+---------+---------+ 9120
      TAACGCGCGAACCGCATTAGTACCAGTATCGACAAAGGACACACTTTAACAATAGGCGAG

ACAATTCCACACAACATACGAGCCGGAAGCATAAAGTGTAAAGCCTGGGGTGCCTAATGA
9121  ---------+---------+---------+---------+---------+---------+ 9180
      TGTTAAGGTGTGTTGTATGCTCGGCCTTCGTATTTCACATTTCGGACCCCACGGATTACT

GTGAGCTAACTCACATTAATTGCGTTGCGCTCACTGCCCGCTTTCCAGTCGGGAAACCTG
9181  ---------+---------+---------+---------+---------+---------+ 9240
      CACTCGATTGAGTGTAATTAACGCAACGCGAGTGACGGGCGAAAGGTCAGCCCTTTGGAC

TCGTGCCAGCTGCATTAATGAATCGGCCAACGCGCGGGGAGAGGCGGTTTGCGTATTGGG
9241  ---------+---------+---------+---------+---------+---------+ 9300
      AGCACGGTCGACGTAATTACTTAGCCGGTTGCGCGCCCCTCTCCGCCAAACGCATAACCC

CGCTCTTCCGCTTCCTCGCTCACTGACTCGCTGCGCTCGGTCGTTCGGCTGCGGCGAGCG
9301  ---------+---------+---------+---------+---------+---------+ 9360
      GCGAGAAGGCGAAGGAGCGAGTGACTGAGCGACGCGAGCCAGCAAGCCGACGCCGCTCGC

GTATCAGCTCACTCAAAGGCGGTAATACGGTTATCCACAGAATCAGGGGATAACGCAGGA
9361  ---------+---------+---------+---------+---------+---------+ 9420
      CATAGTCGAGTGAGTTTCCGCCATTATGCCAATAGGTGTCTTAGTCCCCTATTGCGTCCT

AAGAACATGTGAGCAAAAGGCCAGCAAAAGGCCAGGAACCGTAAAAAGGCCGCGTTGCTG
9421  ---------+---------+---------+---------+---------+---------+ 9480
      TTCTTGTACACTCGTTTTCCGGTCGTTTTCCGGTCCTTGGCATTTTTCCGGCGCAACGAC

GCGTTTTTCCATAGGCTCCGCCCCCCTGACGAGCATCACAAAAATCGACGCTCAAGTCAG
9481  ---------+---------+---------+---------+---------+---------+ 9540
      CGCAAAAAGGTATCCGAGGCGGGGGGACTGCTCGTAGTGTTTTTAGCTGCGAGTTCAGTC

AGGTGGCGAAACCCGACAGGACTATAAAGATACCAGGCGTTTCCCCCTGGAAGCTCCCTC
9541  ---------+---------+---------+---------+---------+---------+ 9600
      TCCACCGCTTTGGGCTGTCCTGATATTTCTATGGTCCGCAAAGGGGGACCTTCGAGGGAG

GTGCGCTCTCCTGTTCCGACCCTGCCGCTTACCGGATACCTGTCCGCCTTTCTCCCTTCG
9601  ---------+---------+---------+---------+---------+---------+ 9660
      CACGCGAGAGGACAAGGCTGGGACGGCGAATGGCCTATGGACAGGCGGAAAGAGGGAAGC

GGAAGCGTGGCGCTTTCTCATAGCTCACGCTGTAGGTATCTCAGTTCGGTGTAGGTCGTT
9661  ---------+---------+---------+---------+---------+---------+ 9720
      CCTTCGCACCGCGAAAGAGTATCGAGTGCGACATCCATAGAGTCAAGCCACATCCAGCAA

CGCTCCAAGCTGGGCTGTGTGCACGAACCCCCCGTTCAGCCCGACCGCTGCGCCTTATCC
9721  ---------+---------+---------+---------+---------+---------+ 9780
      GCGAGGTTCGACCCGACACACGTGCTTGGGGGCAAGTCGGGCTGGCGACGCGGAATAGG

GGTAACTATCGTCTTGAGTCCAACCCGGTAAGACACGACTTATCGCCACTGGCAGCAGCC
9781  ---------+---------+---------+---------+---------+---------+ 9840
      CCATTGATAGCAGAACTCAGGTTGGGCCATTCTGTGCTGAATAGCGGTGACCGTCGTCGG

ACTGGTAACAGGATTAGCAGAGCGAGGTATGTAGGCGGTGCTACAGAGTTCTTGAAGTGG
9841  ---------+---------+---------+---------+---------+---------+ 9900
      TGACCATTGTCCTAATCGTCTCGCTCCATACATCCGCCACGATGTCTCAAGAACTTCACC

TGGCCTAACTACGGCTACACTAGAAGGACAGTATTTGGTATCTGCGCTCTGCTGAAGCCA
9901  ---------+---------+---------+---------+---------+---------+ 9960
      ACCGGATTGATGCCGATGTGATCTTCCTGTCATAAACCATAGACGCGAGACGACTTCGGT
```

FIG. 24J

```
       GTTACCTTCGGAAAAAGAGTTGGTAGCTCTTGATCCGGCAAACAAACCACCGCTGGTAGC
 9961  ------------+---------+---------+---------+---------+---------+ 10020
       CAATGGAAGCCTTTTTCTCAACCATCGAGAACTAGGCCGTTTGTTTGGTGGCGACCATCG

GGTGGTTTTTTTGTTTGCAAGCAGCAGATTACGCGCAGAAAAAAAGGATCTCAAGAAGAT
10021  ------------+---------+---------+---------+---------+---------+ 10080
       CCACCAAAAAAACAAACGTTCGTCGTCTAATGCGCGTCTTTTTTTCCTAGAGTTCTTCTA

CCTTTGATCTTTTCTACGGGGTCTGACGCTCAGTGGAACGAAAACTCACGTTAAGGGATT
10081  ------------+---------+---------+---------+---------+---------+ 10140
       GGAAACTAGAAAAGATGCCCCAGACTGCGAGTCACCTTGCTTTTGAGTGCAATTCCCTAA

TTGGTCATGAGATTATCAAAAAGGATCTTCACCTAGATCCTTTTAAATTAAAAATGAAGT
10141  ------------+---------+---------+---------+---------+---------+ 10200
       AACCAGTACTCTAATAGTTTTTCCTAGAAGTGGATCTAGGAAAATTTAATTTTTACTTCA

TTTAAATCAATCTAAAGTATATATGAGTAAACTTGGTCTGACAGTTACCAATGCTTAATC
10201  ------------+---------+---------+---------+---------+---------+ 10260
       AAATTTAGTTAGATTTCATATATACTCATTTGAACCAGACTGTCAATGGTTACGAATTAG

AGTGAGGCACCTATCTCAGCGATCTGTCTATTTCGTTCATCCATAGTTGCCTGACTCCCC
10261  ------------+---------+---------+---------+---------+---------+ 10320
       TCACTCCGTGGATAGAGTCGCTAGACAGATAAAGCAAGTAGGTATCAACGGACTGAGGGG

GTCGTGTAGATAACTACGATACGGGAGGGCTTACCATCTGGCCCCAGTGCTGCAATGATA
10321  ------------+---------+---------+---------+---------+---------+ 10380
       CAGCACATCTATTGATGCTATGCCCTCCCGAATGGTAGACCGGGGTCACGACGTTACTAT

CCGCGAGACCCACGCTCACCGGCTCCAGATTTATCAGCAATAAACCAGCCAGCCGGAAGG
10381  ------------+---------+---------+---------+---------+---------+ 10440
       GGCGCTCTGGGTGCGAGTGGCCGAGGTCTAAATAGTCGTTATTTGGTCGGTCGGCCTTCC

GCCGAGCGCAGAAGTGGTCCTGCAACTTTATCCGCCTCCATCCAGTCTATTAATTGTTGC
10441  ------------+---------+---------+---------+---------+---------+ 10500
       CGGCTCGCGTCTTCACCAGGACGTTGAAATAGGCGGAGGTAGGTCAGATAATTAACAACG

CGGGAAGCTAGAGTAAGTAGTTCGCCAGTTAATAGTTTGCGCAACGTTGTTGCCATTGCT
10501  ------------+---------+---------+---------+---------+---------+ 10560
       GCCCTTCGATCTCATTCATCAAGCGGTCAATTATCAAACGCGTTGCAACAACGGTAACGA

ACAGGCATCGTGGTGTCACGCTCGTCGTTTGGTATGGCTTCATTCAGCTCCGGTTCCCAA
10561  ------------+---------+---------+---------+---------+---------+ 10620
       TGTCCGTAGCACCACAGTGCGAGCAGCAAACCATACCGAAGTAAGTCGAGGCCAAGGGTT

CGATCAAGGCGAGTTACATGATCCCCCATGTTGTGCAAAAAAGCGGTTAGCTCCTTCGGT
10621  ------------+---------+---------+---------+---------+---------+ 10680
       GCTAGTTCCGCTCAATGTACTAGGGGGTACAACACGTTTTTTCGCCAATCGAGGAAGCCA

CCTCCGATCGTTGTCAGAAGTAAGTTGGCCGCAGTGTTATCACTCATGGTTATGGCAGCA
10681  ------------+---------+---------+---------+---------+---------+ 10740
       GGAGGCTAGCAACAGTCTTCATTCAACCGGCGTCACAATAGTGAGTACCAATACCGTCGT

CTGCATAATTCTCTTACTGTCATGCCATCCGTAAGATGCTTTTCTGTGACTGGTGAGTAC
10741  ------------+---------+---------+---------+---------+---------+ 10800
       GACGTATTAAGAGAATGACAGTACGGTAGGCATTCTACGAAAAGACACTGACCACTCATG

TCAACCAAGTCATTCTGAGAATAGTGTATGCGGCGACCGAGTTGCTCTTGCCCGGCGTCA
10801  ------------+---------+---------+---------+---------+---------+ 10860
       AGTTGGTTCAGTAAGACTCTTATCACATACGCCGCTGGCTCAACGAGAACGGGCCGCAGT

ATACGGGATAATACCGCGCCACATAGCAGAACTTTAAAAGTGCTCATCATTGGAAAACGT
10861  ------------+---------+---------+---------+---------+---------+ 10920
       TATGCCCTATTATGGCGCGGTGTATCGTCTTGAAATTTTCACGAGTAGTAACCTTTTGCA

TCTTCGGGGCGAAAACTCTCAAGGATCTTACCGCTGTTGAGATCCAGTTCGATGTAACCC
10921  ------------+---------+---------+---------+---------+---------+ 10980
       AGAAGCCCCGCTTTTGAGAGTTCCTAGAATGGCGACAACTCTAGGTCAAGCTACATTGGG
```

FIG. 24K

```
       ACTCGTGCACCCAACTGATCTTCAGCATCTTTTACTTTCACCAGCGTTTCTGGGTGAGCA
10981  ----------+---------+---------+---------+---------+---------+ 11040
       TGAGCACGTGGGTTGACTAGAAGTCGTAGAAAATGAAAGTGGTCGCAAAGACCCACTCGT

AAAACAGGAAGGCAAAATGCCGCAAAAAAGGGAATAAGGGCGACACGGAAATGTTGAATA
11041  ----------+---------+---------+---------+---------+---------+ 11100
       TTTTGTCCTTCCGTTTTACGGCGTTTTTTCCCTTATTCCCGCTGTGCCTTTACAACTTAT

CTCATACTCTTCCTTTTTCAATATTATTGAAGCATTTATCAGGGTTATTGTCTCATGAGC
11101  ----------+---------+---------+---------+---------+---------+ 11160
       GAGTATGAGAAGGAAAAAGTTATAATAACTTCGTAAATAGTCCCAATAACAGAGTACTCG

GGATACATATTTGAATGTATTTAGAAAAATAAACAAATAGGGGTTCCGCGCACATTTCCC
11161  ----------+---------+---------+---------+---------+---------+ 11220
       CCTATGTATAAACTTACATAAATCTTTTATTTGTTTATCCCCAAGGCGCGTGTAAAGGG

CGAAAAGTGCCAC
11221  ----------+--- 11233
       GCTTTTCACGGTG
```

```
         crtW1
       MetSerGlyArgLysProGlyThrThrGlyAspThrIleValAlaAsnLeuGlyLeuThrAlaAlaIleLeuLeuCysTrpLeuValLeuHisAlaPheThrLeuTrpLeuLeuAspAlaAla
  1    ATGTCCGGTCGTAAACCGGGTACCACCGGTGACACCATCGTTGCCAACCTGGGTCTGACCGCTGCTATCCTGCTGTGCTGGCTGGTTCTGCACGCTTTCACCCTGTGGCTGCTGGACGCTGCT   120
       ----------+---------+---------+---------+---------+---------+---------+---------+---------+---------+---------+---------+
       TACAGGCCAGCATTTGGCCCATGGTGGCCACTGTGGTAGCAATTGGACCCAGACTGGCGACGATAGGACGACACGACCGACTGGGACACGACCAAGACTGGCGAAAGTGGGACACGACCTGCGACGA
                                                                                   crtW2 crtW3
       AlaHisProLeuLeuAlaValLeuCysLeuLeuValLeuPheIleIleAlaHisAspAlaMetHisGlySerValValProGlyArgProArgAlaAsn
121    GCTCACCCGCTGCTGGCTGTTCTGTGCCTGCTGGTCCTGTTCATCATCGCTCACGACGCTATGCACGGTTCCGTTGTTCCGGGTCGTCCGCGGGCTAAC   240
       ----------+---------+---------+---------+---------+---------+---------+---------+---------+---------+
       CGAGTGGGCGACGACCGACAAGACACGGACGACCAGGACAAGTAGTAGCGAGTGCTGCGATACGTGCCAAGGCAACGCAGTCCAAGGGCCCAGCAGGCGCCCGATTG
                                                                              crtW4 crtW5
       AlaAlaIleGlyGlnLeuAlaLeuTrpLeuTyrAlaGlyPheSerTrpProLysLeuIleAlaAlaLysHisMetThrThrHisArgHisAlaGlyThrAspAsnAspProAspPheGlyHis
241    GCTGCTATCGGTCAGCTGGCTCTGTGGCTGTACGCTGGTTCTCCTGGCCTGGTTTCCTGGCCCAAACTGATCGCTGCTAAACACATGACCACCCACCGTCACGCTGGTACCGACAACGACCCGGACTTCGGTCAC   360
       ----------+---------+---------+---------+---------+---------+---------+---------+---------+---------+---------+---------+
       CGACGATAGCCAGTCGACCGAGACACCGACATGCGACCAAGAGGACCGGGCTTTGACTAGCGACGATTTGTGTACTGGCTAGCGACCATGGCTGTTGCTGGGCCTGAAGCCAGTG
                                                                              crtW6
```

FIG. 25B

```
                                                                                                   crtW7
     GlyGlyProValArgTrpTyrGlySerPheValSerPheGlyTrpArgGluLeuLeuGlyLeuProValIleValThrThrTyrAlaLeuIleLeuGlyAspArgTrpMetTyr
     GGTGGTCCGGTTCGTTGGTTACGGTTCCTTCGTTTGGCCGTGAAGGTCCTGCTCGGTCTGCCGGTTATCGTGACCACCACCTACGCTCTGATCCTCGGTGACCGTTGGATGTAC
361  |----------|----------|----------|----------|----------|----------|----------|----------|----------|----------|----------|----------|  480
     CCACCAGGCCAAGCAACCAATGCCAAGGAAGCAAACCGGCACTTCCAGACGAGCCAATAGCACTGGATCGGAGACTAGGAGCCACTGGCAACCTACATG
                                                                                                   crtW8 crtW9
     ValIlePheTrpProValProAlaValLeuAlaSerIleGlnIleIlePheValPheGlyThrTrpLeuProHisArgProGlyHisAspAspPheProAspArgHisAsnAlaArgSerThr
     GTTATCTTCTGGCCGGTTCCGGCTGTTCTGGCTTCTCATCCAGATCTTCGTTTTCGGTACCTGGCTGCCGCACCGTCCGGGTCACGACGACTTCCCGGACCGTCACAACGCTCGTTCCACC
481  |----------|----------|----------|----------|----------|----------|----------|----------|----------|----------|----------|----------|  600
     CAATAGAAGACCGGCCAAGGCCGACAAGACCGAAGAGTAGGTCTAGAAGCAAAAGCCATGGACCGACGGCGTGGCAGGCCCAGTGCTGCTGAAGGGCCTGGCAGYGTTGCGAGCAAGGTGG
                                                                                                   crtW10 crtW11
     GlyIleGlyAspProLeuSerLeuLeuThrCysPheHisPheGlyGlyTyrHisHisGluHisProHisLeuHisProHisValProTrpTrpArgLeuProArgThrArgLysThrGlyGly
     GGTATCGGTGACCCGCTGTCCCTGCTGACCTGCTTCCACTTCGGTGGCTACCACCACGAACACCCACACCTGCACCCGCACGTTCCGTGGTGGCGTCTGCCGCGTACCCGTAAAACCGGTGGT
601  |----------|----------|----------|----------|----------|----------|----------|----------|----------|----------|----------|----------|  720
     CCATAGCCACTGGGCGACAGGGACGACTGGACGAAGGTGAAGCCACCGATGGTGCTTGTGCTTGTTGCTTGTTGTGACGTGGGCGTGCAAGGCACCACCGCAGAGGCGCATGGGCATTTTGGCCACCA
                                                                                                   crtW12

ArgAla
     CGTGCT
721  ------  726
     GCACGA
```

```
      ACTGTAGTCTGCGCGGATCGCCGGTCCGGGGGACAAGATATGAGCGCACATGCCCTGCCC
  1   ----------+---------+---------+---------+---------+---------+   60
      TGACATCAGACGCGCCTAGCGGCCAGGCCCCCTGTTCTATACTCGCGTGTACGGGACGGG

AAGGCAGATCTGACCGCCACCAGTTTGATCGTCTCGGGCGGCATCATCGCCGCGTGGCTG
 61   ----------+---------+---------+---------+---------+---------+  120
      TTCCGTCTAGACTGGCGGTGGTCAAACTAGCAGAGCCCGCCGTAGTAGCGGCGCACCGAC

GCCCTGCATGTGCATGCGCTGTGGTTTCTGGACGCGGCGGCGCATCCCATCCTGGCGGTC
121   ----------+---------+---------+---------+---------+---------+  180
      CGGGACGTACACGTACGCGACACCAAAGACCTGCGCCGCCGCGTAGGGTAGGACCGCCAG

GCGAATTTCCTGGGGCTGACCTGGCTGTCGGTCGGTCTGTTCATCATCGCGCATGACGCG
181   ----------+---------+---------+---------+---------+---------+  240
      CGCTTAAAGGACCCCGACTGGACCGACAGCCAGCCAGACAAGTAGTAGCGCGTACTGCGC

ATGCATGGGTCGGTCGTGCCGGGGCGCCCGCGCGCCAATGCGGCGATGGGCCAGCTTGTC
241   ----------+---------+---------+---------+---------+---------+  300
      TACGTACCCAGCCAGCACGGCCCCGCGGGCGCGCGGTTACGCCGCTACCCGGTCGAACAG

CTGTGGCTGTATGCCGGATTTTCCTGGCGCAAGATGATCGTCAAGCACATGGCCCATCAT
301   ----------+---------+---------+---------+---------+---------+  360
      GACACCGACATACGGCCTAAAAGGACCGCGTTCTACTAGCAGTTCGTGTACCGGGTAGTA

CGCCATGCCGGAACCGACGACGACCCAGATTTCGACCATGGCGGCCCCGGTCCGCTGGTAC
361   ----------+---------+---------+---------+---------+---------+  420
      GCGGTACGGCCTTGGCTGCTGCTGGGTCTAAAGCTGGTACCGCCGGGCCAGGCGACCATG

GCCCGCTTCATCGGCACCTATTTCGGCTGGCGCGAGGGGCTGCTGCTGCCCGTCATCGTG
421   ----------+---------+---------+---------+---------+---------+  480
      CGGGCGAAGTAGCCGTGGATAAAGCCGACCGCGCTCCCCGACGACGACGGGCAGTAGCAC

ACGGTCTATGCGCTGATGTTGGGGGATCGCTGGATGTACGTGGTCTTCTGGCCGTTGCCG
481   ----------+---------+---------+---------+---------+---------+  540
      TGCCAGATACGCGACTACAACCCCCTAGCGACCTACATGCACCAGAAGACCGGCAACGGC

TCGATCCTGGCGTCGATCCAGCTGTTCGTGTTCGGCATCTGGCTGCCGCACCGCCCCGGC
541   ----------+---------+---------+---------+---------+---------+  600
      AGCTAGGACCGCAGCTAGGTCGACAAGCACAAGCCGTAGACCGACGGCGTGGCGGGGCCG

CACGACGCGTTCCCGGACCGCCACAATGCGCGGTCGTCGCGGATCAGCGACCCCGTGTCG
601   ----------+---------+---------+---------+---------+---------+  660
      GTGCTGCGCAAGGGCCTGGCGGTGTTACGCGCCAGCAGCGCCTAGTCGCTGGGGCACAGC
```

FIG. 30A

```
        CTGCTGACCTGCTTTCACTTTGGCGGTTATCATCACGAACACCACCTGCACCCGACGGTG
  661   ----------+---------+---------+---------+---------+---------+   720
        GACGACTGGACGAAAGTGAAACCGCCAATAGTAGTGCTTGTGGTGGACGTGGGCTGCCAC

CCTTGGTGGCGCCTGCCCAGCACCCGCACCAAGGGGGACACCGCATGACCAATTTCCTGA
  721   ----------+---------+---------+---------+---------+---------+   780
        GGAACCACCGCGGACGGGTCGTGGGCGTGGTTCCCCCTGTGGCGTACTGGTTAAAGGACT

TCGTCGTCGCCACCGTGCTGGTGATGGAGCTGACGGCCTATTCCGTCCACCGCTGGATCA
  781   ----------+---------+---------+---------+---------+---------+   840
        AGCAGCAGCGGTGGCACGACCACTACCTCGACTGCCGGATAAGGCAGGTGGCGACCTAGT

TGCACGGCCCCTTGGGCTGGGGCTGGCACAAGTCCCACCACGAGGAACACGACCACGCGC
  841   ----------+---------+---------+---------+---------+---------+   900
        ACGTGCCGGGGAACCCGACCCCGACCGTGTTCAGGGTGGTGCTCCTTGTGCTGGTGCGCG

TGGAAAAGAACGACCTGTACGGCCTGGTCTTTGCGGTGATCGCCACGGTGCTGTTCACGG
  901   ----------+---------+---------+---------+---------+---------+   960
        ACCTTTTCTTGCTGGACATGCCGGACCAGAAACGCCACTAGCGGTGCCACGACAAGTGCC

TGGGCTGGATCTGGGCACCGGTCCTGTGGTGGATCGCCTTGGGCATGACCGTCTACGGGC
  961   ----------+---------+---------+---------+---------+---------+  1020
        ACCCGACCTAGACCCGTGGCCAGGACACCACCTAGCGGAACCCGTACTGGCAGATGCCCG

TGATCTATTTCGTCCTGCATGACGGGCTGGTGCATCAGCGCTGGCCGTTCCGCTATATCC
 1021   ----------+---------+---------+---------+---------+---------+  1080
        ACTAGATAAAGCAGGACGTACTGCCCGACCACGTAGTCGCGACCGGCAAGGCGATATAGG

CTCGCAAGGGCTATGCCAGACGCCTGTATCAGGCCCACCGCCTGCACCACGCGGTCGAGG
 1081   ----------+---------+---------+---------+---------+---------+  1140
        GAGCGTTCCCGATACGGTCTGCGGACATAGTCCGGGTGGCGGACGTGGTGCGCCAGCTCC

GGCGCGACCATTGCGTCAGCTTCGGCTTCATCTATGCGCCGCCGGTCGACAAGCTGAAGC
 1141   ----------+---------+---------+---------+---------+---------+  1200
        CCGCGCTGGTAACGCAGTCGAAGCCGAAGTAGATACGCGGCGGCCAGCTGTTCGACTTCG

AGGACCTGAAGACGTCGGGCGTGCTGCGGGCCGAGGCGCAGGAGCGCACGTGACCCATGA
 1201   ----------+---------+---------+---------+---------+---------+  1260
        TCCTGGACTTCTGCAGCCCGCACGACGCCCGGCTCCGCGTCCTCGCGTGCACTGGGTACT

```
    ATGAGCGCACATGCCCTGCCCAAGGCAGATCTGACCGCCACCAGTTTGATCGTCTCGGGC
1   ------------+---------+---------+---------+---------+---------+  60
    TACTCGCGTGTACGGGACGGGTTCCGTCTAGACTGGCGGTGGTCAAACTAGCAGAGCCCG

GGCATCATCGCCGCGTGGCTGGCCCTGCATGTGCATGCGCTGTGGTTTCTGGACGCGGCG
61  ------------+---------+---------+---------+---------+---------+ 120
    CCGTAGTAGCGGCGCACCGACCGGGACGTACACGTACGCGACACCAAAGACCTGCGCCGC

GCGCATCCCATCCTGGCGGTCGCGAATTTCCTGGGGCTGACCTGGCTGTCGGTCGGTCTG
121 ------------+---------+---------+---------+---------+---------+ 180
    CGCGTAGGGTAGGACCGCCAGCGCTTAAAGGACCCCGACTGGACCGACAGCCAGCCAGAC

TTCATCATCGCGCATGACGCGATGCATGGGTCGGTCGTGCCGGGGCGCCCGCGCGCCAAT
181 ------------+---------+---------+---------+---------+---------+ 240
    AAGTAGTAGCGCGTACTGCGCTACGTACCCAGCCAGCACGGCCCCGCGGGCGCGCGGTTA

GCGGCGATGGGCCAGCTTGTCCTGTGGCTGTATGCCGGATTTTCCTGGCGCAAGATGATC
241 ------------+---------+---------+---------+---------+---------+ 300
    CGCCGCTACCCGGTCGAACAGGACACCGACATACGGCCTAAAAGGACCGCGTTCTACTAG

GTCAAGCACATGGCCCATCATCGCCATGCCGGAACCGACGACGACCCAGATTTCGACCAT
301 ------------+---------+---------+---------+---------+---------+ 360
    CAGTTCGTGTACCGGGTAGTAGCGGTACGGCCTTGGCTGCTGCTGGGTCTAAAGCTGGTA

GGCGGCCCCGGTCCGCTGGTACGCCCGCTTCATCGGCACCTATTTCGGCTGGCGCGAGGGG
361 ------------+---------+---------+---------+---------+---------+ 420
    CCGCCGGGCCAGGCGACCATGCGGGCGAAGTAGCCGTGGATAAAGCCGACCGCGCTCCCC

CTGCTGCTGCCCGTCATCGTGACGGTCTATGCGCTGATGTTGGGGGATCGCTGGATGTAC
421 ------------+---------+---------+---------+---------+---------+ 480
    GACGACGACGGGCAGTAGCACTGCCAGATACGCGACTACAACCCCCTAGCGACCTACATG

GTGGTCTTCTGGCCGTTGCCGTCGATCCTGGCGTCGATCCAGCTGTTCGTGTTCGGCATC
481 ------------+---------+---------+---------+---------+---------+ 540
    CACCAGAAGACCGGCAACGGCAGCTAGGACCGCAGCTAGGTCGACAAGCACAAGCCGTAG

TGGCTGCCGCACCGCCCCGGCCACGACGCGTTCCCGGACCGCCACAATGCGCGGTCGTCG
541 ------------+---------+---------+---------+---------+---------+ 600
    ACCGACGGCGTGGCGGGGCCGGTGCTGCGCAAGGGCCTGGCGGTGTTACGCGCCAGCAGC

CGGATCAGCGACCCCGTGTCGCTGCTGACCTGCTTTCACTTTGGCGGTTATCATCACGAA
601 ------------+---------+---------+---------+---------+---------+ 660
    GCCTAGTCGCTGGGGCACAGCGACGACTGGACGAAAGTGAAACCGCCAATAGTAGTGCTT

CACCACCTGCACCCGACGGTGCCTTGGTGGCGCCTGCCCAGCACCCGCACCAAGGGGGAC
661 ------------+---------+---------+---------+---------+---------+ 720
    GTGGTGGACGTGGGCTGCCACGGAACCACCGCGGACGGGTCGTGGGCGTGGTTCCCCCTG

ACCGCATGA
721 ---------   729
    TGGCGTACT
```

FIG. 31

```
  1  MSAHALPKAD LTATSLIVSG GIIAAWLALH VHALWFLDAA AHPILAVANF
 51  LGLTWLSVGL FIIAHDAMHG SVVPGRPRAN AAMGQLVLWL YAGFSWRKMI
101  VKHMAHHRHA GTDDDPDFDH GGPVRWYARF IGTYFGWREG LLLPVIVTVY
151  ALMLGDRWMY VVFWPLPSIL ASIQLFVFGI WLPHRPGHDA FPDRHNARSS
201  RISDPVSLLT CFHFGGYHHE HHLHPTVPWW RLPSTRTKGD TA*
```

FIG. 32

```
      ATGACCAATTTCCTGATCGTCGTCGCCACCGTGCTGGTGATGGAGCTGACGGCCTATTCC
  1   ---------+---------+---------+---------+---------+---------+   60
      TACTGGTTAAAGGACTAGCAGCAGCGGTGGCACGACCACTACCTCGACTGCCGGATAAGG

GTCCACCGCTGGATCATGCACGGCCCCTTGGGCTGGGGCTGGCACAAGTCCCACCACGAG
 61   ---------+---------+---------+---------+---------+---------+  120
      CAGGTGGCGACCTAGTACGTGCCGGGGAACCCGACCCCGACCGTGTTCAGGGTGGTGCTC

GAACACGACCACGCGCTGGAAAAGAACGACCTGTACGGCCTGGTCTTTGCGGTGATCGCC
121   ---------+---------+---------+---------+---------+---------+  180
      CTTGTGCTGGTGCGCGACCTTTTCTTGCTGGACATGCCGGACCAGAAACGCCACTAGCGG

ACGGTGCTGTTCACGGTGGGCTGGATCTGGGCACCGGTCCTGTGGTGGATCGCCTTGGGC
181   ---------+---------+---------+---------+---------+---------+  240
      TGCCACGACAAGTGCCACCCGACCTAGACCCGTGGCCAGGACACCACCTAGCGGAACCCG

ATGACCGTCTACGGGCTGATCTATTTCGTCCTGCATGACGGGCTGGTGCATCAGCGCTGG
241   ---------+---------+---------+---------+---------+---------+  300
      TACTGGCAGATGCCCGACTAGATAAAGCAGGACGTACTGCCCGACCACGTAGTCGCGACC

CCGTTCCGCTATATCCCTCGCAAGGGCTATGCCAGACGCCTGTATCAGGCCCACCGCCTG
301   ---------+---------+---------+---------+---------+---------+  360
      GGCAAGGCGATATAGGGAGCGTTCCCGATACGGTCTGCGGACATAGTCCGGGTGGCGGAC

CACCACGCGGTCGAGGGGCGCGACCATTGCGTCAGCTTCGGCTTCATCTATGCGCCGCCG
361   ---------+---------+---------+---------+---------+---------+  420
      GTGGTGCGCCAGCTCCCCGCGCTGGTAACGCAGTCGAAGCCGAAGTAGATACGCGGCGGC

GTCGACAAGCTGAAGCAGGACCTGAAGACGTCGGGCGTGCTGCGGGCCGAGGCGCAGGAG
421   ---------+---------+---------+---------+---------+---------+  480
      CAGCTGTTCGACTTCGTCCTGGACTTCTGCAGCCCGCACGACGCCCGGCTCCGCGTCCTC

CGCACG
481   ------  486
      GCGTGC
```

FIG. 33

```
  1  MTNFLIVVAT VLVMELTAYS VHRWIMHGPL GWGWHKSHHE EHDHALEKND

51  LYGLVFAVIA TVLFTVGWIW APVLWWIALG MTVYGLIYFV LHDGLVHQRW

101  PFRYIPRKGY ARRLYQAHRL HHAVEGRDHC VSFGFIYAPP VDKLKQDLKT

151  SGVLRAEAQE RT
```

FIG. 34

```
       CTGCAGGTCTGACACGGCCAGAAGGCCGCGCCGCGGGcCGGGGGCCGCcGCATCGCGACC
  1    ---------+---------+---------+---------+---------+---------+    60
       GACGTCCAGACTGTGCCGGTCTTCCGGCGCGGCGCCCgGCCCCCGGCGgCGTAGCGCTGG

GGTATCCTTGCCAAGCGCCGCCTGGTCGCCCACaACGTCCAGCAGGTCGTCATAGGACTG
  61   ---------+---------+---------+---------+---------+---------+   120
       CCATAGGAACGGTTCGCGGCGGACCAGCGGGTGtTGCAGGTCGTCCAGCAGTATCCTGAC

GAACACCCGGCCCAGCTGACGGCCAAAGTCGATCATCTGaGTCTGCTCCTCGGCGTCGAA
  121  ---------+---------+---------+---------+---------+---------+   180
       CTTGTGGGCCGGGTCGACTGCCGGTTTCAGCTAGTAGACtCAGACGAGGAGCCGCAGCTT

CTCCTTGATCACGGCCAGCATCTCCAGCCCGGCGATGAACAGCACGCCGGTCTTCAGGTC
  181  ---------+---------+---------+---------+---------+---------+   240
       GAGGAACTAGTGCCGGTCGTAGAGGTCGGGCCGCTACTTGTCGTGCGGCCAGAAGTCCAG

CTGTTCCTGTTCGACCCCCGCGCCGTTCTTGGCCGCGTGCAGGTCCAGGTCCTGGCCGGC
  241  ---------+---------+---------+---------+---------+---------+   300
       GACAAGGACAAGCTGGGGGCGCGGCAAGAACCGGCGCACGTCCAGGTCCAGGACCGGCCG

GCACAGGCCCTGCGGCCCCAGGGACCGCGACAGGATCCgcaccagctgcgcccgcaccgt
  301  ---------+---------+---------+---------+---------+---------+   360
       CGTGTCCGGGACGCCGGGGTCCCTGGCGCTGTCCTAGGCgtggtcgacgcgggcgtggca gcccgacgcgccgcgcgcaccggccagcagggccatcgcctcggtgatcagggcgatgcc
  361  ---------+---------+---------+---------+---------+---------+   420
       cgggctgcgcggcgcgcgtggccggtcgtcccggtagcggagccactagtcccgctacgg gcctagcacggcgcgggctttcgccatgcgccacatgggtcgcgggctggccgcggcgcag
  421  ---------+---------+---------+---------+---------+---------+   480
       cggatcgtgccgcgccgaaagcggtacgcggtgtacccagcgcccgaccggcgccgcgtc cccggcatcgtccatgcagggcaggtcgtcgaagatcagcgatgcggcatgcaccatctc
  481  ---------+---------+---------+---------+---------+---------+   540
       gggccgtagcaggtacgtcccgtccagcagcttctagtcgctacgccgtacgtggtagag gaccgcgcaggcggcgtcgacgatcgtgtcgcagaccccgcccgaggcttctgccgcaag
  541  ---------+---------+---------+---------+---------+---------+   600
       ctggcgcgtccgccgcagctgctagcacagcgtctggggcgggctccgaagacggcgttc cagcatcagcatgccgcggaaacgcttgcccgacgacagcgcgccatggctcatggccgg
  601  ---------+---------+---------+---------+---------+---------+   660
       gtcgtagtcgtacggcgcctttgcgaacgggctgctgtcgcgcggtaccgagtaccggcc gccgagcggctgcgacacggcaccgaatccctgggcgatctcctcaagtctggtctgcag
  661  ---------+---------+---------+---------+---------+---------+   720
       cggctcgccgacgctgtgccgtggcttagggacccgctagaggagttcagaccagacgtc
```

FIG. 38A

```
       aagggtggcgtggatcggggttgacgtctcgtctcatcagtgccttcgcgcttgggttctg
721    ----------+----------+----------+----------+----------+----------+    780
       ttcccaccgcacctaggggaactgcagagcagagtagtcacggaagcgcgaacccaagac accaggcgggaaggtcaggccggggcggcaccccgtgacccgtcatccaccgtcaacagt
781    ----------+----------+----------+----------+----------+----------+    840
       tggtccgcccttccagtccggccccgccgtggggcactgggcagtaggtggcagttgtca ccccatgttggaaggcttcacgcccgattgcgagccttttcgacggcgacgcggggtcgc
841    ----------+----------+----------+----------+----------+----------+    900
       ggggtacaaccttccgaagtgcgggctaacgctcggaaaagctgccgctgcgccccagcg gcggcaatttntccaacaaggtcagtggaccggcgcgccgatggccgcgcgcagccaggc
901    ----------+----------+----------+----------+----------+----------+    960
       cgccgttaaanaggttgttccagtcacctggccgcgcggctaccggcgcgcgtcggtccg atccttggccggaaacacccgcgccgcatcatgatcggccaggatcgtccggcgcgcggc
961    ----------+----------+----------+----------+----------+----------+    1020
       taggaaccggcctttgtgggcgcggcgtagtactagccggtcctagcaggccgcggcgcg gcggcgcaggtcggccgcgtcacccggattgtcaagcacccaggccatcgcgtccgcgac
1021   ----------+----------+----------+----------+----------+----------+    1080
       cgccgcgtccagccggcgcagtgggcctaacagttcgtgggtccggtagcgcaggcgctg ctcgtccgcgtcgtccatgtcgacgatcaggccgttctccatgtcgcggaccagttcgcg
1081   ----------+----------+----------+----------+----------+----------+    1140
       gagcaggcgcagcaggtacagctgctagtccggcaagaggtacagcgcctggtcaagcgc caccggggcggtgttcgatcgatcaccaggcatccggtggccatcgcctcggacagggac
1141   ----------+----------+----------+----------+----------+----------+    1200
       gtggccccgccacaagctagctagtggtccgtaggccaccggtagcggagcctgtccctg caggaggtgacgaagggctcggtgaaatagacatgcgcgtgcgaggcctgcag
1201   ----------+----------+----------+----------+---    1253
       gtcctccactgcttcccgagccactttatctgtacgcgcacgctccggacgtc
```

FIG. 38B

```
    ATGAGACGAGACGTCAACCCGATCCACGCCACCCTTCTGCAGACCAGACTTGAGGAGATC
1   ---------+---------+---------+---------+---------+---------+   60
    TACTCTGCTCTGCAGTTGGGCTAGGTGCGGTGGGAAGACGTCTGGTCTGAACTCCTCTAG

GCCCAGGGATTCGGTGCCGTGTCGCAGCCGCTCGGCCCGGCCATGAGCCATGGCGCGCTG
61  ---------+---------+---------+---------+---------+---------+   120
    CGGGTCCCTAAGCCACGGCACAGCGTCGGCGAGCCGGGCCGGTACTCGGTACCGCGCGAC

TCGTCGGGCAAGCGTTTCCGCGGCATGCTGATGCTGCTTGCGGCAGAAGCCTCCCCCGGG
121 ---------+---------+---------+---------+---------+---------+   180
    AGCAGCCCGTTCGCAAAGGCGCCGTACGACTACGACGAACGCCGTCTTCGGAGCCCGCCC

GTCTGCGACACGATCGTCGACGCCGCCTGCGCGGTCGAGATGGTGCATGCCGCATCGCTG
181 ---------+---------+---------+---------+---------+---------+   240
    CAGACGCTGTGCTAGCAGCTGCGGCGGACGCGCCAGCTCTACCACGTACGGCGTAGCGAC

ATCTTCGACGACCTGCCCTGCATGGACGATGCCGGGCTGCGCCGCGGCCAGCCCGCGACC
241 ---------+---------+---------+---------+---------+---------+   300
    TAGAAGCTGCTGGACGGGACGTACCTGCTACGGCCCGACGCGGCGCCGGTCGGGCGCTGG

CATGTGGCGCATGGCGAAAGCCGCGCCGTGCTAGGCGGCATCGCCCTGATCACCGAGGCG
301 ---------+---------+---------+---------+---------+---------+   360
    GTACACCGCGTACCGCTTTCGGCGCGGCACGATCCGCCGTAGCGGGACTAGTGGCTCCGC

ATGGCCCTGCTGGCCGGTGCGCGCGGCGCGTCGGGCACGGTGCGGGCGCAGCTGGTGCGG
361 ---------+---------+---------+---------+---------+---------+   420
    TACCGGGACGACCGGCCACGCGCGCCGCGCAGCCCGTGCCACGCCCGCGTCGACCACGCC

ATCCTGTCGCGGTCCCTGGGGCCGCAGGGCCTGTGCGCCGGCCAGGGCCTGGACCTGCAC
421 ---------+---------+---------+---------+---------+---------+   480
    TAGGACAGCGCCAGGGACCCCGGCGTCCCGGACACGCGGCCGGTCCTGGACCTGGACGTG

GCGGCCAAGAACGGCGCGGGGGTCGAACAGGAACAGGACCTGAAGACCGGCGTGCTGTTC
481 ---------+---------+---------+---------+---------+---------+   540
    CGCCGGTTCTTGCCGCGCCCCCAGCTTGTCCTTGTCCTGGACTTCTGGCCGCACGACAAG

ATCGCCGGGCTGGAGATGCTGGCCGTGATCAAGGAGTTCGACGCCGAGGAGCAGACTCAG
541 ---------+---------+---------+---------+---------+---------+   600
    TAGCGGCCCGACCTCTACGACCGGCACTAGTTCCTCAAGCTGCGGCTCCTCGTCTGAGTC

ATGATCGACTTTGGCCGTCAGCTGGGCCGGGTGTTCCAGTCCTATGACGACCTGCTGGAC
601 ---------+---------+---------+---------+---------+---------+   660
    TACTAGCTGAAACCGGCAGTCGACCCGGCCCACAAGGTCAGGATACTGCTGGACGACCTG
```

FIG. 39A

```
     GTTGTGGGCGACCAGGCGGCGCTTGGCAAGGATACCGGTCGCGATGCGGCGGCCCCCGGC
661  ------------+---------+---------+---------+---------+---------+  720
     CAACACCCGCTGGTCCGCCGCGAACCGTTCCTATGGCCAGCGCTACGCCGCCGGGGGCCG

CCGCGGCGCGGCCTTCTGGCCGTGTCAGACCTGCAGAACGTGTCCCGTCACTATGAGGCC
721  ---------+---------+---------+---------+---------+---------+  780
     GGCGCCGCGCCGGAAGACCGGCACAGTCTGGACGTCTTGCACAGGGCAGTGATACTCCGG

AGCCGCGCCCAGCTGGACGCGATGCTGCGCAGCAAGCGCCTTCAGGCTCCGGAAATCGCG
781  ---------+---------+---------+---------+---------+---------+  840
     TCGGCGCGGGTCGACCTGCGCTACGACGCGTCGTTCGCGGAAGTCCGAGGCCTTTAGCGC

GCCCTGCTGGAACGGGTTCTGCCCTACGCCGCGCGCGCCTAG
841  ---------+---------+---------+---------+--  882
     CGGGACGACCTTGCCCAAGACGGGATGCGGCGCGCGCGGATC
```

FIG. 39B

```
  1  MRRDVNPIHA TLLQTRLEEI AQGFGAVSQP LGPAMSHGAL SSGKRFRGML

51  MLLAAEASGG VCDTIVDAAC AVEMVHAASL IFDDLPCMDD AGLRRGQPAT

101  HVAHGESRAV LGGIALITEA MALLAGARGA SGTVRAQLVR ILSRSLGPQG

151  LCAGQDLDLH AAKNGAGVEQ EQDLKTGVLF IAGLEMLAVI KEFDAEEQTQ

201  MIDFGRQLGR VFQSYDDLLD VVGDQAALGK DTGRDAAAPG PRRGLLAVSD

251  LQNVSRHYEA SRAQLDAMLR SKRLQAPEIA ALLERVLPYA ARA*
```

FERMENTATIVE CAROTENOID PRODUCTION

BACKGROUND OF THE INVENTION

Over 600 different carotenoids have been described from carotenogenic organisms found among bacteria, yeast, fungi and plants. Currently only two of them, β-carotene and astaxanthin are commercially produced in microorganisms and used in the food and feed industry. β-carotene is obtained from algae and astaxanthin is produced in Pfaffia strains which have been generated by classical mutation. However, fermentation in Pfaffia has the disadvantage of long fermentation cycles and recovery from algae is cumbersome. Therefore it is desirable to develop production systems which have better industrial applicability, e.g. can be manipulated for increased titers and/or reduced fermentation times.

Two such systems using the biosynthetic genes form *Erwinia herbicola* and *Erwinia uredovora* have already been described in WO 91/13078 and EP 393 690, respectively. Furthermore, three β-carotene ketolase genes (β-carotene β-4-oxygenase) of the marine bacteria *Agrobacterium aurantiacum* and Alcaligenes strain PC-1 (crtW) [Misawa, 1995, Biochem. Biophys. Res. Com. 209, 867–876] [Misawa, 1995, J. Bacteriology 177, 6575–6584] and from the green algae *Haematococcus pluvialis* (bkt) [Lotan, 1995, FEBS Letters 364, 125–128][Kajiwara, 1995, Plant Mol. Biol. 29, 343–352] have been cloned. *E. coli* carrying either the carotenogenic genes (crtE, crtB, crtY and crtI) of *E. herbicola* [Hundle, 1994, MGG 245, 406–416] or of *E. uredovora* and complemented with the crtW gene of *A. aurantiacum* [Misawa, 1995] or the bkt gene of *H. pluvialis* [Lotan, 1995][Kajiwara, 1995] resulted in the accumulation of canthaxanthin (β,β-carotene-4,4'-dione), originating from the conversion of β-carotene, via the intermediate echinenone (β,β-carotene-4-one).

Introduction of the above mentioned genes (crtW or bkt) into *E. coli* cells harbouring besides the carotenoid biosynthesis genes mentioned above also the crtZ gene of *E. uredovora* [Kajiwara, 1995][Misawa, 1995], resulted in both cases in the accumulation of astaxanthin (3,3'-dihydroxy-β, β-carotene-4,4'-dione). The results obtained with the bkt gene, are in contrast to the observation made by others [Lotan, 1995], who using the same experimental set-up, but introducing the *H. pluvialis* bkt gene in a zeaxanthin (β,β-carotene-3,3'-diol) synthesising *E. coli* host harbouring the carotenoid biosynthesis genes of *E. herbicola,* a close relative of the above mentioned *E. uredovora* strain, did not observe astaxanthin production.

SUMMARY OF THE INVENTION

Novel proteins of microorganism E-396 (FERM BP-4283) and the DNA sequences which encode these proteins have been discovered which provide an improved biosynthetic pathway from farnesyl pyrophosphate and isopentyl pyrophosphate to various carotenoids, especially zeaxanthin, astaxanthin, adonixanthin and canthaxanthin.

BRIEF DESCRIPTION OF THE FIGURES

FIGS. 7A, 7B, 7C, 7D, 7E, 7F, 7G, 7H, 7I, 7J, 7K, 7L, 7M, 7N, 7O Nucleotide sequence of the Flavobacterium sp. R1534 carotenoid biosynthesis cluster and its flanking regions. The nucleotide sequence is numbered from the first nucleotide shown (see BamHI site of FIG. 6). The deduced amino acid sequence of the ORF's (orf-5, orf-1, crtE, crtB, crtI, crtY, crtZ and orf-16) are shown with the single-letter amino acid code. Arrow (→) indicate the direction of the transcription; asterisks, stop codons.

FIG. 8: Protein sequence of the GGPP synthase (crtE) of Flavobactenum sp. R1534 (SEQ ID NO: 2) with a MW of 31331 Da.

FIG. 9: Protein sequence of the prephytoene synthetase (crtB) of Flavobacterium sp. R1534 (SEQ ID NO: 3) with a MW of 32615 Da.

FIG. 10: Protein sequence of the phytoene desaturase (crtI) of Flavobacterium sp. R1534 (SEQ ID NO: 4) with a MW of 54411 Da.

FIG. 11: Protein sequence of the lycopene cyclase (crtY) of Flavobacterium sp. R1534 (SEQ ID NO: 5) with a MW of 42368 Da.

FIG. 12: Protein sequence of the β-carotene hydroxylase (crtZ) of Flavobacterium sp. R1534 (SEQ ID NO: 6) with a MW of 19282 Da.

FIG. 14: Primers used for PCR reactions (SEQ ID NOs: 7, 8, 9, 10, 11, 12, 13, 14, 15, 16, 17, and 18). The underlined sequence is the recognition site of the indicated restriction enzyme. Small caps indicate nucleotides introduced by mutagenesis. Boxes show the artificial RBS which is recognized in *B. subtilis*. Small caps in bold show the location of the original adenine creating the translation start site (ATG) of the following gene (see original operon). All the ATG's of the original Flavobacter carotenoid biosynthetic genes had to be destroyed to not interfere with the rebuild transcription start site. Arrows indicate start and ends of the indicated Flavobacterium R1534 WT carotenoid genes.

FIG. 15: Linkers used for the different constructions (SEQ ID NOs: 19, 20, 21, 22, 23, 24, 25, and 26). The underlined sequence is the recognition site of the indicated restriction enzyme. Small caps indicate nucleotides introduced by synthetic primers. Boxes show the artificial RBS which is recognized in *B. subtilis*. Arrow indicate start and ends of the indicated Flavobacterium carotenoid genes.

FIGS. 19A, 19B, 19C, 19D Construction of plasmids PHP13-2CARZYIB-EINV and pHP13-2PN25ZYIB-EINV.

FIGS. 20A-1, 20A-2, 20B, 20C-1, 20C-2, 20C-3, 20C-4, 20D Construction of plasmid PXI12-ZYIB-EINVMUTRBS2C.

FIGS. 24A, 24B, 24C, 24D, 24E, 24F, 24G, 24H, 24I, 24J, 24K, 24L Complete nucleotide sequence of plasmid pZea4.

FIGS. 25A, 25B Synthetic crtW gene of Alcaligenes PC-1. The translated protein sequence is shown above the double stranded DNA sequence. The twelve oligonucleotides (crtW1–crtW12) used from the PCR synthesis are underlined.

FIGS. 30A, 30B Shows the sequence obtained containing the $crtW_{E396}$ (from nucleotide 40 to 768) and $crtZ_{E396}$ (from nucleotide 765 to 1253) genes of the bacterium E-396.

FIG. 31: The nucleotide sequence of the $crtW_{E396}$ gene (SEQ ID NO: 31)

FIG. 32: The amino acid sequence encoded by the $crtW_{E396}$ (SEQ ID NO: 32) gene shown in FIG. 31

FIG. 33: The nucleotide sequence of the $crtZ_{E396}$ (SEQ ID NO: 33) gene

FIG. 34: The amino acid sequence (SEQ ID NO: 34) encoded by the $crtZ_{E396}$ gene shown in FIG. 33

FIGS. 39A, 39B The DNA sequence of the complete $crtE_{E396}$ gene.

FIG. 40: The amino acid sequence encoded by the $crtE_{E396}$ gene (SEQ ID NO: 37) shown in FIG. 39 (SEQ ID NO: 36)

DETAILED DESCRIPTION OF THE INVENTION

Figure 1:
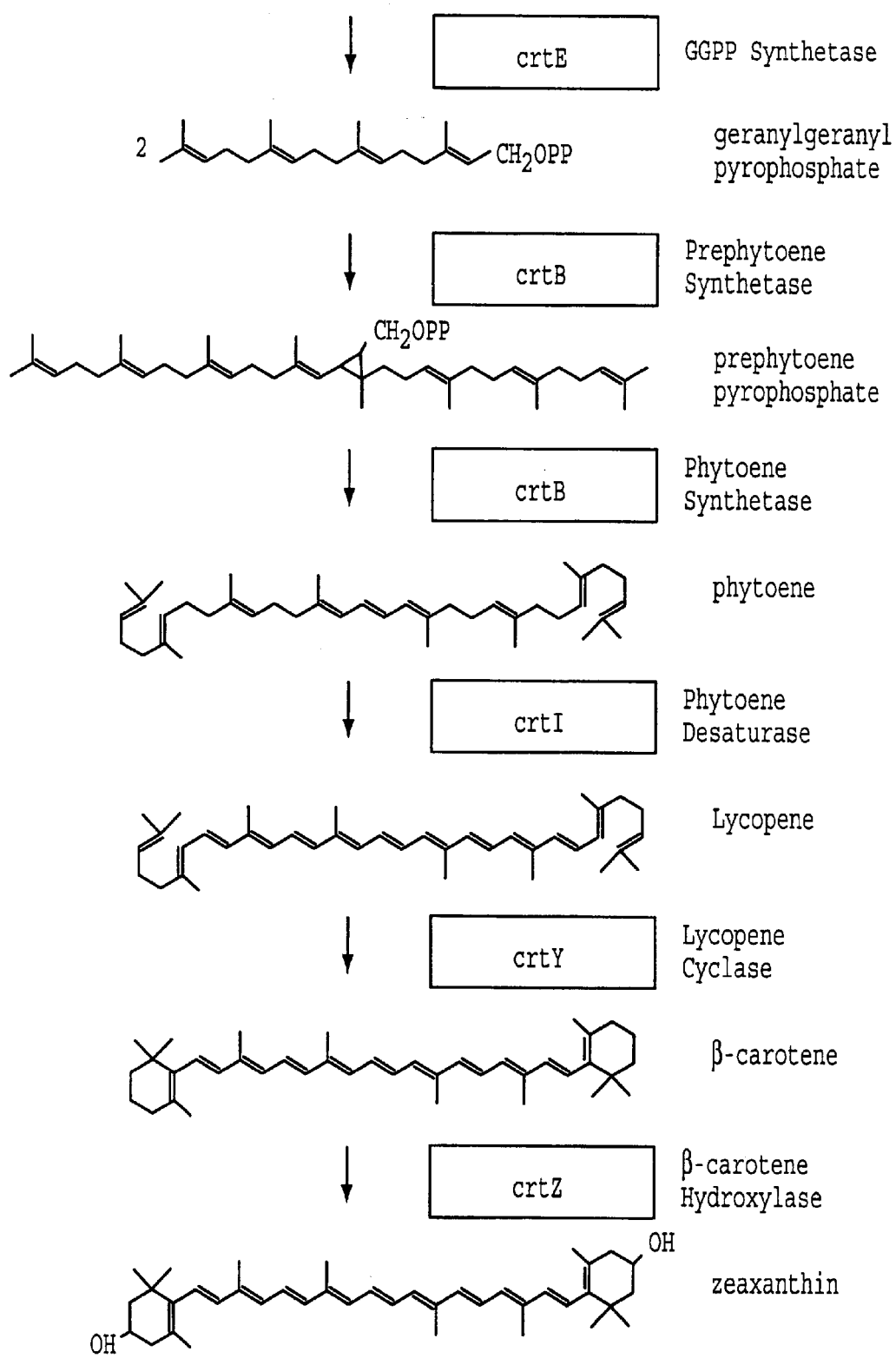
FIG. 1: The biosynthesis pathway for the formation or carotenoids of Flavobacterium sp. R1534 is illustrated explaining the enzymatic activities which are encoded by DNA sequences of the present invention.

Novel proteins of microorganism E-396 (FERM BP-4283) and the DNA sequences which encode these proteins have been discovered which provide an improved biosynthetic pathway from farnesyl pyrophosphate and isopentyl pyrophosphate to various carotenoids, especially zeaxanthin, astaxanthin, adonixanthin and canthaxanthin.

One aspect of the invention is a polynucleotide comprising a DNA sequence which encodes the GGPP synthase ($crtE_{E396}$) (SEQ ID NO: 37) of microorganism E-396, said polynucleotide being substantially free of other polynucleotides of microorganism E-396. Also encompassed by this aspect of the present invention is a polynucleotide comprising a DNA sequence which is substantially homologous to said DNA sequence. Said GGPP synthase catalyzes the condensation of farnesyl pyrophosphate and isopentyl pyrophosphate to obtain geranylgeranyl pyrophosphate, a carotenoid precursor. The preferred GGPP synthase has the amino acid sequence of FIG. 40 (SEQ ID NO: 37), and the preferred DNA sequence encodes said amino acid sequence. The especially preferred DNA sequence is shown in FIG. 39 (SEQ ID NO: 36).

This aspect of the present invention also includes a vector comprising the aforesaid polynucleotide, preferably in the form of an expression vector. Furthermore this aspect of the present invention also includes a recombinant cell comprising a host cell which is transformed by the aforesaid polynucleotide or vector which contains such a polynucleotide. Preferably said host cell is a prokaryotic cell and more preferably said host cell is *E. coli* or a Bacillus strain. However, said host cell may also be a eukaryotic cell, preferably a yeast cell or a fungal cell.

Finally this aspect of the present invention also comprises a process for the preparation of geranylgeranyl pyrophosphate by culturing said recombinant cell of the invention containing farnesyl pyrophosphate and isopentyl pyrophosphate in a culture medium under suitable culture conditions whereby said GGPP synthase is expressed by said cell and catalyzes the condensation of farnesyl pyrophosphate and isopentyl pyrophosphate to geranylgeranyl pyrophosphate, and isolating the geranylgeranyl pyrophosphate from such cells or the culture medium.

Another aspect of the present invention is a polynucleotide comprising a DNA sequence which encodes said β-carotene hydroxylase of microorganism E-396 ($crtZ_{E396}$) (SEQ ID NO: 34), said polynucleotide being substantially free of other polynucleotides of microorganism E-396. Also encompassed by this aspect of the present invention is a polynucleotide comprising a DNA sequence which is substantially homologous to said DNA sequence. Said β-carotene hydroxylase catalyzes the hydroxylation of β-carotene to produce the xanthophyll, zeaxanthin. The preferred β-carotene hydroxylase has the amino acid sequence of FIG. 34 (SEQ ID NO: 34), and the preferred DNA sequence is one which encodes said amino acid sequence. The especially preferred DNA sequence is a DNA sequence comprising the sequence shown in FIG. 33 (SEQ ID NO: 33).

This aspect of the present invention also includes a vector comprising the aforesaid polynucleotide, preferably in the form of an expression vector. Furthermore this aspect of the present invention also includes a recombinant cell comprising a host cell which is transformed by the aforesaid polynucleotide or vector which contains such a DNA sequence. Preferably said host cell is a prokaryotic cell and more preferably said host cell is *E. coli* or a Bacillus strain. However, said host cell may also be a eukaryotic cell, preferably a yeast cell or a fungal cell.

Finally this aspect of the present invention also comprises a process for the preparation of zeaxanthin by culturing said recombinant cell of the invention containing β-carotene in a culture medium under suitable culture conditions whereby said β-carotene hydroxylase is expressed by said cell and catalyzes the hydroxylation of β-carotene to produce the xanthophyll, zeaxanthin, and isolating the zeaxanthin from such cells or the culture medium.

Another aspect of the present invention is a polynucleotide comprising a DNA sequence which encodes said β-carotene β-4-oxygenase of microorganism E-396 ($crtW_{E396}$) (SEQ ID NO:32), said polynucleotide being substantially free of other polynucleotides of microorganism E-396. Also encompassed by this aspect of the present invention is a polynucleotide comprising a DNA sequence which is substantially homologous to said DNA sequence. Said β-carotene β-4-oxygenase catalyzes the conversion of β-carotene to produce the echinenone, and, with the further catalysis of echinenone by the enzyme encoded by $crtW_{E396}$, to canthaxanthin. The preferred β-carotene β-4-oxygenase has the amino acid sequence of FIG. 32 (SEQ ID NO:32), and the preferred DNA sequence is one which encodes said amino acid sequence. The especially preferred DNA sequence is a DNA sequence comprising the sequence shown in FIG. 31 (SEQ ID NO:31).

This aspect of the present invention also includes a vector comprising the aforesaid polynucleotide, preferably in the form of an expression vector. Furthermore this aspect of the present invention also includes a recombinant cell comprising a host cell which is transformed by the aforesaid polynucleotide or vector which contains such a DNA sequence. Preferably said host cell is a prokaryotic cell and more preferably said host cell is *E. coli* or a Bacillus strain. However, said host cell may also be a eukaryotic cell, preferably a yeast cell or a fungal cell.

Finally this aspect of the present invention also comprises a process for the preparation of canthaxanthin by culturing said recombinant cell of the invention containing β-carotene in a culture medium under suitable culture conditions whereby said β-carotene β4-oxygenase is expressed by said cell and catalyzes the conversion of β-carotene to produce echinenone and through further catalysis to produce canthaxanthin, and isolating the canthaxanthin from such cells or the culture medium.

Figure 28:
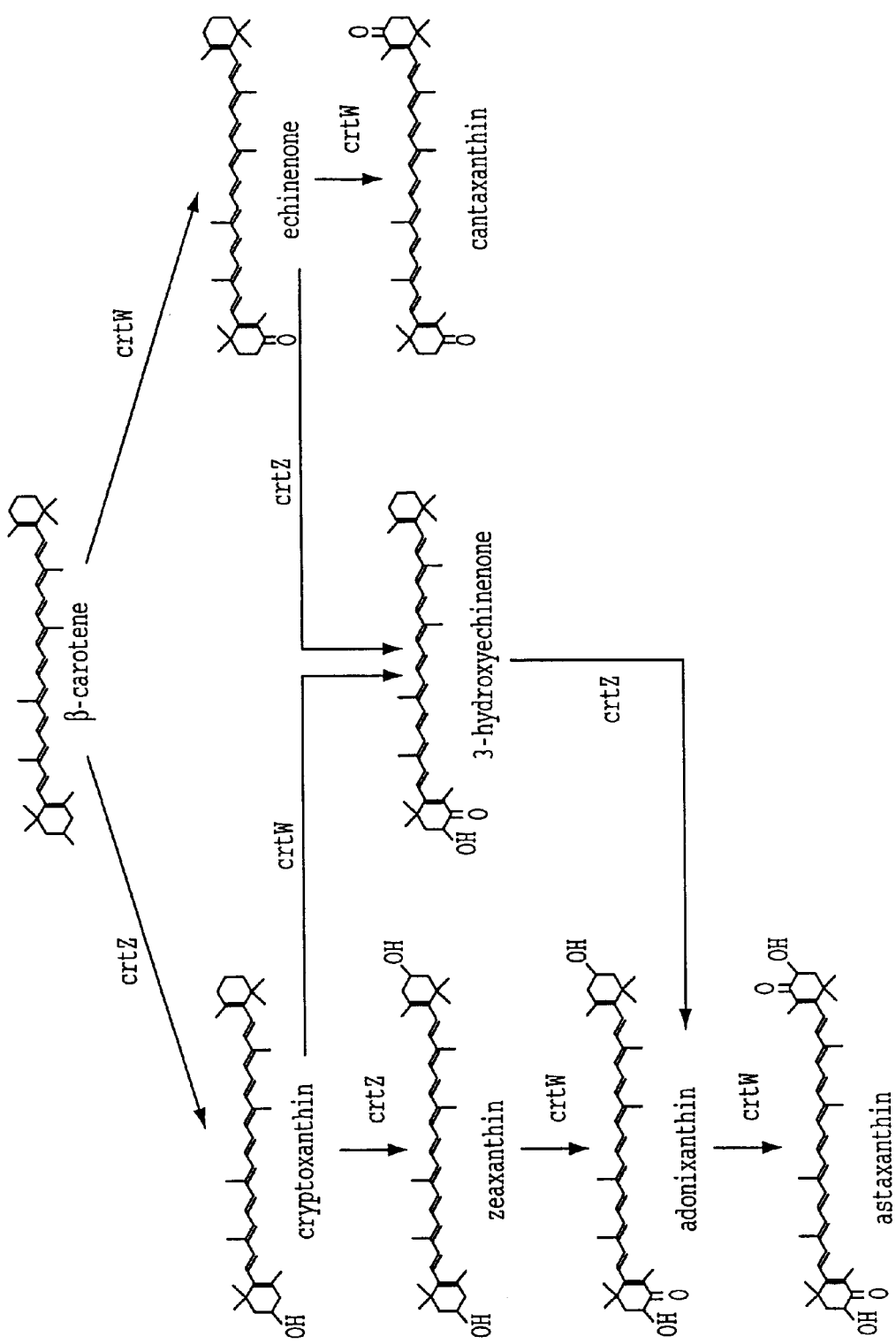
FIG. 28: Reaction products (carotenoids) obtained from β-carotene by the process of the present invention.

It is contemplated, and in fact preferred, that the aforementioned DNA sequences, $crtE_{E396}$, $crtW_{E396}$ and $crtZ_{E396}$, which terms refer to the above-described genes of microorganism E-396 encompassed by the invention herein described, are incorporated, especially $crtW_{E396}$ and $crtZ_{E396}$, with selected DNA sequences from Flavobacterium sp. R1534 into a polynucleotide of the invention whereby two or more of said DNA sequences which encode enzymes catalyzing contiguious steps in the process shown in FIGS. 1 and 28 are contained in said polynucleotide, said polynucleotide being substantially free of other polynucleotides of microorganism E-396 and Flavobacterium sp. R1534, to obtain advantageous production of the carotenoids canthaxanthin, zeaxanthin, astaxanthin and adonixanthin.

Thus, one embodiment of the present invention is a process for the preparation of zeaxanthin which process comprises culturing a recombinant cell containing farnesyl pyrophosphate and isopentyl pyrophosphate under culture conditions sufficient for the expression of enzymes which catalyze the conversion of the farnesyl pyrophosphate and isopentyl pyrophosphate to zeaxanthin, said recombinant cell comprising a host cell transformed by an expression vector comprising a regulatory sequence and a polynucleotide containing DNA sequences which encode said enzymes, as follows:

a) a DNA sequence which encodes the GGPP synthase of Flavobacterium sp. R1534 (crtE) (SEQ ID NO: 2) or a DNA sequence which is substantially homologous, b) a DNA sequence which encodes the prephytoene synthase of Flavobacterium sp. R1534 (crtB) (SEQ ID NO: 3) or a DNA sequence which is substantially homologous, c) a DNA sequence which encodes the phytoene desaturase of Flavobacterium sp. R1534 (crtI) (SEQ ID NO: 4) or a DNA sequence which is substantially homologous, d) a DNA sequence which encodes the lycopene cyclase of Flavobacterium sp. R1534 (crtY) (SEQ ID NO: 5) or a DNA sequence which is substantially homologous, e) a DNA sequence which encodes the β-carotene hydroxylase of microorganism E-396 ($crtZ_{E396}$) (SEQ ID NO: 34) or a DNA sequence which is substantially homologous;

and isolating the zeaxanthin from such cells or the culture medium.

The above-described polynucleotide encodes enzymes which catalyze the conversion of pyrophosphate and isopentyl pyrophosphate to zeaxanthin. It is preferred that this embodiment of the invention utilize a polynucleotide containing crtE, crtB, crtI, crtY, and crtZ$_{E396}$.

It is especially preferred that for this embodiment of the invention:
a) the GGPP synthase has the amino acid sequence of FIG. 8 (SEQ ID NO: 2),
b) the prephytoene synthase has the amino acid sequence of FIG. 9 (SEQ ID NO: 3),
c) the phytoene desaturase has the amino acid sequence of FIG. 10 (SEQ ID NO: 4),
d) the lycopene cyclase has the amino acid sequence of FIG. 11 (SEQ ID NO: 5), and
e) the β-carotene hydroxylase has the amino acid sequence of FIG. 34.

It is most preferred that for this embodiment of the invention:
a) the DNA sequence encoding the GGPP synthase comprises bases 2521–3408 of FIG. 7 (SEQ ID NO: 1),
b) the DNA sequence encoding the prephytoene synthase comprises bases 4316–3405 of FIG. 7 (SEQ ID NO: 1),
c) the DNA sequence encoding the phytoene desaturase comprises bases 4313–5797 of FIG. 7 (SEQ ID NO: 1),
d) the DNA sequence encoding the lycopene cyclase comprises bases 5794–6942 of FIG. 7 (SEQ ID NO: 1), and
e) the DNA sequence encoding the β-carotene hydroxylase comprises the sequence of FIG. 33 (SEQ ID NO: 33).

A second embodiment of the invention is a process for the preparation of canthaxanthin which process comprises culturing a recombinant cell containing farnesyl pyrophosphate and isopentyl pyrophosphate under culture conditions sufficient for the expression of enzymes which catalyze the conversion of the farnesyl pyrophosphate and isopentyl pyrophosphate to canthaxanthin, said recombinant cell comprising a host cell transformed by an expression vector comprising a regulatory sequence and a polynucleotide containing DNA sequences which encode said enzymes, as follows:
a) a DNA sequence which encodes the GGPP synthase of Flavobacterium sp. R1534 (crtE) (SEQ ID NO: 2) or a DNA sequence which is substantially homologous,
b) a DNA sequence which encodes the prephytoene synthase of Flavobacterium sp. R1534 (crtB) (SEQ ID NO: 3) or a DNA sequence which is substantially homologous,
c) a DNA sequence which encodes the phytoene desaturase of Flavobacterium sp. R1534 (crtI) (SEQ ID NO: 4) or a DNA sequence which is substantially homologous,
d) a DNA sequence which encodes the lycopene cyclase of Flavobacterium sp. R1534 (crtY) (SEQ ID NO: 5) or a DNA sequence which is substantially homologous, and
e) a DNA sequence which encodes the β-carotene β4-oxygenase of microorganism E-396 (crtW$_{E396}$) (SEQ ID NO: 32) or a DNA sequence which is substantially homologous;
and isolating the canthaxanthin from such cells or the culture medium.

The above-described polynucleotide encodes enzymes which catalyze the conversion of farnesyl pyrophosphate and isopentyl pyrophosphate to canthaxanthin. It is preferred that this embodiment of the invention utilize a polynucleotide containing crtE, crtB, crtI, crtY, and crtW$_{E396}$.

It is especially preferred that for this embodiment of the invention:
a) the GGPP synthase has the amino acid sequence of FIG. 8 (SEQ ID NO: 2),
b) the prephytoene synthase has the amino acid sequence of FIG. 9 (SEQ ID NO: 3),
c) the phytoene desaturase has the amino acid sequence of FIG. 10 (SEQ ID NO: 4),
d) the lycopene cyclase has the amino acid sequence of FIG. 11 (SEQ ID NO: 5), and
e) the β-carotene β4-oxygenase has the amino acid sequence of FIG. 32 (SEQ ID NO: 32).

For this embodiment of the invention, it is most preferred that:
a) the DNA sequence encoding the GGPP synthase comprises bases 2521–3408 of FIG. 7 (SEQ ID NO: 1),
b) the DNA sequence encoding the prephytoene synthase comprises bases 4316–3405 of FIG. 7 (SEQ ID NO: 1),
c) the DNA sequence encoding the phytoene desaturase comprises bases 4313–5797 of FIG. 7 (SEQ ID NO: 1),
d) the DNA sequence encoding the lycopene cyclase comprises bases 5794–6942 of FIG. 7 (SEQ ID NO: 1), and
e) the DNA sequence encoding the β-carotene β4-oxygenase comprises the sequence of FIG. 31.

A third embodiment of the invention is a process for the preparation of astaxanthin and adonixanthin wherein said process comprises culturing a recombinant cell containing farnesyl pyrophosphate and isopentyl pyrophosphate under culture conditions sufficient for the expression of enzymes which catalyze the conversion of the farnesyl pyrophosphate and isopentyl pyrophosphate to astaxanthin and adonixanthin, said recombinant cell comprising a host cell transformed by an expression vector comprising a regulatory sequence and a polynucleotide containing DNA sequences which encode said enzymes, as follows:
a) a DNA sequence which encodes the GGPP synthase of Flavobacterium sp. R1534 (crtE) (SEQ ID NO. 2) or a DNA sequence which is substantially homologous,
b) a DNA sequence which encodes the prephytoene synthase of Flavobacterium sp. R1534 (crtB) (SEQ ID NO: 3) or a DNA sequence which is substantially homologous,
c) a DNA sequence which encodes the phytoene desaturase of Flavobacterium sp. R1534 (crtI) (SEQ ID NO: 4) or a DNA sequence which is substantially homologous,
d) a DNA sequence which encodes the lycopene cyclase of Flavobacterium sp. R1534 (crtY) (SEQ ID NO: 5) or a DNA sequence which is substantially homologous,
e) a DNA sequence which encodes the β-carotene b4-oxygenase of Flavobacterium sp. R1534 (crtW) or a DNA sequence which is substantially homologous, and
f) a DNA sequence which encodes the β-carotene hydroxylase of microorganism E-396 (crtZ$_{E396}$) or a DNA sequence which is substantially homologous;
and isolating the astaxanthin and adonixanthin from such cells or the culture medium.

The above-described polynucleotide encodes enzymes which catalyze the conversion of farnesyl pyrophosphate and isopentyl pyrophosphate to astaxanthin and adonixanthin. It is preferred that this embodiment of the invention utilize a polynucleotide containing crtE, crtB, crtI, crtY, crtW, and crtZ$_{E396}$ (SEQ ID NO: 34).

It is especially preferred that for this embodiment of the invention:

a) the GGPP synthase has the amino acid sequence of FIG. 8 (SEQ ID NO: 2), b) the prephytoene synthase has the amino acid sequence of FIG. 9 (SEQ ID NO: 3), c) the phytoene desaturase has the amino acid sequence of FIG. 10 (SEQ ID NO: 4), d) the lycopene cyclase has the amino acid sequence of FIG. 11 (SEQ ID NO: 5), e) the β-carotene β4-oxygenase has the amino acid sequence of FIG. 25 (SEQ ID NO: 29), and f) the β-carotene hydroxylase has the amino acid sequence of FIG. 34 (SEQ ID NO: 34).

It is most preferred that for this embodiment of the invention:

a) the DNA sequence encoding the GGPP synthase comprises bases 2521–3408 of FIG. 7 (SEQ ID NO: 1), b) the DNA sequence encoding the prephytoene synthase comprises bases 4316–3405 of FIG. 7 (SEQ ID NO: 1), c) the DNA sequence encoding the phytoene desaturase comprises bases 4313–5797 of FIG. 7 (SEQ ID NO: 1), d) the DNA sequence encoding the lycopene cyclase comprises bases 5794–6942 of FIG. 7 (SEQ ID NO: 1), e) the DNA sequence encoding the β-carotene β4-oxygenase comprises the sequence of FIG. 25 (SEQ ID NO: 28), and f) the DNA sequence encoding the β-carotene hydroxylase comprises the sequence of FIG. 33 (SEQ ID NO: 33).

A fourth embodiment of the invention is a process for the preparation of astaxanthin and adonixanthin wherein said process comprises culturing a recombinant cell containing farnesyl pyrophosphate and isopentyl pyrophosphate under culture conditions sufficient for the expression of enzymes which catalyze the conversion of the farnesyl pyrophosphate and isopentyl pyrophosphate to astaxanthin and adonixanthin, said recombinant cell comprising a host cell transformed by an expression vector comprising a regulatory sequence and a polynucleotide containing DNA sequences which encode said enzymes, as follows:

a) a DNA sequence which encodes the GGPP synthase of Flavobacterium sp. R1534 (crtE) (SEQ ID NO: 2) or a DNA sequence which is substantially homologous, b) a DNA sequence which encodes the prephytoene synthase of Flavobacterium sp. R1534 (crtB) (SEQ ID NO: 3) or a DNA sequence which is substantially homologous, c) a DNA sequence which encodes the phytoene desaturase of Flavobacterium sp. R1534 (crtI) (SEQ ID NO: 4) or a DNA sequence which is substantially homologous, d) a DNA sequence which encodes the lycopene cyclase of Flavobacterium sp. R1534 (crtY) (SEQ ID NO: 5) or a DNA sequence which is substantially homologous, e) a DNA sequence which encodes the β-carotene β4-oxygenase of microorganism E-396 (crtW$_{E396}$) (SEQ ID NO: 32) or a DNA sequence which is substantially homologous, and f) a DNA sequence which encodes the β-carotene hydroxylase of microorganism E-396 (crtZ$_{E396}$) (SEQ ID NO: 34) or a DNA sequence which is substantially homologous;

and isolating the astaxanthin and adonixanthin from such cells or the culture medium. The above-described polynucleotide encodes enzymes which catalyze the conversion of farnesyl pyrophosphate and isopentyl pyrophosphate to astaxanthin and adonixanthin. It is preferred that this embodiment of the invention utilize a polynucleotide containing crtE, crtB, crtI, crtY, crtW$_{E396}$, and crtZ$_{E396}$.

It is especially preferred that for this embodiment of the invention:

a) the GGPP synthase has the amino acid sequence of FIG. 8 (SEQ ID NO: 2), b) the prephytoene synthase has the amino acid sequence of FIG. 9 (SEQ ID NO: 3), c) the phytoene desaturase has the amino acid sequence of FIG. 10 (SEQ ID NO: 4), d) the lycopene cyclase has the amino acid sequence of FIG. 11 (SEQ ID NO: 5), e) the β-carotene β4-oxygenase has the amino acid sequence of FIG. 32 (SEQ ID NO: 32), and f) the β-carotene hydroxylase has the amino acid sequence of FIG. 34 (SEQ ID NO: 34).

It is most preferred that for this embodiment of the invention:

a) the DNA sequence encoding the GGPP synthase comprises bases 2521–3408 of FIG. 7 (SEQ ID NO: 1), b) the DNA sequence encoding the prephytoene synthase comprises bases 4316–3405 of FIG. 7 (SEQ ID NO: 1), c) the DNA sequence encoding the phytoene desaturase comprises bases 4313–5797 of FIG. 7 (SEQ ID NO: 1), d) the DNA sequence encoding the lycopene cyclase comprises bases 5794–6942 of FIG. 7 (SEQ ID NO: 1), e) the DNA sequence encoding the β-carotene β4-oxygenase comprises the sequence of FIG. 31 (SEQ ID NO: 31), and f) the DNA sequence encoding the β4-carotene hydroxylase comprises the sequence of FIG. 33 (SEQ ID NO: 33).

A fifth embodiment of the present invention is a process for the preparation of adonixanthin wherein said process comprises culturing a recombinant cell containing farnesyl pyrophosphate and isopentyl pyrophosphate under culture conditions sufficient for the expression of enzymes which catalyze the conversion of the farnesyl pyrophosphate and isopentyl pyrophosphate to adonixanthin, said recombinant cell comprising a host cell transformed by an expression vector comprising a regulatory sequence and a polynucleotide containing DNA sequences which encode said enzymes, as follows:

a) a DNA sequence which encodes the GGPP synthase of microorganism E-396 (crtE$_{E396}$) (SEQ ID NO: 37) or a DNA sequence which is substantially homologous, b) a DNA sequence which encodes the prephytoene synthase of microorganism E-396 (crtB$_{E396}$) or a DNA sequence which is substantially homologous, c) a DNA sequence which encodes the phytoene desaturase of microorganism E-396 (crtI$_{E396}$) or a DNA sequence which is substantially homologous, d) a DNA sequence which encodes the lycopene cyclase of microorganism E-396 (crtY$_{E396}$) or a DNA sequence which is substantially homologous, e) a DNA sequence which encodes the b-carotene b4-oxygenase of microorganism E-396 (crtW$_{E396}$) (SEQ ID NO: 32) or a DNA sequence which is substantially homologous, and f) a DNA sequence which encodes the β-carotene hydroxylase of microorganism E-396 (crtZ$_{E396}$) (SEQ ID NO: 33) or a DNA sequence which is substantially homologous, said host cell being substantially free of other polynucleotides of microorganism E-396;

and isolating the adonixanthin from such cells or the culture medium. The above-described polynucleotide encodes enzymes which catalyze the conversion of farnesyl pyrophosphate and isopentyl pyrophosphate to adonixanthin. It is preferred that this embodiment of the invention utilize a polynucleotide containing crtE$_{E396}$, crtB$_{E396}$, crtI$_{E396}$, crtY$_{E396}$, crtW$_{E396}$, and crtZ$_{E396}$. It has been found that the use of the above-described process of the invention results in a preferential production of adonixanthin in relation to astaxanthin and other carotenoids. The preferred polynucleotide is plasmid pE396CARcrtW-E whose construction is described in Example 9 herein.

The present invention also comprises the polynucleotides described above for the various embodiments of the invention and a vector comprising such a polynucleotide, preferably in the form of an expression vector. Furthermore the present invention also comprises a recombinant cell wherein said cell is a host cell which is transformed by a polynucleotide of the invention or vector which contains such a polynucleotide. Host cells useful for the expression of heterologous genes normally contain farnesyl pyrophosphate and isopentyl pyrophosphate, which are used for other purposes within the cell. Preferably said host cell is a prokaryotic cell and more preferably said host cell is an *E. coli* or a Bacillus strain. However, said host cell may also be a eukaryotic cell, preferably a yeast cell or a fungal cell.

Finally the present invention also comprises a process for the preparation of a desired carotenoid by culturing a recombinant cell of the invention containing a starting material in a culture medium under suitable culture conditions and isolating the desired carotenoid from such cells or the culture medium wherein the cell utilizes the polynucleotide of the invention which contains said DNA sequences to express the enzymes which catalyze the reactions necessary to produce the desired carotenoid from the starting material. Where an enzyme catalyzes two sequential steps and it is preferred to produce the product of the second step (such as producing astaxanthin preferentially to adonixanthin (see FIG. 28)), a higher copy number of the DNA sequence encoding the enzyme may be used to further production of the product of the second of the two steps in comparison to the first product. The present invention further comprises a process for the preparation of a food or feed composition which process comprises mixing a nutritionally effective amount of the carotenoid isolated from the aforementioned recombinant cells or culture medium with said food or feed.

In this context it should be mentioned that the expression "a DNA sequence is substantially homologous" refers with respect to the crtE encoding DNA sequence to a DNA sequence which encodes an amino acid sequence which shows more than 45%, preferably more than 60% and more preferably more than 75% and most preferably more than 90% identical amino acids when compared to the amino acid sequence of crtE of Flavobacterium sp. 1534 and is the amino acid sequence of a polypeptide which shows the same type of enzymatic activity as the enzyme encoded by crtE of Flavobacterium sp. 1534. In analogy with respect to crtB this means more than 60%, preferably more than 70%, more preferably more than 80% and most preferably more than 90%; with respect to crtI this means more than 70%, preferably more than 80% and most preferably more than 90%; with respect to crtY this means 55%, preferably 70%, more preferably 80% and most preferably 90%.

"DNA sequences which are substantially homologous" refer with respect to the crtW$_{E396}$ encoding DNA sequence to a DNA sequence which encodes an amino acid sequence which shows more than 60%, preferably more than 75% and most preferably more than 90% identical amino acids when compared to the amino acid sequence of crtW of the microorganism E 396 (FERM BP-4283) and is the amino acid sequence of a polypeptide which shows the same type of enzymatic activity as the enzyme encoded by crtW of the microorganism E 396. In analogy with respect to crtZ$_{E396}$ this means more than 75%, preferable more than 80% and most preferably more than 90%; with respect to crtE$_{E396}$, crtB$_{E396}$, crtI$_{E396}$, crtY$_{E396}$ and crtZ$_{E396}$ this means more than 80%, preferably more than 90% and most preferably 95%.

The expression "said polynucleotide being substantially free of other polynucleotides of Flavobacterium sp. R1534" and "said polynucleotide being substantially free of other polynucleotides of microorganism E-396" is meant to preclude the present invention from encompassing the polynucleotides as they exist in Flavobacterium sp. R1534 or in microorganism E-396, themselves. The polynucleotides herein described which are combinations of two or more DNA sequences of Flavobacterium sp. R1534 and/or microorganism E-396 are also substantially free of other polynucleotides of Flavobacterium sp. R1534 and microorganism E-396 in any circumstance where a polynucleotide containing only a single such DNA sequence would be substantially free of other polynucleotides of Flavobacterium sp. R1534 or microorganism E-396.

DNA sequences in form of genomic DNA, cDNA or synthetic DNA can be prepared as known in the art [see e.g. Sambrook et al., Molecular Cloning, Cold Spring Habor Laboratory Press 1989] or, e.g. as specifically described in Examples 1, 2 or 7. In the context of the present invention it should be noted that all DNA sequences used for the process for production of carotenoids of the present invention encoding crt-gene products can also be prepared as synthetic DNA sequences according to known methods or in analogy to the method specifically described for crtW in Example 7.

The cloning of the DNA-sequences of the present invention from such genomic DNA can than be effected, e.g. by using the well known polymerase chain reaction (PCR) method. The principles of this method are outlined e.g. in PCR Protocols: A guide to Methods and Applications, Academic Press, Inc. (1990). PCR is an in vitro method for producing large amounts of a specific DNA of defined length and sequence from a mixture of different DNA-sequences. Thereby, PCR is based on the enzymatic amplification of the specific DNA fragment of interest which is flanked by two oligonucleotide primers which are specific for this sequence and which hybridize to the opposite strand of the target sequence. The primers are oriented with their 3' ends pointing toward each other. Repeated cycles of heat denaturation of the template, annealing of the primers to their complementary sequences and extension of the annealed primers with a DNA polymerase result in the amplification of the segment between the PCR primers. Since the extension product of each primer can serve as a template for the other, each cycle essentially doubles the amount of the DNA fragment produced in the previous cycle.

By utilizing the thermostable Taq DNA polymerase, isolated from the thermophilic bacteria Thermus aquaticus, it has been possible to avoid denaturation of the polymerase which necessitated the addition of enzyme after each heat denaturation step. This development has led to the automation of PCR by a variety of simple temperature-cycling devices. In addition, the specificity of the amplification reaction is increased by allowing the use of higher temperatures for primer annealing and extension. The increased specificity improves the overall yield of amplified products by minimizing the competition by non-target fragments for enzyme and primers. In this way the specific sequence of interest is highly amplified and can be easily separated from the non-specific sequences by methods known in the art, e.g. by separation on an agarose gel and cloned by methods known in the art using vectors as described e.g. by Holten and Graham in Nucleic Acid Res. 19, 1156 (1991), Kovalic et. al. in Nucleic Acid Res. ,19 4560 (1991), Marchuk et al. in Nucleic Acid Res. 19, 1154 (1991) or Mead et al. in Bio/Technology 9, 657–663 (1991).

The oligonucleotide primers used in the PCR procedure can be prepared as known in the art and described e.g. in Sambrook et al., s.a.

Amplified DNA-sequences can than be used to screen DNA libraries by methods known in the art (Sambrook et al., s.a.) or as specifically described in Examples 1 and 2.

Once complete DNA-sequences of the present invention have been obtained they can be used as a guideline to define new PCR primers for the cloning of substantially homologous DNA sequences from other sources. In addition they and such homologous DNA sequences can be integrated into vectors by methods known in the art and described, e.g., in Sambrook et al. (s.a.) to express or overexpress the encoded polypeptide(s) in appropriate host systems. The expression vector into which the polynucleotides of the invention are integrated is not critical. Conventional expression vectors may be selected based upon the size of the polynucleotide of the invention to be inserted into the vector and the host cell to be transformed by the vector. Such conventional expression vectors contain a regulatory sequence for the synthesis of mRNA derived from the polynucleotide of the invention being expressed and possible marker genes. Conventional regulatory sequences generally contain, but are not limited to, one or more of the following: a signal sequence, an origin of replication, one or more marker genes, an enhancer element, a promoter, and a transcription termination sequence.

However, a man skilled in the art knows that also the DNA-sequences themselves can be used to transform the suitable host systems of the invention to get overexpression of the encoded polypeptide. Appropriate host systems are for example Bacteria e.g. *E. coli,* Bacilli as, e.g. *Bacillus subtilis* or Flavobacter strains. *E. coli,* which could be used are *E. coli* K12 strains e.g. M15 [described as DZ 291 by Villarejo et al. in J. Bacteriol. 120, 466–474 (1974)], HB 101 [ATCC No. 33694] or *E. coli* SG13009 [Gottesman et al., J. Bacteriol. 148, 265–273 (1981)].

Suitable Flavobacter strains can be obtained from any of the culture collections known to the man skilled in the art and listed, e.g. in the journal "Industrial Property" (January 1994, pgs 29–40), like the American Type Culture Collection (ATCC) or the Centralbureau voor Schimmelkultures (CBS) and are, e.g. Flavobacterium sp. R 1534 (ATCC No. 21588, classified as unknown bacterium; or as CBS 519.67) or all Flavobacter strains listed as CBS 517.67 to CBS 521.67 and CBS 523.67 to CBS 525.67, especially R 1533 (which is CBS 523.67 or ATCC 21081, classified as unknown bacterium; see also U.S. Pat. No. 3,841,967). Further Flavobacter strains are also described in WO 91/03571. Suitable eukaryotic host systems are for example fungi, like Aspergilli, e.g. Aspergillus niger [ATCC 9142] or yeasts, like Saccharomyces, e.g. *Saccharomyces cerevisiae* or Pichia, like pastoris, all available from ATCC.

Suitable vectors which can be used for expression in *E. coli* are mentioned, e.g., by Sambrook et al. [s.a.] or by Fiers et al. in Procd. 8th Int. Biotechnology Symposium" [Soc. Franc. de Microbiol., Paris (Durand et al., eds.), pp. 680–697 (1988)] or by Bujard et al. in Methods in Enzymology, eds. Wu and Grossmann, Academic Press, Inc. Vol. 155, 416–433 (1987) and Stüber et al. in Immunological Methods, eds. Lefkovits and Pernis, Academic Press, Inc., Vol. IV, 121–152 (1990). Vectors which could be used for expression in Bacilli are known in the art and described, e.g., in EP 405 370, EP 635 572 Procd. Nat. Acad. Sci. USA 81, 439 (1984) by Yansura and Henner, Meth. Enzym. 185, 199–228 (1990) or EP 207 459. Vectors which can be used for expression in fungi are known in the art and described e.g. in EP 420 358 and for yeast in EP 183 070, EP 183 071, EP 248 227, EP 263 311. Vectors which can be used for expression in Flavobacter are known in the art and described in the Examples or, e.g. in Plasmid Technology, edt. by J. Grinsted and P. M. Bennett, Academic Press (1990).

Once such DNA-sequences have been expressed in an appropriate host cell in a suitable medium, the carotenoids can be isolated either from the medium in the case they are secreted into the medium or from the host organism and, if necessary separated from other carotenoids if present in case one specific carotenoid is desired by methods known in the art (see e.g. Carotenoids Vol IA: Isolation and Analysis, G. Britton, S. Liaaen-Jensen, H. Pfander; 1995, Birkhäuser Verlag, Basel).

The carotenoids of the present invention can be used in a process for the preparation of food or feeds. A man skilled in the art is familiar with such processes. Such compound foods or feeds can further comprise additives or components generally used for such purpose and known in the state of the art.

After the invention has been described in general hereinbefore, the following examples are intended to illustrate details of the invention, without thereby limiting it in any matter.

EXAMPLE 1

Materials and General Methods Used

Bacterial strains and plasmids: Flavobacterium sp. R1534 WT (ATCC 21588) was the DNA source for the genes cloned. Partial genomic libraries of Flavobacterium sp. R1534 WT DNA were constructed into the pBluescriptII+ (KS) or (SK) vector (Stratagene, La Jolla, USA) and transformed into *E. coli* XL-1 blue (Stratagene) or JM109.

Media and growth conditions: Transformed *E. coli* were grown in Luria broth (LB) at 37° C. with 100 mg Ampicillin (Amp)/ml for selection. Flavobacterium sp. R1534 WT was grown at 27° C. in medium containing 1% glucose, 1% tryptone (Difco Laboratories), 1% yeast extract (Difco), 0.5% $MgSO_4 7H_2O$ and 3% NaCl.

Colony screening: Screening of the *E. coli* transformants was done by PCR basically according to the method described by Zon et al. [Zon et al., BioTechniques 7, 696–698 (1989)] using the following primers:
Primer #7 (SEQ ID NO: 38):
  5'-CCTGGATGACGTGCTGGAATATTCC-3'
Primer #8 (SEQ ID NO: 39):
  5'-CAAGGCCCAGATCGCAGGCG-3'

Genomic DNA: A 50 ml overnight culture of Flavobacterium sp. R1534 was centrifuged at 10,000 g for 10 minutes. The pellet was washed briefly with 10 ml of lysis buffer (50 mM EDTA, 0.1M NaCl pH7.5), resuspended in 4 ml of the same buffer sumplemented with 10 mg of lysozyme and incubated at 37° C. for 15 minutes. After addition of 0.3 ml of N-Lauroyl sarcosine (20%) the incubation at 37° C. was continued for another 15 minutes before the extraction of the DNA with phenol, phenol/chloroform and chloroform. The DNA was ethanol precipitated at room temperature for 20 minutes in the presence of 0.3 M sodium acetate (pH 5.2), followed by centrifugation at 10,000 g for 15 minutes. The pellet was rinsed with 70% ethanol, dried and resuspended in 1 ml of TE (10 mM Tris, 1 mM EDTA, pH 8.0).

All genomic DNA used in the southern blot analysis and cloning experiments was dialysed against $H_2O$ for 48 hours, using collodium bags (Sartorius, Germany), ethanol precipitated in the presence of 0.3 M sodium acetate and resuspended in $H_2O$.

Probe labelling: DNA probes were labeled with (a-$^{32}$P) dGTP (Amersham) by random-priming according to [Sambrook et al., s.a.].

Figure 6:
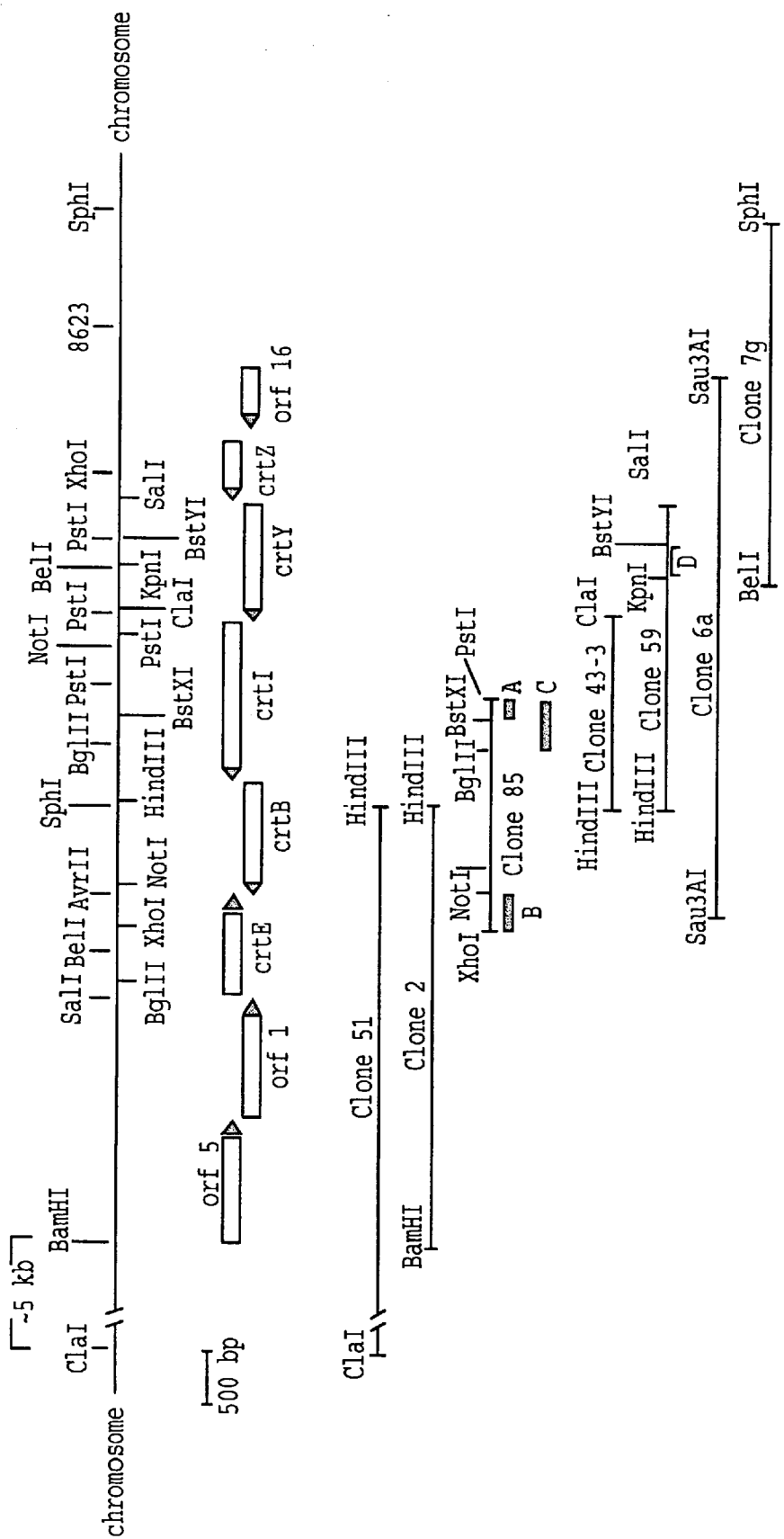
FIG. 6: Physical map of the organization of the carotenoid biosynthesis cluster in Flavobacterium sp. R1534, deduced from the genomic clones obtained. The location of the probes used for the screening are shown as bars on the respective clones.

Probes used to screen the mini-libraries: Probe 46F is a 119 bp fragment obtained by PCR using primer #7 (SEQ ID NO: 38) and #8 (SEQ ID NO: 39) and Flavobacterium sp. R1534 genomic DNA as template. This probe was proposed to be a fragment of the Flavobacterium sp. R1534 phytoene synthase (crtB) gene, since it shows significant homology to the phytoene synthase genes from other species (e.g. *E. uredovora, E. herbicola*). Probe A is a BstXI-PstI fragment of 184 bp originating from the right arm of the insert of clone 85. Probe B is a 397 bp XhoI-NotI fragment obtained from the left end of the insert of clone 85. Probe C is a 536 bp BglII-PstI fragment from the right end of the insert of clone 85. Probe D is a 376 bp KpnI-BstYI fragment isolated from the insert of clone 59. The localization of the individual probes is shown in FIG. 6.

Oligonucleotide synthesis: The oligonucleotides used for PCR reactions or for sequencing were synthesized with an Applied Biosystems 392 DNA synthesizer.

Southern blot analysis: For hybridization experiments Flavobacterium sp. R1534 genomic DNA (3 mg) was digested with the appropiate restriction enzymes and electrophoresed on a 0.75% agarose gel. The transfer to Zeta-Probe blotting membranes (BIO-RAD), was done as described [Sourthern, E. M., J. Mol. Biol. 98, 503 (1975)]. Prehybridization and hybridization was in 7% SDS, 1% BSA (fraction V; Boehringer), 0.5M $Na_2HPO_4$, pH 7.2 at 65° C. After hybridization the membranes were washed twice for 5 minutes in 2×SSC, 1% SDS at room temperature and twice for 15 minutes in 0.1% SSC, 0.1% SDS at 65° C.

DNA sequence analysis: The sequence was determined by the dideoxy chain termination technique [Sanger et al., Proc. Natl. Acad. Sci. USA 74, 5463–5467 (1977)] using the Sequenase Kit (United States Biochemical). Both strands were completely sequenced and the sequence analyzed using the GCG sequence analysis software package (Version 8.0) by Genetics Computer, Inc. [Devereux et al., Nucleic Acids. Res. 12, 387–395 (1984)].

Analysis of carotenoids: *E. coli* XL-1 or JM109 cells (200–400 ml) carrying different plasmid constructs were grown for the times indicated in the text, usually 24 to 60 hours, in LB suplemented with 100 mg Ampicillin/ml, in shake flasks at 37° C. and 220 rpm.

The carotenoids present in the microorganisms were extracted with an adequate volume of acetone using a rotation homogenizer (Polytron, Kinematica AG, CH-Luzern). The homogenate was the filtered through the sintered glass of a suction filter into a round bottom flask. The filtrate was evaporated by means of a rotation evaporator at 50° C. using a water-jet vacuum. For the zeaxanthin detection the residue was dissolved in n-hexane/ acetone (86:14) before analysis with a normalphase HPLC as described in [Weber, S. in Analytical Methods for Vitamins and Carotenoids in Feed, Keller, H. E., Editor, 83–85 (1988)]. For the detection of β-carotene and lycopene the evaporated extract was dissolved in n-hexane/acetone (99:1) and analysed by HPLC as described in [Hengartner et al., Helv. Chim. Acta 75, 1848–1865 (1992)].

EXAMPLE 2

Cloning of the Flavobacterium sp. R1534 Carotenoid Biosynthetic Genes.

Figure 2:
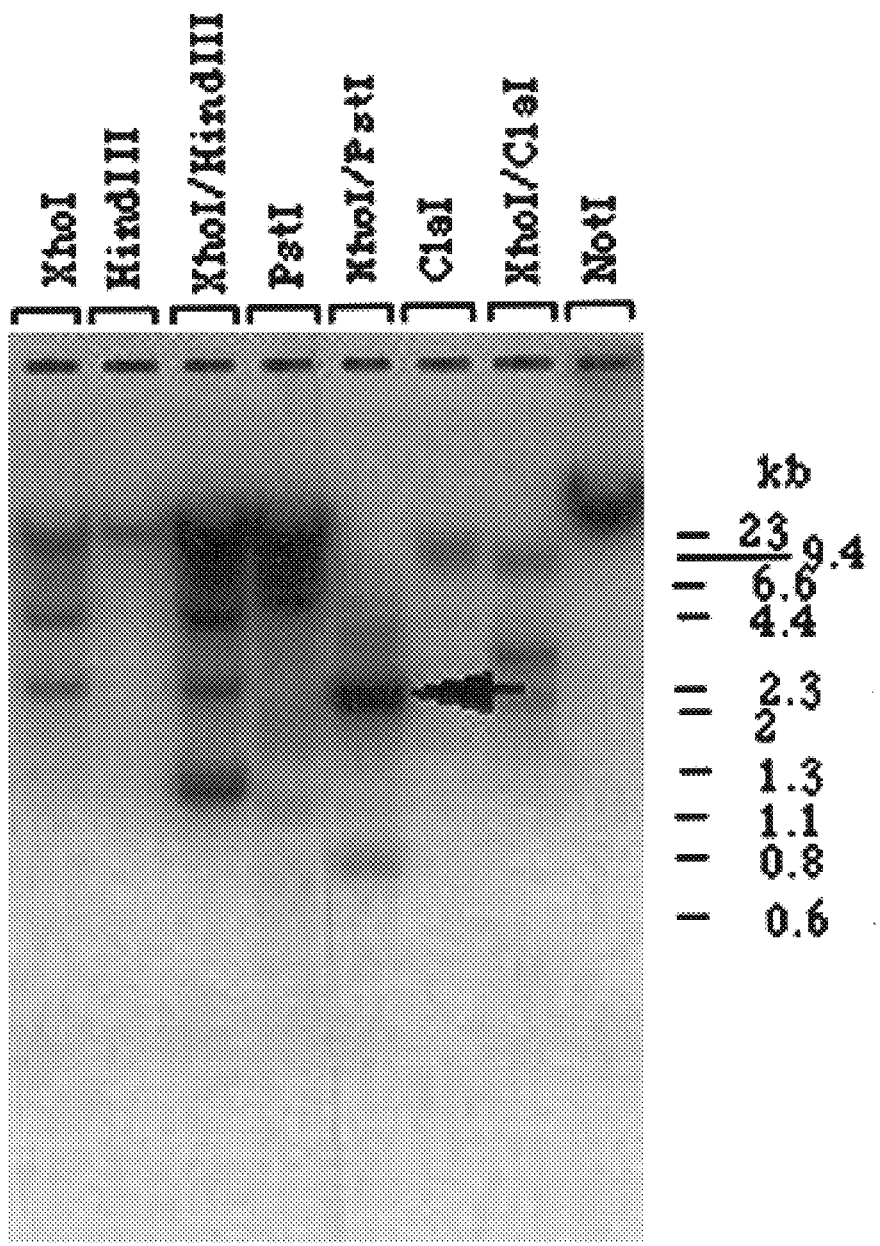
FIG. 2: Southern blot of genomic Flavobacterium sp. R1534 DNA digested with the restriction enzymes shown on top of each lane and hybridized with Probe 46F. The arrow indicated the isolated 2.4 kb XhoI/PstI fragment.
Figures 3A, 3B:
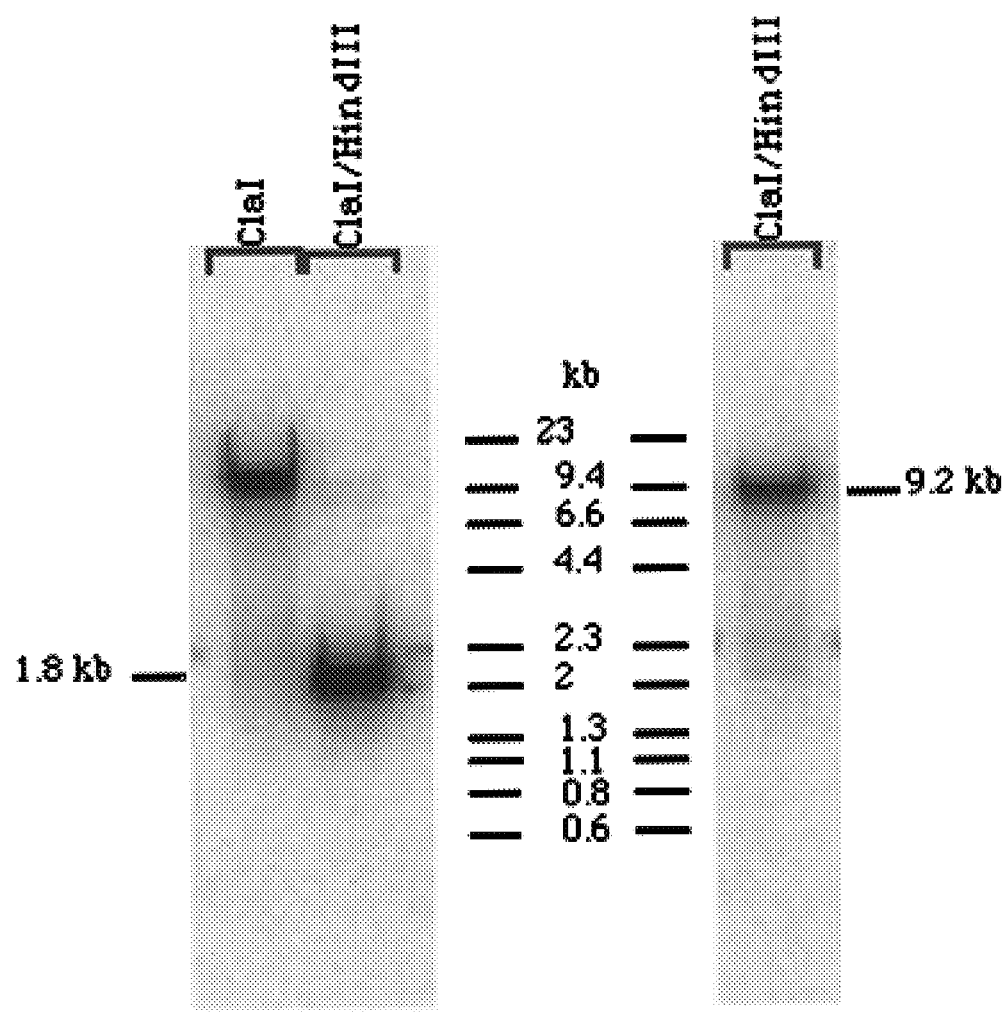
FIGS. 3A, 3B Southern blot of genomic Flavobacterium sp. R1534 DNA digested with ClaI or double digested with ClaI and HindIII. Blots shown in Panel A and B were hybridized to probe A or probe B, respectively (see examples). Both ClaI/HindIII fragments of 1.8 kb and 9.2 kb are indicated.

To identify and isolate DNA fragments carrying the genes of the carotenoid biosynthesis pathway, we used the DNA fragment 46F (see methods) to probe a Southern Blot carrying chromosomal DNA of Flavobacterium sp. R1534 digested with different restriction enzymes FIG. 2. The 2.4 kb XhoI/PstI fragment hybridizing to the probe seemed the most appropiate one to start with. Genomic Flavobacterium sp. R1534 DNA was digested with XhoI/PstI and run on a 1% agarose gel. According to a comigrating DNA marker, the region of about 2.4 kb was cut out of the gel and the DNA isolated. A XhoI/Psti mini library of Flavobacterium sp. R1534 genomic DNA was constructed into XhoI-PstI sites of pBluescriptIISK(+). One hundred *E. coli* XL1 transformants were subsequently screened by PCR with primer #7 (SEQ ID NO: 38) and primer # 8 (SEQ ID NO: 39), the same primers previously used to obtain the 119 bp fragment (46F). One positive transformant, named clone 85, was found. Sequencing of the insert revealed sequences not only homologous to the phytoene synthase (crtB) but also to the phytoene desaturase (crtI) of both *Erwinia* species *herbicola* and *uredovora*. Left and right hand genomic sequences of clone 85 were obtained by the same approach using probe A and probe B. Flavobacterium sp. R1534 genomic DNA was double digested with ClaI and Hind III and subjected to Southern analysis with probe A and probe B. With probe A a ClaI/HindIII fragment of aprox. 1.8 kb was identified (FIG. 3A), isolated and subcloned into the ClaI/HindIII sites of pBluescriptIIKS (+). Screening of the *E. coli* XL1 transformants with probe A gave 6 positive clones. The insert of one of these positives, clone 43-3, was sequenced and showed homology to the N-terminus of crtI genes and to the C-terminus of crtY genes of both Erwinia species mentioned above. With probe B an approx. 9.2 kb ClaI/HindIII fragment was detected (FIG. 3B), isolated and subcloned into pBluescriptIIKS (+).

A screening of the transformants gave one positive, clone 51. Sequencing of the 5' and 3' of the insert, revealed that only the region close to the HindIII site showed relevant homology to genes of the carotenoid biosynthesis of the *Erwinia* species mentioned above (e.g. crtB gene and crtE gene). The sequence around the ClaI site showed no homology to known genes of the carotenoid biosynthesis pathway. Based on this information and to facilitate further sequencing and construction work, the 4.2 kb BamHI/HindIII fragment of clone 51 was subcloned into the respective sites of pBluescriptIIKS(+) resulting in clone 2. Sequencing of the insert of this clone confirmed the presence of genes homologous to Erwinia sp crtB and crtE genes. These genes were located within 1.8 kb from the HindIII site. The remaining 2.4 kb of this insert had no homology to known carotenoid biosynthesis genes.

Figure 4:
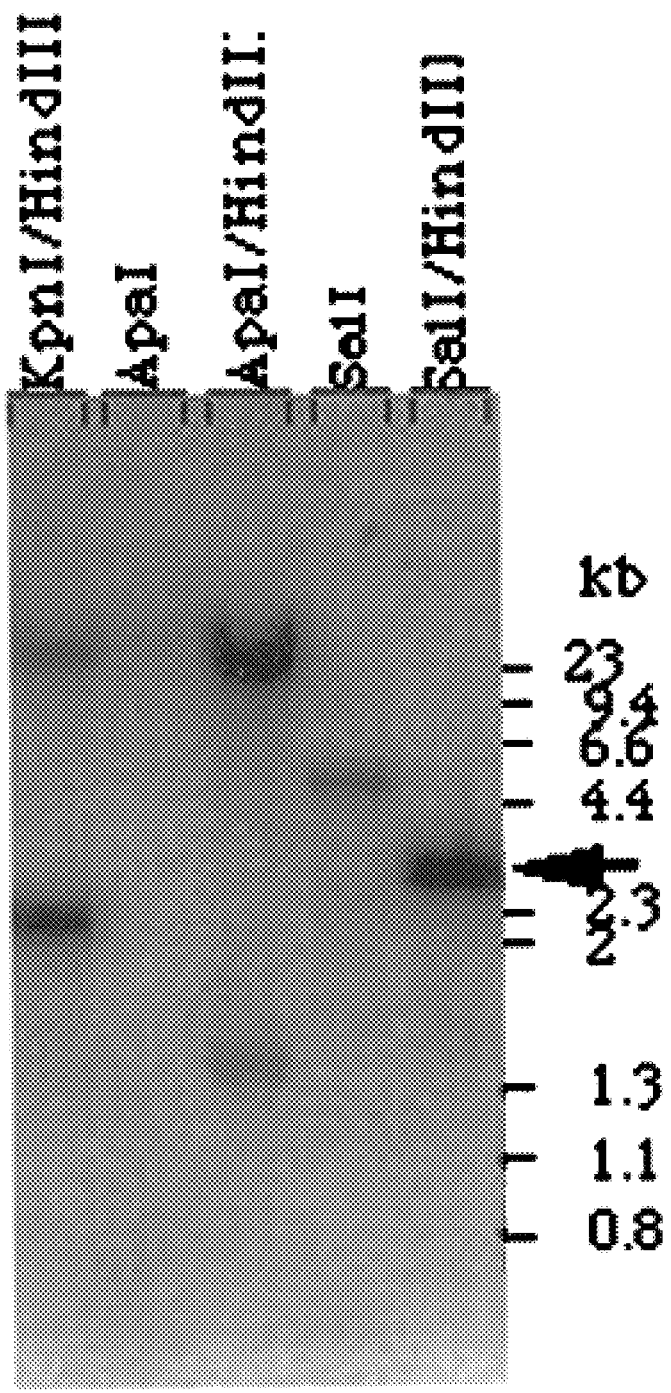
FIG. 4: Southern blot of genomic Flavobacterium sp. R1534 DNA digested with the restriction enzymes shown on top of each lane and hybridized to probe C. The isolated 2.8 kb SalI/HindIII fragment is shown by the arrow.

Additional genomic sequences downstream of the ClaI site were detected using probe C to hybridize to Flavobacterium sp. R1534 genomic DNA digested with different restriction enzymes (see FIG. 4).

Figure 5:
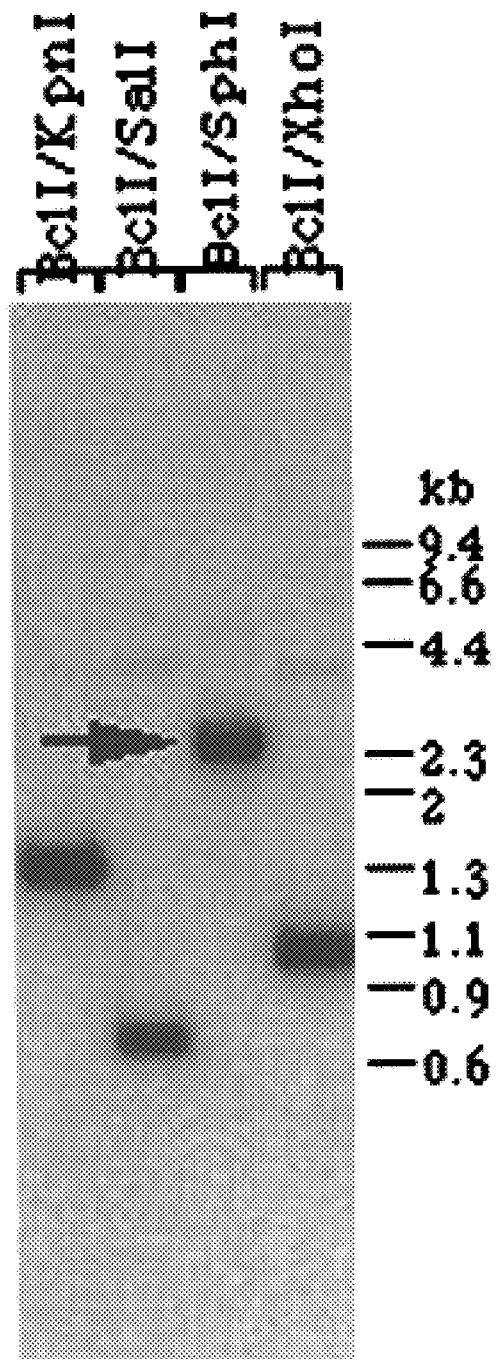
FIG. 5: Southern blot of genomic Flavobacterium sp. R1534 DNA digested with the restriction enzymes shown on top of each lane and hybridized to probe D. The isolated BclI/SphI fragment of approx. 3 kb is shown by the arrow.

A SalI/HindIII fragment of 2.8 kb identified by Southern analysis was isolated and subcloned into the HindIII/XhoI sites of pBluescriptIIKS (+). Screening of the *E. coli* XL1 transformants with probe A gave one positive clone named clone 59. The insert of this clone confirmed the sequence of clone 43-3 and contained in addition sequences homologous to the N-terminus of the crtY gene from other known lycopene cyclases. To obtain the putative missing crtZ gene a Sau3AI partial digestion library of Flavobacterium sp. R1534 was constructed into the BamHI site of pBluescriptIIKS(+). Screening of this library with probe D gave several positive clones. One transformant designated, clone 6a, had an insert of 4.9 kb. Sequencing of the insert revealed besides the already known sequences coding for crtB, crtI and crtY also the missing crtZ gene. Clone 7g was isolated from a mini library carrying BclI/SphI fragments of R1534 (FIG. 5) and screened with probe D. The insert size of clone 7 g is approx. 3 kb.

The six independent inserts of the clones described above covering approx. 14 kb of the Flavobacterium sp. R1534 genome are compiled in FIG. 6.

The determined sequence spanning from the BamHI site (position 1) to base pair 8625 is shown FIG. 7.

Putative protein coding regions of the cloned R1534 sequence.

Computer analysis using the CodonPreference program of the GCG package, which recognizes protein coding regions by virtue of the similarity of their codon usage to a given codon frequency table, revealed eight open reading frames (ORFs) encoding putative proteins: a partial ORF from 1 to 1165 (ORF-5) (SEQ ID NO: 41) coding for a polypeptide larger than 41382 Da; an ORF coding for a polypeptide with a molecular weight of 40081 Da from 1180 to 2352 (ORF-1) (SEQ ID NO: 40); an ORF coding for a polypeptide with a molecular weight of 31331 Da from 2521 to 3405 (crtE); an ORF coding for a polypeptide with a molecular weight of 32615 Da from 4316 to 3408 (crtB); an ORF coding for a polypeptide with a molecular weight of 54411 Da from 5797 to 4316 (crtI); an ORF coding for a polypeptide with a molecular weight of 42368 Da from 6942 to 5797 (crtY); an ORF coding for a polypeptide with a molecular weight of 19282 Da from 7448 to 6942 (crtZ); and an ORF coding for a polypeptide with a molecular weight of 19368 Da from 8315 to 7770 (ORF-16) (SEQ ID NO: 42); ORF-1 and crtE have the opposite transcriptional orientation from the others (FIG. 6). The translation start sites of the ORFs crtI, crtY and crtZ could clearly be determined based on the appropiately located sequences homologous to the Shine/Delgano (S/D) [Shine and Dalgarno, Proc. Natl. Acad. Sci. USA 71, 1342–1346 (1974)] consensus sequence AGG-6-9N-ATG (FIG. 10) and the homology to the N-terminal sequences of the respective enzymes of *E. herbicola* and *E. uredovora*. The translation of the ORF crtB could potentially start from three closely spaced codons ATG (4316), ATG (4241) and ATG (4211). The first one, although not having the best S/D sequence of the three, gives a translation product with the highest homology to the N-terminus of the *E. herbicola* and *E. uredovora* crtB protein, and is therefore the most likely translation start site. The translation of ORF crtE could potentially start from five different start codons found within 150 bp: ATG (2389), ATG (2446), ATG (2473), ATG (2497) and ATG (2521). We believe that based on the following observations, the ATG (2521) is the most likely transcription start site of crtE: this ATG start codon is preceeded by the best consensus S/D sequence of all five putative start sites mentioned; and the putative N-terminal amino acid sequence of the protein encoded has the highest homology to the N-terminus of the crtE enzymes of *E. herbicola* and *E. uredovora*;

Characteristics of the crt translational initiation sites and gene products.

The translational start sites of the five carotenoid biosynthesis genes are shown below and the possible ribosome binding sites are underlined. The genes crtZ, crtY, crtI and crtB are grouped so tightly that the TGA stop codon of the anterior gene overlaps the ATG of the following gene. Only three of the five genes (crtI, crtY and crtZ) fit with the consensus for optimal S/D sequences. The boxed TGA sequence shows the stop condon of the anterior gene.

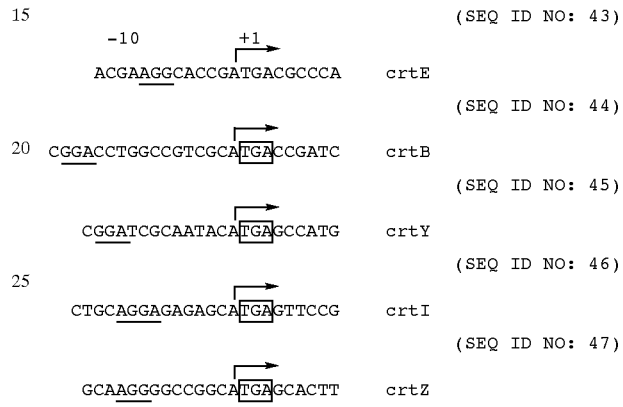

Amino acid sequences of individual crt genes of Flavobacterium sp. R1534.

All five ORFs of Flavobacterium sp. R1534 having homology to known carotenoid biosynthesis genes of other species are clustered in approx. 5.2 kb of the sequence (FIG. 7) (SEQ ID NO: 1).

GGDP synthase (crtE)

The amino acid (aa) sequence of the geranylgeranyl pyrophosphate synthase (crtE gene product) consists of 295 aa and is shown in FIG. 8 (SEQ ID NO: 2). This enzyme condenses farnesyl pyrophosphate and isopentenyl pyrophosphate in a 1'-4.

Phytoene synthase (crtB)

This enzyme catalyzes two enzymatic steps. First it condenses in a head to head reaction two geranylgeranyl pyrophosphates (C20) to the C40 carotenoid prephytoene. Second it rearanges the cyclopropylring of prephytoene to phytoene. The 303 aa encoded by the crtB gene of Flavobacterium sp. R1534 is shown in FIG. 9 (SEQ ID NO: 3).

Phytoene desaturase (crtI)

The phytoene desaturase of Flavobacterium sp. R1534 consisting of 494 aa, shown in FIG. 10 (SEQ ID NO: 4), performs like the crtI enzyme of *E. herbicola* and *E. uredovora*, four desaturation steps, converting the non-coloured carotenoid phytoene to the red coloured lycopene.

Lycopene cyclase (crtY)

The crtY gene product of Flavobacterium sp. R1534 is sufficient to introduce the b-ionone rings at both sides of lycopene to obtain β-carotene. The lycopene cyclase of Flavobacterium sp. R1534 consists of 382 aa (FIG. 11) (SEQ ID NO: 5).

β-carotene hydroxylase (crtZ)

The gene product of crtZ consisting of 169 aa (FIG. 12) (SEQ ID NO: 6) and hydroxylates β-carotene to the xanthophyll zeaxanthin.

Putative enzymatic functions of the ORF's (orf-1 (SEQ ID NO: 40), orf-5 (SEQ ID NO: 41) and orf-16 (SEQ ID NO: 42))

The orf-1 (SEQ ID NO: 40) has at the aa level over 40% identity to acetoacetyl-CoA thiolases of different organisms (e.g. Candida tropicalis, human, rat). This gene is therefore most likely a putative acetoacetyl-CoA thiolase (acetyl-CoA acetyltransferase), which condenses two molecules of acetyl-CoA to Acetoacetyl-CoA. Condensation of acetoacetyl-CoA with a third acetyl-CoA by the HMG-CoA synthase forms β-hydroxy-β-methylglutaryl-CoA (HMG-CoA). This compound is part of the mevalonate pathway which produces besides sterols also numerous kinds of isoprenoids with diverse cellular functions. In bacteria and plants, the isoprenoid pathway is also able to synthesize some unique products like carotenoids, growth regulators (e.g. in plants gibberellins and abcissic acid) and sencodary metabolites like phytoalexins [Riou et al., Gene 148, 293–297 (1994)].

The orf-5 (SEQ ID NO: 41) has a low homology of approx. 30%, to the amino acid sequence of polyketide synthases from different streptomyces (e.g. S. violaceoruber, S. cinnamonensis). These antibiotic synthesizing enzymes (polyketide synthases), have been classified into two groups. Type-I polyketide synthases are large multifunctional proteins, whereas type-II polyketide synthases are multiprotein complexes composed of several individual proteins involved in the subreactions of the polyketide synthesis [Bibb, et al. Gene 142 31–39 (1994)].

The putative protein encoded by the orf-16 (SEQ ID NO: 42) has at the aa level an identity of 42% when compared to the soluble hydrogenase subunit of Anabaena cylindrica.

Functional assignment of the ORF's (crtE, crtB, crtI, crtY and crtZ) to enzymatic activities of the carotenoid biosynthesis pathway.

Figure 13:
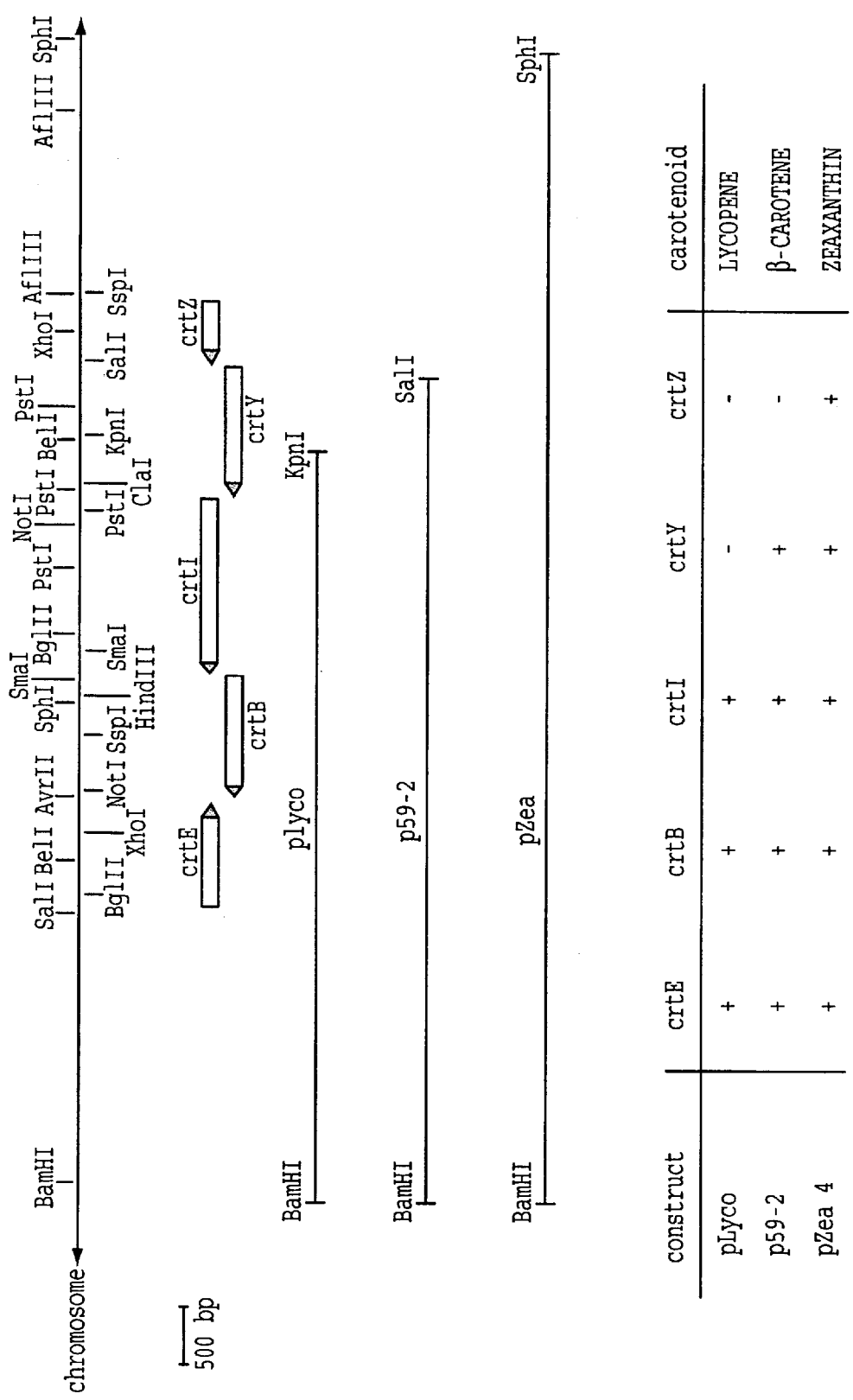
FIG. 13: Recombinant plasmids containing deletions of the Flavobacterium sp. R1534 carotenoid biosynthesis gene cluster.

The biochemical assignment of the gene products of the different ORF's were revealed by analyzing carotenoid accumulation in *E. coli* host strains that were transformed with deleted variants of the Flavobacterium sp. gene cluster and thus expressed not all of the crt genes (FIG. 13).

Three different plasmid were constructed: pLyco, p59-2 and pZea4. Plasmid $p^{59}$-2 was obtained by subcloning the HindIII/BamHI fragment of clone 2 into the HindIII/BamHI sites of clone 59. p59-2 carries the ORF's of the crtE, crtB, crtI and crtY gene and should lead to the production of β-carotene. pLyco was obtained by deleting the KpnI/KpnI fragment, coding for approx. one half (N-terminus) of the crtY gene, from the p59-2 plasmid. *E. coli* cells transformed with pLyco, and therefore having a truncated non-functional crtY gene, should produce lycopene, the precursor of β-carotene. pZea4 was constructed by ligation of the AscI-SpeI fragment of p59-2, containing the crtE, crtB, crtI and most of the crtY gene with the AscI/XbaI fragment of clone 6a, containing the sequences to complete the crtY gene and the crtZ gene. pZea4 [for complete sequence see FIG. 24 (SEQ ID NO: 27); nucleotides 1 to 683 result from pBluescriptIIKS(+), nucleotides 684 to 8961 from Flavobacterium R1534 WT genome, nucleotides 8962 to 11233 from pBluescriptIIKS(+)] has therefore all five ORF's of the zeaxanthin biosynthesis pathway. Plasmid pZea4 has been deposited on May 25, 1995 at the DSM-Deutsche Sammlung von Mikroorganismen und Zellkulturen GmbH (Germany) under accession No. DSM 10012. *E. coli* cells transformed with this latter plasmid should therefore produce zeaxanthin. For the detection of the carotenoid produced, transformants were grown for 48 hours in shake flasks and then subjected to carotenoid analysis as described in the methods section. FIG. 13 summarizes the different inserts of the plasmids described above, and the main carotenoid detected in the cells.

As expected the pLyco carrying *E. coli* cells produced lycopene, those carrying p59-2 produced β-carotene (all-E, 9-Z,13-Z) and the cells having the pZea4 construct produced zeaxanthin. This confirms that all the necessary genes of Flavobacterium sp. R1534 for the synthesis of zeaxanthin or their precursors (phytoene, lycopene and β-carotene) were cloned.

EXAMPLE 3
Materials and Methods Used for Expression of Carotenoid Synthesizing Enzymes Bacterial strains and plasmids: The vectors pBluescriptIIKS (+) or (−) (Stratagene, La Jolla, USA) and pUC18 [Vieira and Messing, Gene ,19 259–268 (1982); Norrander et al., Gene 26, 101–106 (1983)] were used for cloning in different *E. coli* strains, like XL-1 blue (Stratagene), TG1 or JM109. In all *B. subtilis* transformations, strain 1012 was used. Plasmids pHP13 [Haima et al., Mol. Gen. Genet. 209, 335–342 (1987)] and p602/22 [LeGrice, S. F. J. in Gene Expression Technology, Goeddel, D. V., Editor, 201–214. (1990)] are Gram (+)/(−) shuttle vectors able to replicate in *B. subtilis* and *E. coli* cells. Plasmid p205 contains the vegI promoter cloned into the SmaI site of pUC18. Plasmid pXI12 is an integration vector for the constitutive expression of genes in *B. subtilis* [Haiker et al., in 7th Int. Symposium on the Genetics of Industrial Microorganisms, Jun. 26–Jul. 1, 1994. Montreal, Quebec, Canada (1994)]. Plasmid pBEST501 [Itaya et al., Nucleic Acids Res. 17 (11), 4410 (1989)] contains the neomycin resistance gene cassette originating from the plasmid pUB110 (GenBank entry: M19465) of *S. aureus* [McKenzie et al., Plasmid 15, 93–103 (1986); McKenzie et al., Plasmid 17, 83–84 (1987)]. This neomycin gene has been shown to work as a selection marker when present in a single copy in the genome of *B. subtilis*. Plasmid pC194 (ATCC 37034)(GenBank entry: L08860) originates from *S. aureus* [Horinouchi and Weisblaum, J. Bacteriol. 150, 815–825 (1982)] and contains the chloramphenicol acetyltransferase gene.

Media and growth conditions: *E. coli* were grown in Luria broth (LB) at 37° C. with 100 mg Ampicillin (Amp)/ml for selection. *B. subtilis* cells were grown in VY-medium supplemented with either erythromycin (1 mg/ml), neomycin (5–180 mg/ml) or chloramphenicol (10–80 mg/ml).

Transformation: *E. coli* transformations were done by electroporation using the Gene-pulser device of BIO-RAD (Hercules, Calif., USA) with the following parameters (200 W, 250 mFD, 2.5V). *B.subtilis* transformations were done basically according to the standard procedure method 2.8 described by [Cutting and Vander Horn in Molecular Biological Methods for Bacillus, Harwood, C. R. and Cutting, S. M., Editor, John Wiley & Sons: Chichester, England. 61–74 (1990)].

Colony screening: Bacterial colony screening was done as described by [Zon et al., s.a.].

Oligonucleotide synthesis: The oligonucleotides used for PCR reactions or for sequencing were synthesized with an Applied Biosystems 392 DNA synthesizer.

PCR reactions: The PCR reactions were performed using either the UlTma DNA polymerase (Perkin Elmer Cetus) or the Pfu Vent polymerase (New England Biolabs) according to the manufacturers instructions. A typical 50 ml PCR reaction contained: 100 ng of template DNA, 10 pM of each of the primers, all four dNTP's (final conc. 300 mM), $MgCl_2$ (when UlTma polymerase was used; final conc. 2 mM), 1×UlTma reaction buffer or 1×Pfu buffer (supplied by the manufacturer). All components of the reaction with the exception of the DNA polymerase were incubated at 95° C. for 2 min. followed by the cycles indicated in the respective section (see below). In all reactions a hot start was made, by adding the polymerase in the first round of the cycle during the 72° C. elongation step. At the end of the PCR reaction an aliquot was analysed on 1% agarose gel, before extracting once with phenol/chloroform. The amplified fragment in the aqueous phase was precipitated with 1/10 of a 3M NaAcetate solution and two volumes of Ethanol. After centrifugation for 5 min. at 12000 rpm, the pellet was resuspended in an adequate volume of $H_2O$, typically 40 ml, before digestion with the indicated restriction enzymes was performed. After the digestion the mixture was separated on a 1% low melting point agarose. The PCR product of the expected size were excised from the agarose and purified using the glass beads method (GENECLEAN KIT, Bio 101, Vista Calif., USA) when the fragments were above 400 bp or directly spun out of the gel when the fragments were shorter than 400 bp, as described by [Heery et al., TIBS 6 (6), 173 (1990)].

Oligos used for gene amplification and site directed mutagenesis:

All PCR reactions performed to allow the construction of the different plasmids are described below. All the primers used are summarized in FIG. 14.

Primers #100 (SEQ ID NO: 7) and #101 (SEQ ID NO: 8) were used in a PCR reaction to amplify the complete crtE gene having a SpeI restriction site and an artificial ribosomal binding site (RBS) upstream of the transcription start site of this gene. At the 3' end of the amplified fragment, two unique restriction sites were introduced, an AvrII and a SmaI site, to facilitate the further cloning steps. The PCR reaction was done with UlTma polymerase using the following conditions for the amplification: 5 cycles with the profile: 95° C., 1 min./60° C., 45 sec./72° C., 1 min. and 20 cycles with the profile: 95° C., 1 min./72° C., 1 min. Plasmid pBIIKS(+)-clone2 served as template DNA. The final PCR product was digested with SpeI and SmaI and isolated using the GENECLEAN KIT. The size of the fragment was approx. 910 bp.

Primers #104 (SEQ ID NO: 9) and #105 (SEQ ID NO: 10) were used in a PCR reaction to amplify the crtZ gene from the translation start till the SalI restriction site, located in the coding sequence of this gene. At the 5' end of the crtZ gene an EcoRI, a synthetic RBS and a NdeI site was introduced. The PCR conditions were as described above. Plasmid pBIIKS(+)-clone 6a served as template DNA and the final PCR product was digested with EcoRI and SalI. Isolation of the fragment of approx. 480 bp was done with the GENECLEAN KIT.

Primers MUT1 (SEQ ID NO: 11) and MUT5 (SEQ ID NO: 14) were used to amplify the complete crtY gene. At the 5' end, the last 23 nucleotides of the crtZ gene including the SalI site are present, followed by an artificial RBS preceding the translation start site of the crtY gene. The artificial RBS created includes a PmlI restriction site. The 3' end of the amplified fragment contains 22 nucleotides of the crtI gene, preceded by a newly created artifial RBS which contains a MunI restriction site. The conditions used for the PCR reaction were as described above using the following cycling profile: 5 rounds of 95° C., 45 sec./60° C., 45 sec./72° C., 75 sec followed by 22 cycles with the profile: 95° C., 45 sec./66° C., 45 sec./72° C., 75 sec. Plasmid pXI12-ZYIB-EINV4 served as template for the Pfu Vent polymerase. The PCR product of 1225 bp was made blunt and cloned into the SmaI site of pUC18, using the Sure-Clone Kit (Pharmacia) according to the manufacturer.

Primers MUT2 (SEQ ID NO: 15) and MUT6 (SEQ ID NO: 15) were used to amplify the complete crtI gene. At the 5' the last 23 nucleotides of the crtY gene are present, followed by an artificial RBS which precedes the translation start site of the crtI gene. The new RBS created, includes a MunI restriction site. The 3' end of the amplified fragment contains the artificial RBS upstream of the crtB gene including a BamHI restriction site. The conditions used for the PCR reaction were basically as described above including the following cycling profile: 5 rounds of 95° C., 30 sec./60° C., 30 sec./72° C., 75 sec., followed by 25 cycles with the profile: 95° C., 30 sec/66° C., 30 sec./72° C., 75 sec. Plasmid pXI12-ZYIB-EINV4 served as template for the Pfu Vent polymerase. For the further cloning steps the PCR product of 1541 bp was digested with MunI and BamHI.

Primers MUT3 (SEQ ID NO: 13) and CAR17 (SEQ ID NO: 16) were used to amplify the N-terminus of the crtB gene. At the 5' the last 28 nucleotides of the crtI gene are present followed by an artificial RBS, preceding the translation start site of the crtB gene. This new created RBS, includes a BamHI restriction site. The amplified fragment, named PCR-F contains also the HindIII restriction site located at the N-terminus of the crtB gene. The conditions used for the PCR reaction were as described elsewhere in the text, including the following cycling profile: 5 rounds of 95° C., 30 sec./58° C., 30 sec./72° C., 20 sec. followed by 25 cycles with the profile: 95° C., 30 sec./60° C., 30 sec./72° C., 20 sec. Plasmid pXI12-ZYIB-EINV4 served as template for the Pfu Vent polymerase. The PCR product of approx. 160 bp was digested with BamHI and HindIII.

Oligos used to amplify the chloramphenicol resistance gene (cat):

Primers CAT3 (SEQ ID NO: 17) and CAT4 (SEQ ID NO: 18) were used to amplify the chloramphenicol resistance gene of pC194 (ATCC 37034) [Horinouchi and Weisblum, s.a.] a R-plasmid found in *S. aureus*. The conditions used for the PCR reaction were as described previously including the following cycling profile: 5 rounds of 95° C., 60 sec./50° C., 60 sec./72° C., 2 min. followed by 20 cycles with the profile: 95° C., 60 sec./60° C., 60 sec./72° C., 2 min. Plasmid pC198 served as template for the Pfu Vent polymerase. The PCR product of approx. 1050 bp was digested with EcoRI and AatII.

Oligos used to generate linkers: Linkers were obtained by adding 90 ng of each of the two corresponding primers into an Eppendorf tube. The mixture was dried in a speed vac and the pellet resuspended in 1×Ligation buffer (Boehringer, Mannheim, Germany). The solution was incubated at 50° C. for 3 min. before cooling down to RT, to allow the primers to hybridize properly. The linker were now ready to be ligated into the appropriate sites. All the oligos used to generate linkers are shown in FIG. 15.

Primers CS1 (SEQ ID NO: 19) and CS2 (SEQ ID NO: 20) were used to form a linker containing the following restrictions sites HindIII, AflII, ScaI, XbaI, PmeI and EcoRI.

Primers MUT7 (SEQ ID NO: 21) and MUT8 (SEQ ID NO: 22) were used to form a linker containing the restriction sites SalI, AvrII, PmlI, MluI, MunI, BamHI, SphI and HindIII.

Primers MUT9 (SEQ ID NO: 23) and MUT10 (SEQ ID NO: 24) were used to introduce an artificial RBS upstream of crtY.

Primers MUT11 (SEQ ID NO: 25) and MUT12 (SEQ ID NO: 26) were used to introduce an artificial RBS upstream of crtE.

Isolation of RNA: Total RNA was prepared from log phase growing *B. subtilis* according to the method described by [Maes and Messens, Nucleic Acids Res. 20 (16), 4374 (1992)].

Northern Blot analysis: For hybridization experiments up to 30 mg of *B. subtilis* RNA was electrophoreses on a 1% agarose gel made up in 1×MOPS and 0.66 M formaldehyde. Transfer to Zeta-Probe blotting membranes (BIO-RAD), UV cross-linking, pre-hybridization and hybridization was done as described elsewhere in [Farrell, J. R. E., RNA Methodologies. A laboratory Guide for isolation and characterization. San Diego, USA: Academic Press (1993)]. The washing conditions used were: 2×20 min. in 2×SSPE/0.1% SDS followed by 1×20 min. in 0.1% SSPE/0.1% SDS at 65° C. Northern blots were then analyzed either by a Phosphorimager (Molecular Dynamics) or by autoradiography on X-ray films from Kodak.

Isolation of genomic DNA: *B. subtilis* genomic DNA was isolated from 25 ml overnight cultures according to the standard procedure method 2.6 described by [13].

Southern blot analysis: For hybridization experiments *B. subtilis* genomic DNA (3 mg) was digested with the appropriate restriction enzymes and electrophoresed on a 0.75% agarose gel. The transfer to Zeta-Probe blotting membranes (BIO-RAD), was done as described [Southern, E. M., s.a.]. Prehybridization and hybridization was in 7% SDS, 1% BSA (fraction V; Boehringer), 0.5M $Na_2HPO_4$, pH 7.2 at 65° C. After hybridization the membranes were washed twice for 5 min. in 2×SSC, 1% SDS at room temperature and twice for 15 min. in 0.1% SSC, 0.1% SDS at 65° C. Southern blots were then analyzed either by a Phosphorimager (Molecular Dynamics) or by autoradiography on X-ray films from Kodak.

DNA sequence analysis: The sequence was determined by the dideoxy chain termination technique [Sanger et al., s.a.] using the Sequenase Kit Version 1.0 (United States Biochemical). Sequence analysis were done using the GCG sequence analysis software package (Version 8.0) by Genetics Computer, Inc. [Devereux et al., s.a.].

Gene amplification in *B. subtilis*: To amplify the copy number of the SFCO in *B. subtilis* transformants, a single colony was inoculated in 15 ml VY-medium supplemented with 1.5 % glucose and 0.02 mg chloramphenicol or neomycin/ml, dependend on the antibiotic resistance gene present in the amplifiable structure (see results and discussion). The next day 750 ml of this culture were used to inoculate 13 ml VY-medium containing 1.5% glucose supplemented with (60, 80, 120 and 150 mg/ml) for the cat resistant mutants, or 160 mg/ml and 180 mg/ml for the neomycin resistant mutants). The cultures were grown overnight and the next day 50 ml of different dilutions (1:20, 1:400, 1:8000, 1:160,000) were plated on VY agar plates with the appropriate antibiotic concentration. Large single colonies were then further analyzed to determine the number of copies and the amount of carotenoids produced.

Analysis of carotenoids: *E. coli* or *B. subtilis* transformants (200–400 ml) were grown for the times indicated in the text, usually 24 to 72 hours, in LB-medium or VY-medium, respectively, supplemented with antibiotics, in shake flasks at 37° C. and 220 rpm.

The carotenoids produced by the microorganisms were extracted with an adequate volume of acetone using a rotation homogenizer (Polytron, Kinematica AG, CH-Luzern). The homogenate was the filtered through the sintered glass of a suction filter into a round bottom flask. The filtrate was evaporated by means of a rotation evaporator at 50° C. using a water-jet vacuum. For the zeaxanthin detection the residue was dissolved in n-hexane/acetone (86:14) before analysis with a normalphase HPLC as described in [Weber, S., s.a.]. For the detection of β-carotene and lycopene the evaporated extract was dissolved in n-hexane/acetone (99:1) and analysed by HPLC as described in Hengartner et al., s.a.].

EXAMPLE 4

Carotenoid Production in *E. coli*

The biochemical assignment of the gene products of the different open reading frames (ORF's) of the carotenoid biosynthesis cluster of Flavobacterium sp. were revealed by analyzing the carotenoid accumulation in *E. coli* host strains, transformed with plasmids carrying deletions of the Flavobacterium sp. gene cluster, and thus lacking some of the crt gene products. Similar functional assays in *E. coli* have been described by other authors [Misawa et al., s.a.; Perry et al., J. Bacteriol., 168, 607–612 (1986); Hundle, et al., Molecular and General Genetics 254 (4), 406–416 (1994)]. Three different plasmid pLyco, pBIIKS(+)-clone59-2 and pZea4 were constructed from the three genomic isolates pBIIKS(+)-clone2, pBIIKS(+)-clone59 and pBIIKS(+)-clone6a (see FIG. 16).

Figure 16A:
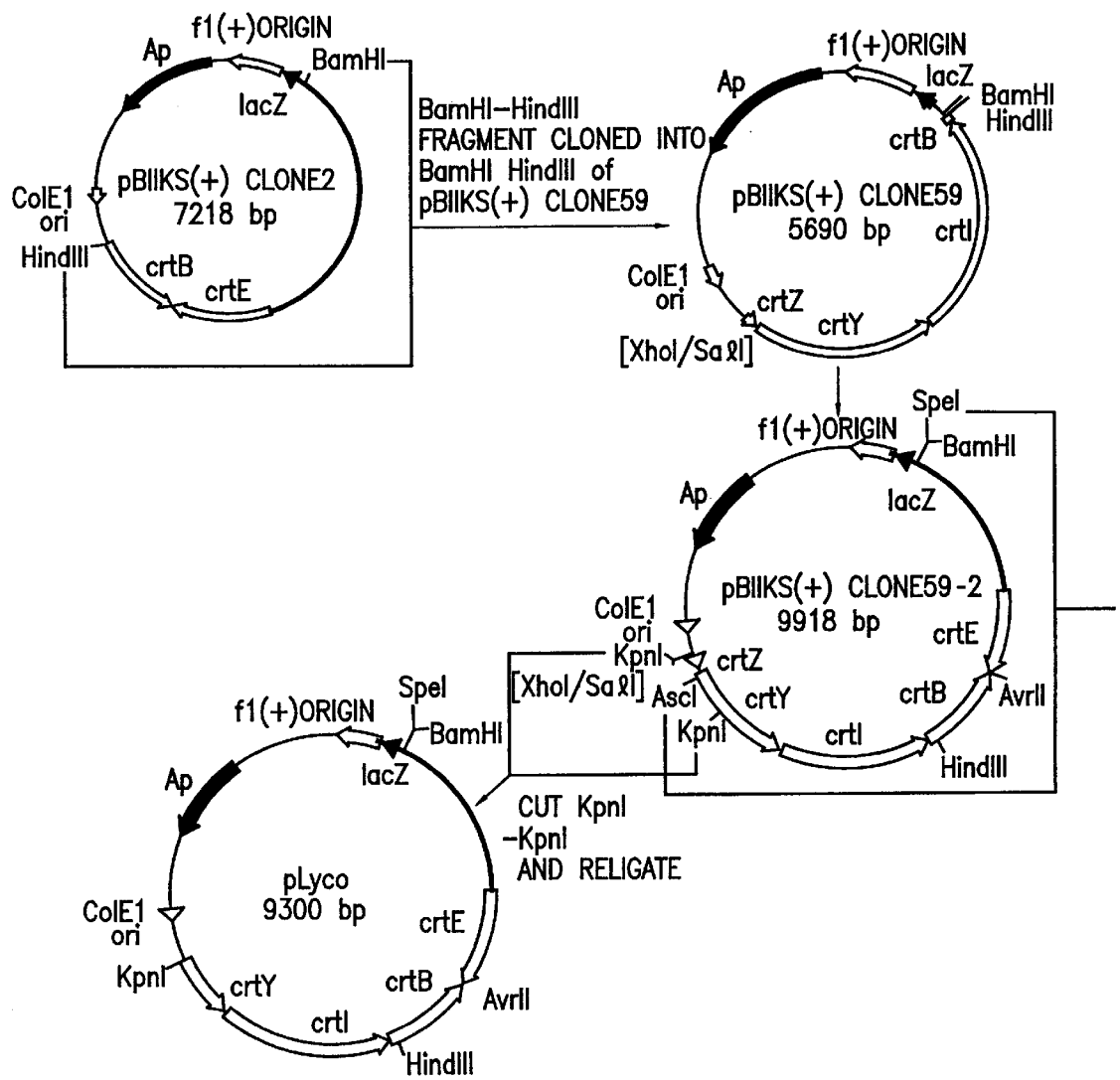
FIGS. 16A, 16B Construction of plasmids pBIIKS(+)-clone59-2, pLyco and pZea4.
Figure 16B:
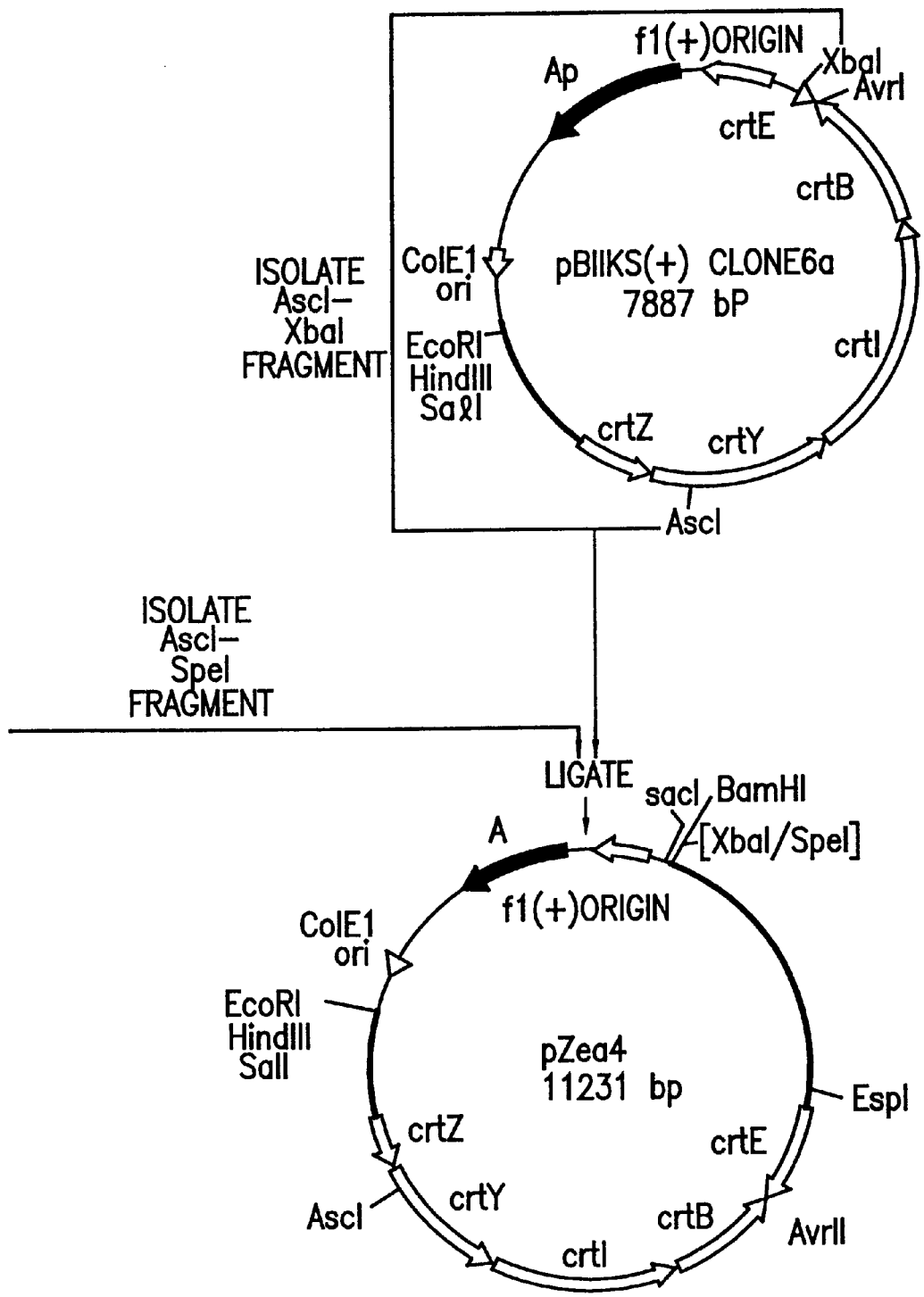

Plasmid pBIIKS(+)-clone59-2 was obtained by subcloning the HindIII/BamHI fragment of pBIIKS(+)-clone 2 into the HindIII/BamHI sites of pBIIKS(+)-clone59. The resulting plasmid pBIIKS(+)-clone59-2 carries the complete ORF's of the crtE, crtB, crtI and crtY gene and should lead to the production of β-carotene. pLyco was obtained by deleting the KpnI/KpnI fragment, coding for approx. one half (N-terminus) of the crtY gene, from the plasmid pBIIKS (+)-clone59-2. *E. coli* cells transformed with pLyco, and therefore having a truncated non-functional crtY gene, should produce lycopene, the precursor of β-carotene. pZea4 was constructed by ligation of the AscI-SpeI fragment of pBIIKS(+)-clone59-2, containing the crtE, crtB, crtI and most of the crtY gene with the AscI/XbaI fragment of clone 6a, containing the crtZ gene and sequences to complete the truncated crtY gene mentioned above. pZea4 has therefore all five ORF's of the zeaxanthin biosynthesis pathway. *E. coli* cells transformed with this latter plasmid should therefore produce zeaxanthin. For the detection of the carotenoid produced, transformants were grown for 43 hours in shake flasks and then subjected to carotenoid analysis as described in the methods section. FIG. 16 summarizes the construction of the plasmids described above.

As expected the pLyco carrying *E. coli* cells produced lycopene, those carrying pBIIKS(+)-clone59-2 produced β-carotene (all-E,9-Z,13-Z) and the cells having the pZea4 construct produced zeaxanthin. This confirms that we have cloned all the necessary genes of Flavobacterium sp. R1534 for the synthesis of zeaxanthin or their precursors (phytoene, lycopene and β-carotene). The production levels obtained are shown in table 1.

TABLE 1

Carotenoid content of *E. coli* transformants, carrying the plasmids pLyco, pBIIKS(+)-clone59-2 and pZea4, after 43 hours of culture in shake flasks. The values indicated show the carotenoid content in % of the total dry cell mass (200 ml).

| plasmid | host | zeaxanthin | β-χαροτενε | lycopene |
|---|---|---|---|---|
| pLyco | *E. coli* JM109 | ND | ND | 0.05% |
| pBIIKS(+)-clone59-2 | " | ND | 0.03% | ND |
| pZea4 | " | 0.033% | 0.0009% | ND |

ND = not detectable.

EXAMPLES 5
Carotenoid Production in B. subtilis

Figure 17:
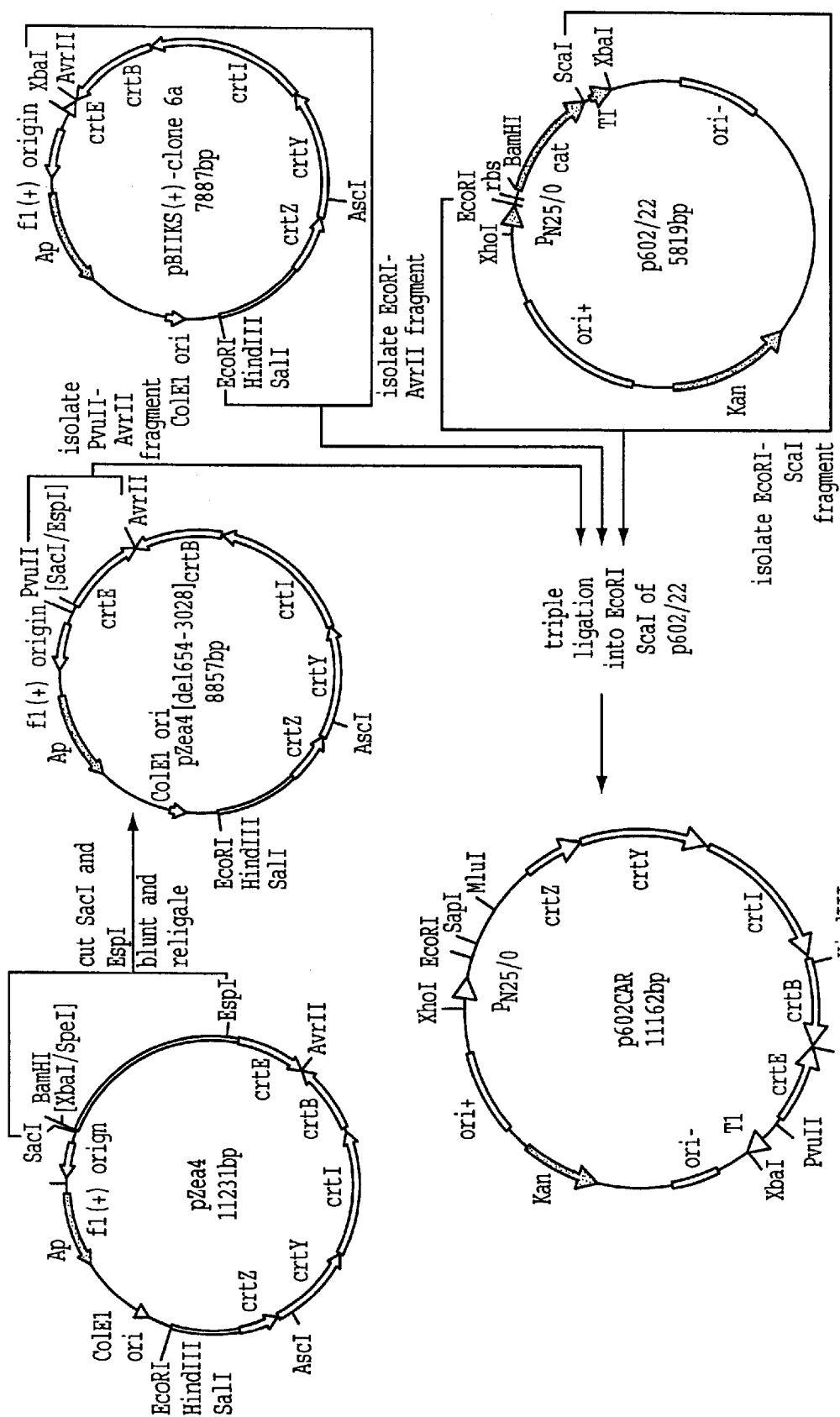
FIG. 17: Construction of plasmid p602CAR.
Figure 18A:
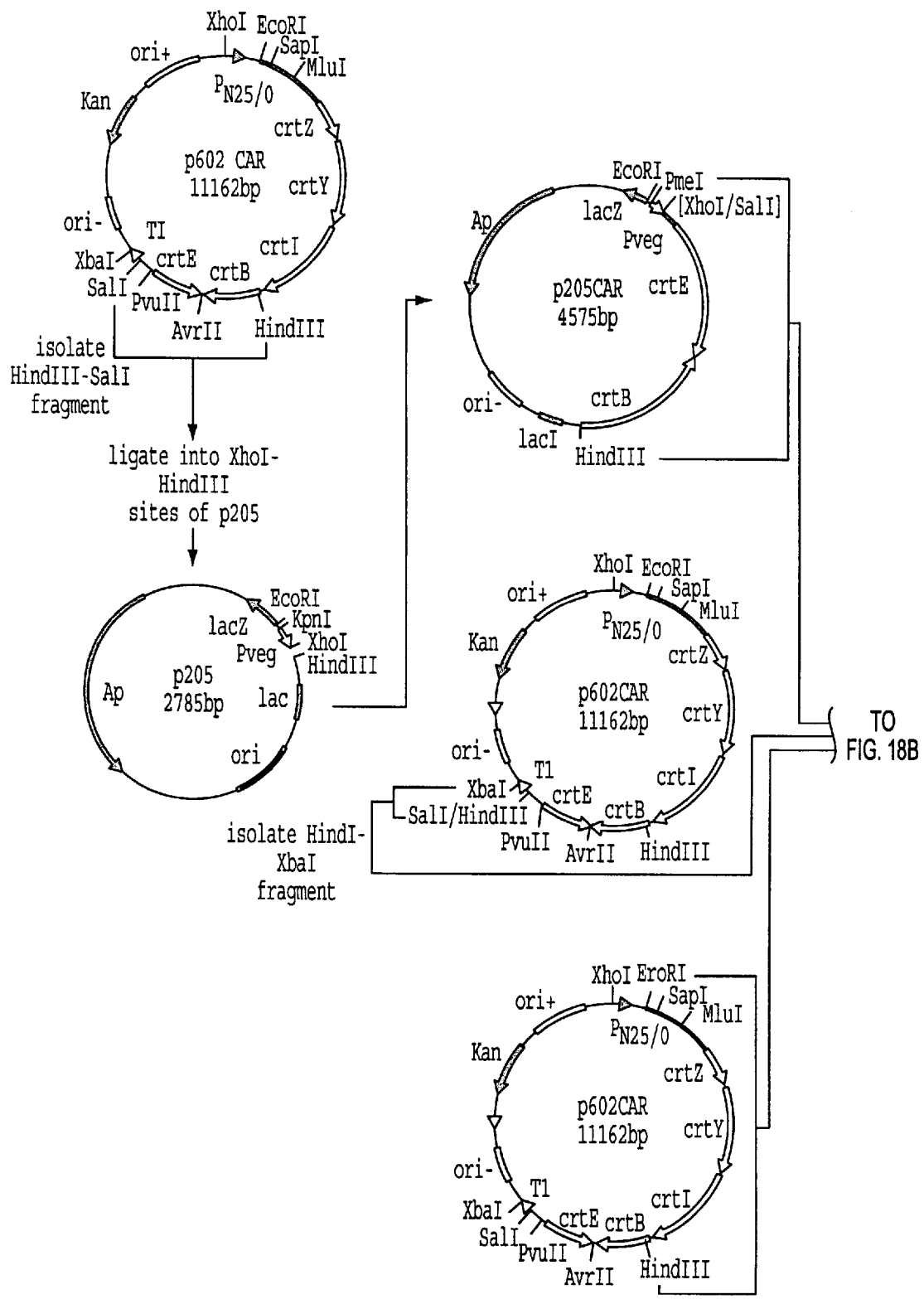
FIGS. 18A, 18B Construction of plasmid pBIIKS(+)-CARVEG-E and p602 CARVEG-E.
Figure 18B:
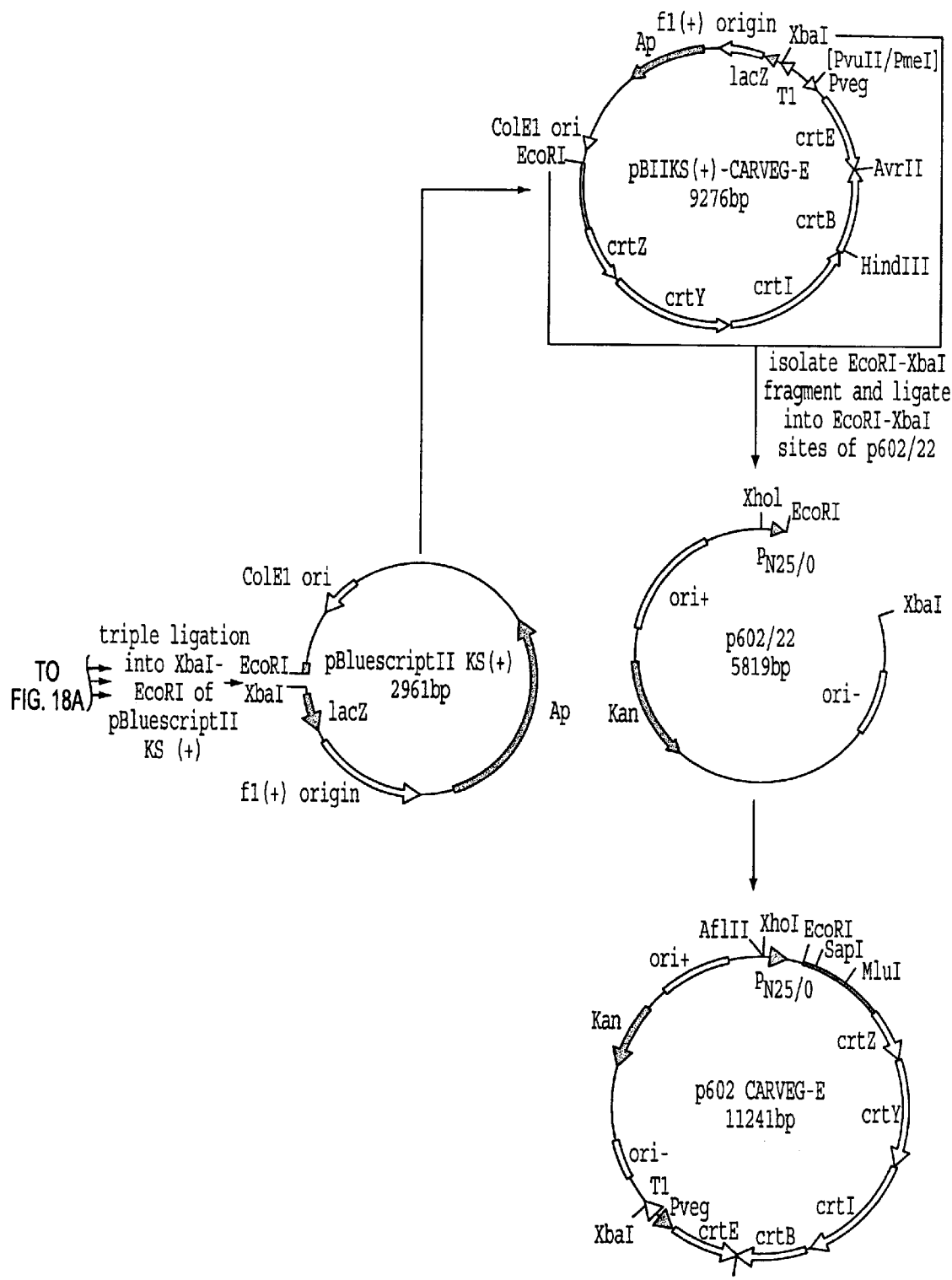

In a first approach to produce carotenoids in B. subtilis, we cloned the carotenoid biosynthesis genes of Flavobacterium into the Gram (+)/(−) shuttle vectors p602/22, a derivative of p602/20 [LeGrice, S. F. J., s.a.]. The assembling of the final construct p602-CARVEG-E, begins with a triple ligation of fragments PvuII-AvrII of pZea4(del654-3028) and the AvrII-EcoRI fragment from plasmid pBIIKS (+)-clone6a, into the EcoRI and ScaI sites of the vector p602/22. The plasmid pZea4(del654-3028) had been obtained by digesting pZea4 with SacI and EspI. The protruding and recessed ends were made blunt with Klenow enzyme and religated. Construct pZea4(del654-3028) lacks most of the sequence upstream of crtE gene, which are not needed for the carotenoid biosynthesis. The plasmid p602CAR has approx. 6.7 kb of genomic Flavobacterium R1534 DNA containing besides all five carotenoid genes (approx. 4.9 kb), additional genomic DNA of 1.2 kb, located upstream of the crtZ translation start site and further 200 bp, located upstream of crtE transcription start. The crtZ, crtY, crtI and crtB genes were cloned downstream of the $P_{N25/O}$ promoter, a regulatable E. coli bacteriophage T5 promoter derivative, fused to a lac operator element, which is functional in B. subtilis [LeGrice, S. F. J., s.a.]. It is obvious that in the p602CAR construct, the distance of over 1200 bp between the $P_{N25/O}$ promoter and the transcription start site of crtZ is not optimal and will be improved at a later stage. An outline of the p602CAR construction is shown in FIG. 17. To ensure transcription of the crtE gene in B. subtilis, the vegI promoter [Moran et al., Mol. Gen. Genet. 186 339–346 (1982); LeGrice et al., Mol. Gen. Genet. 204 229–236 (1986)] was introduced upstream of this gene, resulting in the plasmid construct p602-CARVEG-E. The vegI promoter, which originates from siteI of the veg promoter complex described by [LeGrice et al., s.a.] has been shown to be functional in E. coli [Moran et al., s.a.]. To obtain this new construct, the plasmid p602CAR was digested with SalI and HindIII, and the fragment containing the complete crtE gene and most of the crtB coding sequence, was subcloned into the XhoI and HindIII sites of plasmid p205. The resulting plasmid p205CAR contains the crtE gene just downstream of the PvegI promoter. To reconstitute the carotenoid gene cluster of Flavobacterium sp. The following three pieces were isolated: PmeI/HindIII fragment of p205CAR, the HincII/XbaI fragment and the EcoRI/HindIII fragment of p602CAR and ligated into the EcoRI and XbaI sites of pBluescriptIIKS(+), resulting in the construct pBIIKS(+)-CARVEG-E. Isolation of the EcoRI-XbaI fragment of this latter plasmid and ligation into the EcoRI and XbaI sites of p602/22 gives a plasmid similar to p602CAR but having the crtE gene driven by the PvegI promoter. All the construction steps to get the plasmid p602CARVEG-E are outlined in FIG. 18. E. coli TG1 cells transformed with this plasmid synthesized zeaxanthin. In contrast B. subtilis strain 1012 transformed with the same constructs did not produce any carotenoids. Analysis of several zeaxanthin negative B. subtilis transformants always revealed, that the transformed plasmids had undergone severe deletions. This instability could be due to the large size of the constructs.

Figure 19A:
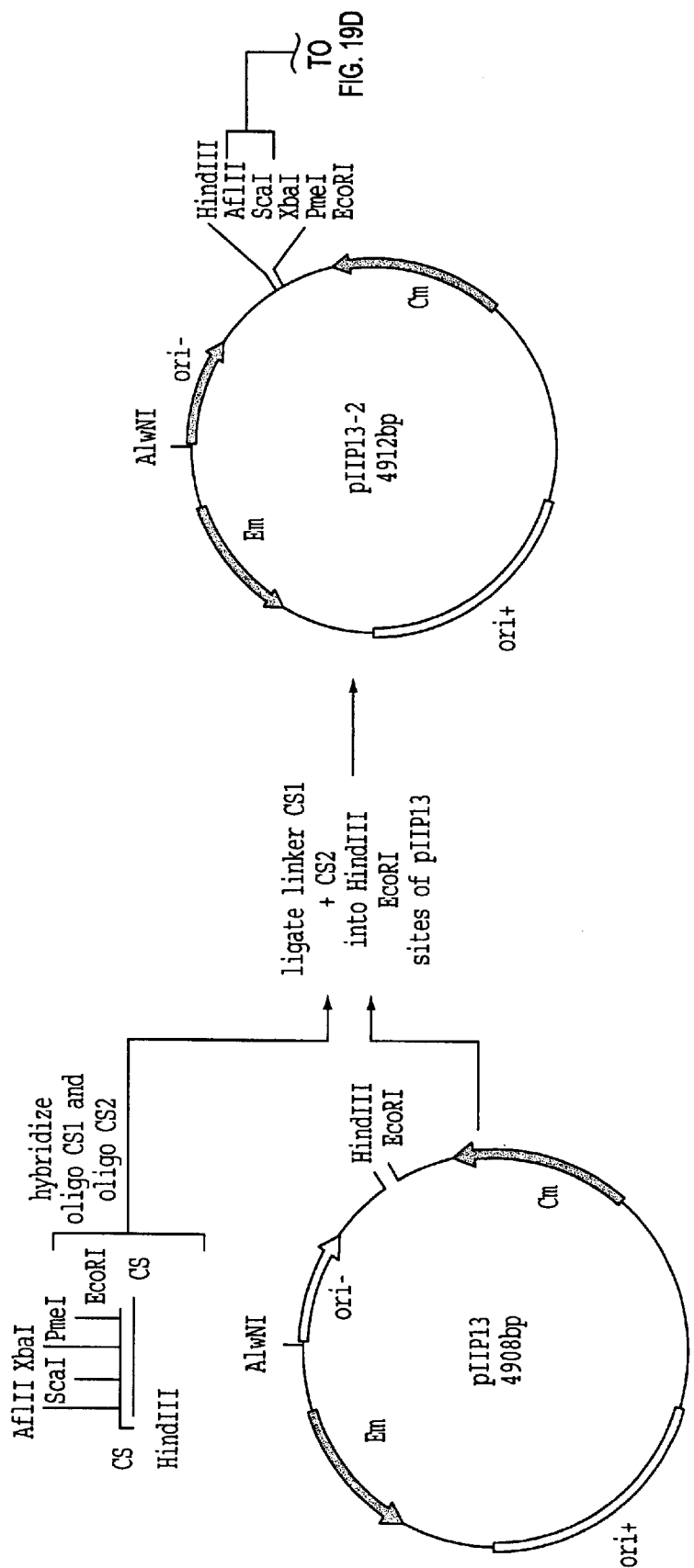
Figure 19B:
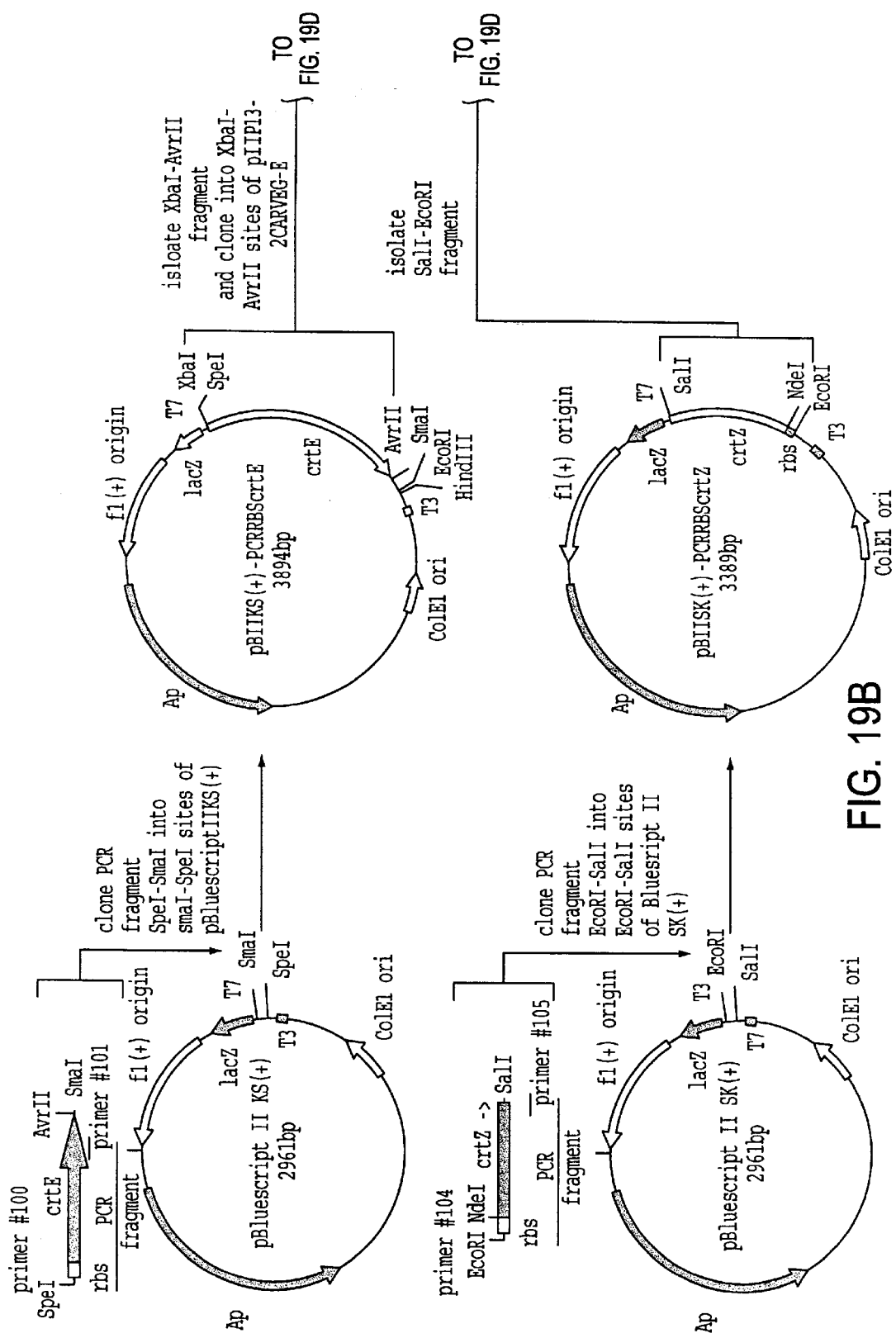
Figures 1, 20A:
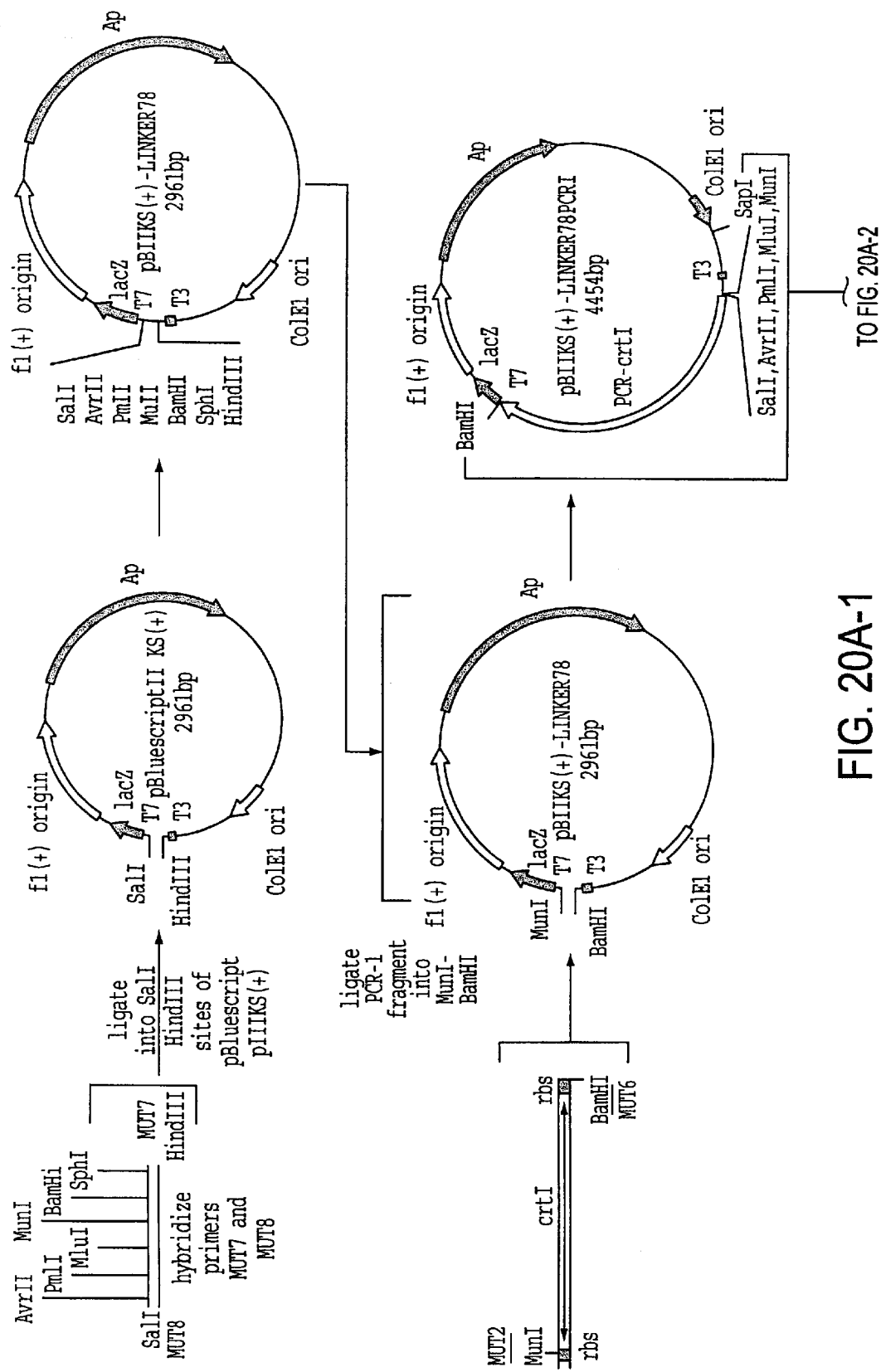
Figures 2, 20A:
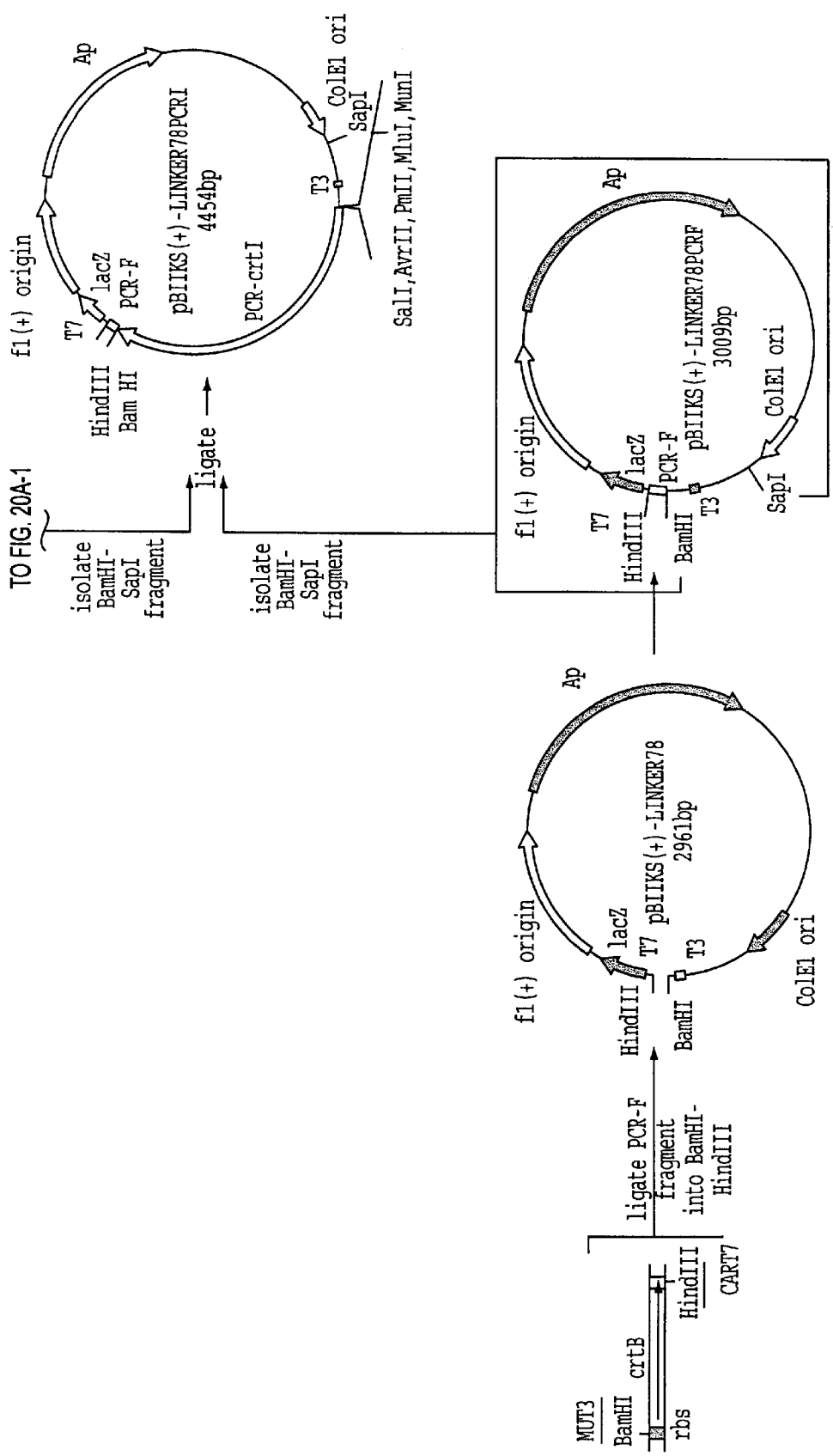
Figure 20B:
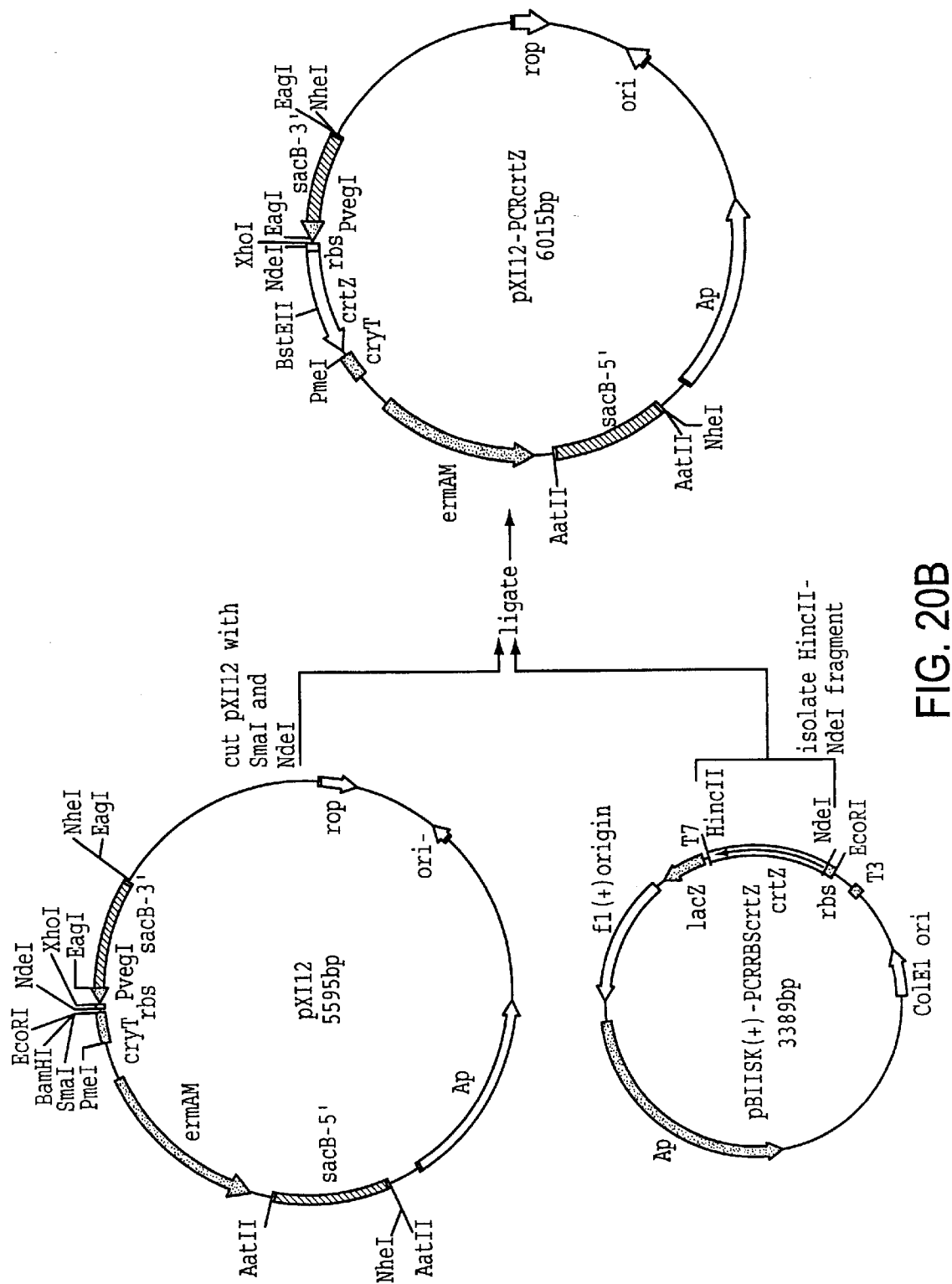
Figures 1, 20C:
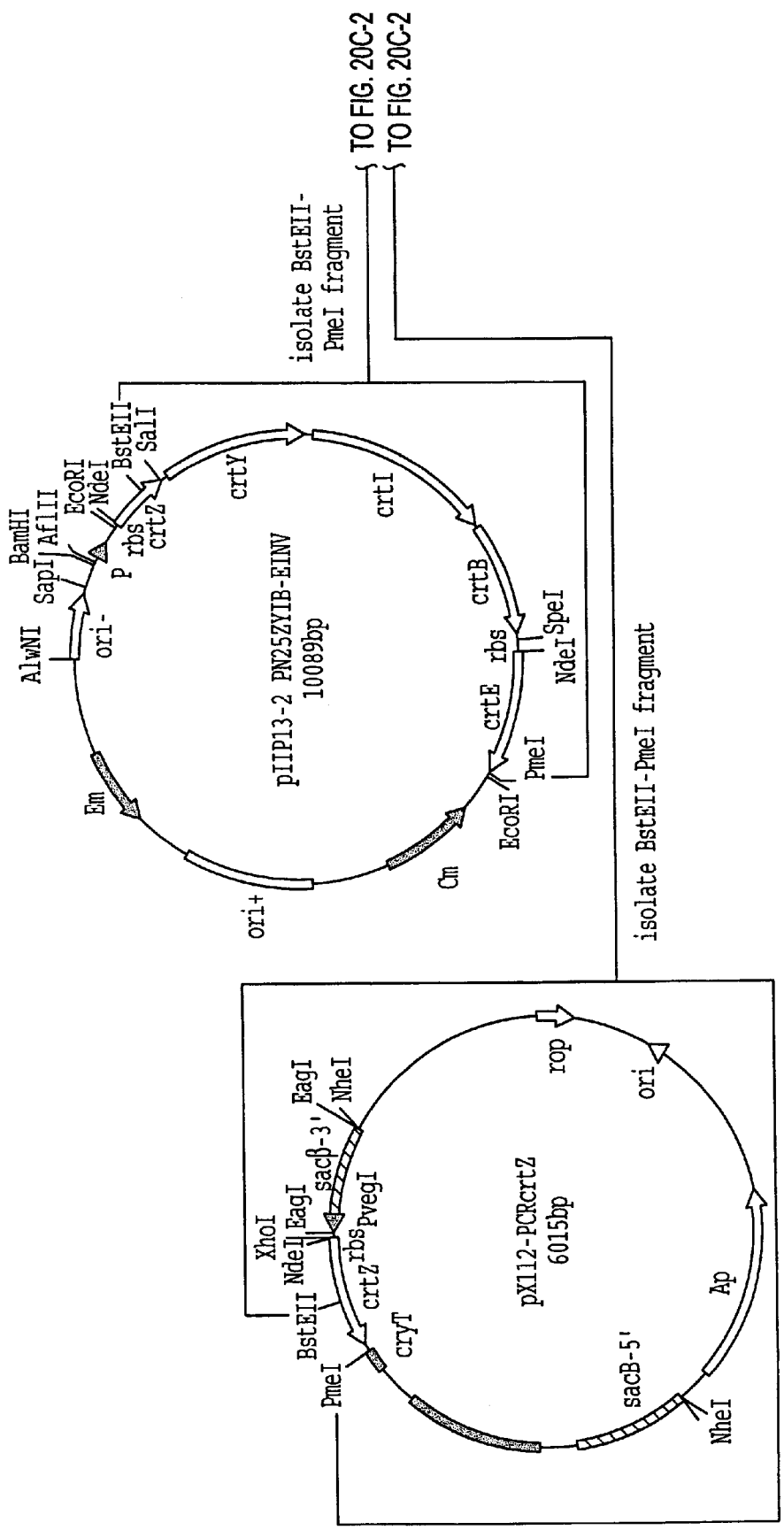
Figures 2, 20C:
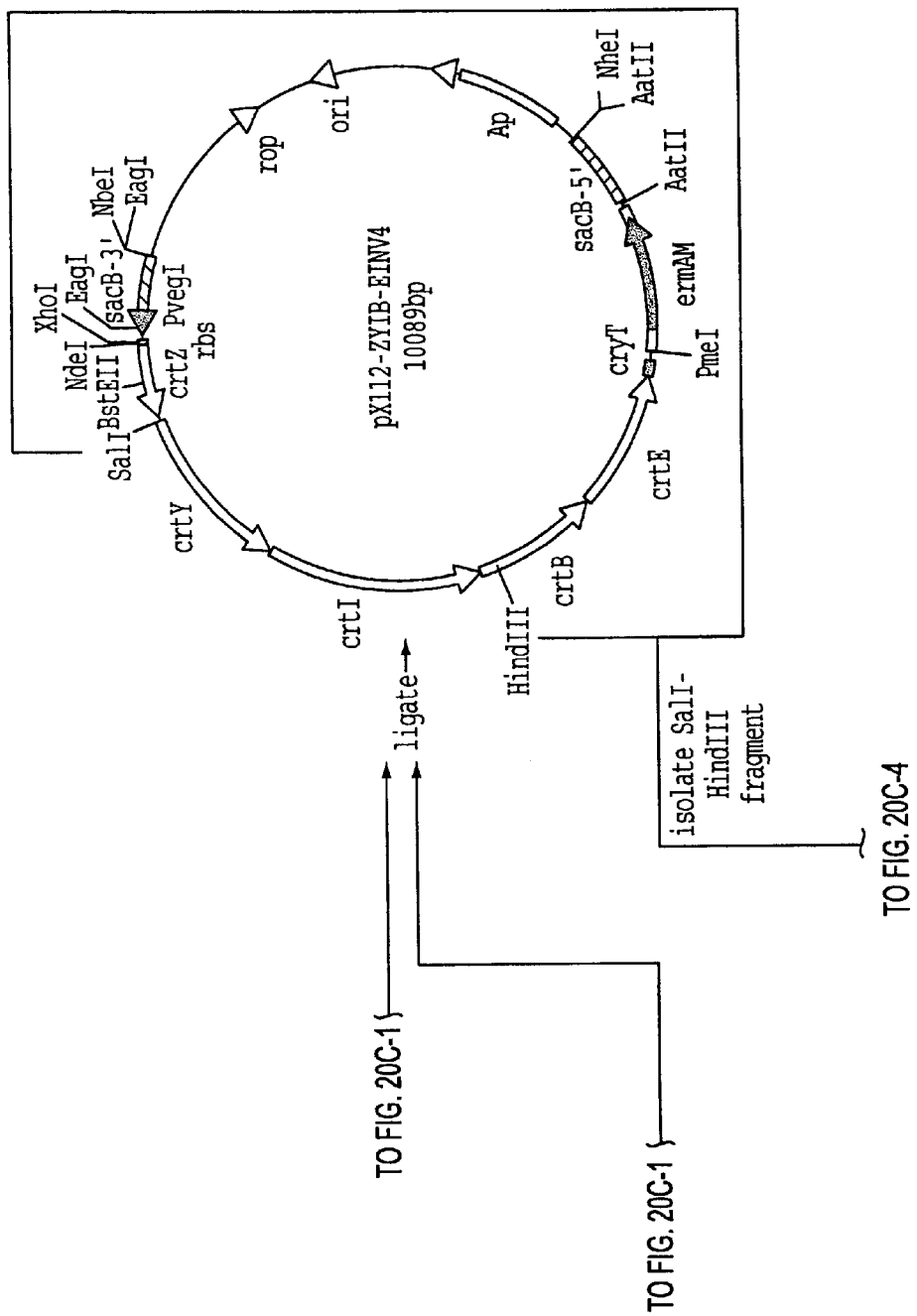
Figures 3, 20C:
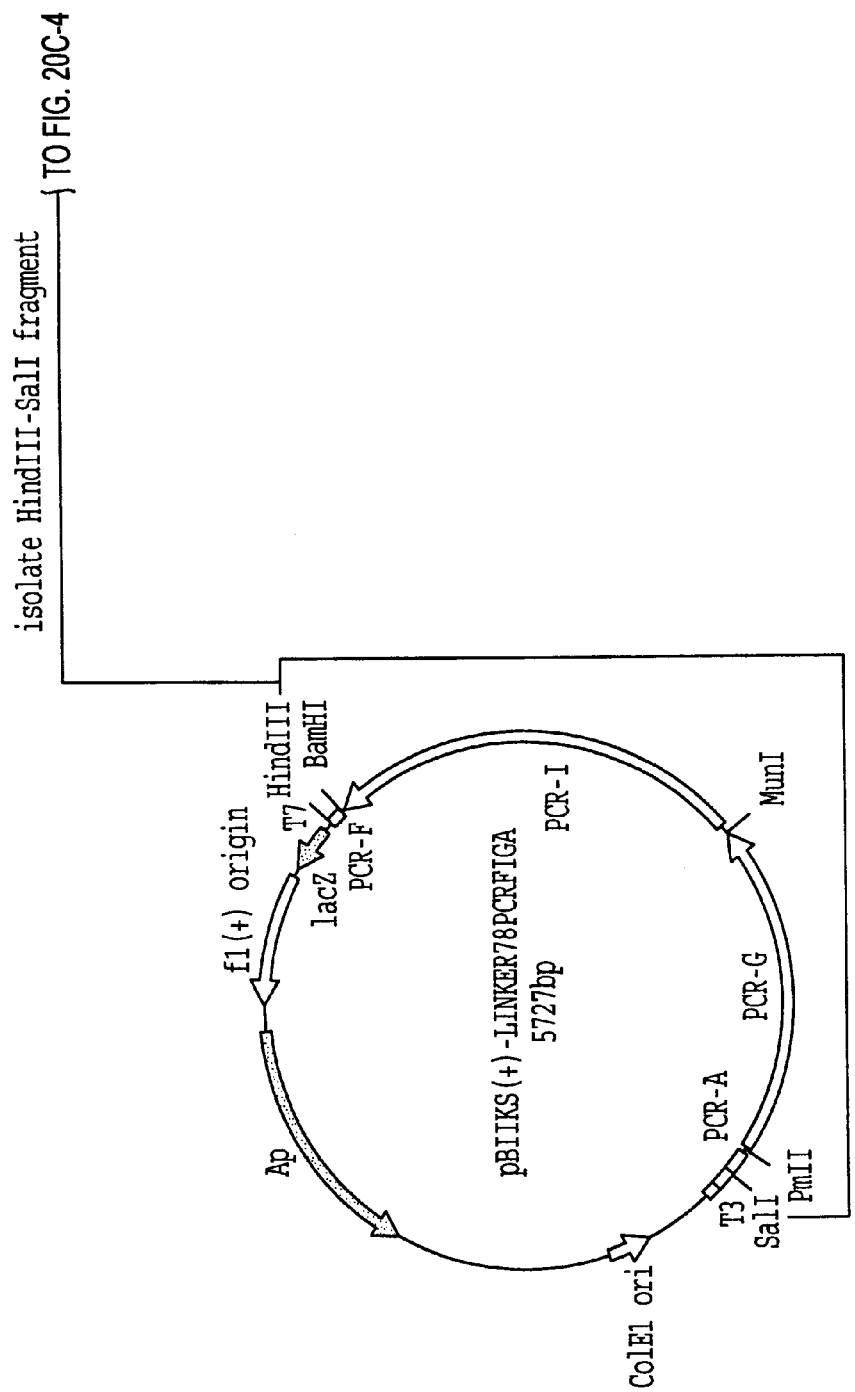
Figures 4, 20C:
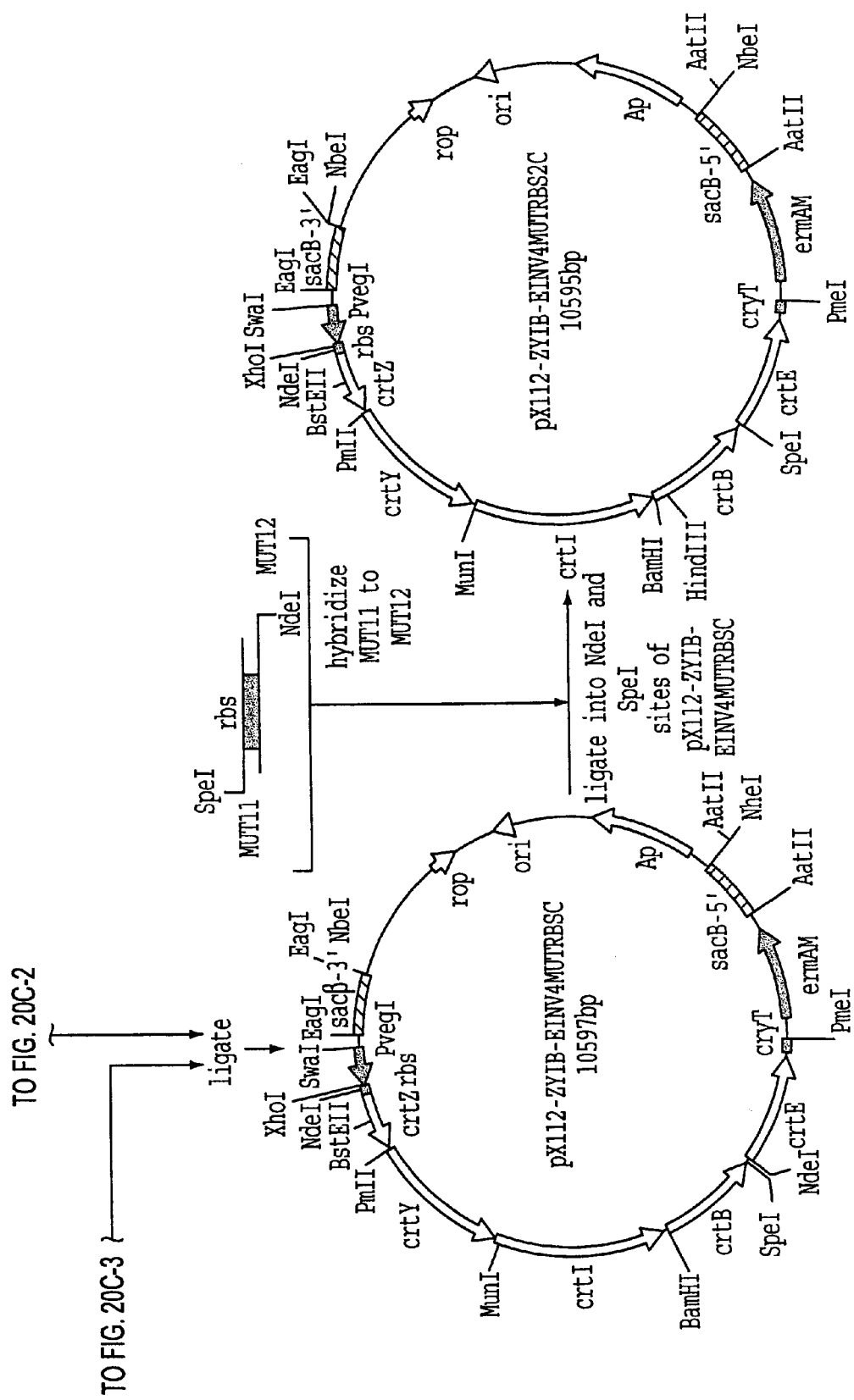
Figure 20D:
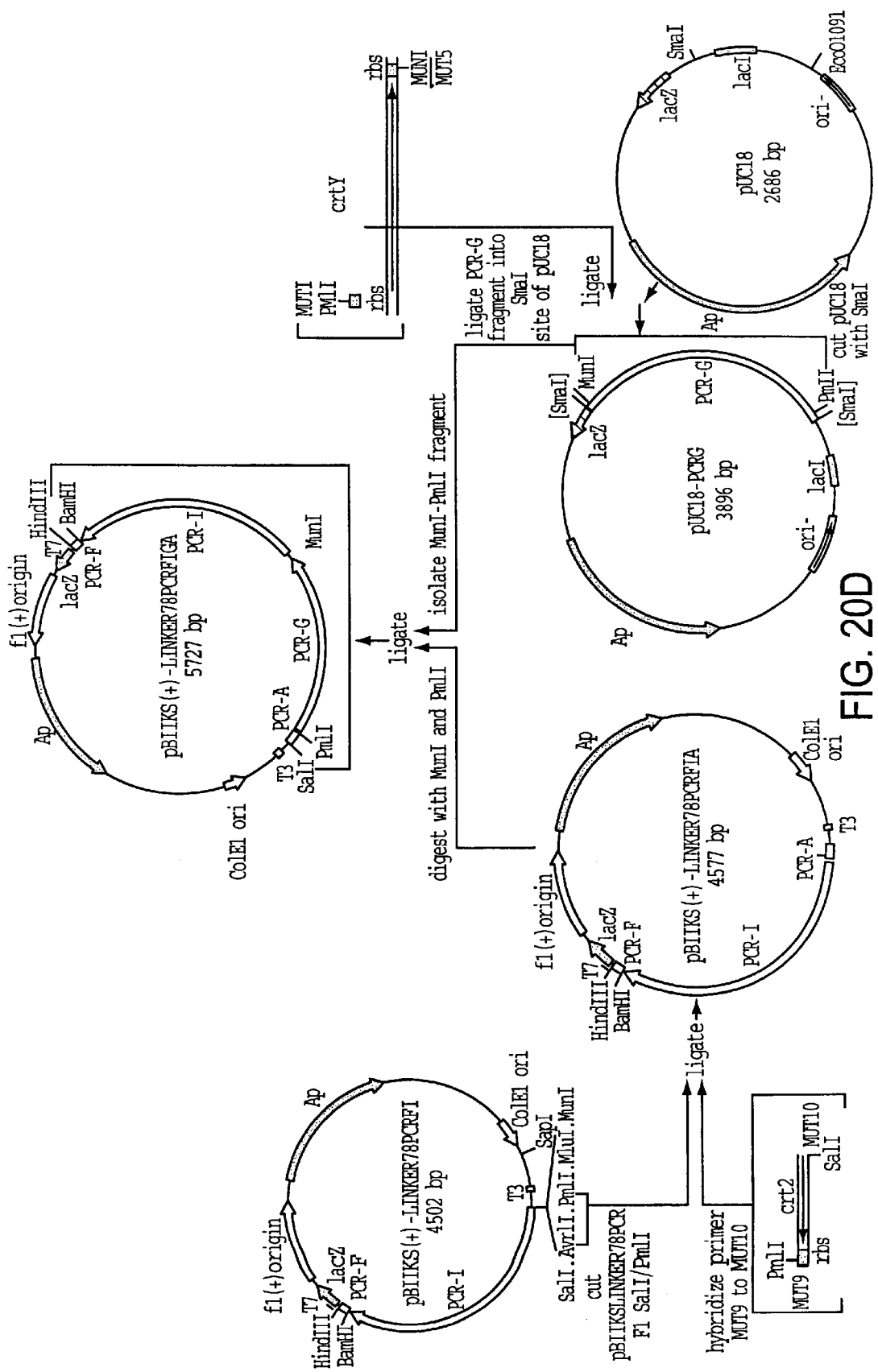

In order to obtain a stable construct in B. subtilis, the carotenoid genes were cloned into the Gram (+)/(−) shuttle vector pHP13 constructed by [Haima et al., s.a.]. The stability problems were thought to be omitted by 1) reducing the size of the cloned insert which carries the carotenoid genes and 2) reversing the orientation of the crtE gene and thus only requiring one promoter for the expression of all five genes, instead of two, like in the previous constructs. Furthermore, the ability of cells transformed by such a plasmid carrying the synthetic Flavobacterium carotenoid operon (SFCO), to produce carotenoids, would answer the question if a modular approach is feasible. FIG. 19 summarizes all the construction steps and intermediate plasmids made to get the final construct pHP13-2PNZYIB-EINV. Briefly: To facilitate the following constructions, a vector pHP13-2 was made, by introducing a synthetic linker obtained with primer CS1 (SEQ ID NO: 19) and CS2 (SEQ ID NO: 20), between the HindIII and EcoRI sites of the shuttle vector pHP13. The intermediate construct pHP13-2CARVEG-E was constructed by subcloning the AflIII-XbaI fragment of p602CARVEG-E into the AflII and XbaI sites of pHP13-2. The next step consisted in the inversion of crtE gene, by removing XbaI and AvrII fragment containing the original crtE gene and replacing it with the XbaI-AvrII fragment of plasmid pBIIKS(+)-PCRRBScrtE. The resulting plasmid was named pHP13-2CARZYIB-EINV and represented the first construction with a functional SFCO. The intermediate construct pBIIKS(+)-PCRRBScrtE mentioned above, was obtained by digesting the PCR product generated with primers #100 (SEQ ID NO: 7) and #101 (SEQ ID NO: 8) with SpeI and SmaI and ligating into the SpeI and SmaI sites of pBluescriptIIKS(+). In order to get the crtZ transcription start close to the promoter $P_{N25/O}$ a triple ligation was done with the BamHI-SalI fragment of pHP13-2CARZYIB-EINV (contains four of the five carotenoid genes), the BamHI-EcoRI fragment of the same plasmid containing the $P_{N25/O}$ promoter and the EcoRI-SalI fragment of pBIIKS(+)-PCRRBScrtZ, having most of the crtZ gene preceded by a synthetic RBS. The aforementioned plasmid pBIISK(+)-PCRRBScrtZ was obtained by digesting the PCR product amplified with primers #104 (SEQ ID NO: 9) and #105 (SEQ ID NO: 10) with EcoRI and SalI and ligating into the EcoRI and SalI sites of pBluescriptIISK(+). In the resulting vector pHP13-2PN25ZYIB-EINV, the SFCO is driven by the bacteriophage T5 promoter $P_{N25/O}$, which should be constitutively expressed, due to the absence of a functional lac repressor in the construct [Peschke and Beuk, J. Mol. Biol. 186, 547–555 (1985)]. E. coli TG1 cells transformed with this construct produced zeaxanthin. Nevertheless, when this plasmid was transformed into B. subtilis, no carotenoid production could be detected. Analysis of the plasmids of these transformants showed severe deletions, pointing towards instability problems, similar to the observations made with the aforementioned plasmids.

EXAMPLES 6
Chromosome Integration Constructs

Figure 21:
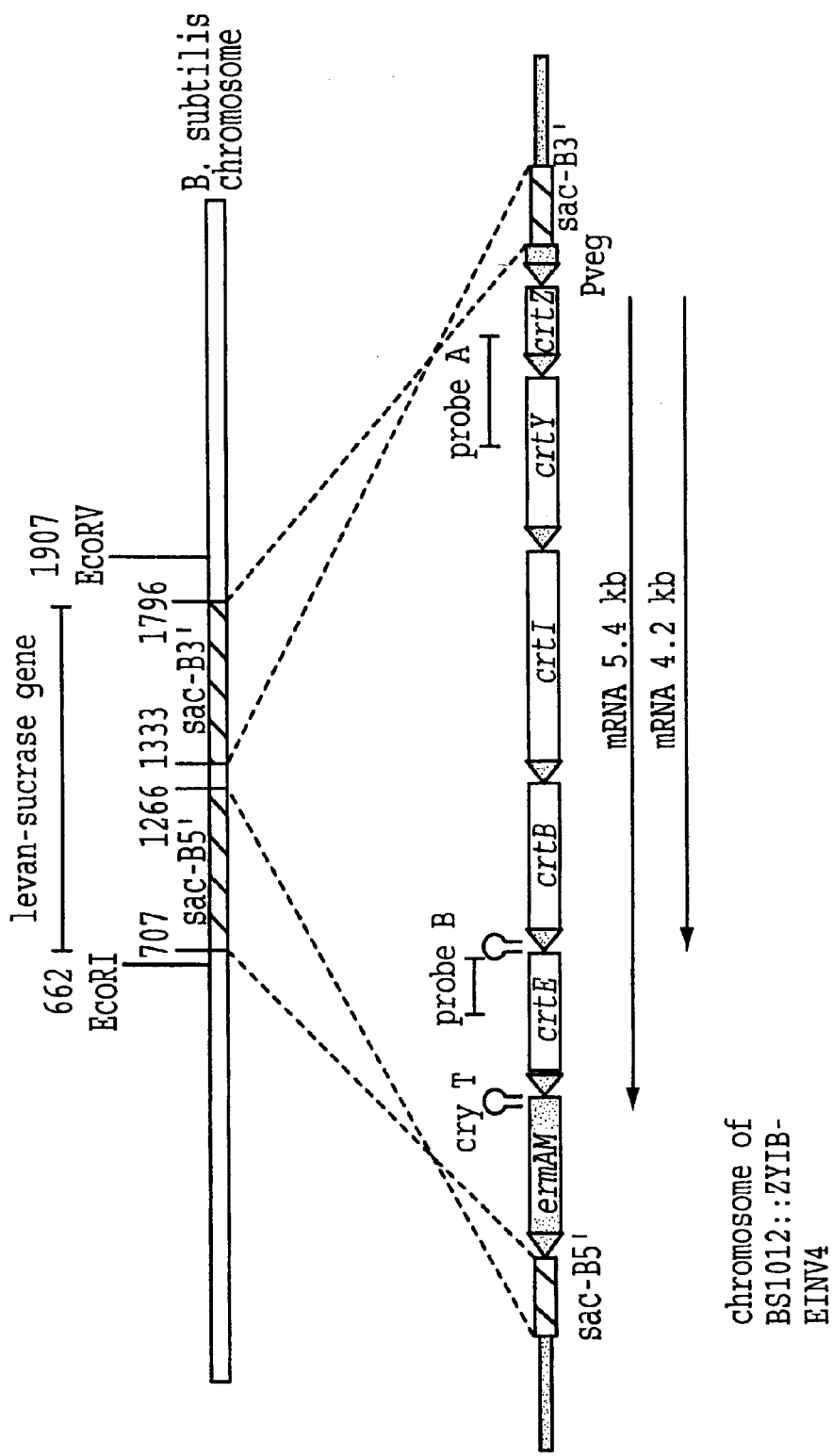
FIGS. 21, 21B Northern blot analysis of *B. subtilis* strain BS1012::ZYIB-EINV4. Panel A: Schematic representation of a reciprocal integration of plasmid pXI12-ZYIB-EINV4 into the levan-sucrase gene of *B-subtilis*. Panel B: Northern blot obtained with probe A (PCR fragment which was obtained with CAR 51 and CAR 76 and hybridizes to the 3' end of crtZ and the 5' end or crtY). Panel C: Northern blot obtained with probe B (BamHI-XhoI fragment isolated from plasmid pBIIKS(+)-crtE/2 and hybridizing to the 5' part of the crtE gene).
Figure 21B:
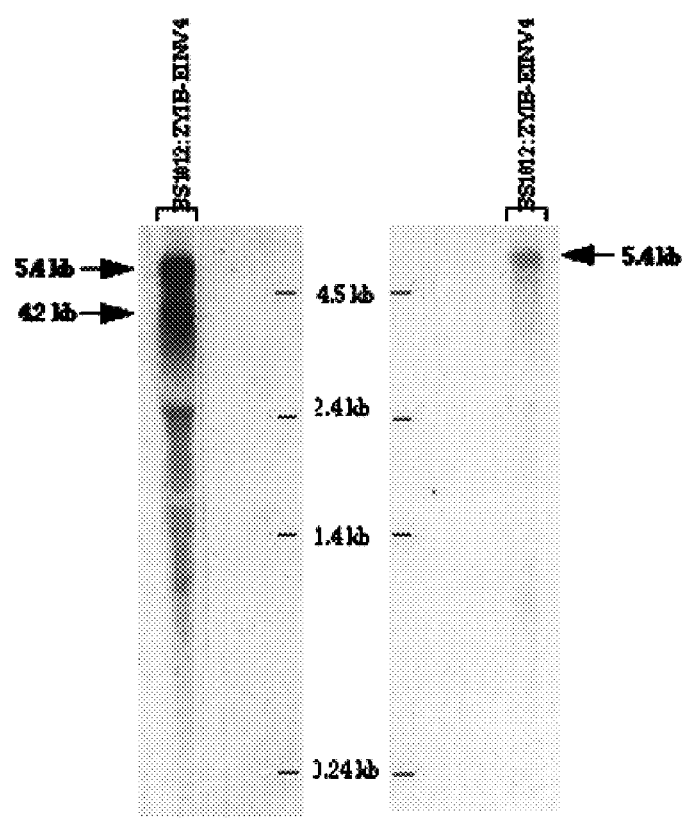

Due to the instability observed with the previous constructs we decided to integrate the carotenoid biosynthesis genes of Flavobacterium sp. into the genome of B. subtilis using the integration/expression vector pXI12. This vector allows the constitutive expression of whole operons after integration into the levan-sucrase gene (sacB) of the B. subtilis genome. The constitutive expression is driven by the vegI promoter and results in medium level expression. The plasmid pXI12-ZYIB-EINV4 containing the synthetic Flavobacterium carotenoid operon (SFCO) was constructed as follows: the NdeI-HincII fragment of pBIISK(+)-PCRRBScrtZ was cloned into the NdeI and SmaI sites of pXI12 and the resulting plasmid was named pXI12-PCRcrtZ. In the next step, the BstEII-PmeI fragment of pHP13-2PN25ZYIB-EINV was ligated to the BstEII-PmeI fragment of pXI12-PCRcrtZ (see FIG. 20). B. subtilis transformed with the resulting construct pXI12-ZYIB-EINV4 can integrate the CAR genes either via a Campbell type reaction or via a reciprocal recombination. One transformant, BS1012::ZYIB-EINV4, having a reciprocal recombination of the carotenoid biosynthesis genes into the levan-sucrase gene was further analyzed (FIG. 21). Although this strain did not synthesize carotenoids, RNA analysis by Northern blots showed the presence of specific polycistronic mRNA's of 5.4 kb and 4.2 kb when hybridized to probe A (see FIG. 21, panel B). Whereas the larger mRNA has the expected message size, the origin of the shorter mRNA was unclear. Hybridization of the same Northern blot to probe B only detected the large mRNA fragment, pointing towards a premature termination of the transcription at the end of the crtB gene. The presence of a termination signal at this location would make sense, since in the original operon organisation in the Flavobacterium sp. R1534 genome, the crtE and the crtB genes are facing each other. With this constellation a transcription termination signal at the 5' end of crtB would make sense, in order to avoid the synthesis of anti-sense RNA which could interfere with the mRNA transcript of the crtE gene. Since this region has been changed considerably with respect to the wild type situation, the sequences constituting this terminator may also have been altered resulting in a "leaky" terminator. Western blot analysis using antisera against the different crt enzymes of the carotenoid pathway, pointed towards the possibility that the ribosomal binding sites might be responsible for the lack of carotenoid synthesis. Out of the five genes introduced only the product of crtZ, the β-carotene hydroxylase was detectable. This is the only gene preceded by a RBS site, originating from the pXI12 vector, known to be functional in *B. subtilis*. Base pairing interactions between a mRNA's Shine-Dalgarno sequence [Shine and Delagarno, s. a.] and the 16S rRNA, which permits the ribosome to select the proper initiation site, have been proposed by [McLaughlin et al., J. Biol. Chem. 256,11283–11291 (1981)] to be much more stable in Gram-positive organisms (*B. subtilis*) than in Gram-negative organisms (*E. coli*). In order to obtain highly stable complexes we exchanged the RBS sites of the Gram-negative Flavobacterium sp., preceding each of the genes crtY, crtI, crtB and crtE, with synthetic RBS's which were designed complementary to the 3' end of the *B. subtilis* 16S rRNA (see table 2). This exchange should allow an effective translation initiation of the different carotenoid genes in *B. subtilis*. The strategy chosen to construct this pXI12-ZYIB-EINV4MUTRBS2C, containing all four altered sites is summarized in FIG. 20. In order to facilitate the further cloning steps in pBluescriptIIKS(+), additional restriction sites were introduced using the linker obtained with primer MUT7 and MUT8, cloned between the SalI and HindIII sites of said vector. The new resulting construct pBIIKS(+)-LINKER78 had the following restriction sites introduced: AvrII, PmlI, MulI MunI, BamHI and SphI. The general approach chosen to create the synthetic RBS's upstream of the different carotenoid genes, was done using a combination of PCR based mutagenesis, where the genes were reconstructed using defined primers carrying the modified RBS sites, or using synthetic linkers having such sequences. Reconstitution of the RBS preceding the crtI and crtB genes was done by amplifying the crtI gene with the primers MUT2 (SEQ ID NO: 12) and MUT6 (SEQ ID NO:15), which include the appropriate altered RBS sites. The PCR-I fragment obtained was digested with MunI and BamHI and ligated into the MunI and BamHI sites of pBIIKS(+)-LINKER78. The resulting intermediate construct was named pBIIKS(+)-LINKER78PCRI. Reconstitution of the RBS preceding the crtB gene was done using a small PCR fragment obtained with primer MUT3 (SEQ ID NO: 13), carrying the altered RBS site upstream of crtB, and primer CAR17 (SEQ ID NO: 16). The amplified PCR-F fragment was digested with BamHI and HindIII and sub cloned into the BamHI and HindIII sites of pBIIKS(+)-LINKER78, resulting in the construct pBIIKS(+)-LINKER78PCRF. The PCR-I fragment was cut out of pBIIKS(+)-LINKER78PCRI with BamHI and SapI and ligated into the BamHI and SapI sites of pBIIKS(+)-LINKER78PCRF. The resulting plasmid pBIIKS(+)-LINKER78PCRFI has the PCR-I fragment fused to the PCR-F fragment. This construct was cut with SalI and PmlI and a synthetic linker obtained by annealing of primer MUT9 (SEQ ID NO: 23) and MUT10 (SEQ ID NO: 24) was introduced. This latter step was done to facilitate the upcoming replacement of the original Flavobacterium RBS in the above mentioned construct. The resulting plasmid was named pBIIKS(+)-LINKER78PCRFIA. Assembling of the synthetic RBS's preceding the crtY and crtI genes was done by PCR, using primers MUT1 (SEQ ID NO: 11) and MUT5 (SEQ ID NO: 14). The amplified fragment PCR-G was made blunt end before cloning into the SmaI site of pUC18, resulting in construct pUC18-PCR-G. The next step was the cloning of the PCR-G fragment between the PCR-A and PCR-I fragments. For this purpose the PCR-G was isolated from pUC18-PCR-G by digesting with MunI and PmlI and ligated into the MunI and PmlI sites of pBIIKS(+)-LINKER78PCRFIA. This construct contains all four fragments, PCR-F, PCR-I, PCR-G and PCR-A, assembled adjacent to each other and containing three of the four artificial RBS sites (crtY, crtI and crtB). The exchange of the Flavobacterium RBS's preceding the genes crtY, crtI and crtB by synthetic ones, was done by replacing the HindIII-SalI fragment of plasmid pXI12-ZYIB-EINV4 with the HindIII-SalI fragment of plasmid pBIIKS(+)-LINKER78PCRFIGA. The resulting plasmid pXI12-ZYIB-EINV4 MUTRBSC was subsequently transformed into *E. coli* TG1 cells and *B. subtilis* 1012. The production of zeaxanthin by these cells confirmed that the PCR amplified genes where functional. The *B. subtilis* strain obtained was named BS1012::SFCO1. The last Flavobacterium RBS to be exchanged was the one preceding the crtE gene. This was done using a linker obtained using primer MUT11 (SEQ ID NO: 25) and MUT12 (SEQ ID NO: 26). The wild type RBS was removed from pXI12-ZYIB-EINV4MUTRBS with NdeI and SpeI and the above mentioned linker was inserted. In the construct pXI12-ZYIB-EINV4MUTRBS2C all Flavobacterium RBS's have been replaced by synthetic RBS's of the consensus sequence AAAGGAGG-7-8 N-ATG (see table 2). *E. coli* TG1 cells transformed with this construct showed that also this last RBS replacement had not interferred

TABLE 2

| mRNA | nucleotide sequence |
|---|---|
| crtZ (SEQ ID NO: 48) | AAAGGAGGGUUUCAU<u>AUG</u>AGC |
| crtY (SEQ ID NO: 49) | AAAGGAGGACACGUG<u>AUG</u>AGC |

TABLE 2-continued

| mRNA | nucleotide sequence |
| --- | --- |
| crtI (SEQ ID NO: 50) | AAAGGAGGCAAUUGAG<u>AUG</u>AGU |
| crtB (SEQ ID NO: 51) | AAAGGAGGAUCCAAUC<u>AUG</u>ACC |
| crtE (SEQ ID NO: 52) | AAAGGAGGGUUUCUU<u>AUG</u>ACG |
| B. subtilis | 16S rRNA (SEQ ID NO: 53) 3' -UCUUUCCUCCACUAG |
| E. coli | 16S rRNA (SEQ ID NO: 54) 3' -AUUCCUCCACUAC |

Table 2: Nucleotide sequences of the synthetic ribosome binding sites in the constructs pXI12-ZYIB-EINV4MUTRBS2C, pXI12-ZYIB-EINV4MUTRBS2CCAT and pXI12-ZYIB-EINV4 MUTRBS2CNEO. Nucleotides of the Shine-Dalgarno sequence preceding the individual carotenoid genes which are complementary to the 3' ends of the 16S rRNA of B. subtilis are shown in bold. The 3' ends of the 16S rRNA of E. coli is also shown as comparison. The underlined AUG is the translation start site of the mentioned gene.

with the ability to produce zeaxanthin. All the regions containing the newly introduced synthetic RBS's were confirmed by sequencing. B. subtilis cells were transformed with plasmid pXI12-ZYIB-EINV4MUTRBS2 and one transformant having integrated the SFCO by reciprocal recombination, into the levan-sucrase gene of the chromosome, was selected. This strain was named BS1012::SFCO2. Analysis of the carotenoid production of this strain show that the amounts zeaxanthin produced is approx. 40% of the zeaxanthin produced by E. coli cells transformed with the plasmid used to get the B. subtilis transformant. Similar was the observation when comparing the BS1012::SFCO1 strain with its E. coli counter part (30%). Although the E. coli cells have 18 times more carotenoid genes, the carotenoid production is only a factor of 2–3 times higher. More drastic was the difference observed in the carotenoid contents, between E. coli cells carrying the pZea4 construct in about 200 copies and the E. coli carrying the plasmid pXI12-ZYIB-EINV4MUTRBS2C in 18 copies. The first transformant produced 48× more zeaxanthin than the latter one. This difference seen can not only be attributed to the roughly 11 times more carotenoid biosynthesis genes present in these transformants. Contributing to this difference is probably also the suboptimal performance of the newly constructed SFCO, in which the overlapping genes of the wild type Flavobacterium operon were separated to introduce the synthetic RBS's. This could have resulted in a lower translation efficiency of the rebuild synthetic operon (e.g. due to elimination of putative translational coupling effects, present in the wild type operon).

Figure 22:
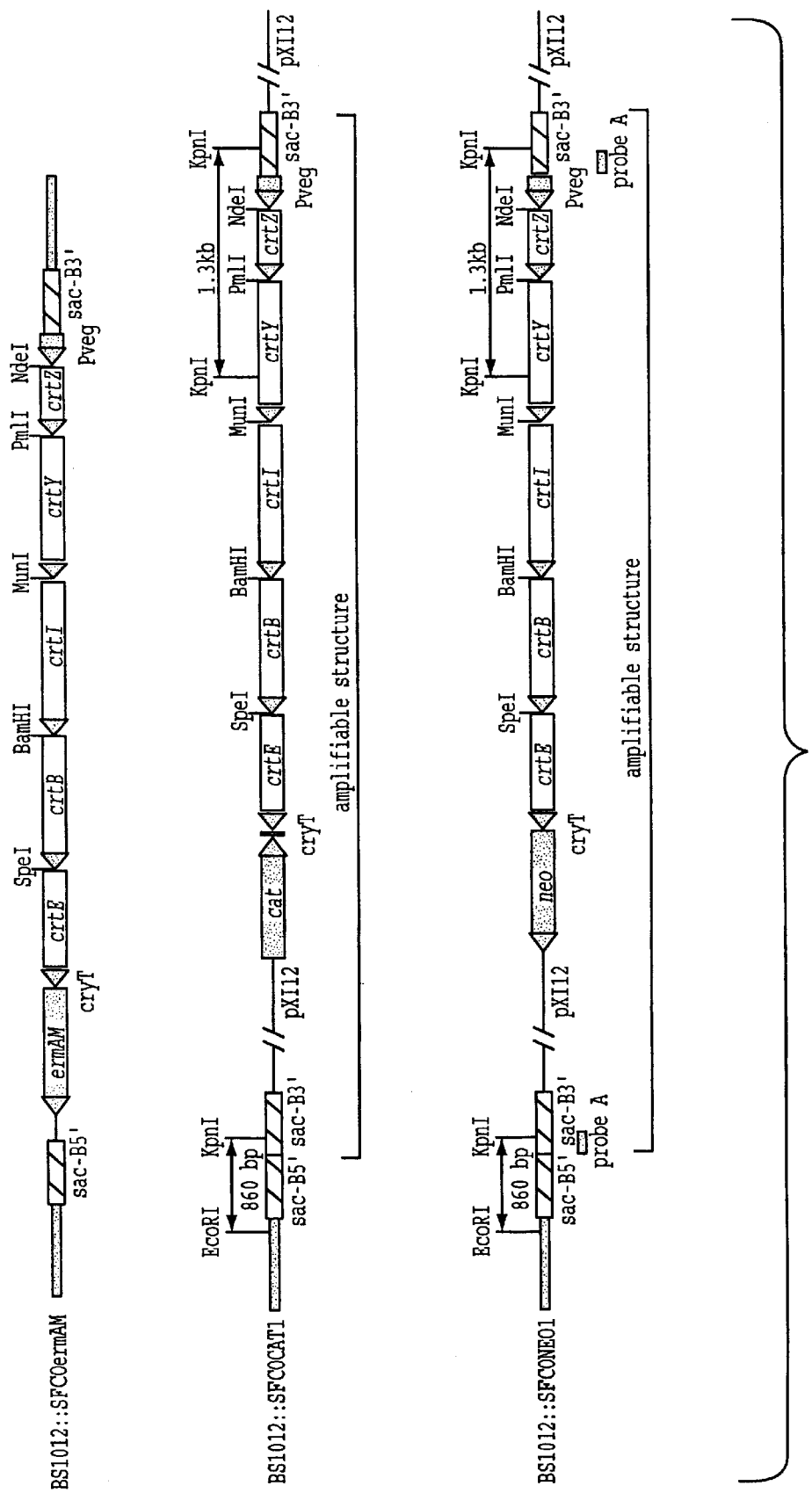
FIG. 22: Schematic representation of the integration sites of three transformed *Bacillus subtilis* strains: BS1012::SFCO, BS1012::SFCOCAT1 and BA1012::SFCONEO1. Amplification of the synthetic Flavobacterium carotenoid operon (SFCO) can only be obtained in those strains having amplifiable structures. Probe A was used to determine the copy number of the integrated SFCO. Erythromycine resistance gene (ermAM), chloramphenicol resistance gene (cat), neomycine resistance gene (neo), terminator of the cryT gene of *B. subtilis* (cryT), levan-sucrase gene (sac-B 5' and sac-B 3'), plasmid sequences of pXI12 (pXI12), promoter originating from site I of the veg promoter complex (Pvegl).
Figure 23A:
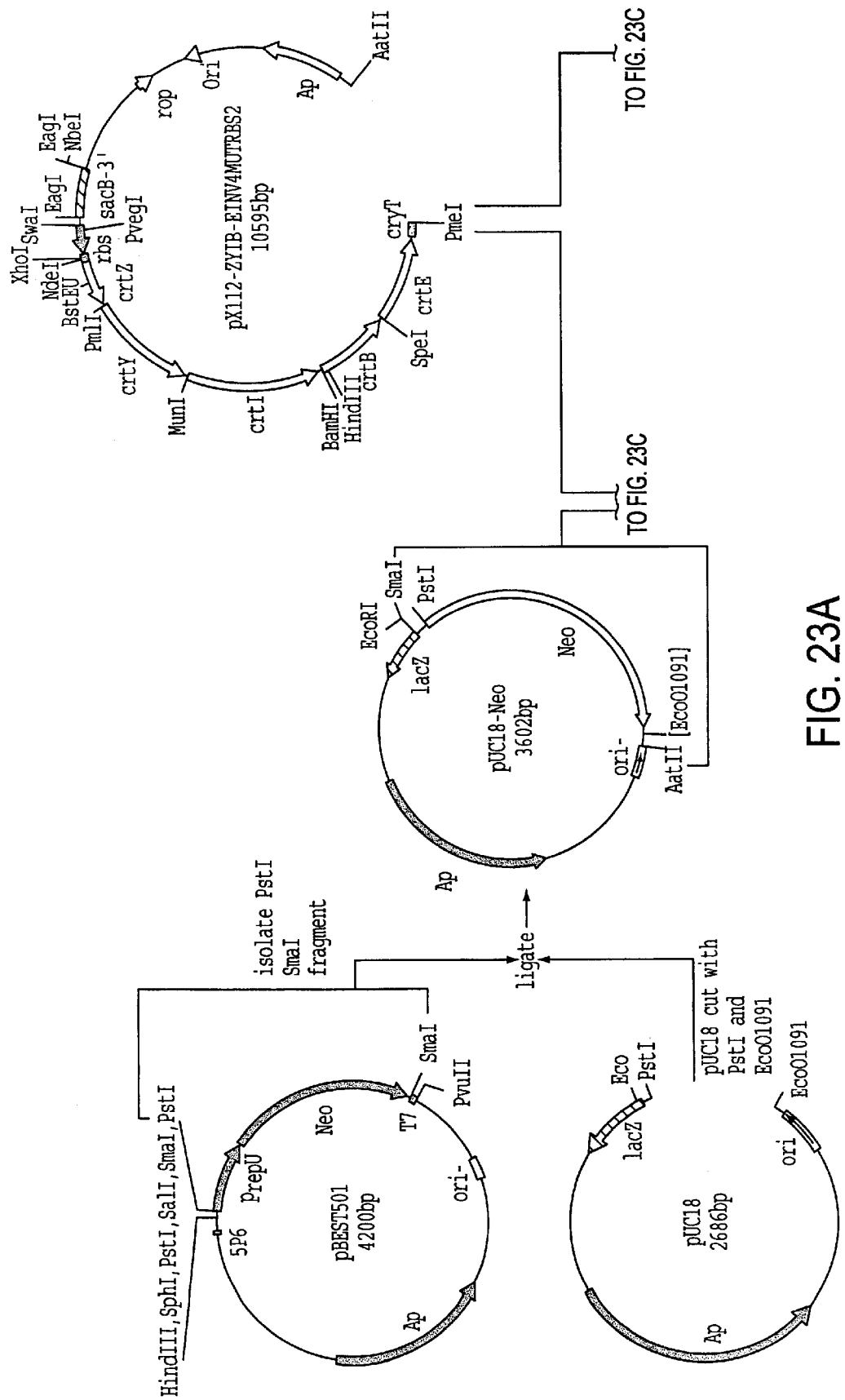
FIGS. 23A, 23B, 23C Construction of plasmids pXI12-ZYIB-EINV4MUTRBS2CNEO and pXI12-ZYIB-EINV4MUTRBS2CCAT.
Figure 23B:
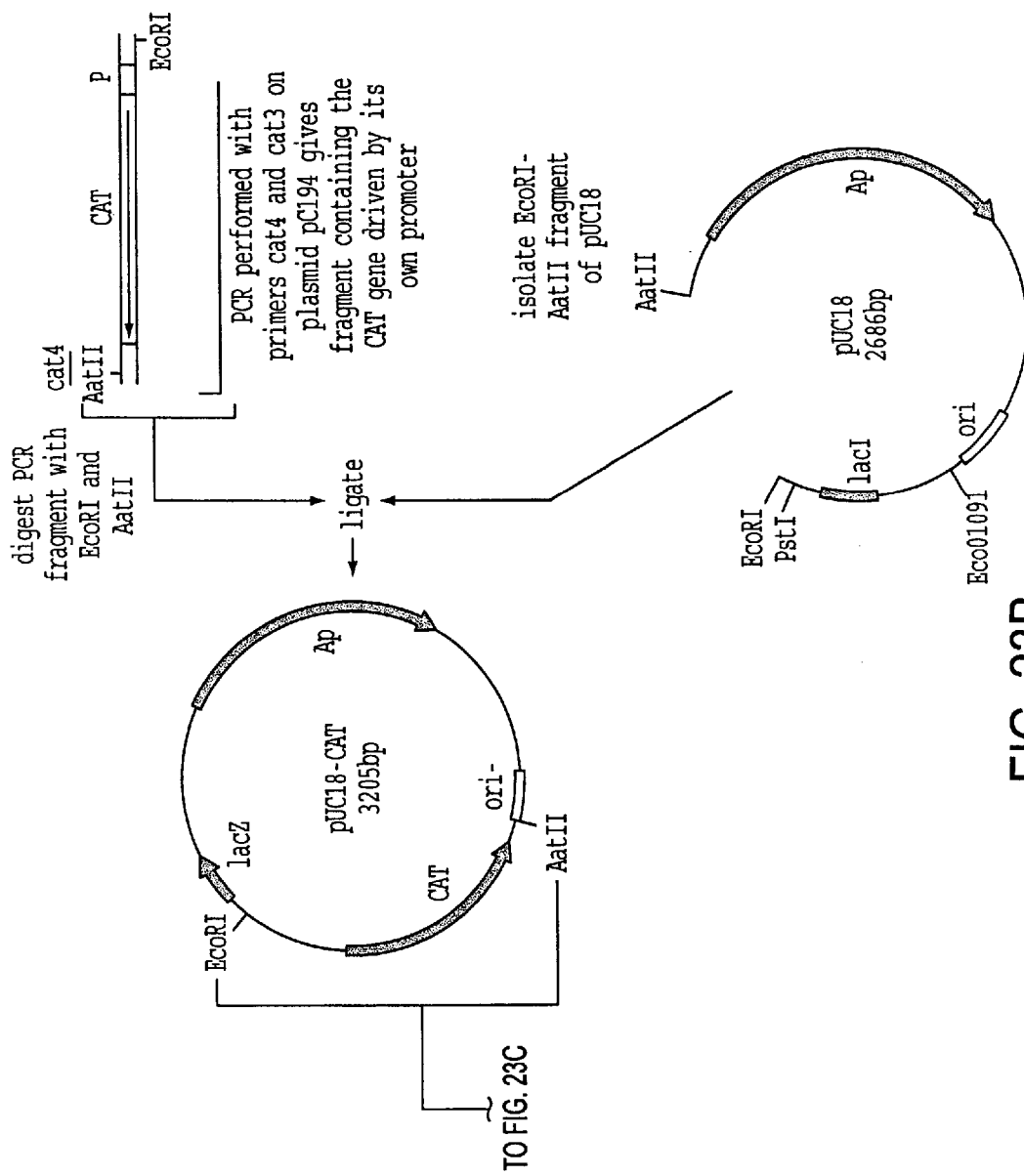
Figure 23C:
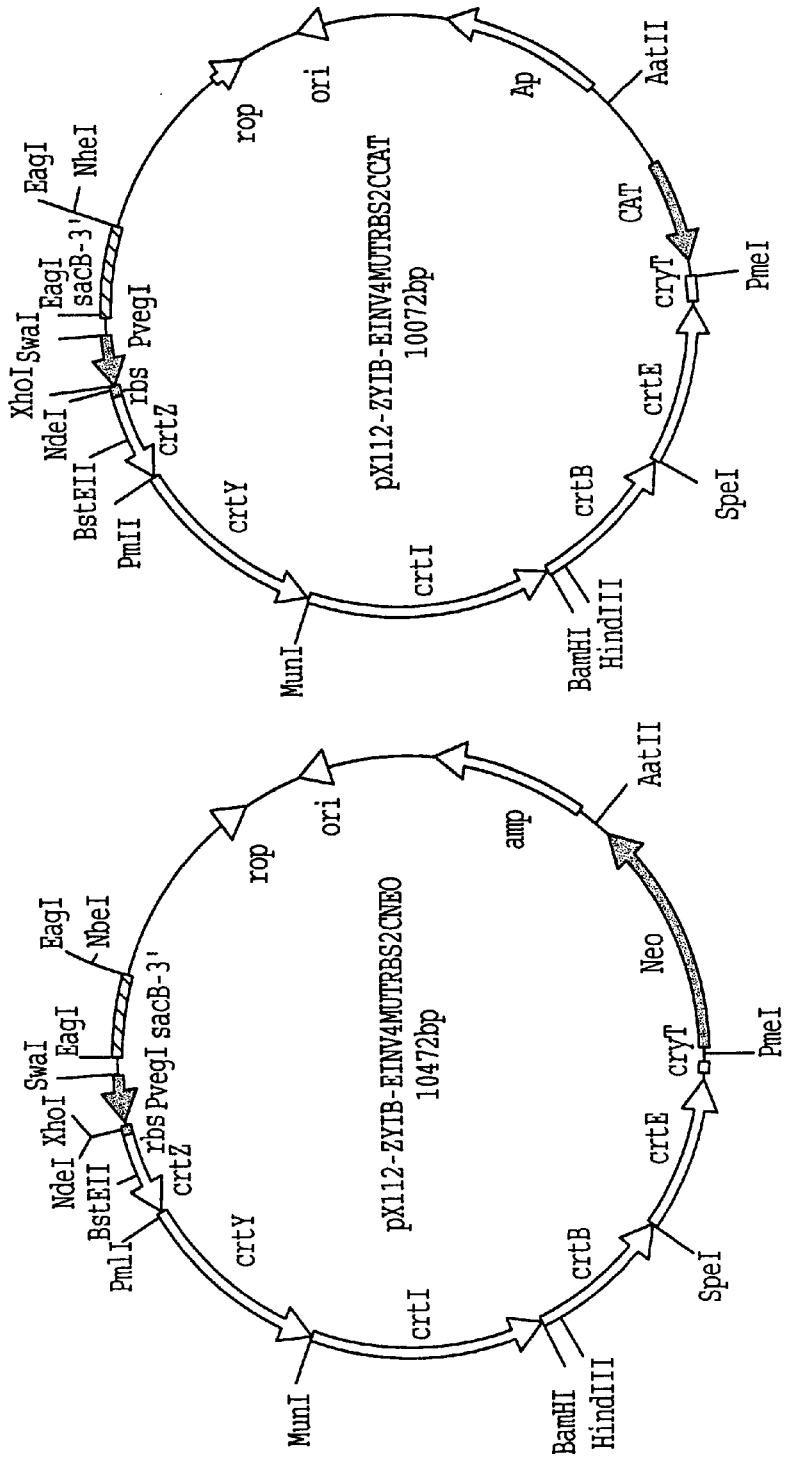

In order to increase the carotenoid production, two new constructs were made, pXI12-ZYIB-EINV4MUTRBS2CNEO and pXI12-ZYIB-EINV4 MUTRBS2CCAT, which after the integration of the SFCO into the levan-sucrase site of the chromosome, generate strains with an amplifiable structure as described by [Janniere et al., Gene 40, 47–55 (1985)]. Plasmid pXI12-ZYIB-EINV4MUTRBS2CNEO has been deposited on May 25,1995 at the DSM-Deutsche Sammlung von Mikroorganismen und Zellkulturen GmbH (Germany) under accession No. DSM 10013. Such amplifiable structures, when linked to a resistance marker (e.g chloramphenicol, neomycin, tetracycline), can be amplified to 20–50 copies per chromosome. The amplifiable structure consist of the SFCO, the resistance gene and the pXI12 sequence, flanked by direct repeats of the sac-B 3' gene (see FIG. 22). New strains having elevated numbers of the SFCO could now be obtained by selecting for transformants with increased level of resistance to the antibiotic. To construct plasmid pXI12-ZYIB-EINV4MUTRBS2CNEO, the neomycin resistance gene was isolated from plasmid pBEST501 with PstI and SmaI and subcloned into the PstI and EcoO109Isites of the pUC18 vector. The resulting construct was named pUC18-Neo. To get the final construct, the PmeI-AatII fragment of plasmid pXI12-ZYIB-EINV4MUTRBS2C was replaced with the SmaI-AatII fragment of pUC18-Neo, containing the neomycin resistance gene. Plasmid pXI12-ZYIB-EINV4MUTRBS2CCAT was obtained as follows: the chloramphenicol resistance gene of pC194 was isolated by PCR using the primer pair cat3 (SEQ ID NO: 17) and cat4 (SEQ ID.NO:,18). The fragment was digested with EcoRI and AatII and subcloned into the EcoRI and AatII sites of pUC18. The resulting plasmid was named pUC18-CAT. The final vector was obtained by replacing the PmeI-AatII fragment of pXI12-ZYIB-EINV4MUTRBS2C with the EcoRI-AatII fragment of pUC18-CAT, carrying the chloramphenicol resistance gene. FIG. 23 summarizes the different steps to obtain aforementioned constructs. Both plasmids were transformed into B. subtilis strain 1012, and transformants resulting from a Campbell-type integration were selected. Two strains BS1012::SFCONEO1 and BS1012::SFCOCAT1 were chosen for further amplification. Individual colonies of both strains were independently amplified by growing them in different concentrations of antibiotics as described in the methods section. For the cat gene carrying strain, the chloramphenicol concentrations were 60, 80, 120 and 150 mg/ml. For the neo gene carrying strain, the neomycin concentrations were 160 and 180 mg/mi. In both strains only strains with minor amplifications of the SFCO's were obtained. In daughter strains generated from strain BS1012::SFCONEO1, the resistance to higher neomycin concentrations correlated with the increase in the number of SFCO's in the chromosome and with higher levels of carotenoids produced by these cells. A different result was obtained with daughter strains obtained from strain BS1012::SFCOCAT1. In these strains an increase up to 150 mg chloramphenicol/ml resulted, as expected, in a higher number of SFCO copies in the chromosome.

EXAMPLE 7

Construction of CrtW Containing Plasmids and Use for Carotenoid Production

Polymerase chain reaction based gene synthesis. The nucleotide sequence of the artificial crtW gene, encoding the β-carotene β-4-oxygenase of Alcaligenes strain PC-1, was obtained by back translating the amino acid sequence outlined in [Misawa, 1995], using the BackTranslate program of the GCG Wisconsin Sequence Analysis Package, Version 8.0 (Genetics Computer Group, Madison, Wis., USA) and a codon frequency reference table of E. coli (supplied by the Bach Translate Program). The synthetic gene consisting of 726 nucleotides was constructed basically according to the method described by [Ye, 1992]. The sequence of the 12 oligonucleotides (crtW1–crtW12) required for the synthesis are shown in FIG. 25 (SEQ ID NO: 28). Briefly, the long oligonucleotides were designed to have short overlaps of 15–20 bases, serving as primers for the extension of the oligonucleotides. After four cycles a few copies of the full length gene should be present which is then amplified by the two terminal oligonucleotides crtW15 (SEQ ID NO: 55) and crtW26. The sequences for these two short oligonucleotides are for the forward primer crtW15 (5'-TATATCTAGAcat atgTCCGGTCGTAAA CCGG-3') and for the reverse primer crtW26 (SEQ ID NO: 56) (5'-TATAgaattccacgtgTCA AGCACGACCACCGGTTTTAC G-3'), where the sequences matching the DNA templates are underlined. Small cap letters show the introduced restriction sites (NdeI for the forward primer and EcoRI and PmlI for the reverse primer) for the latter cloning into the pALTER-Ex2 expression vector.

Polymerase chain reaction. All twelve long oligonucleotides (crtW1–crtW12; 7 nM each) and both terminal primers (crtW15 and crtW26; 0.1 mM each) were mixed and added to a PCR reaction mix containing Expand™ High Fidelity polymerase (Boehringer, Mannheim) (3.5 units) and dNTP's (100 mM each). The PCR reaction was run for 30 cycles with the following profile: 94° C. for 1 min, 50° C. for 2 min and 72° C. for 3 min. The PCR reaction was separated on a 1% agarose gel, and the band of approx. 700 bp was excised and purified using the glass beads method (Geneclean Kit, Bio101, Vista, Calif., USA). The fragment was subsequently cloned into the SmaI site of plasmid pUC18, using the Sure-Clone Kit (Pharmacia, Uppsala, Sweden). The sequence of the resulting crtW synthetic gene was verified by sequencing with the Sequenase Kit Version 1.0 (United States Biochemical, Cleveland, Ohio, USA). The crtW gene constructed by this method was found to contain minor errors, which were subsequently corrected by site-directed mutagenesis.

Figure 26:
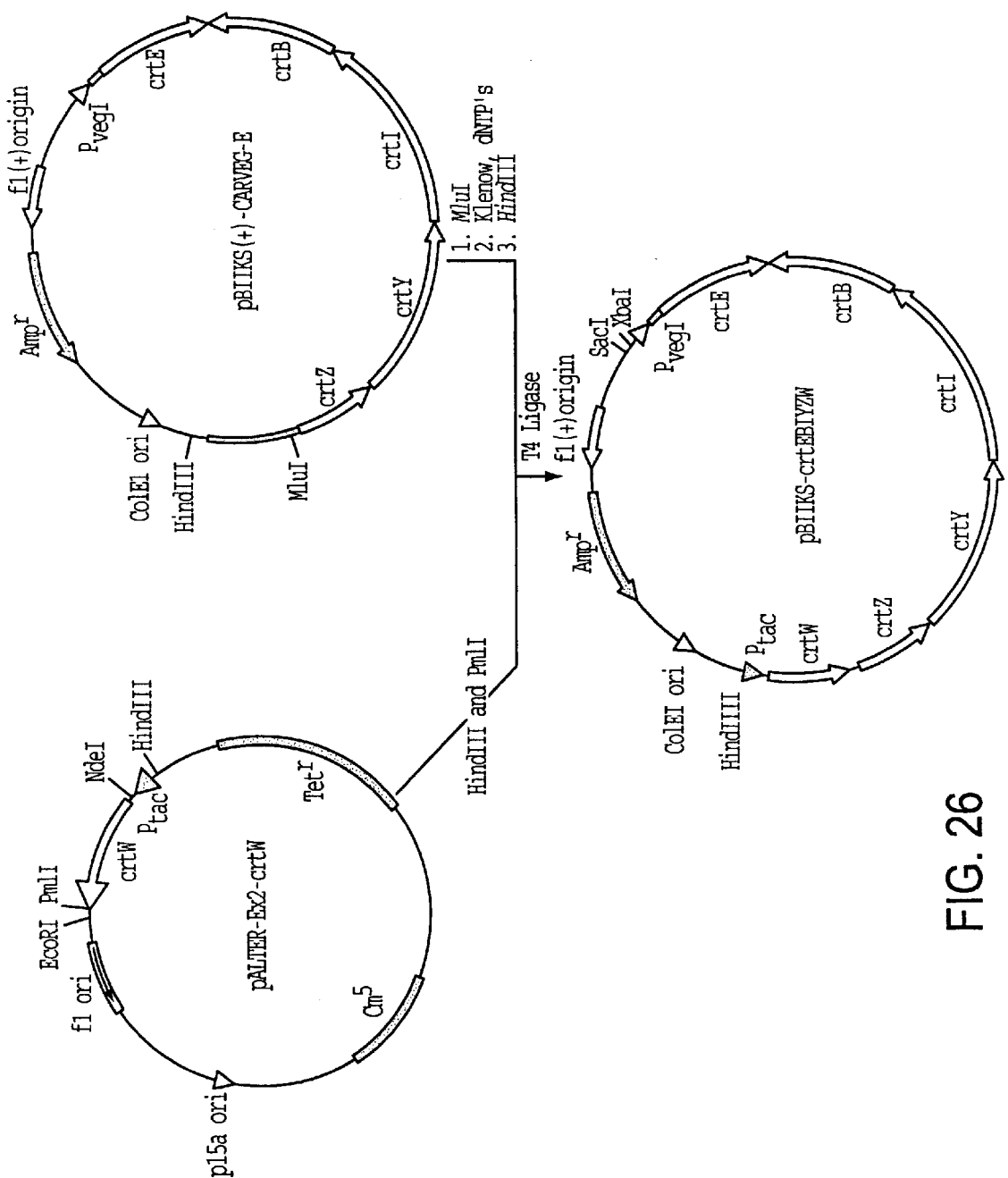
FIG. 26: Construction of plasmid pBIIKS-crtEBIYZW. The HindIII-PmII fragment of pALTER-Ex2-crtW, carrying the synthetic crtW gene, was cloned into the HindIII and MluI (blunt) sites. Pvegl and Ptac are the promoters used for the transcription of the two opera. The ColE1 replication origin of this plasmid is compatible with the p15A origin present in the pALTER-Ex2 constructs.
Figure 27:
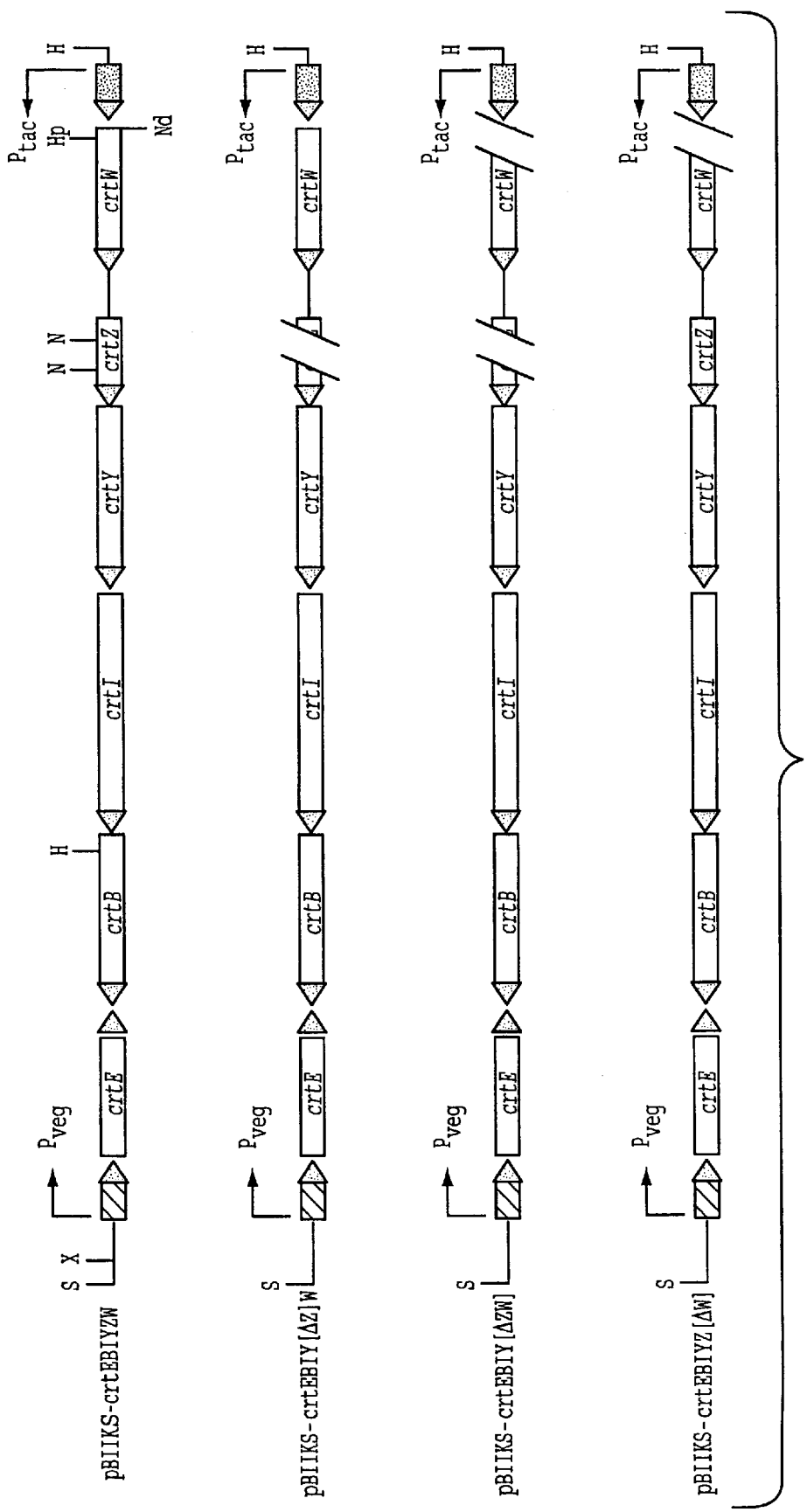
FIG. 27: Relevant inserts of all plasmids constructed in Example 7. Disrupted genes are shown by / /. Restriction sites: S=SacI, X=XbaI, H=HindIII, N=NsiI, Hp=HpaI, Nd=NdeI.

Construction of plasmids. Plasmid pBIIKS(+)-CARVEG-E (see also Example 5) (FIG. 26) contains the carotenoid biosynthesis genes (crtE, crtB, crtY, crtI and crtZ) of the Gram (−) bacterium Flavobacterium sp. strain R1534 WT (ATCC 21588) [Pasamontes, 1995 #732] cloned into a modified pBluescript II KS(+) vector (Stratagene, La Jolla, USA) carrying site I of the B. subtilis veg promoter [LeGrice, 1986 #806]. This constitutive promoter has been shown to be functional in E. coli. Transformants of E. coli strain TG1 carrying plasmid pBIIKS(+)-CARVEG-E synthesise zeaxanthin. Plasmid pALTER-Ex2-crtW was constructed by cloning the NdeI-EcoRI restricted fragment of the synthetic crtW gene into the corresponding sites of plasmid pALTER-Ex2 (Promega, Madison, Wis.). Plasmid pALTER-Ex2 is a low copy plasmid with the p15a origin of replication, which allows it to be maintained with ColE1 vectors in the same host. Plasmid pBIIKS-crtEBIYZW (FIG. 26) was obtained by cloning the HindIII-PmlI fragment of pALTER-Ex2-crtW into the HindIII and the blunt end made MluI site obtained by a fill in reaction with Klenow enzyme, as described elsewhere in [Sambrook, 1989 #505]. Inactivation of the crtZ gene was done by deleting a 285 bp NsiI-NsiI fragment, followed by a fill in reaction and religation, resulting in plasmid pBIIKS-crtEBIY[DZ]W. Plasmid pBIIKS-crtEBIY[DZW] carrying the non-functional genes crtW and crtZ, was constructed by digesting the plasmid pBIIKS-crtEBIY[DZ]W with NdeI and HpaI, and subsequent self religation of the plasmid after filling in the sites with Klenow enzyme. E. coli transformed with this plasmid had a yellow-orange colour due to the accumulation of β-carotene. Plasmid pBIIKS-crtEBIYZ [DW] has a truncated crtW gene obtained by deleting the NdeI-HpaI fragment in plasmid pBIIKS-crtEBIYZW as outlined above. Plasmids pALTER-Ex2-crtEBIY[DZW] and pALTER-Ex2-crtEBIYZ[DW], were obtained by isolating the BamHI-XbaI fragment from pBIIKS-crtEBIY [DZW] and pBIIKS-crtEBIYZ[DW], respectively and cloning them into the BamHI and XbaI sites of pALTER-Ex2. The plasmid pBIIKS-crtW was constructed by digesting pBIIKS-crtEBIYZW with NsiI and SacI, and self-religating the plasmid after recessing the DNA overhangs with Klenow enzyme. FIG. 27 compiles the relevant inserts of all the plasmids used in this paper.

Carotenoid analysis. E. coli TG-1 transformants carrying the different plasmid constructs were grown for 20 hours in Luria-Broth medium supplemented with antibiotics (ampicillin 100 mg/ml, tetracyclin 12.5 mg/ml) in shake flasks at 37° C. and 220 rpm. Carotenoids were extracted from the cells with acetone. The acetone was removed in vacuo and the residue was re dissolved in toluene. The coloured solutions were subjected to high-performance liquid chromatography (HPLC) analysis which was performed on a Hewlett-Packard series 1050 instrument. The carotenoids were separated on a silica column Nucleosil Si-100, 200×4 mm, 3m. The solvent system included two solvents: hexane (A) and hexane/THF, 1:1 (B). A linear gradient was applied running from 13 to 50% (B) within 15 minutes. The flow rate was 1.5 ml/min. Peaks were detected at 450 nm by a photo diode array detector. The individual carotenoid pigments were identified by their absorption spectra and typical retention times as compared to reference samples of chemically pure carotenoids, prepared by chemical synthesis and characterised by NMR, MS and UV-Spectra. HPLC analysis of the pigments isolated from E. coli cells transformed with plasmid pBIIKS-crtEBIYZW, carrying besides the carotenoid biosynthesis genes of Flavobacterium sp. strain R1534, also the crtW gene encoding the β-carotene ketolase of Alcaligenes PC-1 [Misawa, 1995 #670] gave the following major peaks identified as: b-cryptoxanthin, astaxanthin, adonixanthin and zeaxanthin, based on the retention times and on the comparison of the absorbance spectra to given reference samples of chemically pure carotenoids. The relative amount (area percent) of the accumulated pigment in the E. coli transformant carrying pBIIKS-crtEBIYZW is shown in Table 3 ["CRX": cryptoxanthin; "ASX": astaxanthin; "ADX": adonixanthin; "ZXN": zeaxanthin; "ECM": echinenone; "MECH": 3-hydroxyechinenone, "CXN": canthaxanthin]. The Σ of the peak areas of all identified carotenoids was defined as 100%. Numbers shown in Table 3 represent the average value of four independent cultures for each transformant. In contrast to the aforementioned results, E. coli transformants carrying the same genes but on two plasmids namely, pBIIKS-crtEBIYZ[DW] and pALTER-Ex2-crtW, showed a drastical drop in adonixanthin and a complete lack of astaxanthin pigments (Table 3), whereas the relative amount of zeaxanthin (%) had increased. Echinenone, hydroxyechinenone and canthaxanthin levels remained unchanged compared to the transformants carrying all the crt genes on the same plasmid (pBIIKS-crtEBIYZDW). Plasmid pBIIKS-crtEBIYZ[DW] is a high copy plasmid carrying the functional genes of crtE, crtB, crtY, crtI, crtZ of Flavobacterium sp. strain R1534 and a truncated, non-functional version of the crtW gene, whereas the functional copy of the crtW gene is located on the low copy plasmid pALTER-Ex2-crtW. To analyze the effect of overexpression of the crtW gene with respect to the crtZ gene, E. coli cells were co-transformed with plasmid pBIIKS-crtW carrying the crtW gene on the high copy plasmid pBIIKS-crtW and the low copy construct pALTER-Ex2-crtEBIYZ[DW], encoding the Flavobacterium crt genes. Pigment analysis of these transformants by HPLC monitored the presence of β-carotene, cryptoxanthin, astaxanthin, adonixanthin, zeaxanthin, 3-hydroxyechinenone and minute traces of echinenone and canthaxanthin (Table 3).

Transformants harbouring the crtW gene on the low copy plasmid pALTER-Ex2-crtW and the genes crtE, crtB, crtY and crtI on the high copy plasmid pBIIKS-crtEBIY[DZW] expressed only minor amounts of canthaxanthin (6%) but high levels of echinenone (94%), whereas cells carrying the crtW gene on the high copy plasmid pBIIKS-crtW and the other crt genes on the low copy construct pALTER-Ex2-crtEBIY[DZW], had 78.6% and 21.4% of echinenone and canthaxanthin, respectively (Table 3).

crtW100 (SEQ ID NO: 57): 5'-CA(C/T)GA(C/T)GC(A/C)ATGCA(C/T)GG-3'
crtW101 (SEQ ID NO: 58): 5'-CA(C/T)GA(C/T)GC(G/T)ATGCA(C/T)GG-3'

The C-terminal peptide H(W/H)EHH(R/L) corresponding to region II was used design the two 17-mer degenerate primer with the antisense sequences crtW105 (SEQ ID NO: 59) and crtW106 (SEQ ID NO: 60):

crtW105 (SEQ ID NO: 59): 5'-AG(G/A)TG(G/A)TG(T/C)TC(G/A)TG(G/A)TG-3'
crtW106 (SEQ ID NO: 60): 5'-AG(G/A)TG(G/A)TG(T/C)TCCCA(G/A)TG-3'

Polymerase chain reaction. PCR was performed using the GeneAmp Kit (Perkin Elmer Cetus) according to the manufacturer's instructions. The different PCR reactions contained combinations of the degenerate primers (crtW100/crtW105 or crtW100/crtW106 or crtW101/crtW105 or

TABLE 3

| plasmids | CRX | ASX | ADX | ZXN | ECH | HECH | CXN |
|---|---|---|---|---|---|---|---|
| pBIIKS-crtEBIYZW | 1.1 | 2.0 | 44.2 | 52.4 | <1 | <1 | <1 |
| pBIIKS-crtEBIYZ[W] + pALTER-Ex2-crtW | 2.2 | — | 25.4 | 72.4 | <1 | <1 | <1 |
| pBIIKS-crtEBIY[Z]W | — | — | — | — | 66.5 | — | 33.5 |
| pBIIKS-crtEBIY[ZW] + pBIIKS-crtW | — | — | — | — | 94 | — | 6 |

EXAMPLE 8
Selective Carotenoid Production by Using the crtW and crtZ Genes of the Gram Negative Bacterium E-396.

In this section we describe E. coli transformants which accumulate only one (canthaxanthin) or two main carotenoids (astaxanthin, adonixanthin) and minor amounts of adonirubin, rather than the complex variety of carotenoids seen in most carotenoid producing bacteria [Yokoyama et al., Biosci. Biotechnol. Biochem. 58:1842–1844 (1994)] and some of the E. coli transformants shown in Table 3. The ability to construct strains producing only one carotenoid is a major step towards a successful biotechnological carotenoid production process. This increase in the accumulation of individual carotenoids accompanied by a decrease of the intermediates, was obtained by replacing the crtZ of Flavobacterium R1534 and/or the synthetic crtW gene (see example 5) by their homologous genes originating from the astaxanthin producing Gram negative bacterium E-396 (FERM BP-4283) [Tsubokura et al., EP-application 0 635 576 A1]. Both genes, $crtW_{E396}$ and $crtZ_{E396}$, were isolated and used to construct new plasmids as outlined below.

Isolation of a putative fragment of the crtW gene of strain E-396 by the polymerase chain reaction. Based on protein sequence comparison of the crtW enzymes of Agrobacterium aurantiacum, Alcaligenes PC-1 (WO95/18220) [Misawa et al., J.Bacteriol. 177: 6575–6584 (1995)] and Haematococcus pluvialis [Kajiwara et al., Plant Mol. Biol. 29:343–352 (1995)][Lotan et al., FEBS letters, 364:125–128 (1995)], two regions named I and II, having high amino acid conservation and located approx. 140 amino acids appart, were identified and chosen to design the degenerate PCR primers shown below. The N-terminal peptide HDAMHG (region I) was used to design the two 17-mer degenerate primer sequences crtW100 (SEQ ID NO: 57) and crtW101 (SEQ ID NO: 58):

crtW101/crtW106) at a final concentration of 50 pM each, together with genomic DNA of the bacterium E-396 (200 ng) and 2.5 units of Taq polymerase. In total 35 cycles of PCR were performed with the following cycle profile: 95° C. for 30 sec, 55° C. for 30 sec, 72 ° C. for 30 sec. PCR reactions made with the following primer combinations crtW100/crtW105 and crtW101/crtW105 gave PCR amplification products of approx. 500 bp which were in accordance with the expected fragment size. The 500 bp fragment, JAPclone8, obtained in the PCR reaction using primers crtW101 (SEQ ID NO: 58) and crtW105 (SEQ ID NO: 59) was excised from an 1.5% agarose gel and purified using the GENECLEAN Kit and subsequently cloned into the SmaI site of pUC18 using the Sure-Clone Kit, according to the manufacturer's instructions. The resulting plasmid was named pUC18-JAPclone8 and the insert was sequenced. Comparison of the determined sequence to the crtW gene of Agrobacterium aurantiacum (GenBank accession n° D58420) published by Misawa et al. in 1995 (WO95/18220) showed 96% identity at the nucleotide sequence level, indicating that both organisms might be closely related.

Figure 29:
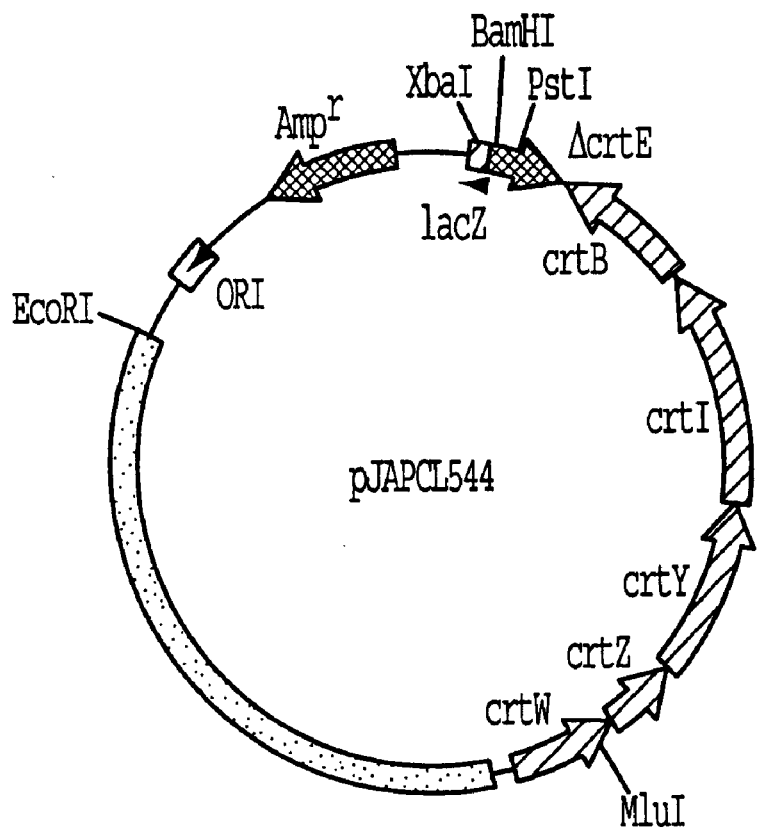
FIG. 29: Isolation of the crt cluster of the strain E-396. Genomic DNA of E-396 was digested overnight with different combinations of restrictions enzymes and separated by agarose gel electrophoresis before transferring the resulting fragments by Southern blotting onto a nitrocellulose membrane. The blot was hybridised with a $^{32}P$ labelled 334 bp fragment obtained by digesting the aforementioned PCR fragment JAPclone8 with BssHII and MluI. An approx. 9.4 kb EcoRI/BamHI fragment hybridizing to the probe was identified as the most appropiate for cloning since it is long enough to potentially carry the complete crt cluster. The fragment was isolated and cloned into the EcoRI and BamHI sites of pBluescriptIIKS resulting in plasmid pJAPCL544.

Isolation of the crt cluster of the strain E-396. Genomic DNA of E-396 was digested overnight with different combinations of restrictions enzymes and separated by agarose gel electrophoresis before transferring the resulting fragments by Southern blotting onto a nitrocellulose membrane. The blot was hybridised with a $^{32}P$ labelled 334 bp fragment obtained by digesting the aforementioned PCR fragment JAPclone8 with BssHII and MluI. An approx. 9,4 kb EcoRI/BamHI fragment hybridizing to the probe was identified as the most appropiate for cloning since it is long enough to potentially carry the complete crt cluster. The fragment was isolated and cloned into the EcoRI and BamHI sites of pBluescriptIIKS resulting in plasmid pJAPCL544 (FIG. 29).

Based on the sequence of the PCR fragment JAPclone8, two primers were synthesized to obtain more sequence information left and right hand of this fragment. FIG. 30 shows the sequence obtained containing the crtW$_{E396}$ (from nucleotide 40 to 768) and crtZ$_{E396}$ (SEQ ID NO: 33) (from nucleotide 765 to 1253) genes of the bacterium E-396. The nucleotide sequence of the crtW$_{E396}$ (SEQ ID NO: 30) gene is shown in FIG. 31 (SEQ ID NO: 31) and the encoded amino acid sequence in FIG. 32 (SEQ ID NO: 32). The nucleotide sequence of the crtZ$_{E396}$ gene is shown in FIG. 33 (SEQ ID NO: 33) and the corresponding amino acid sequence in FIG. 34 (SEQ ID NO: 34). Comparison to the crtW$_{E396}$ gene of E-396 to the crtW gene of *A. aurantiacum* showed 97% identity at the nucleotide level and 99% identity at the amino acid level. For the crtZ gene the values were 98% and 99%, respectively.

Figure 35:
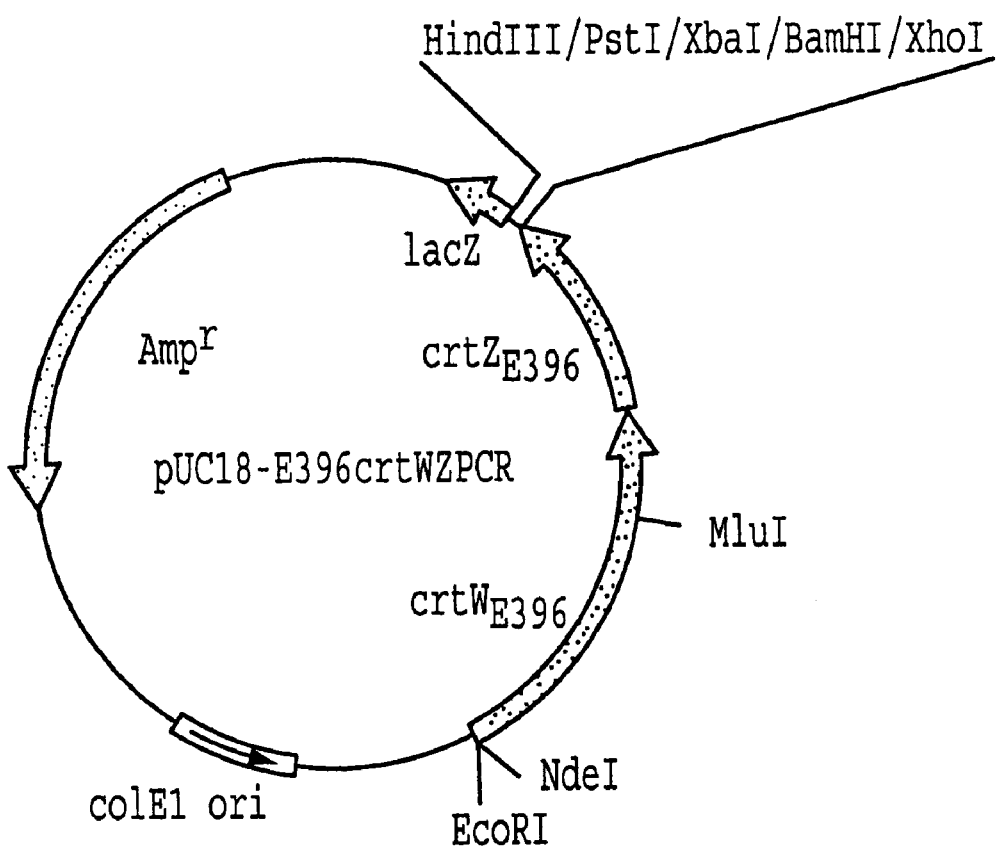
FIG. 35: Diagram of plasmid pUC18-E396crtWZPCR
Figure 36:
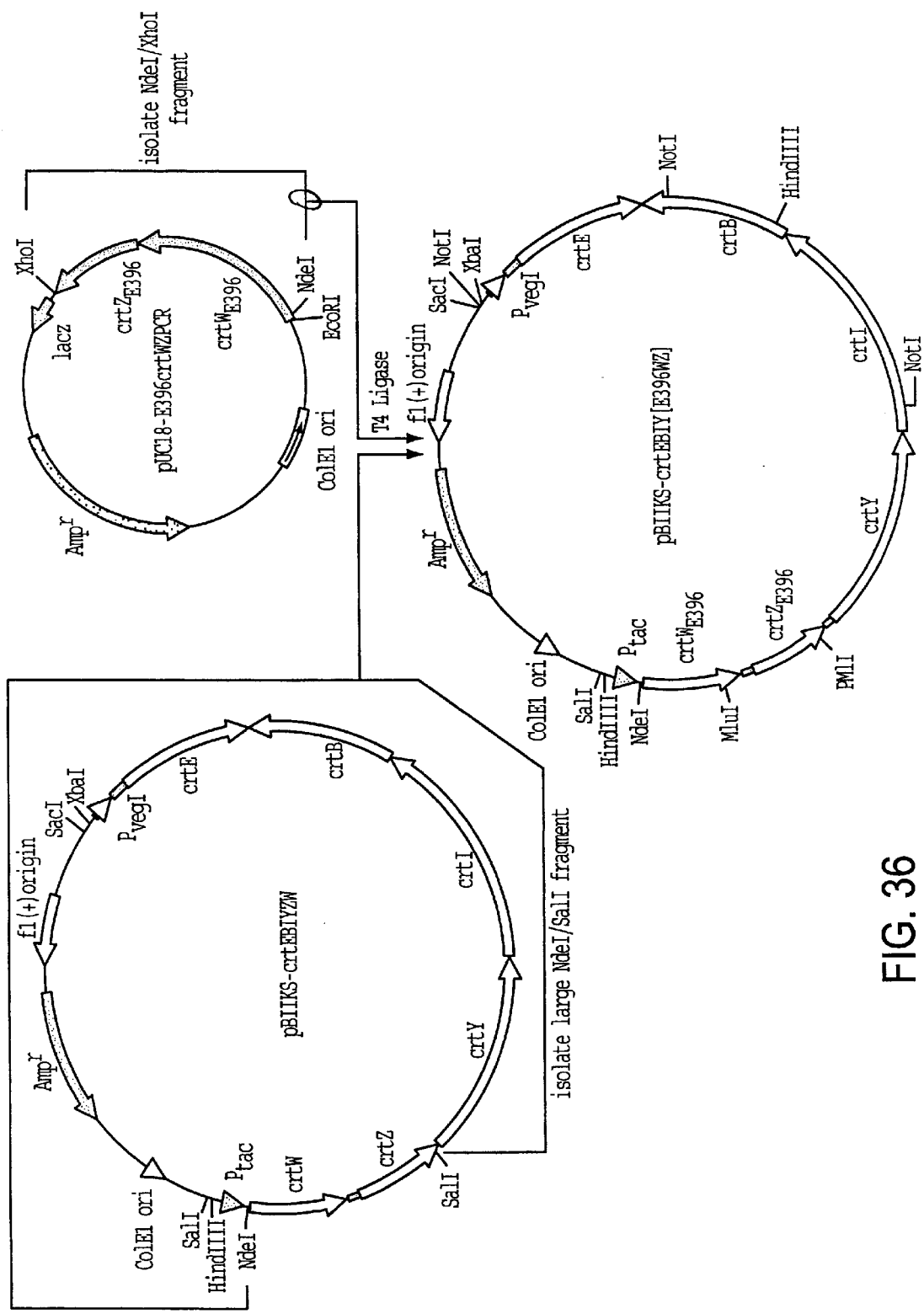
FIG. 36: Construction of plasmid pBIIKS-crtEBIY [E396WZ]

Construction of plasmids: Both genes, crtW$_{E396}$ and crtZ$_{E396}$, which are adjacent in the genome of E-396, were isolated by PCR using primer crtW107 and crtW108 and the ExpandTM High Fidelity PCR system of Boehringer Mannheim, according to the manufacturer's recommendations. To facilitate the subsequent cloning steps (see section below) the primer crt107 (SEQ ID NO: 61) (5'-AT<u>CATATG</u>AGCGCACATGCCCTGCCCAAGGC-3') contains an artificial NdeI site (underlined sequence) spanning the ATG start codon of the crtW$_{E396}$ gene and the reverse primer crtW108 (SEQ ID NO: 62) (5'-AT<u>CTCGAG</u>TCACGTGCGC TCCTGCGCCTCGGCC-3') has an XhoI site (underlined sequence) just downstream of the TGA stop codon of the crtZ$_{E396}$ gene. The final PCR reaction mix had 10 pM of each primer, 2.5 mg genomic DNA of the bacterium E-396 and 3.5 units of the TaqDNA/Pwo DNA polymerase mix. In total 35 cycles were performed with the following cycle profile: 95° C., 1 min; 60° C., 1 min; 72° C. 1 min 30 sec. The PCR product of approx. 1250 bp was isolated from the 1% agarose gel and purified using GENECLEAN before ligation into the SmaI site pUC18 using the Sure-Clone Kit. The resulting construct was named pUC18-E396crtWZPCR (FIG. 35). The functionality of both genes was tested as follows. The crtW$_{E396}$ and crtZ$_{E396}$ gene were isolated from plasmid pUC18-E396crtWZPCR with NdeI and XhoI and cloned into the NdeI and SalI site of plasmid pBIIKS-crtEBIYZW resulting in plasmid pBIIKS-crtEBIY[E396WZ] (FIG. 36). *E. coli* TG1 cells transformed with this plasmid produced astaxanthin, adonixanthin and adonirubin but no zeaxanthin (Table 4).

Figure 37:
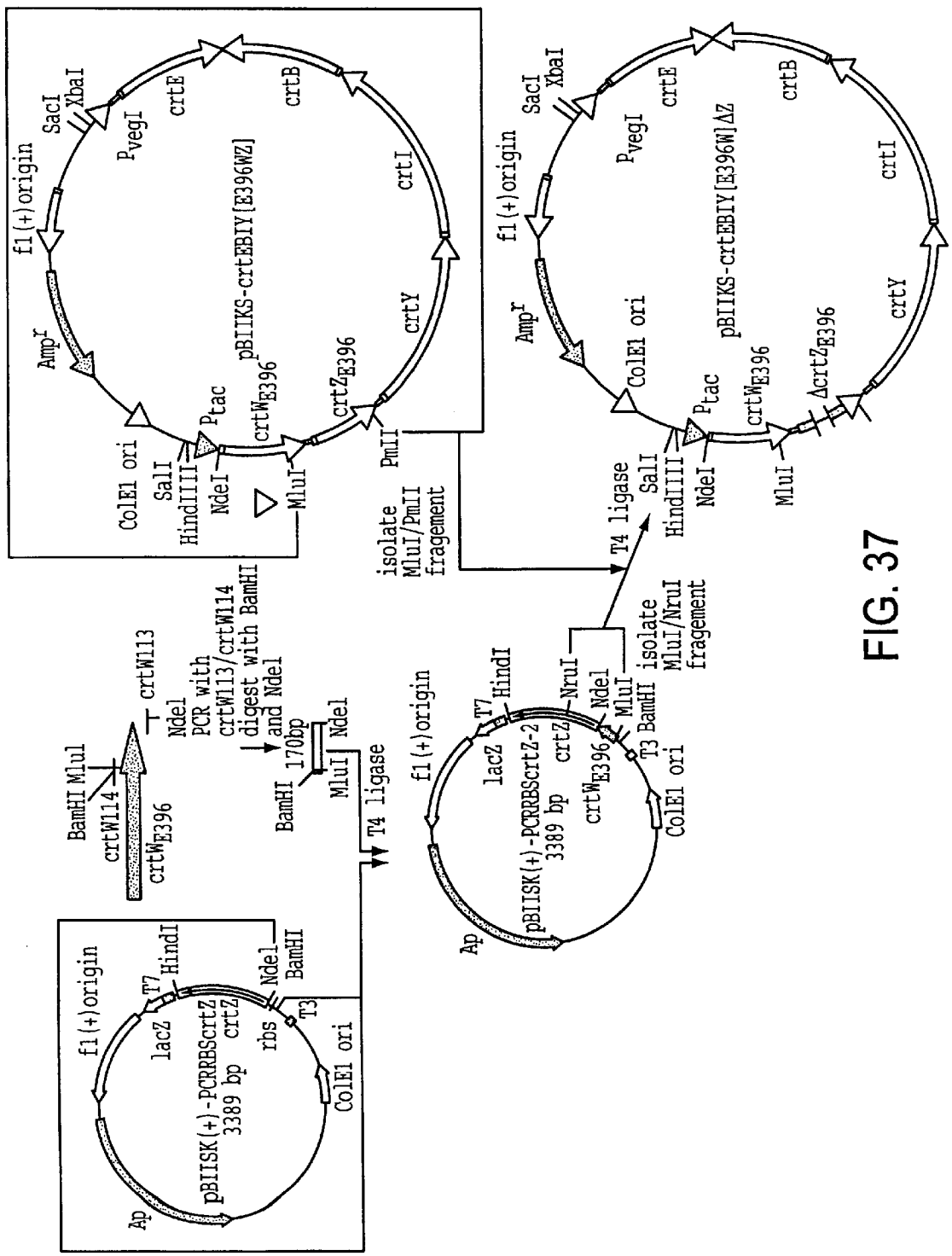
FIG. 37: Construction of plasmid pBIIKS-crtEBIY [E396W]DZ which has a truncated non-functional crtZ gene FIGS. 38A, 38B 463 bp PstI-BamHI fragment originating from the 3' end of the insert of pJAPCL544 (FIG. 29) highlighted a ~1300 bp-long PstI-PstI fragment. This fragment was isolated and cloned into the PstI site of pBSIIKS (+) resulting in plasmid pBSIIKS-#1296. The sequence of the insert is shown (small cap letters refer to new sequence obtained. Capital letters show the sequence also present in the 3' of the insert of plasmid PJAPCL544).

Plasmid pBIIKS-crtEBIY[E396W]DZ has a truncated non-functional crtZ gene. FIG. 37 outlines the construction of this plasmid. The PCR reaction was run as outlined elsewhere in the text using primers crtW113 (SEQ ID NO: 63)/crtW114 (SEQ ID NO: 64) and 200 ng of plasmid pUC18-JAPclone8 as template using 20 cycles with the following protocol: 95° C., 45 sec/ 62° C., 20 sec/ 72° C., 20 sec)

primer crtW113 (SEQ ID NO: 63) (5'-ATATACATATGGTGTCCCCCTTGGTGCGGGTGC-3')
primer crtW114 (SEQ ID NO: 64) (5'-TATGGATCCGACGCGTTCCCGGACCGCCACAATGC-3')

The resulting 150 bp fragment was digested with BamHI and NdeI and cloned into the corresponding sites of pBIISK (+)-PCRRBScrtZ resulting in the construct pBIISK(+)-PCRRBScrtZ-2.The final plasmid carrying the genes crtE, crtB, crtI, crtY of Flavobacterium, the crtW$_{E396}$ gene of E-396 and a truncated non-functional crtZ gene of Flavobacterium was obtained by isolating the MluI/NruI fragment (280 bp) of pBIISK(+)-PCRRBScrtZ-2 and cloning it, into the MluI/PmlI sites of plasmid pBIIKS-crtEBIY[E396WZ]. *E. coli* cells transformed with this plasmid produced 100% canthaxanthin (Table 4; "CRX": cryptoxanthin; "ASX": astaxanthin; "ADX": adonixanthin; "ZXN": zeaxanthin; "ECH": echinenone; "HECH": 3-hydroxyechinenone; "CXN": canthaxanthin; "BCA": β-carotene; "ADR": adonirubin; Numbers indicate the % of the individual carotenoid of the total carotenoids produced in the cell.).

TABLE 4

| plasmid | CRX | ASX | ADX | ZXN | ECH | HECH | CXN | BCA | ADR |
|---|---|---|---|---|---|---|---|---|---|
| pBIIKScrtEBIYZW | 1.1 | 2.0 | 44.2 | 52.4 | <1 | <1 | <1 | | |
| pBIIKS-crtEBIY[E396WZ] | | 74.4 | 19.8 | | | | | | 5.8 |
| pBIIKS-crtEBIY[E396W]DZ | | | | | | | 100 | | |

The results of *E. coli* transformants carrying pBIIKScrtE-BIYZW (see example 7) are also shown in Table 4 to indicate the dramatic effect of the new genes crtW$_{E396}$ and crtZ$_{E396}$ on the carotenoids produced in these new transformants.

EXAMPLE 9

Cloning of the Remaining CRT Genes of the Gram Negative Bacterium E-396.

TG1 *E. coli* transformants carrying the pJAPCL544 plasmid did not produce detectable quantities of carotenoids (results not shown). Sequence analysis and comparison of the 3' (BamHI site) of the insert of plasmid pJAPCL544, to the crt cluster of Flavobacterium R1534 showed that only part of the C-terminus of the crtE gene was present. This result explained the lack of carotenoid production in the aforementioned transformants. To isolate the missing N-terminal part of the gene, genomic DNA of E-396 was digested by 6 restrictions enzymes in different combinations: EcoRI, BamHI, PstI, SacI, SphI and XbaI and transferred by the Southern blot technique to nitrocellulose. Hybridization of this membrane with the $^{32}$P radio-labelled probe (a 463 bp PstI-BamHI fragment originating from the 3' end of the insert of pJAPCL544 (FIG. 29) highlighted a ~1300 bp-long PstI-PstI fragment. This fragment was isolated and cloned into the PstI site of pBSIIKS(+) resulting in plasmid pBSIIKS-#1296. The sequence of the insert is shown in FIG. 38 (SEQ ID NO: 35) (small cap letters refer to new sequence obtained. Capital letters show the sequence also present in the 3' of the insert of plasmid pJAPCL544). The complete crtE gene has therefore a length of 882 bp (see FIG. 39) and encodes a GGPP synthase of 294 amino acids (FIG. 40) (SEQ ID NO: 37). The crtE enzyme has 38% identity with the crtE amino acid sequence of *Erwinia herbicola* and 66% with Flavobacterium R1534 WT.

Figure 41:
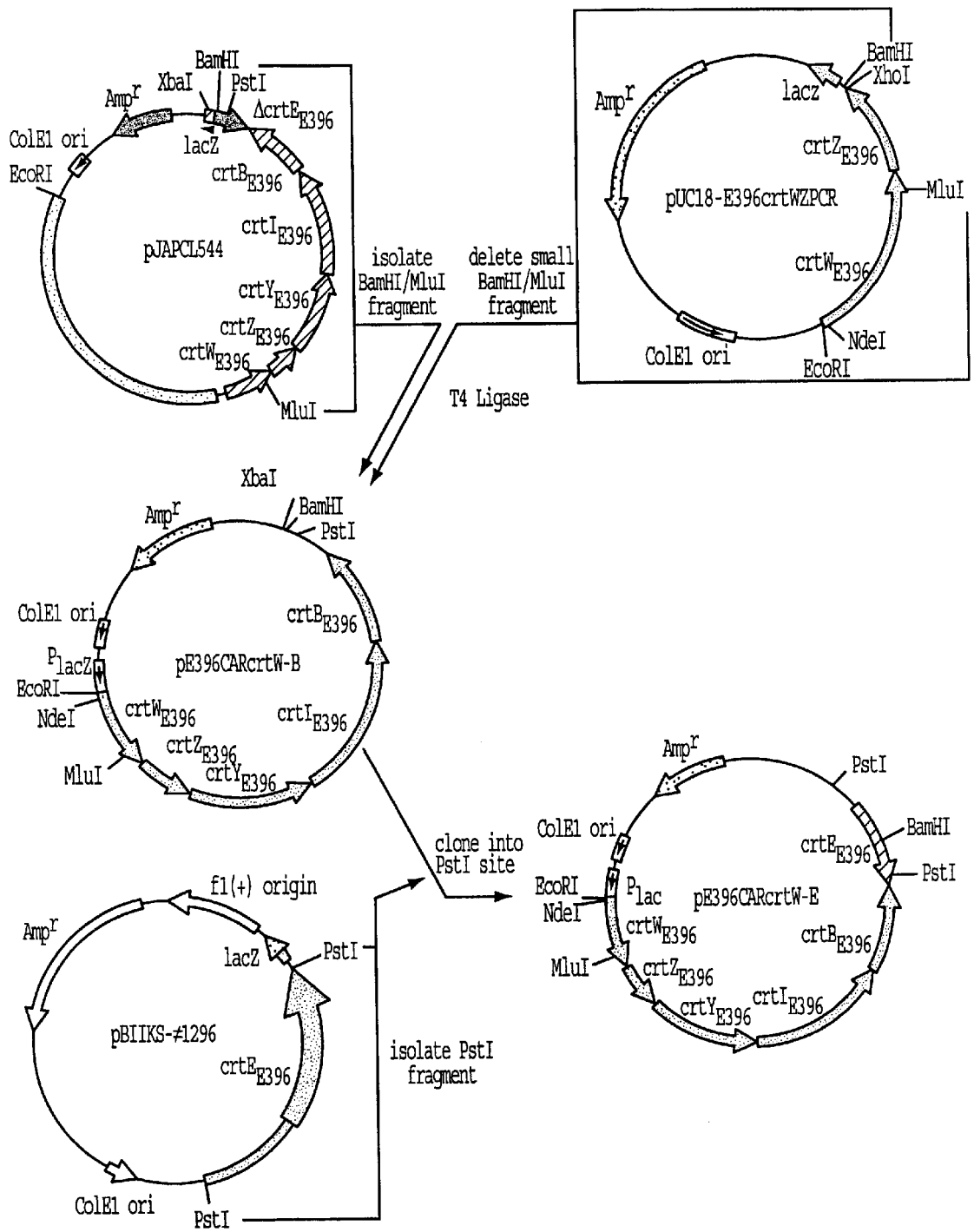
FIG. 41: Construction of plasmid carrying the complete crt cluster of E-396 (pE396CARcrtW-E)

Construction of plasmids. To have a plasmid carrying the complete crt cluster of E-396, the 4.7 kb MluI/BamHI fragment encoding the genes crtW, crtZ, crtY, crtI and crtB was isolated from pJAPCL544 and cloned into the MluI/BamHI sites of pUC18-E396crtWZPCR (see example 8). The new construct was named pE396CARcrtW-B (FIG. 41) and lacked the N-terminus of the crtE gene. The missing C-terminal part of the crtE gene was then introduced by ligation of the aforementioned PstI fragment of pBIIKS-#1296 between the PstI sites of pE396CARcrtW-B. The resulting plasmid was named pE396CARcrtW-E (FIG. 41). The carotenoid distribution of the *E. coli* transformants carrying aforementioned plasmid were: adonixanthin (65%), astaxanthin (8%) and zeaxanthin (3%). The % indicated reflects the proportion of the total amount of carotenoid produced in the cell.

EXAMPLE 10
Astaxanthin and Adonixanthin Production in Flavobacterium R1534

Among bacteria Flavobacterium may represent the best source for the development of a fermentative production process for 3R, 3R' zeaxanthin. Derivatives of Flavobacterium sp. strain R1534, obtained by classical mutagenesis have attracted in the past two decades wide interest for the development of a large scale fermentative production of zeaxanthin, although with little success. Cloning of the carotenoid biosynthesis genes of this organism, as outlined in example 2, may allow replacement of the classical mutagenesis approach by a more rational one, using molecular tools to amplify the copy number of relevant genes, deregulate their expression and eliminate bottlenecks in the carotenoid biosynthesis pathway. Furthermore, the introduction of additional heterologous genes (e.g. crtW) will result in the production of carotenoids normally not synthesised by this bacterium (astaxanthin, adonirubin, adonixanthin, canthaxanthin, echinenone). The construction of such recombinant Flavobacterium R1534 strains producing astaxanthin and adonixanthin will be outlined below.

Gene transfer into Flavobacterium sp.

Plasmid transfer by conjugative mobilization. For the conjugational crosses we constructed plasmid pRSF1010-Amp$^r$, a derivative of the small (8.9 kb) broad host range plasmid RSF1010 (IncQ incompatibility group) [Guerry et al., J. Bacteriol. 117:619–630 (1974)] and used *E. coli* S17-1 as the mobilizing strain [Priefer et al., J. Bacteriol. 163:324–330 (1985)]. In general any of the IncQ plasmids (e.g. RSF1010, R300B, R1162) may be mobilized into rifampicin resistant Flavobacterium if the transfer functions are provided by plasmids of the IncP1 group (e.g. R1, R751).

Rifampicin resistant (Rif$^r$) Flavobacterium R1534 cells were obtained by selection on 100 mg rifampicin/ml. One resistant colony was picked and a stock culture was made. The conjugation protocol was as follows:

Day 1 grow 3 ml culture of Flavobacterium R1534 Rif$^r$ for 24 hours at 30° C. in Flavobacter medium (F-medium) (see example 1)

grow 3 ml mobilizing *E. coli* strain carrying the mobilizable plasmid O/N at 37° C. in LB medium. (e.g *E. coli* S17-1 carrying pRSF1010-Amp$^r$ or *E. coli* TG-1 cells carrying R751 and pRSF1010-Amp$^r$)

Day 2 pellet 1 ml of the Flavobacterium R1534 Rif$^r$ cells and resuspend in 1 ml of fresh F-medium.

pellet 1 ml of *E. coli* cells (see above) and resuspend in 1 ml of LB medium.

donor and recipient cells are then mixed in a ratio of 1:1 and 1:10 in an Eppendorf tube and 30 ml are then applied onto a nitrocellulose filter plated on agar plates containing F-medium and incubated O/N at 30° C.

Day 3 the conjugational mixtures were washed off with F-medium and plated on F-medium containing 100 mg rifampicin and 100 mg ampicillin/ml for selection of transconjugants and inhibition of the donor cells.

Day 6–8

Arising clones are plated once more on F-medium containing 100 mgRif and 100 mg Amp/ml before analysis.

Plasmid transfer by electroporation. The protocol for the eletroporation is as follows:

1. add 10 ml of O/N culture of Flavobacterium sp. R1534 into 500 mlF-medium and incubate at 30° C. until OD600=0.8–0.1
2. harvest cells by centrifugation at 4000 g at 4° C. for 10 min.
3. wash cells in equal volume of ice-cold deionized water (2 times)
4. resuspend bacterial pellet in 1 ml ice-cold deionized water
5. take 50 ml of cells for electroporation with 0.1 mg of plasmid DNA
6. electroporation was done using field strengths between 15 and 25 kV/cm and 1–3 ms.
7. after electroporation cells were immediately diluted in 1 ml of F-medium and incubated for 2 hours at 30° C. at 180 rpm before plating on F-medium plates containing the respective selective antibioticum.

Figure 42:
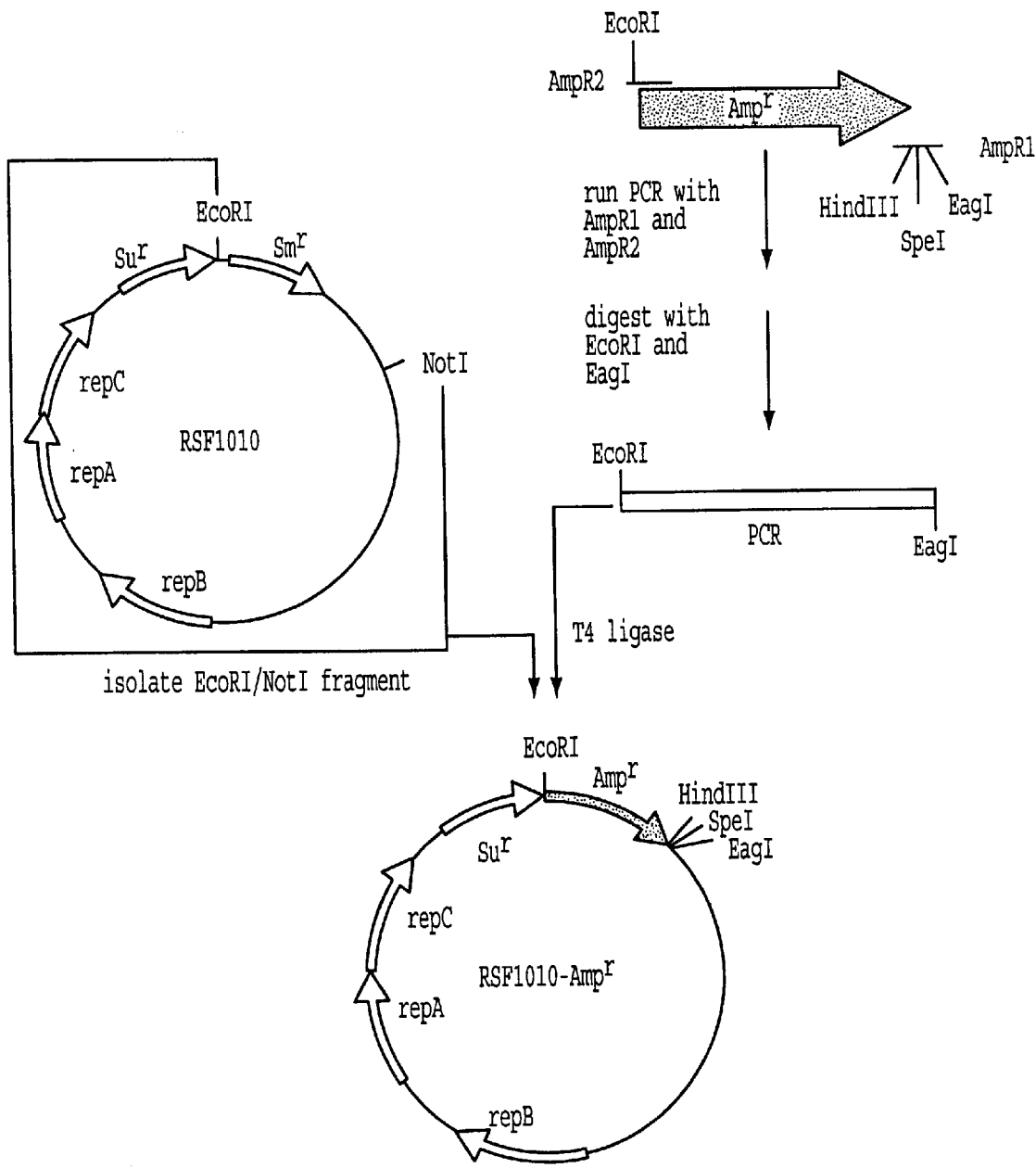
FIG. 42: Construction of plasmid pRSF1010-Amp$^r$

Plasmid constructions: Plasmid pRSF101-Amp$^r$ was obtained by cloning the Amp$^r$ gene of pBR322 between the EcoRI/NotI sites of RSF1010. The Amp$^r$ gene originates from pBR322 and was isolated by PCR using primers AmpR1 (SEQ ID NO: 65) and AmpR2 (SEQ ID NO: 66) as shown in FIG. 42.

AmpR1 (SEQ ID NO: 65):

5'-TATAT<u>CGGCCGACTAGTAAGCTT</u>CAAAAAGGATC TTCACCTAG-3' the underlined sequence contains the introduced restriction sites for EagI, SpeI and HindIII to facilitate subsequent constructions.

AmpR2 (SEQ ID NO: 66):

5'-ATAT<u>GAATTC</u>AATAATATTGAAAAAGGAAG-3' the underlined sequence corresponds to an introduced EcoRI restriction site to facilitate cloning into RSF1010 (see FIG. 42).

The PCR reaction mix had 10 pM of each primer (AmpR1 (SEQ ID NO: 65)/AmpR2 (SEQ ID NO: 66)), 0.5 mg plasmid pBR322 and 3.5 units of the TaqDNA/Pwo DNA polymerase mix. In total 35 amplification cycles were made with the profile: 95° C., 45 sec; 59° C., 45 sec, 72° C., 1 min. The PCR product of approx. 950 was extracted once with phenol/chloroform and precipitated with 0.3 M NaAcetate and 2 vol. Ethanol. The pellet was resuspended in H$_2$O and digested with EcoRI and EagI O/N. The digestion was separated by electrophoresis and the fragment isolated from the 1% agarose gel and purified using GENECLEAN before ligation into the EcoRI and NotI sites of RSF1010. The resulting plasmid was named pRSF1010-Amp$^r$ (FIG. 42).

Figure 43:
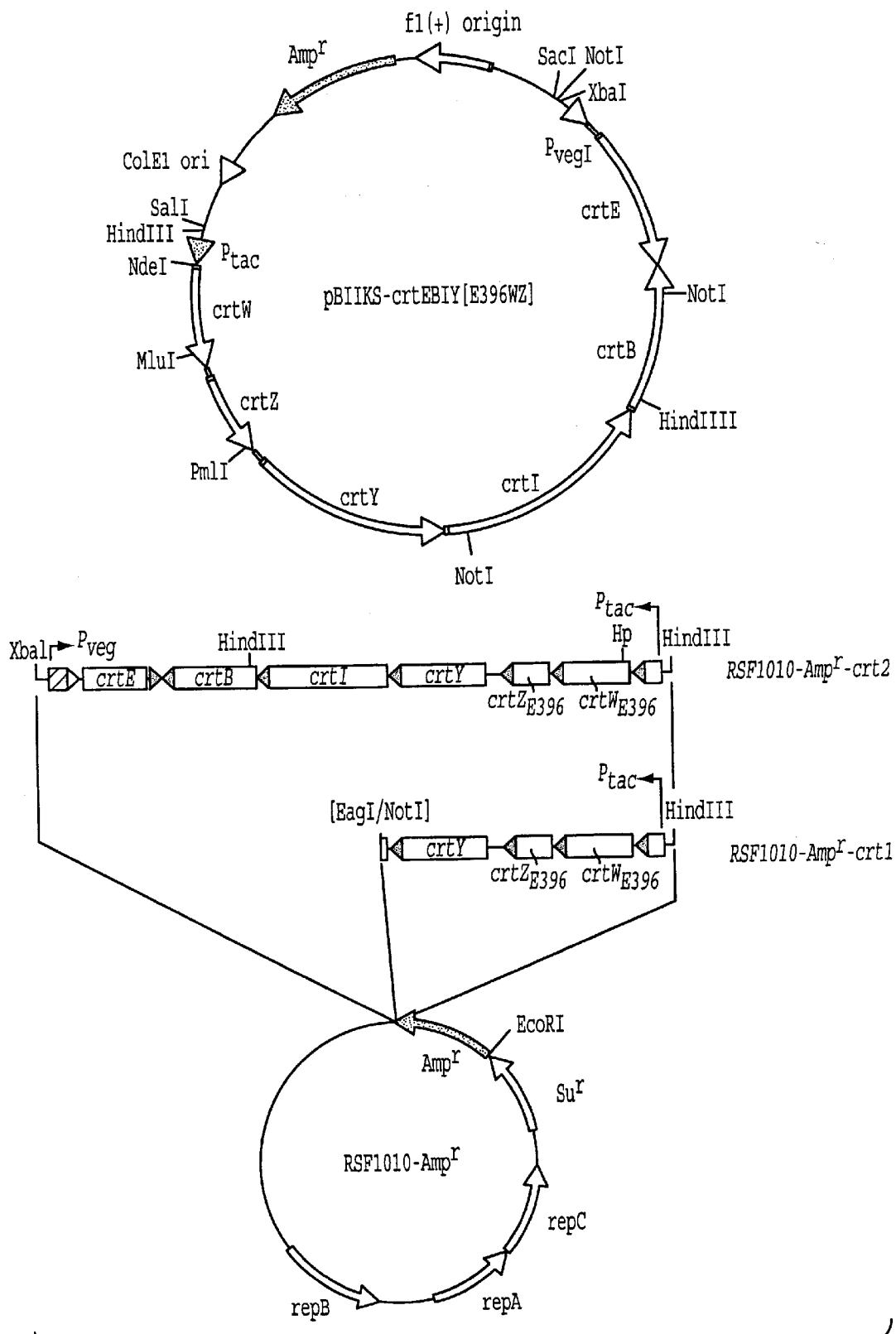
FIG. 43: Construction of plasmids RSF1010-Amp$^r$-crt1 and RSF1010-Ampr-crt2

Plasmid RSF1010-Ampr-crt1 was obtained by isolating the HindIII/NotI fragment of pBIIKS-crtEBIY[E396WZ] and cloning it between the HindIII/EagI sites of RSF1010-Amp$^r$ (FIG. 43). The resulting plasmid RSF1010-Ampr-crt1 carries crtW$_{E396}$, crtZ$_{E396}$, crtY genes and the N-terminus of the crtI gene (non-functional). Plasmid RSF1010-Ampr-crt2 carrying a complete crt cluster composed of the genes crtW$_{E396}$ and crtZ$_{E396}$ of E-396 and the crtY, crtI, crtB and crtE of Flavobacterium R1534 was obtained by isolating the large HindIII/XbaI fragment of pBIIKS-crtEBIY[E396WZ] and cloning it into the SpeI/HindIII sites of RSF1010-Amp$^r$ (FIG. 43).

Flavobacterium R1534 transformants carrying either plasmid RSF1010-Amp$^r$, Plasmid RSF1010-Amp$^r$-crt1 or Plasmid RSF1010-Amp$^r$-crt2 were obtained by conjugation as outlined above using *E. coli* S17-1 as mobilizing strain.

Comparison of the carotenoid production of two Flavobacterium transformants. Overnight cultures of the individual transformants were diluted into 20 ml fresh F-medium to have a final starting OD600 of 0.4. Cells were harvested after growing for 48 hours at 30° C. and carotenoid contents were analysed as outlined in example 7. Table 5 shows the result of the three control cultures Flavobacterium [R1534 WT], [R1534 WT RifR] (rifampicin resistant) and [R1534WT Rifr RSF1010-AmpR] (carries the RSF1010-Amp$^r$ plasmid) and the two transformants [R1534 WT RSF1010-AmpR-crt1] and [R1534 WT RSF1010-AmpR-crt2]. Both latter transformants are able to synthesise astaxanthin and adonixanthin but little zeaxanthin. Most interesting is the [R1534 WT RSF1010-AmpR-crt2] Flavobacterium transformant which produces approx. 4 times more carotenoids than the R1534 WT. This increase in total carotenoid production is most likely due to the increase of the number of carotenoid biosynthesis clusters present in these cell (e.g. corresponds to the total copy number of plasmids in the cell).

TABLE 5

| Transformant | carotenoids % of total dry weight | total carotenoid content in % of dry weight |
| --- | --- | --- |
| R1534 WT | 0.039% b-Carotin 0.001% b-Cryptoxanthin 0.018% Zeaxanthin | 0.06% |
| R1534 Rifr | 0.036% b-Carotin 0.002% b-Cryptoxanthin 0.022% Zeaxanthin | 0.06% |
| R1534 Rifr [RSF1010-Ampr] | 0.021% b-Carotin 0.002% b-Cryptoxanthin 0.032% Zeaxanthin | 0.065% |
| R1534 Rifr [RSF1010-Ampr-crt1] | 0.022% Astaxanthin 0.075% Adonixanthin 0.004% Zeaxanthin | 0.1% |
| R1534 Rifr [RSF1010-Ampr-crt2] | 0.132% b-Carotin 0.006% Echinenon 0.004% Hydroxyechinenon 0.003% b-Cryptoxanthin 0.044% Astaxanthin 0.039% Adonixanthin 0.007% Zeaxanthin | 0.235% |

SEQUENCE LISTING

```
<160> NUMBER OF SEQ ID NOS: 66

<210> SEQ ID NO 1
<211> LENGTH: 8625
<212> TYPE: DNA
<213> ORGANISM: Flavobacterium sp. R1534
<220> FEATURE:
<221> NAME/KEY: unsure
<222> LOCATION: (8348)..(8349)
<220> FEATURE:
<221> NAME/KEY: unsure
<222> LOCATION: (8539)..(8540)
<220> FEATURE:
<221> NAME/KEY: unsure
<222> LOCATION: (8581)
<220> FEATURE:
<221> NAME/KEY: unsure
<222> LOCATION: (8590)
<220> FEATURE:
<221> NAME/KEY: unsure
```

<222> LOCATION: (8592)
<220> FEATURE:
<221> NAME/KEY: unsure
<222> LOCATION: (8602)..(8604)

<400> SEQUENCE: 1

| | | | | | |
|---|---|---|---|---|---|
| ggatccgcgc | ctggccgttc | gcgatcagca | gccgcccttg | cggatcggtc | agcatcatcc   60 |
| ccatgaaccg | cagcgcacga | cgcagcgcgc | gccccagatc | gggcgcgtcc | agcacggcat  120 |
| gcgccatcat | cgcgaaggcc | cccggcggca | tggggcgcgt | gcccattccg | aagaactcgc  180 |
| agcctgtccg | ctgcgcaagg | tcgcgccaga | tcgcgccgta | ttccgatgca | gtgacgggcc  240 |
| cgatgcgcgt | gggcccgccc | tgccccgccg | ccaccagcgc | atcgcgcacg | aaccccttccg  300 |
| agatgatgtg | ctgatccatg | gcccgtcatt | gcaaaaccga | tcaccgatcc | tgtcgcgtga  360 |
| tggcattgtt | tgcaatgccc | cgagggctag | gatggcgcga | aggatcaagg | ggggagaga  420 |
| catgaaaatc | gagggacggg | tctttgtcgt | cacgggcgcc | gcatcgggtc | tggggcggc  480 |
| ctcggcgcgg | atgctggccc | aaggcggcgc | gaaggtcgtg | ctggccgatc | tggcggaacc  540 |
| gaaggacgcg | cccgaaggcg | cggttcacgc | ggcctgcgac | gtgaccgacg | cgaccgctgc  600 |
| gcagacggcc | atcgcgctgg | cgaccgaccg | cttcggcagg | ctggacggcc | ttgtgaactg  660 |
| cgcgggcatc | gcgccggccg | aacggatgct | gggccgcgac | gggccgcatg | gactggacag  720 |
| cttttgcccgt | gcggtcacga | tcaacctgat | cggcagcttc | aacatggccc | gccttgcagc  780 |
| cgaggcgatg | gcccggaacg | agcccgtccg | gggcgagcgt | ggcgtgatcg | tcaacacggc  840 |
| ctcgatcgcg | gcgcaggacg | gacagatcgg | acaggtcgcc | tatgcggcca | gcaaggcggg  900 |
| cgtggcgggc | atgacgctgc | cgatggcccg | cgaccttgcg | cggcacggca | tccgcgtcat  960 |
| gaccatcgcg | cccggcatct | ccgcaccccc | gatgctggag | gggctgccgc | aggacgttca 1020 |
| ggacagcctg | ggcgcggcgg | tgcccttccc | ctcgcggctg | ggagagccgt | cggaatacgc 1080 |
| ggcgctgttg | caccacatca | tcgcgaaccc | catgctgaac | ggagaggtca | tccgcctcga 1140 |
| cggcgcattg | cgcatggccc | ccaagtgaag | gagcgtttca | tggacccccat | cgtcatcacc 1200 |
| ggcgcgatgc | gcaccccgat | ggggggcattc | cagggcgatc | ttgccgcgat | ggatgccccg 1260 |
| acccttggcg | cggacgcgat | ccgcgccgcg | ctgaacggcc | tgtcgcccga | catggtggac 1320 |
| gaggtgctga | tgggctgcgt | cctcgccgcg | ggccagggtc | aggcaccggc | acgtcaggcg 1380 |
| gcgcttggcg | ccggactgcc | gctgtcgacg | ggcacgacca | ccatcaacga | gatgtgcgga 1440 |
| tcgggcatga | aggccgcgat | gctgggccat | gacctgatcg | ccgcgggatc | ggcgggcatc 1500 |
| gtcgtcgccg | gcgggatgga | gagcatgtcg | aacgcccccct | acctgctgcc | caaggcgcgg 1560 |
| tcggggatgc | gcatgggcca | tgaccgtgtg | ctggatcaca | tgttcctcga | cgggttggag 1620 |
| gacgcctatg | acaagggccg | cctgatgggc | accttcgccg | aggattgcgc | cggcgatcac 1680 |
| ggtttcacccc | gcgaggcgca | ggacgactat | gcgctgacca | gcctggcccg | cgcgcaggac 1740 |
| gccatcgcca | gcggtgcctt | cgccgccgag | atcgcgcccg | tgaccgtcac | ggcacgcaag 1800 |
| gtgcagacca | ccgtcgatac | cgacgagatg | cccggcaagg | cccgccccga | aagatccccc 1860 |
| catctgaagc | ccgccttccg | tgacggtggc | acggtcacgg | cggcgaacag | ctcgtcgatc 1920 |
| tcggacgggg | cggcggcgct | ggtgatgatg | cgccagtcgc | aggccgagaa | gctgggcctg 1980 |
| acgccgatcg | cgcggatcat | cggtcatgcg | acccatgccg | accgtccggg | cctgttcccg 2040 |
| acggccccca | tcggcgcgat | cgcaagctg | ctggaccgca | cggacacccg | ccttggcgat 2100 |
| tacgacctgt | tcgaggtgaa | cgaggcattc | gccgtcgtcg | ccatgatcgc | gatgaaggag 2160 |

```
cttggcctgc cacacgatgc cacgaacatc aacggcgggg cctgcgcgct tgggcatccc    2220
atcggcgcgt cggggggcgcg gatcatggtc acgctgctga acgcgatggc ggcgcggggc    2280
gcgacgcgcg gggccgcatc cgtctgcatc ggcggggggcg aggcgacggc catcgcgctg    2340
gaacggctga gctaattcat ttgcgcgaat ccgcgttttt cgtgcacgat ggggggaaccg    2400 gaaacggcca cgcctgttgt ggttgcgtcg acctgtcttc gggccatgcc cgtgacgcga    2460
tgtggcaggc gcatggggcg ttgccgatcc ggtcgcatga ctgacgcaac gaaggcaccg    2520
atgacgccca agcagcaatt cccctacgc gatctggtcg agatcaggct ggcgcagatc    2580
tcgggccagt tcggcgtggt ctcggcccg ctcggcgcgg ccatgagcga tgccgccctg    2640
tcccccggca aacgctttcg cgccgtgctg atgctgatgg tcgccgaaag ctcgggcggg    2700
gtctgcgatg cgatggtcga tgccgcctgc gcggtcgaga tggtccatgc cgcatcgctg    2760
atcttcgacg acatgcccctg catggacgat gccaggaccc gtcgcggtca gcccgccacc    2820
catgtcgccc atggcgaggg gcgcgcggtg cttgcgggca tcgccctgat caccgaggcc    2880
atgcggattt tgggcgaggc gcgcggcgcg acgccggatc agcgcgcaag gctggtcgca    2940
tccatgtcgc gcgcgatggg accggtgggg ctgtgcgcag ggcaggatct ggacctgcac    3000
gcccccaagg acgccgccgg gatcgaacgt gaacaggacc tcaagaccgg cgtgctgttc    3060
gtcgcgggcc tcgagatgct gtccattatt aagggtctgg acaaggccga gaccgagcag    3120
ctcatggcct tcggcgtca gcttggtcgg gtcttccagt cctatgacga cctgctggac    3180
gtgatcggcg acaaggccag caccggcaag gatacgcgc cgacaccgc cgcccccggc    3240 ccaaagggcg gcctgatggc ggtcggacag atgggcgacg tggcgcagca ttaccgcgcc    3300 agccgcgcg aactggacga gctgatgcgc acccggctgt ccgcgggggg gcagatcgcg    3360
gacctgctgg cccgcgtgct gccgcatgac atccgccgca gcgcctaggc gcgcggtcgg    3420
gtccacaggc cgtcgcggct gatttcgccg ccgcgcaggc gcgatgcggc cgcgtccaag    3480
cctccgcgcg ccagaagccc gatcttggca gccttcgacg tgctgatccg ctggcgatag    3540
gcctcggggc caccctgccg gatgcgcgtc ccgattgcgc gatagatacg cagcgcggcg    3600
gcgatcgacc acgcgcagcg cggcggcaga tgcggaagcc cctgccgcgc cgaggcataa    3660
tagggctcgg ccgcgtcaag caggcggatg atgacggaat agagcgcgtc cgaaggcacc    3720
ggaccctcaa ccgtcgcccc cgcctcggcc agccagtcgg caggcagata gcagcgcccg    3780
atggcggcat cgtcgatcac gtcgcgagcg atgttcgtca gctggaacgc aaggcccaga    3840
tcgcaggcgc gatccagcac cgcatcgtcc tgcacgccca tcacccgcgc catcatcacg    3900
cccacgaccc ccgcgacgtg gtaggaatat tccagcacgt catccaggct gcggtattcg    3960
cgatccgcga catccatcgc gaaaccctcg atcaggtcca tcggccaaag gtccgggaaa    4020
tcatgccgcc gggcgacctg gcgcagcgcc gcgaagggcg gcgacatcgg gccgtcctcg    4080
tgcagcgcgg ccagcgtgtc ggcgcgcagc gccccagcc gcgcctgtgg gtcgccgccc    4140
gcctcggggg cagaacccat cacctgcccg tcgatcacgt catccgcatg cctgcaccag    4200
gcatagagca tgaccgtatc ctcgcggatg ccgggcggca tcagcttggc cgcctgcgcg    4260
aagctttgcg aaccctgcgc gatggccgct tcggaagtcg ccgtcagatc ggtcatgcga    4320
cggccaggtc cgacagcatg acctgcgccg tggccttggc gctgccaacg acacccggga    4380
tgcccgcacc cggatgcgtg cccgccccca cgatgtagaa gttcgggatc gcgcggtcgc    4440
ggttatgcgg gcggaaccag gcggattgcg tcaggatcgc ctcgaccgag aaggcgctgc    4500
cgtgatgggc cgacagttcg gtgctgaaat cggcgggggct gaagatgcgg ctgacggtca    4560
```

```
ggtgcttgcg caggtcgggg atggcgcggc gctccagttc ctcgaagatg cgctcggcat      4620
agcccggggc ctcggcttcc caatcgacat cggcgcggcc cagatgcgga acgggcgcaa      4680
ggacgtaatg cgtggacatc ccctcggggg ccaggctggg atcggtcacg cagggcgaat      4740
gcagatacat cgagaaatcg tccggcaggc gtggcccgtt gaagatctcg ttcaccagcc      4800
ccttgtagcg cgggccgaag atgacgctgt ggtgggccag gttctcgggg cgcttggaca      4860
ggccgaaatg cagcacgaac agcgacatcg accagcgctg ccggttcagg atcgcggcct      4920
tggtgcgccc gcggcgggta tggcccagca ggtcgcgata gctgtgcatc acgtcgccgt      4980
tgctggccac cgtatccgcg cgcaactgcc gcccgtccag cagcgtgacg cccgtggcgc      5040
gatcgccctc ggtgtcgatc cgcgtgacgc gggcattcag cagcagcgtg ccgccaagac      5100
gctcgaacag ggcgaccatg cccgcgacca gctggttggt gccgcccttg gcgaaccaga      5160
cgccgccgcg ccgttccagc gcatggatca gcgcatagat cgagctggtc gaaaacgggt      5220
tcccgccgac cagcagcgtg tggaacgaga aggcctgccg cagatgcggg tcctggatga      5280
agcgcgccac catgctgtgg accgagcggt atgcctgcag gcgcatcagc gccggcgcgg      5340
cgttcagcat ctggcccagc ttcaggaagg gcgtggtccc cagcttcaga taccccctcgc     5400
gatagacctc ctcggcgtaa tcgtggaagc ggcgatagcc atcgacatcg gcgggattga      5460
aggaggcgac ctggcggatc agctcgtcgt cgtcgttcac gtattcgaag ctgcggccgt      5520
ccgcccatgt cagccggtag aagggcgaga ccggcagcag cgtcacgtca cgctccatcg      5580
gttggccgct gagggcccac agctctcgca ggctgtcggg gtcggtcacg accgtcgggc      5640
ctgcatcgaa gacgtggccc tgatcgttcc agacataggc gcggccgccg gcttgtcgc      5700
gggcctcgac gatggtggtc gcgatgccgg ccgattgcag gcggatggca agcgcaagcc      5760
cgccgaaacc tgcgccgatg acgatggcgg aactcatgct ctctcctgca gcaggggcg      5820
ttcgggcagg cagcgcacgg cctgcgacag cggaatgggc gggcgtccgg tgacgatgcg      5880
aagccggtcg gccaatgtca ggcgcccggc atagaagcgc tcgatcagcg gctgcggcag      5940
gcggtagaac cgctgcagca ggcgatagcg acggtcgggc gggcagccgc ggaacagcat      6000
ccggttcagc agccgcagga agcggtcgcg atccgcgcga tcgatggccc agccgcgcac      6060
cgcgcgacgg gcggacgcgg tcgtcaggtc gcgcgccgcg atggcatccg cgacctgcgc      6120
ggcatagggc agcgaatatc cggtgacggg gtggaacagc cctgccccca gcccaaccgg      6180
caccgccccc tgcgcgtggt cgcgccagaa gcctatggcg tcatgggcca gcgcgatggg      6240
caggatgccc ctttcgcgcc gcatctcctg cccggtccag ccccgcctgg cggcatagtc      6300
cagcgacgcc tgcgccagcg cgccatcgtc cagatcgccc ccgtcgctgt agcgcgtatc      6360
ctcgatcagg atgcgggtgg gactgaaggg cagcagatag atgaagcggt acccgtccat      6420
ctgcggaacg gtcgcgtcca tgatcatcgg gcgctcgacg ccatgggggg cgtcggtctc      6480
gatctcgacg cccacgaatt tctggaaacc cacggtcagg tgcgggtct cgacggcacc       6540
acgggcgtcg atcacgcagg cagcctcgat ccgcgagccg tccgtcagcg tcgcgccggt      6600
atcgtccagc gtcgcgacat gcgtattcca ccgcagatcg acaccctgca gcagcccgat      6660
cagcgcgccc gcctcgatcg agccatagcc tgtcgtcagg cggcgcgaat ggtcgggaaa      6720
cgcgacctcc tgatccgtcc attcgccgcg acgaatgggc gacaggcgcg ccagccattc      6780
gggcgaaaga tccgtgtcgt ggcaggacca ggtgtgctgg tccgagggc cggaccgcg       6840
gtcgagcatc acgatgcgcg catccggtct gcggtcgcga acggcaagcg cgatcagcgc      6900
```

-continued

```
accggacagc cccgcgcccg cgatcagcag atcatggctc atgtattgcg atccgcccct    6960
tcgcggtcct tcagcagcgc gcccgagcgt ttcagctctg ccttgaggct gtcgaccgag    7020
ggcgcccaga tgaaaccgaa gctgacgcag ttctcgcggc catggaccgc gtgatgcatc    7080
ctgtgtgcct ggtagacgcg acgaagatag ccgcgcttgg ggacatagcg aacggccag     7140 cgcccatgca ccaagccgtc atgcaggaaa tagtagatca gcccgtagca ggtgacccc     7200 accgccagcc accaggccag atccgacccc atcgcgccga tcgcgaacag cacgatcgag    7260
attaccgcga agatgacgcc atagaggtcg ttcttctcga gcgcgtggtc gtgatcctcg    7320
tcgtggtgcg atttatgcca gccccagccc agggggccat gcatgatcca ccgatggacg    7380
gagtaggcca tcagctccat cgcggcgacg gtcaggatga cggtcaggat tgcggcccaa    7440
gtgctcatgc cggcccttg cttgatatga cagggaacag gctacgctgc cgcgcggtgc     7500
atgaccagcc catcggggtg cgaccaaagg gcatcgcgtg acatctgcgt tcagggctca    7560
taggcggatc atccgtgaca ttcgccgccg aacgcggcag gcgcatcacg cgttccgtcg    7620
ctggaaatat taatgttttc ccgaagatgg tcggggcgag aggattcgaa cctccgacct    7680
acggtaccca aaaccgtcgc gctaccaggc tgcgctacgc cccgactgcg gaaggcttta    7740
gccgattgtt ccggcaaggg aaagacctag tcgcaggcca ggaccgcatt gtcgcccatg    7800
cccggatgcg ccatcggctg accgggcttc aggccaaggc gatccgcctc tccgcccgcg    7860
atttcgagga cgaacagccg gtcggggtcc ggatcgccga ccgccgcgcc cggaatgggc    7920
gtctcgtcca gcgggcgcgc attgcggtgg atgtggcgga tgacgccggt ttcatccgca    7980
aagaccatgt ccagcgggat cagtgtgttg cgcatccaga aggacaccgg ctggggcgat    8040
tcgtagatga acagcattcc ggtgcccgca ggcagctcct tgcggaacat caggccctgc    8100
gcgcgctctt cggggctgtc cgcgacctcg acccgaaacc cgagcgtttc cgcaccggta    8160
tcgacgacaa gactgccggg cgcgcattcc accgccgccg cggcggcggg catcaggacc    8220
gcaagaagcg ctgcggcctt actcggccac atgggcaaga taggactgct cggcgccgag    8280
atcctgctga ccctgcgcat cctcgttccg gtcatgcagc gccaggtccc atgccgcgat    8340
ctgcgcgnnc atcagcccgc gcggaccctc gacgacgcgg aggcagatcg cctcgccgat    8400
cacgaggtcc gagaagccgg aatgacggag cacctcgata tggatgaaca cgtcctcggg    8460
gtggccgaag atgttggcga accgggaaaa ggcccttggc cttgtcgaac cacttgacgc    8520
gggccggacg cagcggcann cgtccagatg ctcgatcacc tcggcatcca gatcggcgat    8580
nggggggtgn cngtcgcttt cnnncggttc gatcgacagg acctc                    8625
```

<210> SEQ ID NO 2
<211> LENGTH: 295
<212> TYPE: PRT
<213> ORGANISM: Flavobacterium sp. R1534

<400> SEQUENCE: 2

```
Met Thr Pro Lys Gln Gln Phe Pro Leu Arg Asp Leu Val Glu Ile Arg
  1               5                  10                  15

Leu Ala Gln Ile Ser Gly Gln Phe Gly Val Val Ser Ala Pro Leu Gly
             20                  25                  30

Ala Ala Met Ser Asp Ala Ala Leu Ser Pro Gly Lys Arg Phe Arg Ala
         35                  40                  45

Val Leu Met Leu Met Val Ala Glu Ser Ser Gly Gly Val Cys Asp Ala
     50                  55                  60

Met Val Asp Ala Ala Cys Ala Val Glu Met Val His Ala Ala Ser Leu
```

```
                 65                  70                  75                  80
Ile Phe Asp Asp Met Pro Cys Met Asp Asp Ala Arg Thr Arg Arg Gly
                         85                  90                  95

Gln Pro Ala Thr His Val Ala His Gly Glu Gly Arg Ala Val Leu Ala
                100                 105                 110

Gly Ile Ala Leu Ile Thr Glu Ala Met Arg Ile Leu Gly Glu Ala Arg
            115                 120                 125

Gly Ala Thr Pro Asp Gln Arg Ala Arg Leu Val Ala Ser Met Ser Arg
        130                 135                 140

Ala Met Gly Pro Val Gly Leu Cys Ala Gly Gln Asp Leu Asp Leu His
145                 150                 155                 160

Ala Pro Lys Asp Ala Ala Gly Ile Glu Arg Glu Gln Asp Leu Lys Thr
                165                 170                 175

Gly Val Leu Phe Val Ala Gly Leu Glu Met Leu Ser Ile Ile Lys Gly
            180                 185                 190

Leu Asp Lys Ala Glu Thr Glu Gln Leu Met Ala Phe Gly Arg Gln Leu
        195                 200                 205

Gly Arg Val Phe Gln Ser Tyr Asp Asp Leu Leu Asp Val Ile Gly Asp
    210                 215                 220

Lys Ala Ser Thr Gly Lys Asp Thr Ala Arg Asp Thr Ala Ala Pro Gly
225                 230                 235                 240

Pro Lys Gly Gly Leu Met Ala Val Gly Gln Met Gly Asp Val Ala Gln
                245                 250                 255

His Tyr Arg Ala Ser Arg Ala Gln Leu Asp Glu Leu Met Arg Thr Arg
            260                 265                 270

Leu Phe Arg Gly Gly Gln Ile Ala Asp Leu Leu Ala Arg Val Leu Pro
        275                 280                 285

His Asp Ile Arg Arg Ser Ala
    290                 295

<210> SEQ ID NO 3
<211> LENGTH: 303
<212> TYPE: PRT
<213> ORGANISM: Flavobacterium sp. R1534

<400> SEQUENCE: 3

Met Thr Asp Leu Thr Ala Thr Ser Glu Ala Ala Ile Ala Gln Gly Ser
1               5                   10                  15

Gln Ser Phe Ala Gln Ala Ala Lys Leu Met Pro Pro Gly Ile Arg Glu
            20                  25                  30

Asp Thr Val Met Leu Tyr Ala Trp Cys Arg His Ala Asp Asp Val Ile
        35                  40                  45

Asp Gly Gln Val Met Gly Ser Ala Pro Glu Ala Gly Gly Asp Pro Gln
    50                  55                  60

Ala Arg Leu Gly Ala Leu Arg Ala Asp Thr Leu Ala Ala Leu His Glu
65                  70                  75                  80

Asp Gly Pro Met Ser Pro Pro Phe Ala Ala Leu Arg Gln Val Ala Arg
                85                  90                  95

Arg His Asp Phe Pro Asp Leu Trp Pro Met Asp Leu Ile Glu Gly Phe
            100                 105                 110

Ala Met Asp Val Ala Asp Arg Glu Tyr Arg Ser Leu Asp Asp Val Leu
        115                 120                 125

Glu Tyr Ser Tyr His Val Ala Gly Val Val Gly Val Met Met Ala Arg
    130                 135                 140
```

Val Met Gly Val Gln Asp Asp Ala Val Leu Asp Arg Ala Cys Asp Leu
145                 150                 155                 160

Gly Leu Ala Phe Gln Leu Thr Asn Ile Ala Arg Asp Val Ile Asp Asp
            165                 170                 175

Ala Ala Ile Gly Arg Cys Tyr Leu Pro Ala Asp Trp Leu Ala Glu Ala
            180                 185                 190

Gly Ala Thr Val Glu Gly Pro Val Pro Ser Asp Ala Leu Tyr Ser Val
        195                 200                 205

Ile Ile Arg Leu Leu Asp Ala Ala Glu Pro Tyr Tyr Ala Ser Ala Arg
        210                 215                 220

Gln Gly Leu Pro His Leu Pro Pro Arg Cys Ala Trp Ser Ile Ala Ala
225                 230                 235                 240

Ala Leu Arg Ile Tyr Arg Ala Ile Gly Thr Arg Ile Arg Gln Gly Gly
            245                 250                 255

Pro Glu Ala Tyr Arg Gln Arg Ile Ser Thr Ser Lys Ala Ala Lys Ile
            260                 265                 270

Gly Leu Leu Ala Arg Gly Gly Leu Asp Ala Ala Ser Arg Leu Arg
            275                 280                 285

Gly Gly Glu Ile Ser Arg Asp Gly Leu Trp Thr Arg Pro Arg Ala
290                 295                 300

<210> SEQ ID NO 4
<211> LENGTH: 494
<212> TYPE: PRT
<213> ORGANISM: Flavobacterium sp. R1534

<400> SEQUENCE: 4

Met Ser Ser Ala Ile Val Ile Gly Ala Gly Phe Gly Gly Leu Ala Leu
1               5                   10                  15

Ala Ile Arg Leu Gln Ser Ala Gly Ile Ala Thr Thr Ile Val Glu Ala
            20                  25                  30

Arg Asp Lys Pro Gly Gly Arg Ala Tyr Val Trp Asn Asp Gln Gly His
            35                  40                  45

Val Phe Asp Ala Gly Pro Thr Val Val Thr Asp Pro Asp Ser Leu Arg
        50                  55                  60

Glu Leu Trp Ala Leu Ser Gly Gln Pro Met Glu Arg Asp Val Thr Leu
65                  70                  75                  80

Leu Pro Val Ser Pro Phe Tyr Arg Leu Thr Trp Ala Asp Gly Arg Ser
                85                  90                  95

Phe Glu Tyr Val Asn Asp Asp Glu Leu Ile Arg Gln Val Ala Ser
            100                 105                 110

Phe Asn Pro Ala Asp Val Asp Gly Tyr Arg Arg Phe His Asp Tyr Ala
            115                 120                 125

Glu Glu Val Tyr Arg Glu Gly Tyr Leu Lys Leu Gly Thr Thr Pro Phe
130                 135                 140

Leu Lys Leu Gly Gln Met Leu Asn Ala Ala Pro Ala Leu Met Arg Leu
145                 150                 155                 160

Gln Ala Tyr Arg Ser Val His Ser Met Val Ala Arg Phe Ile Gln Asp
            165                 170                 175

Pro His Leu Arg Gln Ala Phe Ser Phe His Thr Leu Val Gly Gly
            180                 185                 190

Asn Pro Phe Ser Thr Ser Ser Ile Tyr Ala Leu Ile His Ala Leu Glu
            195                 200                 205

Arg Arg Gly Gly Val Trp Phe Ala Lys Gly Gly Thr Asn Gln Leu Val
        210                 215                 220

-continued

```
Ala Gly Met Val Ala Leu Phe Glu Arg Leu Gly Thr Leu Leu Leu
225                 230                 235                 240

Asn Ala Arg Val Thr Arg Ile Asp Thr Glu Gly Asp Arg Ala Thr Gly
                245                 250                 255

Val Thr Leu Leu Asp Gly Arg Gln Leu Arg Ala Asp Thr Val Ala Ser
                260                 265                 270

Asn Gly Asp Val Met His Ser Tyr Arg Asp Leu Leu Gly His Thr Arg
            275                 280                 285

Arg Gly Arg Thr Lys Ala Ala Ile Leu Asn Arg Gln Arg Trp Ser Met
290                 295                 300

Ser Leu Phe Val Leu His Phe Gly Leu Ser Lys Arg Pro Glu Asn Leu
305                 310                 315                 320

Ala His His Ser Val Ile Phe Gly Pro Arg Tyr Lys Gly Leu Val Asn
                325                 330                 335

Glu Ile Phe Asn Gly Pro Arg Leu Pro Asp Asp Phe Ser Met Tyr Leu
            340                 345                 350

His Ser Pro Cys Val Thr Asp Pro Ser Leu Ala Pro Glu Gly Met Ser
        355                 360                 365

Thr His Tyr Val Leu Ala Pro Val Pro His Leu Gly Arg Ala Asp Val
    370                 375                 380

Asp Trp Glu Ala Glu Ala Pro Gly Tyr Ala Glu Arg Ile Phe Glu Glu
385                 390                 395                 400

Leu Glu Arg Arg Ala Ile Pro Asp Leu Arg Lys His Leu Thr Val Ser
                405                 410                 415

Arg Ile Phe Ser Pro Ala Asp Phe Ser Thr Glu Leu Ser Ala His His
            420                 425                 430

Gly Ser Ala Phe Ser Val Glu Pro Ile Leu Thr Gln Ser Ala Trp Phe
        435                 440                 445

Arg Pro His Asn Arg Asp Arg Ala Ile Pro Asn Phe Tyr Ile Val Gly
    450                 455                 460

Ala Gly Thr His Pro Gly Ala Gly Ile Pro Gly Val Val Gly Ser Ala
465                 470                 475                 480

Lys Ala Thr Ala Gln Val Met Leu Ser Asp Leu Ala Val Ala
                485                 490

<210> SEQ ID NO 5
<211> LENGTH: 382
<212> TYPE: PRT
<213> ORGANISM: Flavobacterium sp. R1534

<400> SEQUENCE: 5

Met Ser His Asp Leu Leu Ile Ala Gly Ala Gly Leu Ser Gly Ala Leu
1               5                   10                  15

Ile Ala Leu Ala Val Arg Asp Arg Pro Asp Ala Arg Ile Val Met
            20                  25                  30

Leu Asp Ala Arg Ser Gly Pro Ser Asp Gln His Thr Trp Ser Cys His
        35                  40                  45

Asp Thr Asp Leu Ser Pro Glu Trp Leu Ala Arg Leu Ser Pro Ile Arg
    50                  55                  60

Arg Gly Glu Trp Thr Asp Gln Glu Val Ala Phe Pro Asp His Ser Arg
65                  70                  75                  80

Arg Leu Thr Thr Gly Tyr Gly Ser Ile Glu Ala Gly Ala Leu Ile Gly
                85                  90                  95

Leu Leu Gln Gly Val Asp Leu Arg Trp Asn Thr His Val Ala Thr Leu
```

```
                    100                 105                 110
Asp Asp Thr Gly Ala Thr Leu Thr Asp Gly Ser Arg Ile Glu Ala Ala
            115                 120                 125
Cys Val Ile Asp Ala Arg Gly Ala Val Glu Thr Pro His Leu Thr Val
130                 135                 140
Gly Phe Gln Lys Phe Val Gly Val Glu Ile Glu Thr Asp Ala Pro His
145                 150                 155                 160
Gly Val Glu Arg Pro Met Ile Met Asp Ala Thr Val Pro Gln Met Asp
                165                 170                 175
Gly Tyr Arg Phe Ile Tyr Leu Leu Pro Phe Ser Pro Thr Arg Ile Leu
            180                 185                 190
Ile Glu Asp Thr Arg Tyr Ser Asp Gly Gly Asp Leu Asp Asp Gly Ala
            195                 200                 205
Leu Ala Gln Ala Ser Leu Asp Tyr Ala Ala Arg Arg Gly Trp Thr Gly
        210                 215                 220
Gln Glu Met Arg Arg Glu Arg Gly Ile Leu Pro Ile Ala Leu Ala His
225                 230                 235                 240
Asp Ala Ile Gly Phe Trp Arg Asp His Ala Gln Gly Ala Val Pro Val
                245                 250                 255
Gly Leu Gly Ala Gly Leu Phe His Pro Val Thr Gly Tyr Ser Leu Pro
            260                 265                 270
Tyr Ala Ala Gln Val Ala Asp Ala Ile Ala Ala Arg Asp Leu Thr Thr
            275                 280                 285
Ala Ser Ala Arg Arg Ala Val Arg Gly Trp Ala Ile Asp Arg Ala Asp
        290                 295                 300
Arg Asp Arg Phe Leu Arg Leu Leu Asn Arg Met Leu Phe Arg Gly Cys
305                 310                 315                 320
Pro Pro Asp Arg Arg Tyr Arg Leu Leu Gln Arg Phe Tyr Arg Leu Pro
                325                 330                 335
Gln Pro Leu Ile Glu Arg Phe Tyr Ala Gly Arg Leu Thr Leu Ala Asp
            340                 345                 350
Arg Leu Arg Ile Val Thr Gly Arg Pro Pro Ile Pro Leu Ser Gln Ala
        355                 360                 365
Val Arg Cys Leu Pro Glu Arg Pro Leu Leu Gln Glu Arg Ala
370                 375                 380

<210> SEQ ID NO 6
<211> LENGTH: 169
<212> TYPE: PRT
<213> ORGANISM: Flavobacterium sp. R1534

<400> SEQUENCE: 6

Met Ser Thr Trp Ala Ala Ile Leu Thr Val Ile Leu Thr Val Ala Ala
1               5                   10                  15
Met Glu Leu Thr Ala Tyr Ser Val His Arg Trp Ile Met His Gly Pro
                20                  25                  30
Leu Gly Trp Gly Trp His Lys Ser His His Asp Glu Asp His Asp His
            35                  40                  45
Ala Leu Glu Lys Asn Asp Leu Tyr Gly Val Ile Phe Ala Val Ile Ser
        50                  55                  60
Ile Val Leu Phe Ala Ile Gly Ala Met Gly Ser Asp Leu Ala Trp Trp
65                  70                  75                  80
Leu Ala Val Gly Val Thr Cys Tyr Gly Leu Ile Tyr Tyr Phe Leu His
                85                  90                  95
```

```
Asp Gly Leu Val His Gly Arg Trp Pro Phe Arg Tyr Val Pro Lys Arg
                100                 105                 110

Gly Tyr Leu Arg Arg Val Tyr Gln Ala His Arg Met His His Ala Val
            115                 120                 125

His Gly Arg Glu Asn Cys Val Ser Phe Gly Phe Ile Trp Ala Pro Ser
        130                 135                 140

Val Asp Ser Leu Lys Ala Glu Leu Lys Arg Ser Gly Ala Leu Leu Lys
145                 150                 155                 160

Asp Arg Glu Gly Ala Asp Arg Asn Thr
                165

<210> SEQ ID NO 7
<211> LENGTH: 52
<212> TYPE: DNA
<213> ORGANISM: Artificial Sequence
<220> FEATURE:
<223> OTHER INFORMATION: Description of Artificial Sequence: Primer #100

<400> SEQUENCE: 7
tatatactag taagaggaga aattacatat gacgcccaag cagcagcaat tc          52

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Primer #101

<400> SEQUENCE: 8
tatatacccg ggtcagccgc gacggcctgt gg                                32

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence: Primer #104

<400> SEQUENCE: 9
tatatgaatt caagaggaga aattacatat gagcacttgg gccgcaatcc             50

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Primer #105

<400> SEQUENCE: 10
gtttcagctc tgccttgagg c                                            21

<210> SEQ ID NO 11
<211> LENGTH: 62
<212> TYPE: DNA
<213> ORGANISM: Artificial Sequence
<220> FEATURE:
<223> OTHER INFORMATION: Description of Artificial Sequence: Primer MUT1

<400> SEQUENCE: 11
gcgaaggggc ggatcgcaat acgtgaaagg aggacacgtg atgagccatg atctgctgat  60
cg                                                                62

<210> SEQ ID NO 12
```

```
<211> LENGTH: 63
<212> TYPE: DNA
<213> ORGANISM: Artificial Sequence
<220> FEATURE:
<223> OTHER INFORMATION: Description of Artificial Sequence: Primer MUT2

<400> SEQUENCE: 12
gccccctgct gcaggagaga gcttgaaagg aggcaattga gatgagttcc gccatcgtca        60
tcg                                                                     63

<210> SEQ ID NO 13
<211> LENGTH: 70
<212> TYPE: DNA
<213> ORGANISM: Artificial Sequence
<220> FEATURE:
<223> OTHER INFORMATION: Description of Artificial Sequence: Primer MUT3

<400> SEQUENCE: 13
ggtcatgctg tcggacctgg ccgtcgcttg aaaggaggat ccaatcatga ccgatctgac        60
ggcgacttcc                                                              70

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: Primer MUT5

<400> SEQUENCE: 14
atatatctca attgcctcct ttcaagctct ctcctgcagc aggg                        44

<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence: Primer MUT6

<400> SEQUENCE: 15
atgattggat cctcctttca agcgacggcc aggtccgaca gc                          42

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Primer
      CAR17

<400> SEQUENCE: 16
cagaacccat cacctgcccg tc                                                22

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Primer CATe

<400> SEQUENCE: 17
cgcgaattct cgccggcaat agttacc                                           27

<210> SEQ ID NO 18
<211> LENGTH: 60
<212> TYPE: DNA
```

```
<213> ORGANISM: Artificial Sequence
<220> FEATURE:
<223> OTHER INFORMATION: Description of Artificial Sequence: Primer CAT4

<400> SEQUENCE: 18
gtcacatgca tgcatgttac gagctcataa gcatgtgacg tcttcaacta acggggcagg      60

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Primer CS1

<400> SEQUENCE: 19
agcttggatc cttaagtact ctagagttta aacg                                  34

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Primer CS2

<400> SEQUENCE: 20
aattcgttta aactctagag tacttaagga tcca                                  34

<210> SEQ ID NO 21
<211> LENGTH: 46
<212> TYPE: DNA
<213> ORGANISM: Artificial Sequence
<220> FEATURE:
<223> OTHER INFORMATION: Description of Artificial Sequence: Primer MUT7

<400> SEQUENCE: 21
tcgaccctag gcacgtgacg cgtcaattgg atccgcatgc aagctt                     46

<210> SEQ ID NO 22
<211> LENGTH: 46
<212> TYPE: DNA
<213> ORGANISM: Artificial Sequence
<220> FEATURE:
<223> OTHER INFORMATION: Description of Artificial Sequence: Primer MUT8

<400> SEQUENCE: 22
gatcaagctt gcatgcggat ccaattgacg cgtcacgtgc ctaggg                     46

<210> SEQ ID NO 23
<211> LENGTH: 84
<212> TYPE: DNA
<213> ORGANISM: Artificial Sequence
<220> FEATURE:
<223> OTHER INFORMATION: Description of Artificial Sequence: Primer MUT9

<400> SEQUENCE: 23
gtgtcctcct ttcacgtatt gcgatccgcc ccttcgcggt ccttcagcag cgcgcccgag      60
cgtttcagct ctgccttgag gctg                                             84

<210> SEQ ID NO 24
<211> LENGTH: 88
<212> TYPE: DNA
<213> ORGANISM: Artificial Sequence
<220> FEATURE:
<223> OTHER INFORMATION: Description of Artificial Sequence: Primer
      MUT10
```

<400> SEQUENCE: 24

```
tcgacagcct caaggcagag ctgaaacgct cgggcgcgct gctgaaggac cgcgaagggg      60
cggatcgcaa tacgtgaaag gaggacac                                          88
```

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: Primer
      MUT11

<400> SEQUENCE: 25

```
taagaaaccc tccttta                                                      17
```

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Primer
      MUT12

<400> SEQUENCE: 26

```
ctagtaaagg agggtttct                                                    19
```

<210> SEQ ID NO 27
<211> LENGTH: 11233
<212> TYPE: DNA
<213> ORGANISM: Unknown
<220> FEATURE:
<223> OTHER INFORMATION: Description of Unknown Organism: Plasmid pZea4

<400> SEQUENCE: 27

```
ctaaattgta agcgttaata ttttgttaaa attcgcgtta aatttttgtt aaatcagctc       60 atttttaac caataggccg aaatcggcaa atcccttat aaatcaaaag aatagaccga       120
gatagggttg agtgttgttc cagtttggaa caagagtcca ctattaaaga acgtggactc      180
caacgtcaaa gggcgaaaaa ccgtctatca gggcgatggc ccactacgtg aaccatcacc      240
ctaatcaagt ttttggggt cgaggtgccg taaagcacta aatcggaacc ctaagggag       300 ccccgattt agagcttgac ggggaaagcc ggcgaacgtg gcgagaaagg aagggaagaa      360
agcgaaagga gcggcgcta gggcgctggc aagtgtagcg gtcacgctgc gcgtaaccac      420
cacacccgcc gcgcttaatg cgccgctaca gggcgcgtcc cattcgccat tcaggctgcg      480
caactgttgg gaagggcgat cggtgcgggc ctcttcgcta ttacgccagc tggcgaaagg      540
gggatgtgct gcaaggcgat taagttgggt aacgccaggg ttttcccagt cacgacgttg      600
taaaacgacg gccagtgagc gcgcgtaata cgactcacta tagggcgaat ggagctcca      660 ccgcggtggc ggccgctcta gtggatccgc gcctggccgt tcgcgatcag cagccgccct      720
tgcggatcgg tcagcatcat ccccatgaac cgcagcgcac gacgcagcgc gcgcccaga      780 tcgggcgcgt ccagcacggc atgcgccatc atcgcgaagg ccccggcgg catggggcgc      840 gtgcccattc cgaagaactc gcagcctgtc cgctgcgcaa ggtcgcgcca gatcgcgccg      900
tattccgatg cagtgacggg cccgatgcgc gtgggcccgc cctgccccgc cgccaccagc      960
gcatcgcgca cgaacccttc cgagatgatg tgctgatcca tgcccgtca ttgcaaaacc     1020 gatcaccgat cctgtcgcgt gatggcattg tttgcaatgc cccgagggct aggatggcgc     1080
gaaggatcaa gggggggaga gacatggaaa tcgagggacg ggtctttgtc gtcacgggcg     1140
```

```
ccgcatcggg tctgggggcg gcctcggcgc ggatgctggc ccaaggcggc gcgaaggtcg    1200
tgctggccga tctggcggaa ccgaaggacg cgcccgaagg cgcggttcac gcggcctgcg    1260
acgtgaccga cgcgaccgct gcgcagacgg ccatcgcgct ggcgaccgac cgcttcggca    1320
ggctggacgg ccttgtgaac tgcgcgggca tcgcgccggc cgaacggatg ctggccgcg    1380 acgggccgca tggactggac agctttgccc gtgcggtcac gatcaacctg atcggcagct    1440
tcaacatggc ccgccttgca gccgaggcga tggcccggaa cgagcccgtc cggggcgagc    1500
gtggcgtgat cgtcaacacg gcctcgatcg cggcgcagga cggacagatc ggacaggtcg    1560
cctatgcggc cagcaaggcg ggcgtggcgg gcatgacgct gccgatggcc cgcgaccttg    1620
cgcggcacgg catccgcgtc atgaccatcg cgcccggcat cttccgcacc ccgatgctgg    1680
aggggctgcc gcaggacgtt caggacagcc tgggcgcggc ggtgcccttc ccctcgcggc    1740
tgggagagcc gtcggaatac gcggcgctgt tgcaccacat catcgcgaac cccatgctga    1800
acggagaggt catccgcctc gacggcgcat tgcgcatggc ccccaagtga aggagcgttt    1860
catggacccc atcgtcatca ccggcgcgat gcgcacccg atgggggcat tccagggcga    1920
tcttgccgcg atggatgccc cgacccttgg cgcggacgcg atccgcgccg cgctgaacgg    1980
cctgtcgccc gacatggtgg acgaggtgct gatgggctgc gtcctcgccg cgggccaggg    2040
tcaggcaccg gcacgtcagg cggcgcttgg cgccggactg ccgctgtcga cgggcacgac    2100
caccatcaac gagatgtgcg gatcgggcat gaaggccgcg atgctgggcc atgacctgat    2160
cgccgcggga tcggcgggca tcgtcgtcgc cggcgggatg gagagcatgt cgaacgcccc    2220
ctacctgctg cccaaggcgc ggtcggggat gcgcatgggc catgaccgtg tgctggatca    2280
catgttcctc gacgggttgg aggacgccta tgacaagggc cgcctgatgg gcaccttcgc    2340
cgaggattgc gccggcgatc acggtttcac ccgcgaggcg caggacgact atgcgctgac    2400
cagcctggcc cgcgcgcagg acgccatcgc cagcggtgcc ttcgccgccg agatcgcgcc    2460
cgtgaccgtc acggcacgca aggtgcagac caccgtcgat accgacgaga tgcccggcaa    2520
ggcccgcccc gagaagatcc cccatctgaa gcccgccttc cgtgacggtg gcacggtcac    2580
ggcggcgaac agctcgtcga tctcggacgg ggcggcggcg ctggtgatga tgcgccagtc    2640
gcaggccgag aagctgggcc tgacgccgat cgcgcggatc atcggtcatg cgacccatgc    2700
cgaccgtccc ggcctgttcc cgacggcccc catcggcgcg atgcgcaagc tgctggaccg    2760
cacggacacc cgccttggcg attacgacct gttcgaggtg aacgaggcat tcgccgtcgt    2820
cgccatgatc gcgatgaagg agcttggcct gccacacgat gccacgaaca tcaacgcgcg    2880
ggcctgcgcg cttgggcatc ccatcggcgc gtcggggcg cggatcatgg tcacgctgct    2940
gaacgcgatg gcggcgcggg gcgcgacgcg cggggccgca tccgtctgca tcggcggggg    3000
cgaggcgacg gccatcgcgc tggaacggct gagctaattc atttgcgcga atccgcgttt    3060
ttcgtgcacg atgggggaac cggaaacggc cacgcctgtt gtggttgcgt cgacctgtct    3120
tcgggccatg cccgtgacgc gatgtggcag gcgcatgggg cgttgccgat ccggtcgcat    3180
gactgacgca acgaaggcac cgatgacgcc caagcagcaa ttcccctac gcgatctggt    3240 cgagatcagg ctgcgcagag tctcgggcca gttcggcgtg gtctcggccc cgctcggcgc    3300
ggccatgagc gatgccgccc tgtccccgg caaacgcttt cgcgccgtgc tgatgctgat    3360
ggtcgccgaa agctcgggcg gggtctgcga tgcgatggtc gatgccgcct gcgcggtcga    3420
gatggtccat gccgcatcgc tgatcttcga cgacatgccc tgcatggacg atgccaggac    3480
```

-continued

| | |
|---|---|
| ccgtcgcggt cagcccgcca cccatgtcgc ccatggcgag gggcgcgcgg tgcttgcggg | 3540 |
| catcgccctg atcaccgagg ccatgcggat tttgggcgag gcgcgcggcg cgacgccgga | 3600 |
| tcagcgcgca aggctggtcg catccatgtc gcgcgcgatg ggaccggtgg ggctgtgcgc | 3660 |
| agggcaggat ctggacctgc acgcccccaa ggacgccgcc gggatcgaac gtgaacagga | 3720 |
| cctcaagacc ggcgtgctgt tcgtcgcggg cctcgagatg ctgtccatta ttaagggtct | 3780 |
| ggacaaggcc gagaccgagc agctcatggc cttcgggcgt cagcttggtc gggtcttcca | 3840 |
| gtcctatgac gacctgctgg acgtgatcgg cgacaaggcc agcaccggca aggatacggc | 3900 |
| gcgcgacacc gccgcccccg gcccaaaggg cggcctgatg gcggtcggac agatgggcga | 3960 |
| cgtggcgcag cattaccgcg ccagccgcgc gcaactggac gagctgatgc gcacccggct | 4020 |
| gttccgcggg gggcagatcg cggacctgct ggcccgcgtg ctgccgcatg acatccgccg | 4080 |
| cagcgcctag gcgcgcggtc gggtccacag gccgtcgcgg ctgatttcgc cgccgcgcag | 4140 |
| gcgcgatgcg gccgcgtcca agcctccgcg cgccagaagc ccgatcttgg cagccttcga | 4200 |
| cgtgctgatc cgctggcgat aggcctcggg gccaccctgc cggatgcgcg tcccgattgc | 4260 |
| gcgatagata cgcagcgcgg cggcgatcga ccacgcgcag cgcggcggca gatgcggaag | 4320 |
| cccctgccgc gccgaggcat aatagggctc ggccgcgtca gcaggcggga tgatgacgga | 4380 |
| atagagcgcg tccgaaggca ccggaccctc aaccgtcgcc cccgctcgg ccagccagtc | 4440 |
| ggcaggcaga tagcagcgcc cgatggcggc atcgtcgatc acgtcgcgag cgatgttcgt | 4500 |
| cagctggaac gcaaggccca gatcgcaggc gcgatccagc accgcatcgt cctgcacgcc | 4560 |
| catcacccgc gccatcatca cgcccacgac ccccgcgacg tggtaggaat attccagcac | 4620 |
| gtcatccagg ctgcggtatt cgcgatccgc gacatccatc gcgaaaccct cgatcaggtc | 4680 |
| catcggccaa aggtccggga aatcatgccg ccgggcgacc tggcgcagcg ccgcgaaggg | 4740 |
| cggcgacatc gggccgtcct cgtgcagcgc ggccagcgtg tcggcgcgca gcgccccag | 4800 |
| ccgcgcctgt gggtcgccgc ccgcctcggg ggcagaaccc atcacctgcc cgtcgatcac | 4860 |
| gtcatccgca tgcctgcacc aggcatagag catgaccgta tcctcgcgga tgccgggcgg | 4920 |
| catcagcttg gccgcctgcg cgaagctttg cgaaccctgc gcgatggccg cttcggaagt | 4980 |
| cgccgtcaga tcggtcatgc gacggccagg tccgacagca tgacctgcgc cgtggccttg | 5040 |
| gcgctgccaa cgacacccgg gatgcccgca cccggatgcg tgcccgcccc cacgatgtag | 5100 |
| aagttcggga tcgcgcggtc gcggttatgc gggcggaacc aggcggattg cgtcaggatc | 5160 |
| ggctcgaccg agaaggcgct gccgtgatgg gccgacagtt cggtgctgaa atcggcgggg | 5220 |
| ctgaagatgc ggctgacggt cagtgcttg cgcaggtcgg ggatggcgcg cgctccagt | 5280 |
| tcctcgaaga tgcgctcggc atagcccggg gcctcggctt cccaatcgac atcggcgcgg | 5340 |
| cccagatgcg gaacgggcgc aaggacgtaa tgcgtggaca tccctcgggg gccaggctg | 5400 |
| ggatcggtca cgcagggcga atgcagatac atcgagaaat cgtccggcag gcgtggcccg | 5460 |
| ttgaagatct cgttcaccag ccccttgtag cgcgggccga agatgacgct gtggtgggcc | 5520 |
| aggttctcgg ggcgcttgga caggccgaaa tgcagcacga acagcgacat cgaccagcgc | 5580 |
| tgccggttca ggatcgcggc cttggtgcgc ccgcggcggg tatggcccag caggtcgcga | 5640 |
| tagctgtgca tcacgtcgcc gttgctggcc accgtatccg cgcgcaactg ccgcccgtcc | 5700 |
| agcagcgtga cgcccgtggc gcgatcgccc tcggtgtcga tccgcgtgac gcgggcattc | 5760 |
| agcagcagcg tgccgccaag acgctcgaac agggcgacca tgcccgcgac cagctggttg | 5820 |
| gtgccgccct tggcgaacca gacgccgccg cgccgttcca gcgcatggat cagcgcatag | 5880 |

```
atcgagctgg tcgaaaacgg gttcccgccg accagcagcg tgtggaacga gaaggcctgc    5940
cgcagatgcg ggtcctggat gaagcgcgcc accatgctgt ggaccgagcg gtatgcctgc    6000
aggcgcatca gcgccggcgc ggcgttcagc atctggccca gcttcaggaa gggcgtggtc    6060
cccagcttca gataccccctc gcgatagacc tcctcggcgt aatcgtggaa gcggcgatag    6120
ccatcgacat cggcgggatt gaaggaggcg acctggcgga tcagctcgtc gtcgtcgttc    6180
acgtattcga agctgcggcc gtccgcccat gtcagccggt agaagggcga gaccggcagc    6240
agcgtcacgt cacgctccat cggttggccg ctgagggccc acagctctcg caggctgtcg    6300
gggtcggtca cgaccgtcgg gcctgcatcg aagacgtggc cctgatcgtt ccagacatag    6360
gcgcggccgc cgggcttgtc gcgggcctcg acgatggtgg tcgcgatgcc ggccgattgc    6420
aggcggatgg caagcgcaag cccgccgaaa cctgcgccga tgacgatggc ggaactcatg    6480
ctctctcctg cagcagggg cgttcgggca ggcagcgcac ggcctgcgac agcggaatgg    6540
gcgggcgtcc ggtgacgatg cgaagccggt cggccaatgt caggcgcccg gcatagaagc    6600
gctcgatcag cggctgcggc aggcggtaga accgctgcag caggcgatag cgacggtcgg    6660
gcgggcagcc gcggaacagc atccggttca gcagccgcag gaagcggtcg cgatccgcgc    6720
gatcgatggc ccagccgcgc accgcgcgac gggcggacgg ggtcgtcagg tcgcgcgccg    6780
cgatggcatc cgcgacctgc gcggcatagg gcagcgaata tccggtgacg gggtggaaca    6840
gccctgcccc cagcccaacc ggcaccgccc ctgcgcgtg gtcgcgccag aagcctatgg    6900
cgtcatgggc cagcgcgatg ggcaggatgc ccctttcgcg ccgcatctcc tgcccggtcc    6960
agccccgcct ggcggcatag tccagcgacg cctgcgccag cgcgccatcg tccagatcgc    7020
cgccgtcgct gtagcgcgta tcctcgatca ggatgcgggt gggactgaag ggcagcagat    7080
agatgaagcg gtacccgtcc atctgcggaa cggtcgcgtc catgatcatc gggcgctcga    7140
cgccatgggg ggcgtcggtc tcgatctcga cgcccacgaa tttctggaaa cccacggtca    7200
ggtgcgggt ctcgacggca ccacgggcgt cgatcacgca ggcagcctcg atccgcgagc    7260
cgtccgtcag cgtcgcgccg gtatcgtcca gcgtcgcgac atgcgtattc caccgcagat    7320
cgacaccctg cagcagcccg atcagcgcgc ccgcctcgat cgagccatag cctgtcgtca    7380
ggcggcgcga atggtcggga aacgcgacct cctgatccgt ccattcgccg cgacgaatgg    7440
gcgacaggcg cgccagccat tcgggcgaaa gatccgtgtc gtggcaggac caggtgtgct    7500
ggtccgaggg gccggaccgc gcgtcgagca tcacgatgcg cgcatccggt ctgcggtcgc    7560
gaacggcaag cgcgatcagc gcaccggaca gccccgcgcc cgcgatcagc agatcatggc    7620
tcatgtattg cgatccgccc cttcgcggtc cttcagcagc gcgcccgagc gtttcagctc    7680
tgccttgagg ctgtcgaccg agggcgccca gatgaaaccg aagctgacgc agttctcgcg    7740
gccatggacc gcgtgatgca tcctgtgtgc ctggtagacg cgacgaagat agccgcgctt    7800
ggggacatag cggaacggcc agcgcccatg caccaagccg tcatgcagga aatagtagat    7860
cagcccgtag caggtgaccc ccaccgccag ccaccaggcc agatccgacc ccatcgcgcc    7920
gatcgcgaac agcacgatcg agattaccgc gaagatgacg ccatagaggt cgttcttctc    7980
gagcgcgtgg tcgtgatcct cgtcgtggtg cgatttatgc cagccccagc ccaggggcc    8040
atgcatgatc caccgatgga cggagtaggc cgtcagctcc atcgcggcga cggtcaggat    8100
gacggtcagg attgcggccc aagtgctcat gccggcccct tgcttgatat gacagggaac    8160
aggctacgct gccgcgcggt gcatgaccag cccatcgggg tgcgaccaaa gggcatcgcg    8220
```

-continued

```
tgacatctgc gttcagggct cataggcgga tcatccgtga cattcgccgc cgaacgcggc    8280
aggcgcatca cgcgttccgt cgctggaaat attaatgttt tcccgaagat ggtcggggcg    8340
agaggattcg aacctccgac ctacggtacc caaaaccgtc gcgctaccag gctgcgctac    8400
gccccgactg cggaaggctt tagccgattg ttccggcaag ggaaagacct agtcgcaggc    8460
caggaccgca ttgtcgccca tgcccggatg cgccatcggc tgaccgggct tcaggccaag    8520
gcgatccgcc tctccgcccg cgatttcgag gacgaacagc cggtcggggt ccggatcgcc    8580
gaccgccgcg cccggaatgg gcgtctcgtc cagcgggcgc gcattgcggt ggatgtggcg    8640
gatgacgccg gtttcatccg caaagaccat gtccagcggg atcagtgtgt tgcgcatcca    8700
gaaggacacc ggctggggcg attcgtagat gaacagcatt ccggtgcccg caggcagctc    8760
cttgcggaac atcaggccct gcgcgcgctc ttcggggctg tccgcgacct cgacccgaaa    8820
cccgagcgtt tccgcaccgg tatcgacgac aagactgccg ggcgcgcatt ccaccgccgc    8880
cgcggcggcg ggcatcagga ccgcaagaag cgctgcggcc ttactcggcc acatgggcaa    8940
gataggactg ctcggcgccg agatcccccg ggctgcagga attcgatatc aagcttatcg    9000
ataccgtcga cctcgagggg gggcccggta cccagctttt gttccctttta gtgagggtta    9060
attgcgcgct tggcgtaatc atggtcatag ctgtttcctg tgtgaaattg ttatccgctc    9120
acaattccac acaacatacg agccggaagc ataaagtgta aagcctgggg tgcctaatga    9180
gtgagctaac tcacattaat tgcgttgcgc tcactgcccg ctttccagtc gggaaacctg    9240
tcgtgccagc tgcattaatg aatcggccaa cgcgcgggga gaggcggttt gcgtattggg    9300
cgctcttccg cttcctcgct cactgactcg ctgcgctcgg tcgttcggct gcggcgagcg    9360
gtatcagctc actcaaaggc ggtaatacgg ttatccacag aatcagggga taacgcagga    9420
aagaacatgt gagcaaaagg ccagcaaaag gccaggaacc gtaaaaaggc cgcgttgctg    9480
gcgttttttcc ataggctccg ccccctgac gagcatcaca aaaatcgacg ctcaagtcag    9540
aggtggcgaa acccgacagg actataaaga taccaggcgt ttccccctgg aagctccctc    9600
gtgcgctctc ctgttccgac cctgccgctt accggatacc tgtccgcctt tctcccttcg    9660
ggaagcgtgg cgctttctca tagctcacgc tgtaggtatc tcagttcggt gtaggtcgtt    9720
cgctccaagc tgggctgtgt gcacgaaccc cccgttcagc ccgaccgctg cgccttatcc    9780
ggtaactatc gtcttgagtc aacccggta agacacgact tatcgccact ggcagcagcc    9840
actggtaaca ggattagcag agcgaggtat gtaggcggtg ctacagagtt cttgaagtgg    9900
tggcctaact acggctacac tagaaggaca gtatttggta tctgcgctct gctgaagcca    9960
gttaccttcg gaaaaagagt tggtagctct tgatccggca acaaaccac cgctggtagc    10020
ggtggttttt ttgtttgcaa gcagcagatt acgcgcagaa aaaaaggatc tcaagaagat    10080
cctttgatct tttctacggg gtctgacgct cagtggaacg aaaactcacg ttaagggatt    10140
ttggtcatga gattatcaaa aaggatcttc acctagatcc ttttaaatta aaaatgaagt    10200
tttaaatcaa tctaaagtat atatgagtaa acttggtctg acagttacca atgcttaatc    10260
agtgaggcac ctatctcagc gatctgtcta tttcgttcat ccatagttgc ctgactcccc    10320
gtcgtgtaga taactacgat acgggagggc ttaccatctg gccccagtgc tgcaatgata    10380
ccgcgagacc cacgctcacc ggctccagat ttatcagcaa taaaccagcc agccggaagg    10440
gccgagcgca gaagtggtcc tgcaacttta tccgcctcca tccagtctat taattgttgc    10500
cgggaagcta gagtaagtag ttcgccagtt aatagtttgc gcaacgttgt tgccattgct    10560
acaggcatcg tggtgtcacg ctcgtcgttt ggtatggctt cattcagctc cggttcccaa    10620
```

```
cgatcaaggc gagttacatg atcccccatg ttgtgcaaaa aagcggttag ctccttcggt   10680
cctccgatcg ttgtcagaag taagttggcc gcagtgttat cactcatggt tatggcagca   10740
ctgcataatt ctcttactgt catgccatcc gtaagatgct tttctgtgac tggtgagtac   10800
tcaaccaagt cattctgaga atagtgtatg cggcgaccga gttgctcttg cccggcgtca   10860
atacgggata ataccgcgcc acatagcaga actttaaaag tgctcatcat tggaaaacgt   10920
tcttcggggc gaaaactctc aaggatctta ccgctgttga gatccagttc gatgtaaccc   10980
actcgtgcac ccaactgatc ttcagcatct tttactttca ccagcgtttc tgggtgagca   11040
aaaacaggaa ggcaaaatgc cgcaaaaaag ggaataaggg cgacacggaa atgttgaata   11100
ctcatactct tcctttttca atattattga agcatttatc agggttattg tctcatgagc   11160
ggatacatat ttgaatgtat ttagaaaaat aaacaaatag gggttccgcg cacatttccc   11220 gtgc cac                                                            11233

<210> SEQ ID NO 28
<211> LENGTH: 726
<212> TYPE: DNA
<213> ORGANISM: Alcaligenes PC-1

<400> SEQUENCE: 28
atgtccggtc gtaaaccggg taccaccggt gacaccatcg ttaacctggg tctgaccgct     60
gctatcctgc tgtgctggct ggttctgcac gctttcaccc tgtggctgct ggacgctgct    120
gctcacccgc tgctggctgt tctgtgcctg gctggtctga cctggctgtc cgttggtctg    180
ttcatcatcg ctcacgacgc tatgcacggt tccgttgttc cgggtcgtcc gcgggctaac    240
gctgctatcg gtcagctggc tctgtggctg tacgctggtt tctcctggcc gaaactgatc    300
gctaaacaca tgacccacca ccgtcacgct ggtaccgaca cgacccgga cttcggtcac    360 ggtggtccgg ttcgttggta cggttccttc gtttccacct acttcggttg gcgtgaaggt    420
ctgctgctgc cggttatcgt taccacctac gctctgatcc tgggtgaccg ttggatgtac    480
gttatcttct ggccggttcc ggctgttctg gcttccatcc agatcttcgt tttcggtacc    540
tggctgccgc accgtccggg tcacgacgac ttcccggacc gtcacaacgc tcgttccacc    600
ggtatcggtg acccgctgtc cctgctgacc tgcttccact cggtggtta ccaccacgaa    660 caccacctgc acccgcacgt tccgtggtgg cgtctgccgc gtacccgtaa aaccggtggt    720
cgtgct                                                              726

<210> SEQ ID NO 29
<211> LENGTH: 242
<212> TYPE: PRT
<213> ORGANISM: Alcaligenes PC-1

<400> SEQUENCE: 29

Met Ser Gly Arg Lys Pro Gly Thr Thr Gly Asp Thr Ile Val Asn Leu
  1               5                  10                  15

Gly Leu Thr Ala Ala Ile Leu Leu Cys Trp Leu Val Leu His Ala Phe
             20                  25                  30

Thr Leu Trp Leu Leu Asp Ala Ala Ala His Pro Leu Leu Ala Val Leu
         35                  40                  45

Cys Leu Ala Gly Leu Thr Trp Leu Ser Val Gly Leu Phe Ile Ile Ala
     50                  55                  60

His Asp Ala Met His Gly Ser Val Val Pro Gly Arg Pro Arg Ala Asn
 65                  70                  75                  80
```

-continued

```
Ala Ala Ile Gly Gln Leu Ala Leu Trp Leu Tyr Ala Gly Phe Ser Trp
                 85                  90                  95

Pro Lys Leu Ile Ala Lys His Met Thr His His Arg His Ala Gly Thr
            100                 105                 110

Asp Asn Asp Pro Asp Phe Gly His Gly Gly Pro Val Arg Trp Tyr Gly
        115                 120                 125

Ser Phe Val Ser Thr Tyr Phe Gly Trp Arg Glu Gly Leu Leu Leu Pro
    130                 135                 140

Val Ile Val Thr Thr Tyr Ala Leu Ile Leu Gly Asp Arg Trp Met Tyr
145                 150                 155                 160

Val Ile Phe Trp Pro Val Pro Ala Val Leu Ala Ser Ile Gln Ile Phe
                165                 170                 175

Val Phe Gly Thr Trp Leu Pro His Arg Pro Gly His Asp Asp Phe Pro
            180                 185                 190

Asp Arg His Asn Ala Arg Ser Thr Gly Ile Gly Asp Pro Leu Ser Leu
        195                 200                 205

Leu Thr Cys Phe His Phe Gly Gly Tyr His His Glu His His Leu His
    210                 215                 220

Pro His Val Pro Trp Trp Arg Leu Pro Arg Thr Arg Lys Thr Gly Gly
225                 230                 235                 240

Arg Ala
```

<210> SEQ ID NO 30
<211> LENGTH: 1261
<212> TYPE: DNA
<213> ORGANISM: Alcaligenes PC-1

<400> SEQUENCE: 30

```
actgtagtct gcgcggatcg ccggtccggg ggacaagata tgagcgcaca tgccctgccc     60
aaggcagatc tgaccgccac cagtttgatc gtctcgggcg gcatcatcgc cgcgtggctg    120
gccctgcatg tgcatgcgct gtggtttctg gacgcggcgg cgcatcccat cctggcggtc    180
gcgaatttcc tggggctgac ctggctgtcg gtcggtctgt tcatcatcgc gcatgacgcg    240
atgcatgggt cggtcgtgcc ggggcgcccg cgcgccaatg cggcgatggg ccagcttgtc    300
ctgtggctgt atgccggatt ttcctggcgc aagatgatcg tcaagcacat ggcccatcat    360
cgccatgccg gaaccgacga cgacccagat ttcgaccatg gcggcccggt ccgctggtac    420
gcccgcttca tcggcaccta tttcggctgg cgcgaggggc tgctgctgcc cgtcatcgtg    480
acggtctatg cgctgatgtt gggggatcgc tggatgtacg tggtcttctg gccgttgccg    540
tcgatcctgg cgtcgatcca gctgttcgtg ttcggcatct ggctgccgca ccgccccggc    600
cacgacgcgt tcccggaccg ccacaatgcg cggtcgtcgc ggatcagcga ccccgtgtcg    660
ctgctgacct gctttcactt tggcggttat catcacgaac accacctgca cccgacggtg    720
ccttggtggc gcctgcccag cacccgcacc aaggggggaca ccgcatgacc aatttcctga    780
tcgtcgtcgc caccgtgctg gtgatggagc tgacggccta ttccgtccac cgctggatca    840
tgcacggccc cttgggctgg ggctggcaca gtcccaccac gaggaacacc gaccacgcgc    900
tggaaaagaa cgacctgtac ggcctggtct ttgcggtgat cgccacggtg ctgttcacgg    960
tgggctggat ctgggcaccg gtcctgtggt ggatcgcctt gggcatgacc gtctacgggc   1020
tgatctattt cgtcctgcat gacgggctgg tgcatcagcg ctggccgttc cgctatatcc   1080
ctcgcaaggg ctatgccaga cgcctgtatc aggcccaccg cctgcaccac gcggtcgagg   1140
```

-continued

| | |
|---|---|
| ggcgcgacca ttgcgtcagc ttcggcttca tctatgcgcc gccggtcgac aagctgaagc | 1200 |
| aggacctgaa gacgtcgggc gtgctgcggg ccgaggcgca ggagcgcacg tgacccatga | 1260 |
| c | 1261 |

<210> SEQ ID NO 31
<211> LENGTH: 1458
<212> TYPE: DNA
<213> ORGANISM: E-396
<220> FEATURE:
<223> OTHER INFORMATION: Description of Unknown Organism: Unkown

<400> SEQUENCE: 31

| | |
|---|---|
| atgagcgcac atgccctgcc caaggcagat ctgaccgcca ccagtttgat cgtctcgggc | 60 |
| tactcgcgtg tacgggacgg gttccgtcta gactggcggt ggtcaaacta gcagagcccg | 120 |
| ggcatcatcg ccgcgtggct ggccctgcat gtgcatgcgc tgtggtttct ggacgcggcg | 180 |
| ccgtagtagc ggcgcaccga ccgggacgta cacgtacgcg acaccaaaga cctgcgccgc | 240 |
| gcgcatccca tcctggcggt cgcgaatttc ctggggctga cctggctgtc ggtcggtctg | 300 |
| cgcgtagggt aggaccgcca gcgcttaaag gaccccgact ggaccgacag ccagccagac | 360 |
| ttcatcatcg cgcatgacgc gatgcatggg tcggtcgtgc cggggcgccc gcgcgccaat | 420 |
| aagtagtagc gcgtactgcg ctacgtaccc agccagcacg gccccgcggg cgcgcggtta | 480 |
| gcggcgatgg gccagcttgt cctgtggctg tatgccggat tttcctggcg caagatgatc | 540 |
| cgccgctacc cggtcgaaca ggacaccgac atacggccta aaaggaccgc gttctactag | 600 |
| gtcaagcaca tggcccatca tcgccatgcc ggaaccgacg acgacccaga tttcgaccat | 660 |
| cagttcgtgt accgggtagt agcggtacgg ccttggctgc tgctgggtct aaagctggta | 720 |
| ggcggcccgg tccgctggta cgcccgcttc atcggcacct atttcggctg gcgcgagggg | 780 |
| ccgccgggcc aggcgaccat gcgggcgaag tagccgtgga taaagccgac gcgctcccc | 840 |
| ctgctgctgc ccgtcatcgt gacggtctat gcgctgatgt tggggatcg ctggatgtac | 900 |
| gacgacgacg gcagtagca ctgccagata cgcgactaca acccctagc gacctacatg | 960 |
| gtggtcttct ggccgttgcc gtcgatcctg gcgtcgatcc agctgttcgt gttcggcatc | 1020 |
| caccagaaga ccggcaacgg cagctaggac cgcagctagg tcgacaagca caagccgtag | 1080 |
| tggctgccgc accgccccgg ccacgacgcg ttcccggacc gccacaatgc gcggtcgtcg | 1140 |
| accgacggcg tggcggggcc ggtgctgcgc aagggcctgg cggtgttacg cgccagcagc | 1200 |
| cggatcagcg accccgtgtc gctgctgacc tgctttcact ttgcggtta tcatcacgaa | 1260 |
| gcctagtcgc tggggcacag cgacgactgg acgaaagtga aaccgccaat agtagtgctt | 1320 |
| caccacctgc acccgacggt gccttggtgg cgcctgccca gcacccgcac caaggggac | 1380 |
| gtggtggacg tgggctgcca cggaaccacc gcggacgggt cgtgggcgtg gttccccctg | 1440 |
| accgcatgat ggcgtact | 1458 |

<210> SEQ ID NO 32
<211> LENGTH: 242
<212> TYPE: PRT
<213> ORGANISM: E-396
<220> FEATURE:
<223> OTHER INFORMATION: Description of Unknown Organism: Unkown

<400> SEQUENCE: 32

Met Ser Ala His Ala Leu Pro Lys Ala Asp Leu Thr Ala Thr Ser Leu
1               5                   10                  15

```
Ile Val Ser Gly Gly Ile Ile Ala Ala Trp Leu Ala Leu His Val His
            20                  25                  30
Ala Leu Trp Phe Leu Asp Ala Ala His Pro Ile Leu Ala Val Ala
        35                  40                  45
Asn Phe Leu Gly Leu Thr Trp Leu Ser Val Gly Leu Phe Ile Ile Ala
    50                  55                  60
His Asp Ala Met His Gly Ser Val Val Pro Gly Arg Pro Arg Ala Asn
65                  70                  75                  80
Ala Ala Met Gly Gln Leu Val Leu Trp Leu Tyr Ala Gly Phe Ser Trp
                85                  90                  95
Arg Lys Met Ile Val Lys His Met Ala His Arg His Ala Gly Thr
            100                 105                 110
Asp Asp Asp Pro Asp Phe Asp His Gly Gly Pro Val Arg Trp Tyr Ala
            115                 120                 125
Arg Phe Ile Gly Thr Tyr Phe Gly Trp Arg Glu Gly Leu Leu Leu Pro
        130                 135                 140
Val Ile Val Thr Val Tyr Ala Leu Met Leu Gly Asp Arg Trp Met Tyr
145                 150                 155                 160
Val Val Phe Trp Pro Leu Pro Ser Ile Leu Ala Ser Ile Gln Leu Phe
                165                 170                 175
Val Phe Gly Ile Trp Leu Pro His Arg Pro Gly His Asp Ala Phe Pro
            180                 185                 190
Asp Arg His Asn Ala Arg Ser Ser Arg Ile Ser Asp Pro Val Ser Leu
        195                 200                 205
Leu Thr Cys Phe His Phe Gly Gly Tyr His His Glu His His Leu His
    210                 215                 220
Pro Thr Val Pro Trp Trp Arg Leu Pro Ser Thr Arg Thr Lys Gly Asp
225                 230                 235                 240
Thr Ala
```

<210> SEQ ID NO 33
<211> LENGTH: 972
<212> TYPE: DNA
<213> ORGANISM: E-396
<220> FEATURE:
<223> OTHER INFORMATION: Description of Unknown Organism: Unknown

<400> SEQUENCE: 33

```
atgaccaatt tcctgatcgt cgtcgccacc gtgctggtga tggagctgac ggcctattcc      60
tactggttaa aggactagca gcagcggtgg cacgaccact acctcgactg ccggataagg     120
gtccaccgct ggatcatgca cggccccttg ggctggggct ggcacaagtc ccaccacgag     180
caggtggcga cctagtacgt gccggggaac ccgaccccga ccgtgttcag ggtggtgctc     240
gaacacgacc acgcgctgga aaagaacgac ctgtacggcc tggtctttgc ggtgatcgcc     300
cttgtgctgg tgcgcgacct tttcttgctg gacatgccgg accagaaacg ccactagcgg     360
acggtgctgt tcacggtggg ctggatctgg caccggtcc tgtggtggat cgccttgggc      420
tgccacgaca agtgccaccc gacctagacc cgtggccagg acaccaccta gcggaacccg     480
atgaccgtct acgggctgat ctatttcgtc ctgcatgacg ggctggtgca tcagcgctgg     540
tactggcaga tgcccgacta gataaagcag gacgtactgc ccgaccacgt agtcgcgacc     600
ccgttccgct atatccctcg caagggctat gccagacgcc tgtatcaggc ccaccgcctg     660
ggcaaggcga tagggagc gttcccgata cggtctgcg acatagtccg ggtggcggac       720
caccacgcgg tcgaggggcg cgaccattgc gtcagcttcg gcttcatcta tgcgccgccg     780
```

```
gtggtgcgcc agctccccgc gctggtaacg cagtcgaagc cgaagtagat acgcggcggc      840
gtcgacaagc tgaagcagga cctgaagacg tcgggcgtgc tgcgggccga ggcgcaggag      900
cagctgttcg acttcgtcct ggacttctgc agcccgcacg acgcccggct ccgcgtcctc      960
cgcacggcgt gc                                                          972
```

<210> SEQ ID NO 34
<211> LENGTH: 162
<212> TYPE: PRT
<213> ORGANISM: E-396
<220> FEATURE:
<223> OTHER INFORMATION: Description of Unknown Organism: Unknown

<400> SEQUENCE: 34

```
Met Thr Asn Phe Leu Ile Val Val Ala Thr Val Leu Val Met Glu Leu
 1               5                  10                  15

Thr Ala Tyr Ser Val His Arg Trp Ile Met His Gly Pro Leu Gly Trp
            20                  25                  30

Gly Trp His Lys Ser His Glu Glu His Asp His Ala Leu Glu Lys
        35                  40                  45

Asn Asp Leu Tyr Gly Leu Val Phe Ala Val Ile Ala Thr Val Leu Phe
    50                  55                  60

Thr Val Gly Trp Ile Trp Ala Pro Val Leu Trp Trp Ile Ala Leu Gly
65                  70                  75                  80

Met Thr Val Tyr Gly Leu Ile Tyr Phe Val Leu His Asp Gly Leu Val
                85                  90                  95

His Gln Arg Trp Pro Phe Arg Tyr Ile Pro Arg Lys Gly Tyr Ala Arg
            100                 105                 110

Arg Leu Tyr Gln Ala His Arg Leu His His Ala Val Glu Gly Arg Asp
        115                 120                 125

His Cys Val Ser Phe Gly Phe Ile Tyr Ala Pro Val Asp Lys Leu
    130                 135                 140

Lys Gln Asp Leu Lys Thr Ser Gly Val Leu Arg Ala Glu Ala Gln Glu
145                 150                 155                 160

Arg Thr
```

<210> SEQ ID NO 35
<211> LENGTH: 1253
<212> TYPE: DNA
<213> ORGANISM: E-396
<220> FEATURE:
<221> NAME/KEY: unsure
<222> LOCATION: (911)

<400> SEQUENCE: 35

```
ctgcaggtct gacacggcca gaaggccgcg ccgcgggccg ggggccgccg catcgcgacc       60
ggtatccttg ccaagcgccg cctggtcgcc cacaacgtcc agcaggtcgt cataggactg      120
gaacacccgg cccagctgac ggccaaagtc gatcatctga gtctgctcct cggcgtcgaa      180
ctccttgatc acgccagca tctccagccc ggcgatgaac agcacgccgg tcttcaggtc       240
ctgttcctgt tcgaccccg cgccgttctt ggccgcgtgc aggtccaggt cctgccggc        300 gcacaggccc tgcggcccca gggaccgcga caggatccgc accagctgcg cccgcaccgt      360
gcccgacgcg ccgcgcgcac cggccagcag ggccatcgcc tcggtgatca gggcgatgcc      420
gcctagcacg gcgcggcttt cgccatgcgc cacatgggtc gcgggctggc cgcggcgcag      480
cccggcatcg tccatgcagg gcaggtcgtc gaagatcagc gatgcggcat gcaccatctc      540
```

```
gaccgcgcag gcggcgtcga cgatcgtgtc gcagaccccg cccgaggctt ctgccgcaag      600
cagcatcagc atgccgcgga aacgcttgcc cgacgacagc gcgccatggc tcatggccgg      660
gccgagcggc tgcgacacgg caccgaatcc ctgggcgatc tcctcaagtc tggtctgcag      720
aagggtggcg tggatcgggt tgacgtctcg tctcatcagt gccttcgcgc ttgggttctg      780
accaggcggg aaggtcaggc cggggcggca ccccgtgacc cgtcatccac cgtcaacagt      840
ccccatgttg gaaggcttca cgcccgattg cgagccttt cgacggcgac gcgggtcgc       900 gcggcaattt ntccaacaag gtcagtggac cggcgcgccg atggccgcgc gcagccaggc      960
atccttggcc ggaaacaccc gcgccgcatc atgatcggcc aggatcgtcc ggcgcgcggc     1020
gcggcgcagg tcggccgcgt cacccggatt gtcaagcacc caggccatcg cgtccgcgac     1080
ctcgtccgcg tcgtccatgt cgacgatcag gccgttctcc atgtcgcgga ccagttcgcg     1140
caccggggcg gtgttcgatc gatcaccagg catccggtgg ccatcgcctc ggacagggac     1200
caggaggtga cgaagggctc ggtgaaatag acatgcgcgt gcgaggcctg cag            1253

<210> SEQ ID NO 36
<211> LENGTH: 1764
<212> TYPE: DNA
<213> ORGANISM: E-396
<220> FEATURE:
<223> OTHER INFORMATION: Description of Unknown Organism: Unknown

<400> SEQUENCE: 36
atgagacgag acgtcaaccc gatccacgcc acccttctgc agaccagact tgaggagatc       60
tactctgctc tgcagttggg ctaggtgcgg tgggaagacg tctggtctga actcctctag      120
gcccagggat tcggtgccgt gtcgcagccg ctcgcccgg ccatgagcca tggcgcgctg       180
cgggtcccta agccacggca cagcgtcggc gagccgggcc ggtactcggt accgcgcgac      240
tcgtcgggca agcgtttccg cggcatgctg atgctgcttg cggcagaagc ctcgggcggg      300
agcagcccgt tcgcaaaggc gccgtacgac tacgacgaac gccgtcttcg gagcccgccc      360
gtctgcgaca cgatcgtcga cgccgcctgc gcggtcgaga tggtgcatgc cgcatcgctg      420
cagacgctgt gctagcagct gcggcggacg cgccagctct accacgtacg gcgtagcgac      480
atcttcgacg acctgccctg catggacgat gccgggctgc gccgcggcca gcccgcgacc      540
tagaagctgc tggacgggac gtacctgcta cggcccgacg cggcgccggt cgggcgctgg      600
catgtggcgc atggcgaaag ccgcgccgtg ctaggcggca tcgccctgat caccgaggcg      660
gtacaccgcg taccgctttc ggcgcggcac gatccgccgt agcggactga gtggctccgc      720
atggccctgc tggccggtgc gcgcggcgcg tcggcacgtg tgcgggcgca gctggtgcgg      780
taccgggacg accggccacg cgcgccgcgc agcccgtgcc acgcccgcgt cgaccacgcc      840
atcctgtcgc ggtccctggg gccgcagggc ctgtgcgccg ccaggacct ggacctgcac       900 taggacagcg ccagggaccc cggcgtcccg gacacgcggc cggtcctgga cctggacgtg      960
gcggccaaga acgcgcgggg ggtcgaacag gaacaggacc tgaagaccgg cgtgctgttc     1020
cgccggttct tgccgcgcc ccagcttgtc cttgtcctgg acttctggcc gcacgacaag      1080 atcgccggc tggagatgct ggccgtgatc aaggagttcg acgccgagga gcagactcag      1140
tagcggcccg acctctacga ccggcactag ttcctcaagc tgcggctcct cgtctgagtc     1200
atgatcgact ttgccgtca gctgggccgg tgttccagt cctatgacga cctgctggac      1260
tactagctga aaccggcagt cgacccggcc cacaaggtca ggatactgct ggacgacctg     1320
```

-continued

```
gttgtgggcg accaggcggc gcttggcaag gataccggtc gcgatgcggc ggcccccggc    1380
caacacccgc tggtccgccg cgaaccgttc ctatggccag cgctacgccg ccggggggccg    1440 ccgcggcgcg gccttctggc cgtgtcagac ctgcagaacg tgtcccgtca ctatgaggcc    1500
ggcgccgcgc cggaagaccg gcacagtctg gacgtcttgc acagggcagt gatactccgg    1560
agccgcgccc agctggacgc gatgctgcgc agcaagcgcc ttcaggctcc ggaaatcgcg    1620
tcggcgcggg tcgacctgcg ctacgacgcg tcgttcgcgg aagtccgagg cctttagcgc    1680
gccctgctgg aacgggttct gccctacgcc gcgcgcgcct agcgggacga ccttgcccaa    1740
gacgggatgc ggcgcgcgcg gatc                                            1764
```

<210> SEQ ID NO 37
<211> LENGTH: 293
<212> TYPE: PRT
<213> ORGANISM: E-396
<220> FEATURE:
<223> OTHER INFORMATION: Description of Unknown Organism: Unkown

<400> SEQUENCE: 37

```
Met Arg Arg Asp Val Asn Pro Ile His Ala Thr Leu Leu Gln Thr Arg
 1               5                  10                  15

Leu Glu Glu Ile Ala Gln Gly Phe Gly Ala Val Ser Gln Pro Leu Gly
                20                  25                  30

Pro Ala Met Ser His Gly Ala Leu Ser Ser Gly Lys Arg Phe Arg Gly
            35                  40                  45

Met Leu Met Leu Leu Ala Ala Glu Ala Ser Gly Gly Val Cys Asp Thr
        50                  55                  60

Ile Val Asp Ala Ala Cys Ala Val Glu Met Val His Ala Ala Ser Leu
 65                  70                  75                  80

Ile Phe Asp Asp Leu Pro Cys Met Asp Ala Gly Leu Arg Arg Gly
                85                  90                  95

Gln Pro Ala Thr His Val Ala His Gly Glu Ser Arg Ala Val Leu Gly
            100                 105                 110

Gly Ile Ala Leu Ile Thr Glu Ala Met Ala Leu Leu Ala Gly Ala Arg
        115                 120                 125

Gly Ala Ser Gly Thr Val Arg Ala Gln Leu Val Arg Ile Leu Ser Arg
    130                 135                 140

Ser Leu Gly Pro Gln Gly Leu Cys Ala Gly Gln Asp Leu Asp Leu His
145                 150                 155                 160

Ala Ala Lys Asn Gly Ala Gly Val Glu Gln Glu Gln Asp Leu Lys Thr
                165                 170                 175

Gly Val Leu Phe Ile Ala Gly Leu Glu Met Leu Ala Val Ile Lys Glu
            180                 185                 190

Phe Asp Ala Glu Glu Gln Thr Gln Met Ile Asp Phe Gly Arg Gln Leu
        195                 200                 205

Gly Arg Val Phe Gln Ser Tyr Asp Asp Leu Leu Asp Val Val Gly Asp
    210                 215                 220

Gln Ala Ala Leu Gly Lys Asp Thr Gly Arg Asp Ala Ala Pro Gly
225                 230                 235                 240

Pro Arg Arg Gly Leu Leu Ala Val Ser Asp Leu Gln Asn Val Ser Arg
                245                 250                 255

His Tyr Glu Ala Ser Arg Ala Gln Leu Asp Ala Met Leu Arg Ser Lys
            260                 265                 270

Arg Leu Gln Ala Pro Glu Ile Ala Ala Leu Leu Glu Arg Val Leu Pro
        275                 280                 285
```

Tyr Ala Ala Arg Ala
    290

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Primer #7

<400> SEQUENCE: 38
cctggatgac gtgctggaat attcc                                              25

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Primer #8

<400> SEQUENCE: 39
caaggcccag atcgcaggcg                                                    20

<210> SEQ ID NO 40
<211> LENGTH: 391
<212> TYPE: PRT
<213> ORGANISM: Flavobacterium sp. R1534

<400> SEQUENCE: 40

Met Asp Pro Ile Val Ile Thr Gly Ala Met Arg Thr Pro Met Gly Ala
 1               5                  10                  15

Phe Gln Gly Asp Leu Ala Ala Met Asp Ala Pro Thr Leu Gly Ala Asp
            20                  25                  30

Ala Ile Arg Ala Ala Leu Asn Gly Leu Ser Pro Asp Met Val Asp Glu
        35                  40                  45

Val Leu Met Gly Cys Val Leu Ala Ala Gly Gln Gly Gln Ala Pro Ala
    50                  55                  60

Arg Gln Ala Ala Leu Gly Ala Gly Leu Pro Leu Ser Thr Gly Thr Thr
65                  70                  75                  80

Thr Ile Asn Glu Met Cys Gly Ser Gly Met Lys Ala Ala Met Leu Gly
                85                  90                  95

His Asp Leu Ile Ala Ala Gly Ser Ala Gly Ile Val Val Ala Gly Gly
            100                 105                 110

Met Glu Ser Met Ser Asn Ala Pro Tyr Leu Leu Pro Lys Ala Arg Ser
        115                 120                 125

Gly Met Arg Met Gly His Asp Arg Val Leu Asp His Met Phe Leu Asp
    130                 135                 140

Gly Leu Glu Asp Ala Tyr Asp Lys Gly Arg Leu Met Gly Thr Phe Ala
145                 150                 155                 160

Glu Asp Cys Ala Gly Asp His Gly Phe Thr Arg Glu Ala Gln Asp Asp
                165                 170                 175

Tyr Ala Leu Thr Ser Leu Ala Arg Ala Gln Asp Ala Ile Ala Ser Gly
            180                 185                 190

Ala Phe Ala Ala Glu Ile Ala Pro Val Thr Val Thr Ala Arg Lys Val
        195                 200                 205

Gln Thr Thr Val Asp Thr Asp Glu Met Pro Gly Lys Ala Arg Pro Glu
    210                 215                 220

Lys Ile Pro His Leu Lys Pro Ala Phe Arg Asp Gly Gly Thr Val Thr

-continued

```
225                 230                 235                 240
Ala Ala Asn Ser Ser Ile Ser Asp Gly Ala Ala Leu Val Met
                245                 250                 255

Met Arg Gln Ser Gln Ala Glu Lys Leu Gly Leu Thr Pro Ile Ala Arg
                260                 265                 270

Ile Ile Gly His Ala Thr His Ala Asp Arg Pro Gly Leu Phe Pro Thr
                275                 280                 285

Ala Pro Ile Gly Ala Met Arg Lys Leu Leu Asp Arg Thr Asp Thr Arg
        290                 295                 300

Leu Gly Asp Tyr Asp Leu Phe Glu Val Asn Glu Ala Phe Ala Val Val
305                 310                 315                 320

Ala Met Ile Ala Met Lys Glu Leu Gly Leu Pro His Asp Ala Thr Asn
                325                 330                 335

Ile Asn Gly Gly Ala Cys Ala Leu Gly His Pro Ile Gly Ala Ser Gly
                340                 345                 350

Ala Arg Ile Met Val Thr Leu Leu Asn Ala Met Ala Ala Arg Gly Ala
            355                 360                 365

Thr Arg Gly Ala Ala Ser Val Cys Ile Gly Gly Gly Glu Ala Thr Ala
        370                 375                 380

Ile Ala Leu Glu Arg Leu Ser
385                 390

<210> SEQ ID NO 41
<211> LENGTH: 388
<212> TYPE: PRT
<213> ORGANISM: Flavobacterium sp. R1534

<400> SEQUENCE: 41

Asp Pro Arg Leu Ala Val Arg Asp Gln Gln Pro Pro Leu Arg Ile Gly
  1               5                  10                  15

Gln His His Pro His Glu Pro Gln Arg Thr Thr Gln Arg Ala Pro Gln
                20                  25                  30

Ile Gly Arg Val Gln His Gly Met Arg His His Arg Glu Gly Pro Arg
            35                  40                  45

Arg His Gly Ala Arg Ala His Ser Glu Glu Leu Ala Ala Cys Pro Leu
    50                  55                  60

Arg Lys Val Ala Pro Asp Arg Ala Val Phe Arg Cys Ser Asp Gly Pro
65                  70                  75                  80

Asp Ala Arg Gly Pro Ala Leu Pro Arg Arg His Gln Arg Ile Ala His
                85                  90                  95

Glu Pro Phe Arg Asp Asp Val Leu Ile His Gly Pro Ser Leu Gln Asn
                100                 105                 110

Arg Ser Pro Ile Leu Ser Arg Asp Gly Ile Val Cys Asn Ala Pro Arg
            115                 120                 125

Ala Arg Met Ala Arg Ile Lys Gly Gly Arg Asp Met Glu Ile Glu
    130                 135                 140

Gly Arg Val Phe Val Val Thr Gly Ala Ala Ser Gly Leu Gly Ala Ala
145                 150                 155                 160

Ser Ala Arg Met Leu Ala Gln Gly Gly Ala Lys Val Val Leu Ala Asp
                165                 170                 175

Leu Ala Glu Pro Lys Asp Ala Pro Glu Gly Ala Val His Ala Ala Cys
                180                 185                 190

Asp Val Thr Asp Ala Thr Ala Ala Gln Thr Ala Ile Ala Leu Ala Thr
            195                 200                 205
```

```
Asp Arg Phe Gly Arg Leu Asp Gly Leu Val Asn Cys Ala Gly Ile Ala
    210                 215                 220
Pro Ala Glu Arg Met Leu Gly Arg Asp Gly Pro His Gly Leu Asp Ser
225                 230                 235                 240
Phe Ala Arg Ala Val Thr Ile Asn Leu Ile Gly Ser Phe Asn Met Ala
                245                 250                 255
Arg Leu Ala Ala Glu Ala Met Ala Arg Asn Glu Pro Val Arg Gly Glu
            260                 265                 270
Arg Gly Val Ile Val Asn Thr Ala Ser Ile Ala Ala Gln Asp Gly Gln
        275                 280                 285
Ile Gly Gln Val Ala Tyr Ala Ala Ser Lys Ala Gly Val Ala Gly Met
    290                 295                 300
Thr Leu Pro Met Ala Arg Asp Leu Ala Arg His Gly Ile Arg Val Met
305                 310                 315                 320
Thr Ile Ala Pro Gly Ile Phe Arg Thr Pro Met Leu Glu Gly Leu Pro
                325                 330                 335
Gln Asp Val Gln Asp Ser Leu Gly Ala Ala Val Pro Phe Pro Ser Arg
            340                 345                 350
Leu Gly Glu Pro Ser Glu Tyr Ala Ala Leu Leu His His Ile Ile Ala
        355                 360                 365
Asn Pro Met Leu Asn Gly Glu Val Ile Arg Leu Asp Gly Ala Leu Arg
    370                 375                 380
Met Ala Pro Lys
385

<210> SEQ ID NO 42
<211> LENGTH: 182
<212> TYPE: PRT
<213> ORGANISM: Flavobacterium sp. R1534

<400> SEQUENCE: 42

Met Thr Gly Thr Arg Met Arg Arg Val Ser Arg Ile Ser Ala Pro Ser
  1               5                  10                  15
Ser Pro Ile Leu Pro Met Trp Pro Ser Lys Ala Ala Leu Leu Ala
                 20                  25                  30
Val Leu Met Pro Ala Ala Ala Ala Val Glu Cys Ala Pro Gly Ser
             35                  40                  45
Leu Val Val Asp Thr Gly Ala Glu Thr Leu Gly Phe Arg Val Glu Val
         50                  55                  60
Ala Asp Ser Pro Glu Glu Arg Ala Gln Gly Leu Met Phe Arg Lys Glu
 65                  70                  75                  80
Leu Pro Ala Gly Thr Gly Met Leu Phe Ile Tyr Glu Ser Pro Gln Pro
                 85                  90                  95
Val Ser Phe Trp Met Arg Asn Thr Leu Ile Pro Leu Asp Met Val Phe
                100                 105                 110
Ala Asp Glu Thr Gly Val Ile Arg His Ile His Arg Asn Ala Arg Pro
            115                 120                 125
Leu Asp Glu Thr Pro Ile Pro Gly Ala Ala Val Gly Asp Pro Asp Pro
        130                 135                 140
Asp Arg Leu Phe Val Leu Glu Ile Ala Gly Gly Glu Ala Asp Arg Leu
145                 150                 155                 160
Gly Leu Lys Pro Gly Gln Pro Met Ala His Pro Gly Met Gly Asp Asn
                165                 170                 175
Ala Val Leu Ala Cys Asp
            180
```

<210> SEQ ID NO 43
<211> LENGTH: 22
<212> TYPE: DNA
<213> ORGANISM: Flavobacterium sp. R1534

<400> SEQUENCE: 43
acgaaggcac cgatgacgcc ca                                    22

<210> SEQ ID NO 44
<211> LENGTH: 25
<212> TYPE: DNA
<213> ORGANISM: Flavobacterium sp. R1534

<400> SEQUENCE: 44
cggacctggc cgtcgcatga ccatc                                 25

<210> SEQ ID NO 45
<211> LENGTH: 23
<212> TYPE: DNA
<213> ORGANISM: Flavobacterium sp. R1534

<400> SEQUENCE: 45
cggatcgcaa tacatgagcc atg                                   23

<210> SEQ ID NO 46
<211> LENGTH: 24
<212> TYPE: DNA
<213> ORGANISM: Flavobacterium sp. R1534

<400> SEQUENCE: 46
ctgcaggaga gagcatgagt tccg                                  24

<210> SEQ ID NO 47
<211> LENGTH: 23
<212> TYPE: DNA
<213> ORGANISM: Flavobacterium sp. R1534

<400> SEQUENCE: 47
gcaaggggcc ggcatgagca ctt                                   23

<210> SEQ ID NO 48
<211> LENGTH: 21
<212> TYPE: RNA
<213> ORGANISM: Flavobacterium sp.

<400> SEQUENCE: 48
aaaggagggu uucauaugag c                                     21

<210> SEQ ID NO 49
<211> LENGTH: 21
<212> TYPE: RNA
<213> ORGANISM: Flavobacterium sp.

<400> SEQUENCE: 49
aaaggaggac acgugaugag c                                     21

<210> SEQ ID NO 50
<211> LENGTH: 22
<212> TYPE: RNA
<213> ORGANISM: Flavobacterium sp.

<400> SEQUENCE: 50

-continued aaaggaggca auugagauga gu    22

<210> SEQ ID NO 51
<211> LENGTH: 22
<212> TYPE: RNA
<213> ORGANISM: Flavobacterium sp.

<400> SEQUENCE: 51
aaaggaggau ccaaucauga cc    22

<210> SEQ ID NO 52
<211> LENGTH: 21
<212> TYPE: RNA
<213> ORGANISM: Flavobacterium sp.

<400> SEQUENCE: 52
aaaggagggu uucuuaugac g    21

<210> SEQ ID NO 53
<211> LENGTH: 15
<212> TYPE: RNA
<213> ORGANISM: Bacillus subtilis

<400> SEQUENCE: 53
ucuuuccucc acuag    15

<210> SEQ ID NO 54
<211> LENGTH: 13
<212> TYPE: RNA
<213> ORGANISM: Escherichia coli

<400> SEQUENCE: 54
auuccuccac uag    13

<210> SEQ ID NO 55
<211> LENGTH: 32
<212> TYPE: DNA
<213> ORGANISM: Artificial Sequence
<220> FEATURE:
<223> OTHER INFORMATION: Description of Artificial Sequence: Primer
      crtW15

<400> SEQUENCE: 55
tatatctaga catatgtccg gtcgtaaacc gg    32

<210> SEQ ID NO 56
<211> LENGTH: 40
<212> TYPE: DNA
<213> ORGANISM: Artificial Sequence
<220> FEATURE:
<223> OTHER INFORMATION: Description of Artificial Sequence: Primer
      crtW26

<400> SEQUENCE: 56
tatagaattc cacgtgtcaa gcacgaccac cggttttacg    40

<210> SEQ ID NO 57
<211> LENGTH: 17
<212> TYPE: DNA
<213> ORGANISM: Artificial Sequence
<220> FEATURE:
<223> OTHER INFORMATION: Description of Artificial Sequence: Primet
      crtW100

<400> SEQUENCE: 57
caygaygcma tgcaygg                                                          17

<210> SEQ ID NO 58
<211> LENGTH: 17
<212> TYPE: DNA
<213> ORGANISM: Artificial Sequence
<220> FEATURE:
<223> OTHER INFORMATION: Description of Artificial Sequence: Primer
      crtW101

<400> SEQUENCE: 58
caygaygcka tgcaygg                                                          17

<210> SEQ ID NO 59
<211> LENGTH: 17
<212> TYPE: DNA
<213> ORGANISM: Artificial Sequence
<220> FEATURE:
<223> OTHER INFORMATION: Description of Artificial Sequence: Primer
      crtW105

<400> SEQUENCE: 59
agrtgrtgyt crtgrtg                                                          17

<210> SEQ ID NO 60
<211> LENGTH: 17
<212> TYPE: DNA
<213> ORGANISM: Artificial Sequence
<220> FEATURE:
<223> OTHER INFORMATION: Description of Artificial Sequence: Primer
      crtW106

<400> SEQUENCE: 60
agrtgrtgyt cccartg                                                          17

<210> SEQ ID NO 61
<211> LENGTH: 31
<212> TYPE: DNA
<213> ORGANISM: Artificial Sequence
<220> FEATURE:
<223> OTHER INFORMATION: Description of Artificial Sequence: Primer
      crtW107

<400> SEQUENCE: 61
atcatatgag cgcacatgcc ctgcccaagg c                                          31

<210> SEQ ID NO 62
<211> LENGTH: 33
<212> TYPE: DNA
<213> ORGANISM: Artificial Sequence
<220> FEATURE:
<223> OTHER INFORMATION: Description of Artificial Sequence: Primer
      crtW108

<400> SEQUENCE: 62
atctcgagtc acgtgcgctc ctgcgcctcg gcc                                        33

<210> SEQ ID NO 63
<211> LENGTH: 33
<212> TYPE: DNA
<213> ORGANISM: Artificial Sequence
<220> FEATURE:
<223> OTHER INFORMATION: Description of Artificial Sequence: Primer
      crtW113

<400> SEQUENCE: 63
atatacatat ggtgtccccc ttggtgcggg tgc                                        33

-continued

```
<210> SEQ ID NO 64
<211> LENGTH: 35
<212> TYPE: DNA
<213> ORGANISM: Artificial Sequence
<220> FEATURE:
<223> OTHER INFORMATION: Description of Artificial Sequence: Primer
      crtW114

<400> SEQUENCE: 64
tatggatccg acgcgttccc ggaccgccac aatgc                              35

<210> SEQ ID NO 65
<211> LENGTH: 43
<212> TYPE: DNA
<213> ORGANISM: Artificial Sequence
<220> FEATURE:
<223> OTHER INFORMATION: Description of Artificial Sequence: Primer
      AmpR1

<400> SEQUENCE: 65
tatatcggcc gactagtaag cttcaaaaag gatcttcacc tag                     43

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Primer
      AmpR2

<400> SEQUENCE: 66
atatgaattc aataatattg aaaaaggaag                                    30
```

What is claimed is:

1. A process for the preparation of zeaxanthin wherein the process comprises culturing a recombinant cell containing farnesyl pyrophosphate and isopentyl pyrophosphate under culture conditions sufficient for the expression of enzymes which catalyze the conversion of the farnesyl pyrophosphate and isopentyl pyrophosphate to zeaxanthin, the recombinant cell being a host cell transformed by an expression vector comprising a regulatory sequence and a polynucleotide containing the following DNA sequences which encode the enzymes:

(a) a DNA sequence which encodes the geranylgeranyl pyrophosphate (GGPP) synthase of Flavobacterium sp. R1534 (crtE) (SEQ ID NO: 2) or a DNA sequence that hybridizes to a complementary strand of SEQ ID NO: 1 under the following conditions: hybridization. in 7% sodium dodecyl sulfate (SDS), 1% bovine serum albumin (BSA), 0.5 M $Na_2HPO_4$, pH 7.2, at 65° C., washing twice for 5 minutes each in 2×SSC, 1% SDS, at room temperature, followed by two additional washes for 15 minutes each in 0.1% SSC, 0.1% SDS, at 65° C., wherein the hybrid DNA encodes a polypeptide having geranylgeranyl pyrophosphate (GGPP) synthase activity, (b) a DNA sequence which encodes the prephytoene synthase of Flavobacterium sp. R1534 (crtB) (SEQ ID NO: 3) or a DNA sequence that hybridizes to a complementary strand of SEQ ID NO: 1 under the following conditions: hybridization in 7% sodium dodecyl sulfate (SDS), 1% bovine serum albumin (BSA), 0.5 M $Na_2HPO_4$, pH 7.2, at 65° C., washing twice for 5 minutes each in 2×SSC, 1% SDS, at room temperature, followed by two additional washes for 15 minutes each in 0.1% SSC, 0.1% SDS, at 65° C., wherein the hybrid DNA encodes a polypeptide having prephytoene synthase activity, (c) a DNA sequence which encodes the phytoene desaturase of Flavobacterium sp. R1534 (crtI) (SEQ ID NO: 4) or a DNA sequence that hybridizes to a complementary strand of SEQ ID NO: 1 under the following conditions: hybridization in 7% sodium dodecyl sulfate (SDS), 1% bovine serum albumin (BSA), 0.5 M $Na_2HPO_4$, pH 7.2, at 65° C., washing twice for 5 minutes each in 2×SSC, 1% SDS, at room temperature, followed by two additional washes for 15 minutes each in 0.1% SSC, 0.1% SDS, at 65° C., wherein the hybrid DNA encodes a polypeptide having phytoene desaturase activity, (d) a DNA sequence which encodes the lycopene cyclase of Flavobacterium sp. R1534 (crtY) (SEQ ID NO: 5) or a DNA sequence that hybridizes to a complementary strand of SEQ ID NO: 1 under the following conditions: hybridization in 7% sodium dodecyl sulfate (SDS), 1% bovine serum albumin (BSA), 0.5 M $Na_2HPO_4$, pH 7.2, at 65° C., washing twice for 5 minutes each in 2×SSC, 1% SDS, at room temperature, followed by two additional washes for 15 minutes each in 0.1% SSC, 0.1% SDS, at 65° C., wherein the hybrid DNA encodes a polypeptide having lycopene cyclase activity, and (e) a DNA sequence which encodes the β-carotene hydroxylase of microorganism E-396 ($crtZ_{E396}$) (SEQ ID NO: 34) or a DNA sequence that hybridizes to a complementary strand of SEQ ID NO: 33 under the following conditions: hybridization in 7% sodium dodecyl sulfate (SDS), 1% bovine serum albumin (BSA), 0.5 M $Na_2HPO_4$, pH 7.2, at 65° C., washing twice for 5 minutes each in 2×SSC, 1% SDS, at room temperature, followed by two additional washes for 15 minutes each in 0.1% SSC, 0.1% SDS, at 65° C., wherein the hybrid DNA encodes a polypeptide having β-carotene hydroxylase activity; and isolating the zeaxanthin from such cells or culture medium.

2. A process according to claim 1 wherein the DNA sequences are:

(a) the DNA sequence which encodes the GGPP synthase of Flavobacterium sp. R1534 (crtE) (SEQ ID NO: 2), (b) the DNA sequence which encodes the prephytoene synthase of Flavobacterium sp. R1534 (crtB) (SEQ ID NO: 3), (c) the DNA sequence which encodes the phytoene desaturase of Flavobacterium sp. R1534 (crtI) (SEQ ID NO: 4), (d) the DNA sequence which encodes the lycopene cyclase of Flavobacterium sp. R1534 (crtY) (SEQ ID NO: 5), and (e) the DNA sequence which encodes the β-carotene hydroxylase of microorganism E-396 ($crtZ_{E396}$) (SEQ ID NO: 34).

3. The process of claim 2 wherein:

(a) the DNA sequence encoding the GGPP synthase comprises nucleotides 2521–3408 of FIG. 7 (SEQ ID NO: 1), (b) the DNA sequence encoding prephytoene synthase comprises nucleotides 4316–3405 of FIG. 7 (SEQ ID NO: 1), (c) the DNA sequence encoding the phytoene desaturase comprises nucleotides 4313–5797 of FIG. 7 (SEQ ID NO: 1), (d) the DNA sequence encoding the lycopene cyclase comprises nucleotides 5794–6942 of FIG. 7 (SEQ ID NO: 1), and (e) the DNA sequence encoding the β-carotene hydroxylase comprises the sequence of FIG. 33 (SEQ ID NO: 33).

* * * * *

UNITED STATES PATENT AND TRADEMARK OFFICE
CERTIFICATE OF CORRECTION

PATENT NO. : 6,291,204 B1
DATED : September 18, 2001
INVENTOR(S) : Luis Pasamontes and Yuri Tsygankov It is certified that error appears in the above-identified patent and that said Letters Patent is hereby corrected as shown below:

<u>Title page,</u>
Item [56], References Cited, FOREIGN PATENT DOCUMENTS, please change "747-483" to -- 0 747 483 A2 --;
Throughout the patent, please italicize every occurrence of "Flavobacterium sp.;"

Signed and Sealed this

Twenty-fourth Day of September, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 6,291,204 B1
DATED : September 18, 2001
INVENTOR(S) : Luis Pasamontes and Yuri Tsygankov It is certified that error appears in the above-identified patent and that said Letters Patent is hereby corrected as shown below:

Title page,
Item [56], References Cited, FOREIGN PATENT DOCUMENTS, please change "747-483" to -- 0 747 483 A2 --;

Columns 1-102,
Please italicize every occurrence of "Flavobacterium sp.;"

Signed and Sealed this

Eighth Day of March, 2005

JON W. DUDAS
*Director of the United States Patent and Trademark Office*